(12) United States Patent
Strong et al.

(10) Patent No.: US 11,235,076 B2
(45) Date of Patent: Feb. 1, 2022

(54) CHELATING PLATFORM FOR DELIVERY OF RADIONUCLIDES

(71) Applicants: Fred Hutchinson Cancer Research Center, Seattle, WA (US); The Regents of the University of California, Oakland, CA (US)

(72) Inventors: Roland K. Strong, Seattle, WA (US); Peter Rupert, Seattle, WA (US); Rebecca J. Abergel, Berkeley, CA (US); Ilya Captain, Moraga, CA (US); Gauthier J P Deblonde, Berkeley, CA (US)

(73) Assignees: Fred Hutchinson Cancer Research Center, Seattle, WA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 16/329,178

(22) PCT Filed: Aug. 28, 2017

(86) PCT No.: PCT/US2017/048954
§ 371 (c)(1),
(2) Date: Feb. 27, 2019

(87) PCT Pub. No.: WO2018/044812
PCT Pub. Date: Mar. 8, 2018

(65) Prior Publication Data
US 2019/0184041 A1 Jun. 20, 2019

Related U.S. Application Data

(60) Provisional application No. 62/380,885, filed on Aug. 29, 2016, provisional application No. 62/401,687, filed on Sep. 29, 2016, provisional application No. 62/505,458, filed on May 12, 2017.

(51) Int. Cl.
| | | |
|---|---|---|
| A61K 51/04 | (2006.01) |
| B01D 15/34 | (2006.01) |
| B01D 15/38 | (2006.01) |
| C07K 14/47 | (2006.01) |
| C22B 60/02 | (2006.01) |

(52) U.S. Cl.
CPC ...... *A61K 51/0482* (2013.01); *A61K 51/0478* (2013.01); *B01D 15/34* (2013.01); *B01D 15/3804* (2013.01); *C07K 14/47* (2013.01); *C22B 60/02* (2013.01)

(58) Field of Classification Search
CPC .... A61K 51/00; A61K 51/04; A61K 51/0482; A61K 51/0478; C07K 14/47; B01D 15/34; B01D 15/3804; A61P 35/00; C22B 60/02
USPC .......... 424/1.11, 1.65, 1.69, 1.81, 1.85, 1.89, 424/9.1, 9.2, 9.3, 9.4, 9.5; 534/7, 10–16; 514/1, 1.1, 19.2, 19.3, 19.4, 19.5, 19.6, 514/21.2; 530/300, 350
See application file for complete search history.

(56) References Cited

U.S. PATENT DOCUMENTS

| | | |
|---|---|---|
| 4,278,559 A | 7/1981 | Levenson et al. |
| 4,454,106 A | 6/1984 | Gansow et al. |
| 4,472,509 A | 9/1984 | Gansow et al. |
| 4,698,431 A | 10/1987 | Raymond et al. |
| 4,831,175 A | 5/1989 | Gansow et al. |
| 4,891,075 A | 1/1990 | Dakubu |
| 5,246,692 A | 9/1993 | Gansow et al. |
| 5,250,285 A | 10/1993 | Lauffer et al. |
| 5,442,116 A | 8/1995 | Welch et al. |
| 5,482,570 A | 1/1996 | Saurer et al. |
| 5,514,363 A | 5/1996 | Shochat et al. |
| 5,571,894 A | 11/1996 | Wels et al. |
| 5,587,458 A | 12/1996 | King et al. |
| 5,591,828 A | 1/1997 | Bosslet et al. |
| 5,634,901 A | 6/1997 | Alba et al. |
| 5,753,204 A | 5/1998 | Huston et al. |
| 5,826,161 A | 10/1998 | Madic et al. |
| 5,837,218 A | 11/1998 | Peers et al. |
| 5,869,046 A | 2/1999 | Presta et al. |
| 5,891,418 A | 4/1999 | Sharma |
| 5,892,029 A | 4/1999 | Raymond et al. |
| 5,922,302 A | 7/1999 | Goldenberg et al. |
| 6,180,082 B1 | 1/2001 | Woltering et al. |
| 6,183,721 B1 | 2/2001 | Albert et al. |
| 6,203,775 B1 | 3/2001 | Torchilin et al. |

(Continued)

FOREIGN PATENT DOCUMENTS

| | | |
|---|---|---|
| CN | 104825389 | 8/2015 |
| CN | 104998251 | 10/2015 |

(Continued)

OTHER PUBLICATIONS

Holmes et al, Structure, vol. 14, pp. 29-41 (Year: 2005).*
Deri et al, Journal of Medicinal Chemistry, 2014, vol. 57, pp. 4849-4860 (Year: 2014).*
International Search Report and Written Opinion dated Nov. 13, 2017 in International patent application PCT/US2017/050121.
International Search Report dated Dec. 21, 2017 in International Patent Application No. PCT/US2017/048910.

(Continued)

*Primary Examiner* — D. L. Jones
(74) *Attorney, Agent, or Firm* — Lee & Hayes PC; C. Rachal Winger

(57) ABSTRACT

Siderocalin-metal chelator combinations that bind metallic radioisotopes used in nuclear medicine with high affinity are described. The high affinity siderocalin-metal chelator combinations include a number of chelator backbone arrangements with functional groups that coordinate with metals. The siderocalin-metal chelator combinations can be used to deliver radionuclides for imaging and therapeutic purposes.

21 Claims, 35 Drawing Sheets
Specification includes a Sequence Listing.

(56) References Cited

U.S. PATENT DOCUMENTS

| | | | |
|---|---|---|---|
| 6,843,917 | B1 | 1/2005 | Guy et al. |
| 6,846,915 | B2 | 1/2005 | Raymond et al. |
| 8,361,794 | B2 | 1/2013 | Jakobsen |
| 8,394,606 | B2 | 3/2013 | Ali et al. |
| 8,475,747 | B1 | 7/2013 | Johnson et al. |
| 8,933,526 | B2 | 1/2015 | Tsakalakos et al. |
| 9,123,846 | B2 | 9/2015 | Le Perchec et al. |
| 9,260,492 | B2 | 2/2016 | Matschiner et al. |
| 9,472,694 | B2 | 10/2016 | Dionne et al. |
| 2002/0122752 | A1 | 9/2002 | Taylor et al. |
| 2005/0008570 | A1 | 1/2005 | Raymond et al. |
| 2009/0184051 | A1 | 7/2009 | Heres et al. |
| 2009/0320646 | A1 | 12/2009 | Yaita et al. |
| 2010/0015725 | A1 | 1/2010 | Raymond et al. |
| 2010/0261902 | A1 | 10/2010 | Xu et al. |
| 2011/0189088 | A1 | 8/2011 | Xu et al. |
| 2011/0250138 | A1 | 10/2011 | Fan et al. |
| 2011/0262353 | A1 | 10/2011 | Skerra et al. |
| 2011/0319985 | A1 | 12/2011 | Oepen |
| 2012/0132277 | A1 | 5/2012 | Sulima et al. |
| 2012/0214843 | A1 | 8/2012 | Durbin-Heavey et al. |
| 2014/0235680 | A1 | 8/2014 | Bergeron, Jr. |
| 2014/0294759 | A1 | 10/2014 | Chu et al. |
| 2016/0289223 | A1 | 10/2016 | Bergeron, Jr. |
| 2016/0362491 | A1 | 12/2016 | Mudde et al. |
| 2017/0298272 | A1 | 10/2017 | Agbo et al. |
| 2019/0183868 | A1 | 6/2019 | Abergel et al. |
| 2019/0287691 | A1 | 9/2019 | Abergel et al. |
| 2019/0382470 | A1 | 12/2019 | Himmler et al. |
| 2021/0009510 | A1 | 1/2021 | Abergel et al. |

FOREIGN PATENT DOCUMENTS

| | | |
|---|---|---|
| EP | 0404097 B1 | 9/1996 |
| JP | 2019514944 A | 6/2019 |
| JP | 2019532040 A | 11/2019 |
| JP | 2019532182 A | 11/2019 |
| WO | WO9301161 A1 | 1/1993 |
| WO | WO9316185 A2 | 8/1993 |
| WO | WO2006028523 A2 | 3/2006 |
| WO | WO2006072620 A1 | 7/2006 |
| WO | WO2007098934 A1 | 9/2007 |
| WO | WO2009156456 | 12/2009 |
| WO | WO2010129962 A2 | 11/2010 |
| WO | WO2014093403 A1 | 6/2014 |
| WO | WO2015077655 A1 | 5/2015 |
| WO | WO2017105565 A2 | 6/2017 |
| WO | WO2017192581 A1 | 11/2017 |
| WO | WO2018048812 A1 | 3/2018 |
| WO | WO2018063638 A1 | 4/2018 |
| WO | WO2018097871 A2 | 5/2018 |

OTHER PUBLICATIONS

International Search Report dated May 11, 2018 in International Patent Application No. PCT/US2017/048934.

Iqbal, et al., Synthesis and Am/Eu extraction of novel TODGA derivatives, Supramolecualr Chemistry, vol. 22, pp. 827-837, 2010.

Jang, et al. Bright dual-mode green emission from selective set of dopant ions in Beta-Na(Y,Gd)F4:Yb,Er/ß-NaGdF4: Ce,Tb core/shell nanocrystals, Optics Express, vol. 20, No. 15, pp. 17107-17118, (2012).

Jarvis, et al., Significance of Single Variables in Defining Adequate Animal Models to Assess the Efficacy of New Radionuclide Decorporation Agents: Using the Contamination Dose as an Example. Drug Development Research, vol. 73, No. 5, pp. 281-299, 2012.

Jurcic, et al., "Phase I Trial of the Targeted Alpha-Particle Nano-Generator Actinium-225 (225Ac)-Lintuzumab (Anti-CD33) in Combination With Low-Dose Cytarabine (LDAC) for Older Patients With Untreated Acute Myeloid Leukemia (AML)," Blood, vol. 122, No. 21, 2013, pp. 1460-1460.

Jursich, et al.., Laser induced fluorescence of 249 Bk 4+ in CeF 4, Inorganica Chim. Acta. vol. 139, pp. 27✓ 274. 1987.

Kim and Brechbiel, "An overview of targeted alpha therapy," Tumor Biol., vol. 33, No. 3, 2012, pp. 573-590.

Konzen, et al, Development of the Plutonium-DTPA Biokinetic Model. Health Physics, vol. 108, No. 6, pp. 565-573, 2015.

Kruijff, et. al., "A Critical Review of Alpha Radionuclide Therapy-How to Deal with Recoiling Daughters?" Pharmaceuticals, vol. 8, 2015, pp. 321-336.

Kullgren, et al., "Actinide chelation: biodistribution and in vivo complex stability of the targeted metal ions," Toxicol. Mech. Methods, vol. 23, No. 1, 2013, pp. 18-26.

Kurkoti, et al., Gadolinium and nephrogenic systemic fibrosis: Association or causation. 1-10 Nephrology, vol. 13, pp. 235-241, 2008.

Lake, et al., Construction and Binding Analysis of Recombinant Single-Chain TCR Derived From Tumor-Infiltrating Lymphocytes and a Cytotoxic T Lymphocyte Clone Directed Against MAGE-1, International Immunology, Vo. 11, pp. 745-751, 1999.

Lakowicz, et al., Energy Transfer, Principles of Fluorescence Spectroscopy, pp. 367-394, 2006.

Lakshminarayana, et al., Cooperative downconversion luminescence in Pr3+/Yb3+:SiO2—Al2O3—BaF2—GdF3 glasses, Journal of Materials Research, vol. 23, Issue 11, pp. 3090-3095, 2008.

Laskowski, et al., "PROCHECK: a program to check the stereochemical quality of protein structures," J. Appl. Cryst., vol. 26, 1993, pp. 283-291.

Li, et al. Nd3+ Sensitized Up/Down Converting Dual-Mode Nanomaterials for Efficient Invitro and In-vivo Bioimaging Excited at 800 nm, Scientific Reports, vol. 3, pp. 3536, 2013.

Li, et al., Engineering Homogeneous Doping in Single Nanoparticle to Enhance Upconversion Efficiency, Nano Lett., vol. 14, No. 6, pp. 3634-3639, 2014.

Li, et al., Enhanced NIR downconversion luminescence by precipitating nano Ca5(PO4)3F crystals in Eu2+Yb3+ co-doped glass, Spectrochimica Acta Part A: Molecular and Biomolecular Spectroscopy, vol. 114, pp. 575-578, 2013.

Liepe, "Alpharadin, a 223Ra-based alpha-particle-emitting pharmaceutical for the treatment of bone metastases in patients with cancer," Curr. Opin. Investig. Drugs, vol. 10, No. 12, 2009, pp. 1346-1358.

Liu et al., Procedures for a fast separation of berkelium from complex mixtures of reaction products, J. Radioanal. Nucl. Chem. 76, pp. 119-124, 1983.

Liu, et al. A Strategy to Achieve Efficent Dual-Mode Luminescence of EU3+ in Lanthanides Doped Multifunctional NAGdF4 Nanocrystals, Adv Matter, vol. 22, pp. 3266-3271, 2010.

Liu, et al. Morphology and Phase-Controlled Synthesis of Monodisperse Lanthanide-Doped NaGdF4 Nanocrystals with Multicolor Photo Luminesence, Journal of Materials Chemistry, vol. 19, pp. 489-496, 2009.

Lohithakshan, et al., Solvent extraction studies of plutonium(IV) and americium(III) in room temperature ionic liquid (RTIL) by di-2-ethyl hexyl phosphoric acid (HDEHP) as Extractant, Journal of Radioanalytical and Nuclear Chemistry, vol. 301, pp. 153-157, 2014.

Loomis and Raymond, "Solution equilibria of enterobactin and metal-enterobactin complexes," Inorg. Chem., vol. 30, No. 5, 1991, pp. 906-911.

Lumetta, et al., An Advanced TALSPEAK Concept Using 2-Ethylhexylphosphonic Acid Mono-2-Ethylhexyl Ester as the Extractant, Solvent Extraction and Ion Exchange, vol. 33, No. 3, pp. 211-223, 2015.

Lundberg, et al., Structural Study of the N,N'-Dimethylpropyleneurea Solvated Lanthanoid(III) Ions in Solution and Solid State with an Analysis of the Ionic Radii of Lanthanoid(III) Ions, Inorganic Chemistry, vol. 49, pp. 4420-4432, 2010.

Lundberg, et al., The size of actinoid(III) ions—structural analysis vs. common misinterpretations, Coordination Chemistry Reviews, vol. 318, pp. 131-134, 2016.

Maynard, et al., High-Level Bacterial Secretion of Single-Chain Alpha Beta T-Cell Receptors, Journal of Immunological Methods, vol. 306, pp. 51-67, 2005.

McDevitt, et al., "Tumor therapy with targeted atomic nanogenerators," Science, vol. 294, No. 5546, 2001, pp. 1537-1540.

(56) References Cited

OTHER PUBLICATIONS

Milyukova, et al. Extraction of Bk(IV) with POM—Milyukova, 1986.pdf, J. Radioanal. Nucl. Chem. 104 pp. 81-90, (1986).

Mimum, et al., Bimodal imaging using neodymium doped gadolinium fluoride nanocrystals with near-infrared to near-infrared downconversion luminescence and magnetic resonance properties, Journals of Materials Chemistry B, vol. 1, pp. 5702-5710, 2013.

Modolo, et al., Recovery of Actinides and Lanthanides From High-Level Liquid Waste by Extraction Chromatography Using TODGA+TBP Impregnated Resins, Radiochimica Acta, vol. 95, pp. 391-397, 2007.

Moore, et al. An octadentate luminescent Eu(III) 1,2-HOPO chelate with potent aqueous stability, Inorganic Chemistry, vol. 46, No. 14, pp. 5468-5470, 2007.

Moore, et al. Liquid-liquid Extraction Method for the Separation of Cerium (IV) From Berkelium (IV) and Other Elements, Analytical Chemistry, vol. 41, pp. 1658-1661, 1969.

Moore, et al., Application of dual affinity retargeting molecules to achieve optimal redirected T-cell killing of B-cell lymphoma, Blood, Vo. 117, pp. 4542-4551, 2011.

Moore, et al., New Method for Rapid Separation of Berkelium (IV) From Cerium (IV) by Anion Exchange, Analytical Chemistry, vol. 39, pp. 1874-1876, 1967.

Moos, et al., Radiation Drugs—A Hot Topic. Drug Development Research, vol. 73, No. 5, pp. 229-231, 2012.

Morita, et al. Development of Todga Extraction Process for High-Level Liquid Waste—Preliminary Evaluation of Actinide Separation by Calculation, 2000.

Morris, et al., Voltammetric Investigation of the Berkelium(IV/III) Couple in Concentrated Aqueous Carbonate Solutions, Radiochimica Acta, pp. 125-134, 1990.

Mulford, et al., "The promise of targeted {alpha}-particle therapy," J. Nucl. Med., vol. 46, Suppl. 1, 2005, pp. 199S-204S.

Murshudov, et al., "Refinement of macromolecular structures by the maximum-likelihood method," Acta Crystallogr. D. Biol. Crystallogr, vol. 53, Part 3, 1997, pp. 240-255.

Nash, et al., The Chemistry of TALSPEAK: A Review of the Science, Solvent Extraction. Ion Exchange Journal, vol. 33, No. 1, pp. 1-55, 2015.

Nord, et al., A combinatorial library of an alpha-helical bacterial receptor domain, Protein Engineering, Design and Selection, vol. 8, No. 6, pp. 601, 1995.

Nord, et al., Binding proteins selected from combinatorial libraries of an a-helical bacterial receptor domain, Nature Biotechnology, vol. 15, pp. 772-777, 1997.

Nord, et al., Recombinant human factor VIII-specific affinity ligands selected from phagedisplayed combinatorial libraries of protein A, European Journal of Biochemistry, vol. 268, pp. 4269-4277, 2001.

Nugent, et al., Electron-transfer and fd Absorption Bands of Some Lanthanide and Actinide Complexes and the Standard (II-III) Oxidation Potential for Each Member of the Lanthanide and Actinide Series, The Journal of Physical Chemistry A, vol. 77, pp. 1528-1539, 1973.

Nugent, et al., Intramolecular Energy Transfer and Sensitized Luminescence in Actinide (III). Beta.-Diketone Chelates, The Journal of Physical Chemistry A, vol. 73, pp. 1540-1549, 1969.

Office Action dated Apr. 9, 2020 in U.S. Appl. No. 15/442,441.
Office Action dated Aug. 23, 2019 in U.S. Appl. No. 15/442,441.
Office Action dated Jan. 2, 2020 in U.S. Appl. No. 15/442,441.
Office Action dated Jun. 25, 2019 in U.S. Appl. No. 16/097,782.
Office Action dated Mar. 10, 2020 in U.S. Appl. No. 16/097,782.
Office Action dated May 6, 2019 in U.S. Appl. No. 15/442,441.
Office Action dated Nov. 21, 2018 in U.S. Appl. No. 15/442,441.
Office Action dated Oct. 15, 2019 in U.S. Appl. No. 16/097,782.

Ostapenko, et al., Extraction Chromatographic Behavior of Actinium and REE on DGA, Ln and TRU Resins in Nitric Acid Solutions, Journal of Radioanalytical and Nuclear Chemistry, vol. 306, pp. 707-711, 2015.

Otwinowski & Minor, "Processing of X-ray Diffraction Data Collected in Oscillation Mode," Methods Enzymol., vol. 276, 1997, pp. 307-326.

Paragas et al. "NGAL-Siderocalin in kidney disease" Biochimica et Biophysica Acta, vol. 1823, 2012, pp. 1451-1458.

Payne & Peterson, Possible Stabilization of the Tetravalent Oxidation State of Berkelium and Californium in Acetonitrile With Triphenylarsine Oxide, Inorganica Chimica Acta, vol. 139, pp. 111-112, 1987.

Invitation to Pay Additional Fees dated Mar. 5, 2018 for International Application No. PCT/US2017/048954, 3 pages.

Peppard, et al. Isolation of Berkelium by Solvent Extraction of the Tetravalent Species, Journal of Inorganic and Nuclear Chemistry, vol. 4, pp. 344-348, 1957.

Pezutto, et al., "CD19 monoclonal antibody HD37 inhibits anti-immunoglobulin-induced B cell activation and proliferation," J. Immunol., vol. 138, No. 9, 1987, pp. 2793-2799.

Pham, et al., "A macrocyclic chelator with unprecedented Th4plus affinity," J. Am. Chem. Soc., vol. 136, No. 25, 2014, pp. 9106-9115.

Plueckthon the Pharmacology of Monoclonal Antibodies, vol. 113, Rosenburg and Moore, 269-315, 1994.

Pokhrel, et al. Stokes emission inGdF3:Nd3+ nanoparticles for bioimaging probe, Nanoscale, vol. 6, No. 3, pp. 1667-1674, 2014.

Pourmand, et al., Distribution coefficients of 60 elements on TODGA resin: Application to Ca, Lu, Hf, U and Th isotope geochemistry, Talanta, vol. 81, pp. 741-753, 2010.

Radchenko et al., Application of Ion Exchange and Extraction Chromatography to the Separation of Actinium From Proton-Irradiated Thorium Metal for Analytical Purposes, Journal of Chromatography, pp. 55-63, 2015.

Ricano, et al. Combinatorial Design of Multimeric Chelating Peptoids for Selective Metal Coordination, Chemical Science, 2019.

Sam II, AD et al. Safety of gadolinium contrast angiography in patients with chronic renal Insufficiency Journal of Vascular Surgery, vol. 38, pp. 313-318, (2003).

Shannon, et al., Revised Effective Ionic Radii and Systematic Studies of Interatomic Distances in Halides and Chalcogenides, Acta Crystallographica A32, pp. 751-757, 1976.

Shockley, et al. Detailed Balance Limit of Efficiency of p-n Junction Solar Cells, Journal of Applied Physics, vol. 32, No. 3, pp. 510-519, 1961.

Smith, et al., NIST standard reference database 46. NIST Critically selected stability constants of metal complexes database ver 2004, 27 pages.

Search Report and Written Opinion dated Apr. 26, 2018 for International Application No. PCT/US2017/048954, 13 pages.

Stather, et al., Use of DTPAfor increasing the rate of elimination ofplutonium-238 and americium-241from rodents after their inhalation as the nitrates, Human & Experimental Toxicology, vol. 4, No. 6, pp. 573-582, 1985.

Sturzbecher-Hoehne, et al Intramolecular Sensitization of Americium Luminescence in Solution: Shining Light on Short-Lived Forbidden 5f Transitions, Dalton Transactions, vol. 45, pp. 9912-9919, 2016.

Sturzbecher-Hoehne, et al., "3,4,3-LI(1,2-HOPO): in vitro formation of highly stable lanthanide complexes translates into efficacious in vivo europium decorporation," Dalton Transactions, vol. 40, No. 33, 2011, pp. 8340-8346.

Sturzbecher-Hoehne, et al., "Hydroxypyridinonate complex stability of group (IV) metals and tetravalent f-block elements: the key to the next generation of chelating agents for radiopharmaceuticals," Inorganic chemistry, vol. 54, No. 7, 2015, pp. 3462-3468.

Sturzbecher-Hoehne, et al., "Solution thermodynamic evaluation of hydroxypyridinonate chelators 3,4,3-LI(1,2-HOPO) and 5-LIO(Me-3,2-HOPO) for UO2(VI) and Th(IV) decorporation," Radiochimica Acta., vol. 101, No. 6, 2013, pp. 359-366.

Sturzbecher-Hoehne, et al., Highly Luminescent and Stable Hydroxypyridinonate Complexes: A Step Towards New Curium Decontamination Strategies, Chemistry A European Journal, vol. 20, No. 32, pp. 9962-9968, 2014.

Supplementary European Search Report, dated Nov. 15, 2019, in European Application No. EP 17793154.

(56) References Cited

OTHER PUBLICATIONS

Supplementary Partial European Search Report, re Application No. 17873523.9, dated May 27, 2020.
Suzuki, et al., Extraction and separation of Am(III) and Sr(II) by N,N,N N-tetraoctyl-3-oxapentanediamide (TODGA), Radiochimica Acta vol. 92, pp. 463-466, 2004.
Tachimori, et al. Modification of Todga-N-Dodecane Solvent With a Monoamide for High Loading of Lanthanides (Iii) and Actinides(III), Solvent Extraction and Ion Exchange, 2007.
Taylor, et al., Treatment of Human Contamination With Plutonium and Americium: Would Orally Administered Ca- or Zn-DTPA be effective? Radiation Protection Dosimetry, vol. 127, pp. 469-471, 2007.
Thompson, et al, Chemical properties of Berkelium, Journal of the American Chemical Society, vol. 72, pp. 2798-2801, 1950.
Thompson, et al, Element 97, Physics Review, vol. 77, pp. 838, 1950.
Trissel, L. et al., ASHP Handbook on Injectable Drugs 4th ed, pp. 622-630, 1986.
Turanov, et al., Synergistic Extraction of U(VI), Th(IV), and Lanthanides(III) from Nitric Acid Solutions Using Mixtures of TODGA and Dinonylnaphthalene Sulfonic Acid, Solvent Extraction and Ion Exchange, 2018.
U.S. Food and Drug Administration, Approval of New Drugs When Human Efficacy Studies Are Not Ethical or Feasible 2015, U.S. FDA: Washington, DC.
U.S. Food and Drug Administration, Guidance for Industry Product Development Under the Animal Rule 2015.
U.S. Food and Drug Administration, Guidance for Industry Calcium DTPA and Zinc DTPA Drug Products—Submitting a New Drug Application. 2004.
U.S. Food and Drug Administration, Guidance for Industry Internal Radioactive Contamination—Development of Decorporation Agents. 2006.
Umeda, et al., Separation of Americium from Plutonium-Solvent Extraction Raffinate by Extraction Chromatography using TODGA Absorbent, Atlantate, 2004.
Vagin and Teplyakov, "MOLREP: an Automated Program for Molecular Replacement," J. Appl. Cryst., vol. 30, 1997, pp. 1022-1025.
Van Der Ende, et al., Lanthanide ions as spectral converters for solar cells, Physical Chemistry Chemical Physics, vol. 11, pp. 11081-11095, 2009.
Van Wijngaarden, et al. Energy Transfer Mechanism for Downconversion in the (Pr3+, Yb3+) couple, Physics Review, vol. 81, Issue 15, pp. 155112, 2010.
Wadsworth, et al., Present Status of Cerium (IV)-Cerium (III) Potentials, Analytical Chemistry, vol. 29, pp. 1824-1825, 1957.
Partial Supplementary European Search Report dated Oct. 7, 2020 for International Application No. PCT/US2017/048910, 24 pages.
Uhlir, et al., "Specific sequestering agents for the actinides. 21. Synthesis and initial biological testing of octadentate mixed catecholate-hydroxypyridinonate ligands," Journal of Medicinal Chemistry, vol. 36, No. 4, 1993, pp. 504-509.
Abergel, et al., "Anthrax pathogen evades the mammalian immune system through stealth siderophore production," PNAS, vol. 103, No. 49, 2006, pp. 18499-18503.
Abergel, et al., "Microbial evasion of the immune system: structural modifications of enterobactin impair siderocalin recognition," J. Am. Chem. Soc., vol. 128, No. 34, 2006, pp. 10998-10999.
Abergel, et al., "Using the antenna effect as a spectroscopic tool: photophysics and solution thermodynamics of the model luminescent hydroxypyridonate complex [Eu(III)(3,4,3-LI(1,2-HOPO))]-," Inorg. Chem., vol. 48, No. 23, 2009, pp. 10868-10870.
Alderighi, et al., "Hyperquad simulation and speciation (HySS): a utility program for the investigation of equilibria involving soluble and partially soluble species," Coordination Chemistry Reviews, vol. 184, No. 1, 1999, pp. 311-318.
Allred, et al., "Siderocalin-mediated recognition, sensitization, and cellular uptake of actinides," PNAS, vol. 112, No. 33, 2015, pp. 10342-10347.
Bejcek, et al., "Development and characterization of three recombinant single chain antibody fragments (scFvs) directed against the CD19 antigen," Cancer Res., vol. 55, No. 11, 2005, pp. 2346-2351.
Bunin, et al., "Dose-dependent efficacy and safety toxicology of hydroxypyridinonate actinide decorporation agents in rodents: towards a safe and effective human dosing regimen," Rad Res., vol. 179, No. 2, 2013, pp. 171-182.
Clifton, et al., "Siderocalins: siderophore-binding proteins of the innate immune system," Biometals, vol. 22, No. 4, 2009, pp. 557-564.
Correnti and Strong, "Iron Sequestration in Immunity," Metals in Cells, 2016, pp. 349-359.
Davis, et al., "MolProbity: all-atom contacts and structure validation for proteins and nucleic acids," Nucleic Acids Res., vol. 35, 2007, pp. W375-W383.
Deblonde, et al., "Solution thermodynamic stability of complexes formed with the octadentate hydroxypyridinonate ligand 3,4,3-LI(1,2-HOPO): a critical feature for efficient chelation of lanthanide(IV) and actinide(IV) ions," Inorg. Chem., vol. 52, No. 15, 2013, pp. 8805-8811.
Deri, et al., "Alternative chelator for 89Zr radiopharmaceuticals: radiolabeling and evaluation of 3,4,3-(LI-1,2-HOPO)," J. Med. Chem., vol. 57, No. 11, 2014, pp. 4849-4860.
Deri, et al., "p-SCN-Bn-HOPO: A Superior Bifunctional Chelator for (89)Zr ImmunoPET," Bioconjug. Chem., vol. 26, No. 12, 2015, pp. 2579-2591.
Durbin, et al., "Chelating agents for uranium(VI): 2. Efficacy and toxicity of tetradentate catecholate and hydroxypyridinonate ligands in mice," Health Phys., vol. 78, No. 5, 2000, pp. 511-521.
Fattal, et al., "Novel drug delivery systems for actinides (uranium and plutonium) decontamination agents," Advanced Drug Delivery Reviews, Elsevier, 2015, pp. 40-54.
Gans & O'Sullivan, "GLEE, a new computer program for glass electrode calibration," Talanta, vol. 51, No. 1, 2000, pp. 33-37.
Gans, et al., "Investigation of equilibria in solution. Determination of equilibrium constants with the HYPERQUAD suite of programs," Talanta, vol. 43, No. 10, 1996, pp. 1739-1753.
Goetz, et al., "The neutrophil lipocalin NGAL is a bacteriostatic agent that interferes with siderophore-mediated iron acquisition," Mol. Cell, vol. 10, No. 5, 2002, pp. 1033-1043.
Heyerdahl, et al., "Fractionated therapy of HER2-expressing breast and ovarian cancer xenografts in mice with targeted alpha emitting 227Th-DOTA-p-benzyl-trastuzumab," PloS One, vol. 7, No. 8, 2012, 14 pages.
Holmes, et al., "Siderocalin (Lcn 2) also binds carboxymycobactins, potentially defending against mycobacterial infections through iron sequestration," Structure, vol. 13, No. 1, 2005, pp. 29-41.
Liepe & Alpharadin, "Alpharadin, a 223Ra-based alpha-particle-emitting pharmaceutical for the treatment of bone metastases in patients with cancer," Curr. Opin. Investig. Drugs, vol. 10, No. 12, 2009, pp. 1346-1358.
Ravandi, et al., "Phase I Trial of the Targeted Alpha-Particle Nano-Generator Actinium-225 (225Ac)-Lintuzumab (Anti-CD33) in Combination With Low-Dose Cytarabine (LDAC) for Older Patients With Untreated Acute Myeloid Leukemia (AML)," Blood, vol. 122, No. 21, 2013, pp. 1460-1460.
Smith, et al., NIST standard reference database 46. NIST Critically selected stability constants of metal complexes database ver 2004, 2.
Weitl, et al., "Specific sequestering agents for the actinides. 3. Polycatecholate ligands derived from 2,3-dihydroxy-5-sulfobenzoyl conjugates of diaza- and tetraazaalkanes," J. Am. Chem. Soc., vol. 102, No. 7, 1980, pp. 2289-2293.
Chen, et al., Carboxylate-Derived Calixarenes With High Selectivity for Actinium-225, Chemical Communications pp. 377-378, 1998.
Wang, et al. Down- and Up-Conversion Photoluminescence, Cathodoluminescence and Paramagnetic Properties of NaGdF4 : Yb3+,Er3+ Submicron Disks Assembled From Primary nanocrystals, Journal of Materials Chemistry, Issue 16, pp. 3178-3185, 2010.

(56) References Cited

OTHER PUBLICATIONS

Wang, et al. Extraction of Trivalent Americium and Europium With TODGA Homologs From HNO3 Solution, Journal of Radioanalytical and Nuclear Chemistry, vol. 313, pp. 309-318, 2017.

Wang, et al. Preparation of Core-Shell NaGdF4 Nanoparticles Doped with Luminescent Lanthanide Ions to be Used as Upconversion-Based Probes, Nature Protocols, vol. 9, No. 7, pp. 1634-1644, 2014.

Wawrzynczyk, et al. Ligand-dependent luminescence of ultra-small Eu3+-doped NaYF4 nanoparticles, Journal of Nanoparticle Research, vol. 15, pp. 1707, 2013.

Weidle et al., The Emerging Role of New Protein Scaffold-based Agents for Treatment of Cancer, Cancer Genomics and Proteomics. vol. 10, pp. 155, 2013.

Weitl et al, "Specific Sequestering Agents for Actinides. 3. Polycatecholate Ligands Derived from 2, 3-Dihydroxy-5-Sulfobenzoyl Conjugates of Diaza- and Tetraazaalkanes", Journal of the American Chemical Society, vol. 102, No. 7, American Chemical Society, US, Jan. 1, 1980, pp. 2289-2293.

Wermuth, C. et al., Designing Prodrugs and Bioprecursors, pp. 561-586, 2003.

Whitaker, et al., Applications of Diglycolamide Based Solvent Extraction Processes in Spent Nuclear Fuel Reprocessing, Part 1: Todga, Solvent Extraction and Ion Exchange, 2018.

Whitcomb, et al., A Public Health Perspective on the U.S. Response to the Fukushima radiological emergency. Health Phys, vol. 108, No. 3, pp. 357-363, 2015.

White, et al., Specific Sequestering Agents for the Actinides. 16. Synthesis and Initial Biological Testing of Polydentate Oxohydroxypyridinecarboxylate Ligands, Journal of Medicinal Chemistry, vol. 31, No. 1, pp. 11-18, 1988.

Wilden, A. et al. Unprecedented Inversion of Selectivity and Extraordinary Difference in the Complexation of Trivalent f-Elements by Diastereomers of a Methylated Diglycolamide, Chemistry a European Journal, 2019.

Xu et a l. "Synthesis and Initial Evaluation for In Vivo Chelation of Pu( IV) of a Mixed Ocladentate Spermine-Based Ligand Containing 4-Carbamoyl-3-hydroxy-1-methyl-2(1H)-pyridinone and 6-Carbamoyl-1-hydroxy-2(1H)-pyrldinone" Journal or Medicinal Chemistry, vol. 45, 2002, pp. 3963-3971.

Xu, et al., Specific Sequestering Agents for the Actinides. 28. Synthesis and Initial Evaluation of Multidentate 4-Carbamoyl-3-hydroxy-1-methyl-2(1H)-pyridinone Ligands for in Vivo Plutonium (IV) Chelation, Journal of Medicinal Chemistry, vol. 38, No. 14, pp. 2606-2614, 1995.

Yantasee, et al., Novel Sorbents for Removal of Gadolinium-Based Contrast Agents in Sorbent Dialysis and Hemoperfusion: Preventive Approaches to Nephrogenic Systemic Fibrosis (NSF), Nanomedicine, vol. 6, No. 1, pp. 1-8, 2010.

Ye, et al. Down conversion luminescence of Tb3+—Yb3+ codoped SrF2 precipitated glass ceramics, Journal of Non-Crystalline Solids, vol. 357, Issues 11-13, pp. 2268-2271, 2011.

Ye, et al. Enhanced cooperative quantum cutting in Tm3+—Yb3+ codoped glass ceramics containing LaF3nanocrystals, Optics Express, vol. 16, No. 12, pp. 8989-8994, 2008.

Zhang et al, Novel enterobactin analogues as potential therapeutic chelating agents: Synthesis, thermodynamic and antioxidant studies Scientific Reports, vol. 6, pp. 1-12, 2016.

Zhu, et al. An active-core/active-shell structure with enhanced quantum-cutting luminescence in Pr—Yb co-doped monodisperse nanoparticles, Nanoscale, vol. 6, pp. 10500-10504, 2014.

Zhu, X et al. Cumulative study on solvent extraction of elements by N,N,N ,N-tetraoctyl-3-oxapentanediamide (TODGA) from nitric acid into n-dodecane, Analytica Chimica Acta 527, pp. 163-168, 2004.

Zou, et al. Broadband Dye-Sensitized Upconversion of Near-Infrared Light, Nature Photonics, vol. 6, pp. 560-564, 2012.

Deblonde, et al., 1387—Hydropyridinonate ligands: From iron(III) to berkelium(IV) chemistry, Abstract.

Deblonde, et al., A New Strategy for the Purification of Heavy Actinides and Medical Radioisotopes, Advanced Techniques in Actinide Spectroscopy, 2018.

Deblonde, et al., Complexation, Characterization and Separation of the Lanthanides and Actinides: Shedding Light to Subtle Differences within the f-element Series, Actinides and Rare Earths Focus Topic, 2018.

Deblonde, et al., Inducing Selectivity and Chirality in Group IV Metal Coordination With High-Denticity Hydroxypyridinone, Dalton Transactions, No. 23, 2019.

Deblonde, et al., Solution Thermodynamics and Kinetics of Metal Complexation with a Hydroxypyridinone Chelator Designed for Thorium-227 Targeted Alpha Therapy, Inorganic Chemistry, vol. 57, pp. 14337-14346, 2018.

Deblonde, et al., Solution thermodynamics of hydropyridinonate 4f and 5f complexes, 28th Rare Earth Research Conference, 2017.

Deblonde, et al., Toxic heavy metal—Pb, Cd, Sn-complexation by the octadentate hydroxypyridinonate ligand archetype 3,4,3-LI(1,2-HOPO, New Journal of Chemistry, vol. 42, pp. 7649-7658, 2018.

Deblonde, et al., Ultra-selective Ligand-driven Separation of Strategic Actinides, Nature Communications, 2019.

Delmau, et al., Extraction of Trivalent Actinides and Lanthanides from Californium Campaign Rework Solution Using TODGA-based Solvent Extraction System, Oak Ridge National Laboratory, 2017.

Deri, et al., A Superior Bifunctional Chelator for 89Zr ImmunoPET, Bioconjugate Chemistry, vol. 26, No. 12, pp. 2579-2591, 2015.

Deri, et al., Bioconjugate Chemistry, vol. 26, No. 12, pp. 2579-2591, 2015.

Designing a Process for Selecting a Site for a Deep-Mined, Geologic Repository for High Level Radioactive Waste and Spent Nuclear Fuel, United States Nuclear Waste Technical Review Board, pp. 1-228, 2015.

Durbin et al, "Chelation of Plutonium-238 IV In-Vivo by 3 4 3 Licam-C Effects of Ligand Methylation and Ph", Health Physics, vol. 56, No. 6, 1989, Philadelphia , PA, US, pp. 839-856.

Durbin, et al., Gross Composition and Plasma and Extracellular Water Volumes of Tissues of a Reference Mouse, Health Physics, vol. 63, No. 4, pp. 427-442, 1992.

Durbin, et al., Lecture: The Quest for Therapeutic Actinide Chelators, Health Physics, vol. 95, No. 5, pp. 465-492, 2008.

Durbin et al, "Octadentate catechol amide ligands for Pu(IV) based on linear or preorganized molecular backbones", Human Toxicology, vol. 15, No. 4, MacMillan Publishers, Basingstoke, GB, Jan. 1, 1996, pp. 352-360.

Dutta, et al., Studies on separation of 90Y and 90Sr separation from hydrochloric acid solutions using TODGA as the extractant by SLM method, Procedia Chemistry, vol. 7, pp. 191-194, 2012.

Partial Supplementary Search Report dated May 27, 2020 in European Application No. 17873523.9, 12 pages.

Extended European Search Report dated Mar. 24, 2020, for European Application No. 17849400.1, 3 pages.

European Search Report dated Apr. 6, 2020 for European Patent Application No. 17847318.7, 17 pages.

Extended European Search Report dated Jul. 8, 2020 for European Patent Application No. 17847318.7, 16 pages.

Fritsch, et al., Simplified Structure of a New Model to Describe Urinary Excretion of Plutonium After Systemic, Liver or Pulmonary Contamination of Rats Associated With Ca-DTPA Treatments, Radiation Research, vol. 171, No. 6, pp. 674-686, 2009.

Fritsch, et al., Structure of a Single Model to Describe Plutonium and Americium Decorporation by DTPA treatments, Health Physics, vol. 99, No. 4, pp. 553-559, 2010.

Gorden, et al., Rational Design of Sequestering Agents for Plutonium and Other Actinides, Chemical Reviews, vol. 103, pp. 4207-4282, 2003.

Grappin, et al., Treatment of actinide exposures: A review oJCa-DTPA injections inside CEA-COGEMA plants, Radiation Protection Dosimetry, vol. 127, pp. 435-439, 2007.

Gregoric, et al., Characterization and Leaching of Neodymium Magnet Waste and Solvent Extinction of the Rare-Earth Elements Using TODGA, Journal of Sustain. Metall, vol. 3, pp. 638-645, 2017.

(56) References Cited

OTHER PUBLICATIONS

Grimes, et al., Trivalent Lanthanide/Actinide Separation Using Aqueous-Modified TALSPEAK Chemistry, Solvent Extraction and Ion Exchange, vol. 32, No. 4, pp. 378-390, 2014.

Gutmacher, et al., Stability of Tetravalent Berkelium in Acid Solution and the Absorption Spectra of Bk(IV) and Bk(III), Journal of Inorganic and Nuclear Chemistry, pp. 979-994, 1973.

Gutmacher, et al., The absorption spectra of Bk3+ and Bk4+ in solution, Journal of Inorganic and Nuclear Chemistry, vol. 29, pp. 2341-2345, 1967.

Harvey, Production of Actinium-225 via High Energy Proton Induced Spallation of Thorium-232. Final Technical Report DE-SC0003602, Northstar Medical Radioisotopes, LLC, https://world wide web www.osti.gov/scitech/servlets/purl/1032445/).

Hobart, et al., The Chemistry of the Actinide and Transactinide Elements—Chapter X—Berkelium, Springer, 2006.

Hoet, et al., Generation of High-Affinity Human Antibodies by Combining Donor-Derived and Synthetic Complementarity-Determining-Region Diversity, Nature Biotechnology, vol. 23, pp. 344-348, 2005.

Holliger, et al., "Diabodies": small bivalent and bispecific antibody fragments, Proceedings of the National Academy of Sciences of the USA, vol. 90, pp. 6444-6448, 1993.

Hudson, et al., Engineered antibodies, Nature Medicine, vol. 9, pp. 129-134, 2003.

Husain, et al., Extraction chromatography of lanthanides using N,N,N',N'-tetraoctyl diglycolamide (TODGA) as the stationary phase, Desalination, vol. 229, pp. 294-301, 2008.

Huston, et al., Protein Engineering of Antibody Binding Sites: Recovery of Specific Activity in an Anti-Digoxin Single-Chain Fv Analogue Produced in *Escherichia coli*, Proceedings of the National Academy of Sciences of the USA, vol. 85, pp. 5879-5883, 1988.

International Preliminary Report on Patentability dated Nov. 6, 2018 in International Patent Application No. PCT/US2017/030628.

International Preliminary Report on Patentability dated Mar. 12, 2019 in International Patent Application No. PCT/US2017/050121.

International Preliminary Report on Patentability dated Apr. 2, 2019 in International Patent Application No. PCT/US2017/048910.

International Preliminary Report on Patentability dated Apr. 2, 2019 in International Patent Application No. PCT/US2017/048934.

International Search Report and Written Opinion dated Jul. 27, 2017 in International Patent Application No. PCT/US2017/030628.

Abergel, et al. Biomimetic Actinide Chelators: An Update on the Preclinical Development of the Orally Active Hydroxypyridonate Decorporation Agents 3,4,3-L/(1,2-HOPO) and 5-LIO(Me-3,2-HOPO). Health Physics, vol. 99, No. 3, pp. 401-417, 2010.

Abergel, et al., Multidentate Terephthalamidate and Hydroxypyridonate Ligands: Towards New Orally Active Chelators, Hemoglobin, vol. 35, No. 3, pp. 276-290, 2011.

Agbo et al., Enhanced ultraviolet photon capture in ligand-sensitized nanocrystals, ACS Photonics, vol. 3, pp. 547-552, 2016.

Agbo et al., Ligand-Sensitized Lanthanide Nanocrystals: Merging Solid-State Photophysics and Molecular Solution Chemistry, Inorganic Chemistry, vol. 55, No. 20, pp. 9973-9980, 2016.

Agency for Toxic Substances and Disease Registry (ATSDR), Toxicological profile for Plutonium. 2010, U.S. Department of Health and Human Services, Public Health Service: Atlanta, GA.

Allred et al, "Siderocalin-mediated recognition, sensitization, and cellular uptake of actinides", Proceedings of the National Academy of Science, vol. 112, No. 33, Aug. 3, 2015, pp. 10342-10347.

An, et al., Pu Elimination Profiles After Delayed Treatment With 3,4,3L/(1,2HOPO) in Female and Male Swiss-Webster Mice. International Journal of Radiation Biology, vol. 90, No. 11, pp. 1055-1061, 2014.

An et al, "From early prophylaxis to delayed treatment: Establishing the plutonium decorporation activity window of hydroxypyridinonate chelating agents", Chemico-Biological Interactions, vol. 267, Elsevier Science Irland, IR, Mar. 31, 2016, pp. 80-88.

Ansari, et al., Extraction of actinides using N, N,N , N-Tetraoctyl Diglycolamide (TODGA): A Thermodynamic Study Radiochimica. Acta Journal, vol. 94, pp. 30x 312, 2006.

Ansari, et al., N,N,N',N'-Tetraoctyl Diglycolamide (TODGA): A Promising Extractant for Actinide-Partitioning from High-Level Waste (HLW), Solvent Extraction and Ion Exchange, pp. 463-479, 2006.

Antonio, M. et al., Berkelium redox speciation, Radiochim. Acta, vol. 90, pp. 851-856, (2002).

Argonne National Laboratory Division of Biological and Medical Research, Annual Report, Argonne National Laboratory. Division of Biological and Medical Research: Argonne, Illinois. 1979.

Bago, et al., Diphenyl-Benzo[1,3]dioxole-4-Carboxylic Acid Pentafluorophenyl Ester: A Convenient Catechol Precursor in the Synthesis of Siderophore Vectors Suitable for Antibiotic Trojan Horse Strategies, Organic and Biomolecular Chemistry, vol. 12, pp. 749, 2014.

Banker, et al., Pharmaceutics and Pharmacy Practice, pp. 238-250, 1982.

Banski, M. et al., NaYF4 nanocrystals with TOPO ligands: synthesis-dependent structural and luminescent properties, Physical Chemistry Chemical Physics, vol. 15, No. 47, pp. 19232-19241, 2013.

Baral, T. et al., Experimental Therapy of African Trypanosomiasis With a Nanobody-Conjugated Human Trypanolytic Factor, Nature Medicine, vol. 12, pp. 580-584, 2006.

Barthelemy, et al., "Comprehensive Analysis of the Factors Contributing to the Stability and Solubility of Autonomous Human VH Domains," Journal of Biological Chemistry, vol. 283, No. 6, 3639-3654.

Baybarz, et al. Absorption Spectra of Bk(III) and Bk(IV) in Several Media, Journal of Inorganic and Nuclear Chemistry, Vo. 34, pp. 734+ 746, 1972.

Bhattacharyya, M. et al., Action of DTPA on Hepatic Plutonium: III. Evidence for a Direct Chelation Mechanism for DTPA-Induced Excretion of Monomeric Plutonium into Rat Bile, Radiation Research, vol. 80, pp. 108-115, 1979.

Binz, et al., Engineering Novel Binding Proteins From Nonimmunoglobulin Domains, Nature Biotechnology, vol. 23, pp. 1257-1268, 2005.

Bird, et al., Single-chain antigen-binding proteins, Science, vol. 242, No. 4877, pp. 423-426, 1988.

Boersma, et al., DARPins and Other Repeat Protein Scaffolds: Advances in Engineering and Applications, Current Opinion in Biotechnology, vol. 22, No. 4, pp. 849-857, 2011.

Bunzlil, et al. Taking Advantage of Luminescent Lanthanide Ions, Chemical Society Reviews, vol. 34, No. 12, pp. 1048-1077, 2005.

Bunzlil, et al., Lanthanide Luminescence for Biomedical Analyses and Imaging, Chemical Reviews, vol. 110, No. 5, pp. 2729-2755, 2010.

Burgada, et al., Journal of Labelled Compounds and Radiopharmaceuticals, vol. 44, pp. 13-19, 2001.

Captain, et al., Engineered Recognition of Tetravalent Zirconium and Thorium by Chelator-Protein Systems: Toward Flexible Radiotherapy and Imaging Platforms, Inorganic Chemistry, vol. 55, pp. 11930-11936, 2016.

Carnall, et al., A Systematic Analysis of the Spectra the Trivalent Actinide Chlorides in D3h Site Symetry, Argonne National Laboratory, Argonne , Illinois, USA, 1989.

Carott, et al., Distribution of plutonium, americium and interfering fission products between nitric acid and a mixed organic phase of TODGA and DMDOHEMA in kerosene, and implications for the design of the EURO-GANEX process, Hydrometallurgy, vol. 152, pp. 139-148, 2015.

Carrot, et al. Neptunium Extraction and Stability in the GANEX Solvent: 0.2 M TODGA/0.5M DMDOHEMA/Kerosene, Solvent Extraction and Ion Exchange, 2012.

Cassatt, et al., Medical Countermeasures Against Nuclear Threats Radionuclide Decorporation Agents., Radiation Research, vol. 170, No. 4, pp. 540-548, 2008.

Chang, et al., Analytical Methods for the Bioavailability Evaluation of Hydroxypyridinonate Actinide Decorporation Agents in Pre-Clinical Pharmacokinetic Studies, Journal Chromatography Separation Technique Journal, 2012.

(56) References Cited

OTHER PUBLICATIONS

Chen, et al. Core/Shell NaGdF4:Nd3+/NaGdF4 Nanocrystals with Efficient Near-Infrared to Near-Infrared Downconversion Photoluminescence for Bioimaging Applications, ACS Nano, vol. 6, No. 4, pp. 2969-2977, 2012.

Choi, et al., Biodistribution of the Multidentate Hydroxypyridinonate Ligand [(14)C]-3,4,3-LI/(1,2-HOPO), A Potent Actinide Decorporation Agent, Drug Development Research, vol. 76, No. 3, pp. 107-122, 2015.

Choi, et al., In vitro metabolism and stability of the actinide chelating agent 3,4,3-Lf {1,2-I-/OPO). Journal of pharmaceutical sciences, vol. 104, No. 5, pp. 1832-1838, 2015.

Choi, et al., Understanding the Health Impacts and Risks of Exposure to Radiation, in Reflections on the Fukushima Daiichi Nuclear Accident, Chemical Sciences Division, Lawrence Berkeley National Laboratory, pp. 259-281, 2015.

Chudinov, et al., The separation of berkelium (III) from cerium (III), Journal of Radioanalytical and Nuclear Chemistry, vol. 10, pp. 41-46, 1972.

Cortez-Retamozo, V. et al., Efficient Cancer Therapy with a Nanobody-Based Conjugate, Cancer Research, vol. 64, pp. 2853-2857, 2004.

Daumann, et al. New Insights into Structure and Luminescence of Eu(III) and Sm(III) Complexes of the 3,4,3-Li(1,2-HOPO) Ligand, Journal of the American Chemical Society, vol. 137, pp. 2816-2819, 2015.

Deblonde, "Chelation and stabilization of berkelium in oxidation state +IV", Nature Chemistry, vol. 9, No. 9, Apr. 10, 2017, pp. 843-849.

Deblonde, et al., "Solution thermodynamic stability of complexes formed with the octadentate hydroxypyridinonate ligand 3,4,3-LI(1,2-HOPO): A critical feature for efficient chelation of lanthanide(IV) and actinide(IV) ions," Inorganic Chemistry, vol. 52, No. 15, 2013, pp. 8805-8811.

Extended European Search Report dated Jan. 19, 2021 for European Patent Application No. 17857076.8, 22 pages.

European Search Report dated Aug. 27, 2020 in European Application No. 17873523.9, 10 pages.

Office Action dated Jul. 22, 2020 in U.S. Appl. No. 16/097,782, 12 pages.

Supplementary Partial European Search Report dated Oct. 7, 2020 in European Application No. 17857076.8, 22 pages.

Office Action dated Jul. 28, 2021 in Japanese Application No. 2019-512761, 8 pages.

Naasani, et al., "Improving the Oral Bioavailability of Sulpiride by Sodium Oleate in Rabbits," J. Pharm., vol. 47, 1995, pp. 469-473.

Office Action dated Jul. 13, 2021 in U.S. Appl. No. 16/330,601, 8 pages.

Office Action dated May 14, 2021 in European Patent Application No. 17793154.0, 3 pages.

Rejection dated Apr. 26, 2021 in Japanese Patent Application No. JP 2018-557384, 7 pages.

Office Action dated Jun. 10, 2021 in U.S. Appl. No. 16/365,132, 5 pages.

* cited by examiner

FIG. 9

| | 232Th-Ent | 232Th-TRENCAM | 238Pu-Ent | Sm-HOPO | 243Am-HOPO | 248Cm-HOPO |
|---|---|---|---|---|---|---|
| PDB accession code Data collection* | 4ZFX | 4ZHC | 4ZHD | 4ZHH | 4ZHG | 4ZHF |
| Space group | P4₃2₁2 | P4₃2₁2 | P4₃2₁2 | P4₃2₁2 | P4₃2₁2 | P4₃2₁2 |
| Cell dimensions a, b, c (Å) | 114.5, 114.5, 119.5 | 114.7, 114.7, 119.2 | 114.6, 114.6, 118.8 | 107.7, 117.8, 121.2 | 110.7, 115.3, 120.5 | 107.7, 117.7, 121.2 |
| Wavelength | CuKα | 1.00000 Å | 1.00000 Å | 1.00000 Å | 1.00000 Å | 1.00000 Å |
| Resolution (Å) | 50.0-2.55 (2.59-2.55) | 50.0-2.04 (2.08-2.04) | 50.0-2.05 (2.09-2.05) | 50.0-2.4 (2.49-2.45) | 50.0-2.04 (2.08-2.04) | 50.0-2.05 (2.09-2.05) |
| $R_{merge}$ (%) | 8.2 (49.0) | 9.7 (48.8) | 6.3 (34.8) | 13.5 (46.3) | 7.1 (20.8) | 11.4 (34.8) |
| I / σI | 27.8 (5.1) | 25.4 (5.6) | 38.2 (7.3) | 13.7 (3.4) | 38.7 (9.8) | 16.5 (4.4) |
| Completeness (%) | 99.7 (100) | 99.7 (97.0) | 99.1 (95.3) | 98.8 (100) | 99.2 (93.2) | 99.1 (81.7) |
| Redundancy | 7.6 (6.7) | 9.6 (8.7) | 9.5 (7.3) | 4.9 (5.0) | 4.8 (4.6) | 4.8 (3.6) |
| Refinement | | | | | | |
| No. reflections | 26,474 (1,289) | 51,169 (2,430) | 49,864 (2,341) | 56,438 (2,806) | 98,255 (4,564) | 96,900 (3,939) |
| $R_{work}$ / $R_{free}$ (%) | 23.9/26.8 | 20.7/22.9 | 20.4/22.6 | 20.3/22.4 | 17.4/19.9 | 19.5/21.7 |
| No. atoms | | | | | | |
| Protein | 4,166 | 4,167 | 4,162 | 8,562 | 8,535 | 8,584 |
| Ligand/ion | 34 | 71 | 63 | 330 | 330 | 330 |
| Water | 26 | 138 | 118 | 326 | 565 | 332 |
| B-factors (Å²) | | | | | | |
| Protein | 59 | 50 | 46 | 30 | 28 | 27 |
| Ligand/ion | 48 | 63 | 57 | 38 | 25 | 28 |
| Water | 41 | 48 | 43 | 29 | 32 | 27 |
| R.m.s. deviations | | | | | | |
| Bond lengths (Å) / angles (°) | 0.01/1.45 | 0.01/0.90 | 0.01/1.15 | 0.01/0.97 | 0.01/1.25 | 0.01/1.19 |
| MolProbity | | | | | | |
| Percentile | 100 | 99 | 97 | 99 | 99 | 98 |
| Score | 1.27 | 1.37 | 1.49 | 1.64 | 1.28 | 1.45 |
| Residues in most favored regions (%) | 98 | 97 | 98 | 98 | 98 | 98 |
| Res. in disallowed regions (%) | 0 | 0 | 0 | 0 | 0 | 0 |
| Est. coordinate error (max. likelihood ESU(c) (Å) | 0.2 | 0.1 | 0.1 | 0.2 | 0.1 | 0.1 |

*One crystal was used per data set. Values in parentheses are for the highest-resolution shell.

FIG. 11

| species | mlh | log $\beta_{mlh}$ | $pK_a$ |
|---|---|---|---|
| 3,4,3-LI(CAM) | | | |
| $LH^{7-}$ | 011 | 12.50 ± 0.30 | 12.50 ± 0.30 |
| $LH_2^{6-}$ | 012 | 24.50 ± 0.35 | 12.00 ± 0.30 |
| $LH_3^{5-}$ | 013 | 35.81 ± 0.55 | 11.31 ± 0.55 |
| $LH_4^{4-}$ | 014 | 45.41 ± 0.47 | 9.60 ± 0.12 |
| $LH_5^{3-}$ | 015 | 54.11 ± 0.23 | 8.70 ± 0.27 |
| $LH_6^{2-}$ | 016 | 61.93 ± 0.56 | 7.82 ± 0.57 |
| $LH_7^-$ | 017 | 68.67 ± 1.45 | 6.73 ± 0.61 |
| $LH_8$ | 018 | 73.24 ± 1.38 | 4.57 ± 0.29 |
| $[EuL]^{5-}$ | 110 | 29.65 ± 0.65 | - |
| $[EuLH]^{4-}$ | 111 | 41.75 ± 0.06 | - |
| $[EuLH_2]^{3-}$ | 112 | 46.79 ± 0.14 | - |
| $[ZrL]^{4-}$ | 110 | 57.26 ± 0.20 | - |
| $[ZrLH]^{3-}$ | 111 | 64.25 ± 0.32 | - |
| $[ThL]^{4-}$ | 110 | 47.71 ± 0.08 | - |
| $[ThLH]^{3-}$ | 111 | 55.36 ± 0.09 | - |
| 3,4,3-LI(1,2-HOPO) | | | |
| $LH^{3-}$ | 011 | 6.64 | 6.64 |
| $LH_2^{2-}$ | 012 | 12.32 | 5.68 |
| $LH_3^-$ | 013 | 17.33 | 5.01 |
| $LH_4$ | 014 | 21.20 | 3.87 |
| $[EuL]^-$ | 110 | 20.2 | - |
| $[EuLH]$ | 111 | 24.8 | - |
| $[ZrL]$ | 110 | 43.1 | - |
| $[ThL]$ | 110 | 40.1 | - |

FIG. 15

SEQ ID NO: 1: *H. sapiens* Scn
QDSTSDLIPAPPLSKVPLQQNFQDNQFQGKWYVVGLAGNAILREDKDPQKMYATIYELK
EDKSYNVTSVLFRKKKCDYWIRTFVPGCQPGEFTLGNIKSYPGLTSYLVRVVSTNYNQH
AMVFFKKVSQNREYFKITLYGRTKELTSELKENFIRFSKSLGLPENHIVFPVPIDQCIDGG SEQ ID NO: 2: *P. troglodytes* Scn
QDSTSDLIPAPPLSKVPLQQNFQDNQFQGKWYVVGLAGNAILREDKDPQKMYATIYELK
EDKSYNVTSVLFRKKKCDYWIRTFVPGRQPGEFTLGNIKSYPGLTSYLVRVVSTNYNQH
AMVFFKKVSQNREYFKITLYGRTKELTSELQENFIRFSKSLGLPENHIVFPVPIDQCIDG SEQ ID NO: 3: *G. gorilla* Scn
QDSTSDLIPAPPLSKVPLQQNFQDNQFQGKWYVVGLAGNAILREDKDPQKMYATIYELK
EDKSYNVTSVLFREKAQKCDYWIRTFVPGSQPGEFTLGNIKSYPGLTSYLVRVVSTNYN
QHAMVFFKKVSQNREYFKITLYGRTKELTSELKENFIRFSKSLGLPENHIVFPVPIDQCID
G SEQ ID NO: 4: *P. pygmaeus* Scn
QDSTSDLIPAPPLSKVPLQQNFQDNQFQGKWYVVGLAGNAIRREDKDSQKMYATIYELK
EDKSYNVTSVLFRKKKCDYWIRTFVPGSQPGEFTLGNTKGYPGLTSYLVRVVSTNYNQY
AMVFFKKVSQNREYFKITLYGRTKELTSELKENFIRFSKSLGLPENHIVFPAPIDQCIDG SEQ ID NO: 5: *M. mulatta* Scn
QDSSSDLIPAPPLSKVPLQQNFQDNQFQGKWYVVGLSGNAVGRKDEAPLKMYATIYEL
KEDKSYNVTSILFRKEKCDYWIRTFVPGSQPGEFTLGNIQNHPGLTSYVVRVVSTNYKQ
YAMVFFKKVSQNKEYFKITLYGRTKELTSELKENFIRFSKSLGLPENHIVFSVPIDQCING SEQ ID NO: 6: *C. jacchus* Scn
QDSPSPLIPAPPLSKVPLQQNFQDNQFQGKWYVVGLAGNAIRREDQDSLKMYATIYELK
EDKSYNVTSVLFRKGKCDYWIRTFVPSSRPGEFKLGNIESHPGLTSYIVRVVNTDYKQH
AMVFFMKASHNRKYFKVTLYGRTKELTSDLKENFTSFSKSLGLTENHIIFPVPIDQCIDG SEQ ID NO: 7: *M. musculus* Scn
QDSTQNLIPAPSLLTVPLQPDFRSDQFRGRWYVVGLAGNAVQKKTEGSFTMYSTIYELQ
ENNSYNVTSILVRDQDQGCRYWIRTFVPSSRAGQFTLGNMHRYPQVQSYNVQVATTDY
NQFAMVFFRKTSENKQYFKITLYGRTKELSPELKERFTRFAKSLGLKDDNIIFSVPTDQCI
DN SEQ ID NO: 8: *R. norvegicus* Scn
QDSTQNLIPAPPLISVPLQPGFWTERFQGRWFVVGLAANAVQKERQSRFTMYSTIYELQ
EDNSYNVTSILVRGQGCRYWIRTFVPSSRPGQFTLGNIHSYPQIQSYDVQVADTDYDQF
AMVFFQKTSENKQYFKVTLYGRTKGLSDELKERFVSFAKSLGLKDNNIVFSVPTDQCIDN SEQ ID NO: 9: *O. princeps* Scn
QELTMDPTPSPRLIPVPSLRKIHVQKNFQSDQFQGKWYVVGLAGNNIHNSDQEHQQMY
STTYELKEDGSYNVTSTLLRNQQCDHWIRTFVPGSKLGHFNLGNIKSYPTLKSYLIRVVT
TDYNQFAIVFFRKVYKNNKKFFKIVLYGRTKELSPELRGRFTSFAKTLGLTDNHIVFPAPI
GQCIDD

FIG. 15 cont'd

SEQ ID NO: 10: *O. cuniculus* Scn
QDPTPKLIPAPSLRRVPLQRNFQDEQFQGKWYVVGLAGNAVQKREEGQEPMYSTTYE
LNEDRSFNVTSTLLRDQRCDHWIRTFVPTSRPGQYNLGNIKSYPGVKNYIVRVVATDYS
QYAMMFFRKGSRNKQFFKTTLYGRTKELSPELRERFTRFAKSLGLPDDRIVFPTPIDQCI
DD SEQ ID NO: 11: *B. taurus* Scn
RSSSSRLLRAPPLSRIPLQPNFQADQFQGKWYTVGVAGNAIKKEEQDPLKMYSSNYEL
KEDGSYNVTSILLKDDLCDYWIRTFVPSSQPGQFTLGNIKSYRGIRSYTVRVVNTDYNQF
AIVYFKKVQRKKTYFKITLYGRTKELTPEVRENFINFAKSLGLTDDHIVFTVPIDRCIDDQ SEQ ID NO: 12: *S. scrofa* Scn
QGTIPNWIPAPPLSKVPLQPNFQADQFQGKWYVVGLAGNAVKKEEQGRFKMYTTTYEL
KEDGSYNVISTLLRGQLCDNWIRTFVPSLQPGQFKLGDIKKYSGLQSYVVRVVSTNYSQ
FAIVFFKKVSNNQEYFKTTLYGRTKVLSPELKENFVRFAKSLGLSDDNIIFPVAIDQCIDG
Q SEQ ID NO: 13: *T. truncatus* Scn
QDSTPNLIPAPPLFRVPLQPNFQPDQFQGKWYIVGLAGNAFKKEKQGQFKMYATTYEL
KEDRSYNVTSALLRDERCDHWIRTFVPSSRPGQFTLGNIKGFPGVQSYTVRVATTNYN
QFAIVYFKKVYKNQEYFKTTLYGRTKELTPQLKENFIHFAKSLGLTDEYILFPVPIDKCIDD
Q SEQ ID NO: 14 *E. caballus* Scn
RDPAPKLIPAPPLDRVPLQPDFKDDQFQGKWYVVGVAGNAFKKEEQGQFTMYTTTYEL
KEDHSYNVTSILLRDQNCDHWIRTFIPSSQPGQFNLGDIKRYFGVQSYIVRVADTDYNQ
FAIVFFRKVYKNQEYFKTTLYRRTKELTPELREKFISFAKSLGLTDDHIIFPVPIDQCIDEE SEQ ID NO: 15: *M. murinus* Scn
QDSKEKLIPAPPLLRVPLQPDFQDDQFQGKWYVVGLAGNAVSKEEQGQFTMYTTTYEL
KDHSYNVTSTLLRNGKCDYWIRTFVLTSQPGQFALGNINRYPGIQSYTVRVVTTNYNQF
AIVFFKKVSENKEYFKTTLYGRTKELPPELKENFIRFAKSLGLTEDHIIYPVPIDQCIDD SEQ ID NO: 16: *L. africana* Scn
QTHSPTLIPAPPLLRVPLQPDFQDDKFQGKWYVIGLAGNAVEKKEQGQFKMYTTTYELK
EDGSYNVTSTLLQEDGKCSYWIRTFVPSFQPGQFNLGNIKNFPGLQSYTVRVTATNYN
QFAIVFFKKVSKNGEYFKTTLYGRTKELTPELKERFIRFAKSLGLSDHIIFPVPIDRCIDDA SEQ ID NO: 17: *P. capensis* Scn
QEPTPLIPAPPLSSIPLKPNFHNDKFQGKWYVVGVAGNAITKEKDPSLMYTTTYELRDD
GSYNVTSTQFREKINCTHWTRTFVPTSQPGQFSLGNIDKYPHLSSYTVRVTATNYNYFA
IVYFKKVSKNQEYFKTTLYKRIKKLTHGLKKHFIQFAKSLGLPDNHITFLVPTDRCIDDA SEQ ID NO: 18: *C. familiaris* Scn
QDSTPSLIPAPPPLKVPLQPDFQHDQFQGKWYVIGIAGNILKKEGHGQLKMYTTTYELK
DDQSYNVTSTLLRNERCDYWNRDFVPSFQPGQFSLGDIQLYPGVQSYLVQVVATNYN
QYALVYFRKVYKSQEYFKITLYGRTKELPLELKKEFIRFAKSIGLTEDHIIFPVPIDQCIDE

FIG. 16

SEQ ID NO: 19: SEQ ID NO: 1 with T54C mutation (underlined)
QDSTSDLIPAPPLSKVPLQQNFQDNQFQGKWYVVGLAGNAILREDKDPQKMYA<u>C</u>IYELKEDK
SYNVTSVLFRKKKCDYWIRTFVPGCQPGEFTLGNIKSYPGLTSYLVRVVSTNYNQHAMVFFK
KVSQNREYFKITLYGRTKELTSELKENFIRFSKSLGLPENHIVFPVPIDQCIDGG SEQ ID NO: 20: SEQ ID NO: 1 with S68C mutation (underlined)
QDSTSDLIPAPPLSKVPLQQNFQDNQFQGKWYVVGLAGNAILREDKDPQKMYATIYELKEDK
SYNVT<u>C</u>VLFRKKKCDYWIRTFVPGCQPGEFTLGNIKSYPGLTSYLVRVVSTNYNQHAMVFFK
KVSQNREYFKITLYGRTKELTSELKENFIRFSKSLGLPENHIVFPVPIDQCIDGG SEQ ID NO: 21: SEQ ID NO: 1 with T54C and S68C mutations (both underlined)
QDSTSDLIPAPPLSKVPLQQNFQDNQFQGKWYVVGLAGNAILREDKDPQKMYA<u>C</u>IYELKEDK
SYNVT<u>C</u>VLFRKKKCDYWIRTFVPGCQPGEFTLGNIKSYPGLTSYLVRVVSTNYNQHAMVFFK
KVSQNREYFKITLYGRTKELTSELKENFIRFSKSLGLPENHIVFPVPIDQCIDGG SEQ ID NO: 22: SEQ ID NO: 1 with C87S mutation (underlined)
QDSTSDLIPAPPLSKVPLQQNFQDNQFQGKWYVVGLAGNAILREDKDPQKMYATIYELKEDK
SYNVTSVLFRKKKCDYWIRTFVPG<u>S</u>QPGEFTLGNIKSYPGLTSYLVRVVSTNYNQHAMVFFK
KVSQNREYFKITLYGRTKELTSELKENFIRFSKSLGLPENHIVFPVPIDQCIDGG SEQ ID NO: 23: SEQ ID NO:1 with a leader sequence (bold), and mutations K125A and C87S (underlined)
MPLGLLWLGLALLGALHAQAQDSTSDLIPAPPLSKVPLQQNFQDNQFQGKWYVVGLAGNAI
LREDKDPQKMYATIYELKEDKSYNVTSVLFRKKKCDYWIRTFVPG<u>S</u>QPGEFTLGNIKSYPGLT
SYLVRVVSTNYNQHAMVFFK<u>A</u>VSQNREYFAITLYGRTKELTSELKENFIRFSKSLGLPENHIVF
PVPIDQCIDG SEQ ID NO: 24: SEQ ID NO:1 with a leader sequence (bold), and mutations T54C, S68C, C87S, and K125A (underlined)
MPLGLLWLGLALLGALHAQAQDSTSDLIPAPPLSKVPLQQNFQDNQFQGKWYVVGLAGNAI
LREDKDPQKMYA<u>C</u>IYELKEDKSYNVT<u>C</u>VLFRKKKCDYWIRTFVPG<u>S</u>QPGEFTLGNIKSYPGLT
SYLVRVVSTNYNQHAMVFFK<u>A</u>VSQNREYFAITLYGRTKELTSELKENFIRFSKSLGLPENHIVF
PVPIDQCIDG SEQ ID NO: 25: Scn-CD19 fusion protein: SEQ ID NO: 1 with a leader sequence (bold, underlined); T54C and C87S mutations (italic, underlined), a GGS linker (underlined), and CD19 scFv sequence (bold)
<u>MPLGLLWLGLALLGALHAQA</u>QDSTSDLIPAPPLSKVPLQQNFQDNQFQGKWYVVGLAGNAI
LREDKDPQKMYA<u>*C*</u>IYELKEDKSYNVTSVLFRKKKCDYWIRTFVPG<u>*S*</u>QPGEFTLGNIKSYPGLT
SYLVRVVSTNYNQHAMVFFKKVSQNREYFKITLYGRTKELTSELKENFIRFSKSLGLPENHIVF
PVPIDQCIDG<u>GGS</u>**DIQMTQTTSSLSASLGDRVTISCRASQDISKYLNWYQQKPDGTVKLLIY
HTSRLHSGVPSRFSGSGSGTDYSLTISNLEQEDIATYFCQQGNTLPYTFGGGTKLEITGSTS
GSGKPGSGEGSTKGEVKLQESGPGLVAPSQSLSVTCTVSGVSLPDYGVSWIRQPPRKGLE
WLGVIWGSETTYYNSALKSRLTIIKDNSKSQVFLKMNSLQTDDTAIYYCAKHYYYGGSYAM
DYWGQGTSVTVSS**

SEQUENCE LISTING

<160> NUMBER OF SEQ ID NOS: 46

<210> SEQ ID NO 1
<211> LENGTH: 179
<212> TYPE: PRT
<213> ORGANISM: Homo sapiens

<400> SEQUENCE: 1

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly

<210> SEQ ID NO 2
<211> LENGTH: 178
<212> TYPE: PRT
<213> ORGANISM: Pan troglodytes

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Arg Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 3
<211> LENGTH: 180
<212> TYPE: PRT
<213> ORGANISM: Gorilla gorilla

<400> SEQUENCE: 3

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
             20                  25                  30

Val Val Gly Leu Ala Gly Asn Ala Ile Leu Arg Glu Asp Lys Asp Pro
         35                  40                  45

Gln Lys Met Tyr Ala Thr Ile Tyr Glu Leu Lys Glu Asp Lys Ser Tyr
     50                  55                  60

Asn Val Thr Ser Val Leu Phe Arg Glu Lys Ala Gln Lys Cys Asp Tyr
 65                  70                  75                  80

Trp Ile Arg Thr Phe Val Pro Gly Ser Gln Pro Gly Glu Phe Thr Leu
                 85                  90                  95

Gly Asn Ile Lys Ser Tyr Pro Gly Leu Thr Ser Tyr Leu Val Arg Val
            100                 105                 110

Val Ser Thr Asn Tyr Asn Gln His Ala Met Val Phe Phe Lys Lys Val
        115                 120                 125

Ser Gln Asn Arg Glu Tyr Phe Lys Ile Thr Leu Tyr Gly Arg Thr Lys
    130                 135                 140

Glu Leu Thr Ser Glu Leu Lys Glu Asn Phe Ile Arg Phe Ser Lys Ser
145                 150                 155                 160

Leu Gly Leu Pro Glu Asn His Ile Val Phe Pro Val Pro Ile Asp Gln
                165                 170                 175

Cys Ile Asp Gly
            180
```

<210> SEQ ID NO 4
<211> LENGTH: 178
<212> TYPE: PRT
<213> ORGANISM: Pongo pygmaeus

<400> SEQUENCE: 4

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
             20                  25                  30

Val Val Gly Leu Ala Gly Asn Ala Ile Arg Arg Glu Asp Lys Asp Ser
         35                  40                  45

Gln Lys Met Tyr Ala Thr Ile Tyr Glu Leu Lys Glu Asp Lys Ser Tyr
     50                  55                  60

Asn Val Thr Ser Val Leu Phe Arg Lys Lys Lys Cys Asp Tyr Trp Ile
 65                  70                  75                  80

Arg Thr Phe Val Pro Gly Ser Gln Pro Gly Glu Phe Thr Leu Gly Asn
                 85                  90                  95

Thr Lys Gly Tyr Pro Gly Leu Thr Ser Tyr Leu Val Arg Val Val Ser
            100                 105                 110

Thr Asn Tyr Asn Gln Tyr Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Ala Pro Ile Asp Gln Cys Ile
                165                 170                 175

Asp Gly
```

<210> SEQ ID NO 5
<211> LENGTH: 178
<212> TYPE: PRT
<213> ORGANISM: Macaca mulatta

<400> SEQUENCE: 5

```
Gln Asp Ser Ser Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ser Gly Asn Ala Val Gly Arg Lys Asp Glu Ala Pro
            35                  40                  45

Leu Lys Met Tyr Ala Thr Ile Tyr Glu Leu Lys Glu Asp Lys Ser Tyr
    50                  55                  60

Asn Val Thr Ser Ile Leu Phe Arg Lys Glu Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Gln Asn His Pro Gly Leu Thr Ser Tyr Val Val Arg Val Val Ser
                100                 105                 110

Thr Asn Tyr Lys Gln Tyr Ala Met Val Phe Phe Lys Lys Val Ser Gln
                115                 120                 125

Asn Lys Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Ser Val Pro Ile Asp Gln Cys Ile
                165                 170                 175

Asn Gly
```

<210> SEQ ID NO 6
<211> LENGTH: 178
<212> TYPE: PRT
<213> ORGANISM: Callithrix jacchus

<400> SEQUENCE: 6

```
Gln Asp Ser Pro Ser Pro Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Arg Arg Glu Asp Gln Asp Ser
            35                  40                  45

Leu Lys Met Tyr Ala Thr Ile Tyr Glu Leu Lys Glu Asp Lys Ser Tyr
    50                  55                  60

Asn Val Thr Ser Val Leu Phe Arg Lys Gly Lys Cys Asp Tyr Trp Ile
65                  70                  75                  80

Arg Thr Phe Val Pro Ser Ser Arg Pro Gly Glu Phe Lys Leu Gly Asn
                85                  90                  95

Ile Glu Ser His Pro Gly Leu Thr Ser Tyr Ile Val Arg Val Val Asn
                100                 105                 110
```

```
Thr Asp Tyr Lys Gln His Ala Met Val Phe Met Lys Ala Ser His
        115                 120                 125

Asn Arg Lys Tyr Phe Lys Val Thr Leu Tyr Gly Arg Thr Lys Glu Leu
130                 135                 140

Thr Ser Asp Leu Lys Glu Asn Phe Thr Ser Phe Ser Lys Ser Leu Gly
145                 150                 155                 160

Leu Thr Glu Asn His Ile Ile Phe Pro Val Pro Ile Asp Gln Cys Ile
                165                 170                 175

Asp Gly

<210> SEQ ID NO 7
<211> LENGTH: 180
<212> TYPE: PRT
<213> ORGANISM: Mus musculus

<400> SEQUENCE: 7

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
                20                  25                  30

Val Val Gly Leu Ala Gly Asn Ala Val Gln Lys Lys Thr Glu Gly Ser
            35                  40                  45

Phe Thr Met Tyr Ser Thr Ile Tyr Glu Leu Gln Glu Asn Asn Ser Tyr
    50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95

Gly Asn Met His Arg Tyr Pro Gln Val Gln Ser Tyr Asn Val Gln Val
            100                 105                 110

Ala Thr Thr Asp Tyr Asn Gln Phe Ala Met Val Phe Phe Arg Lys Thr
    115                 120                 125

Ser Glu Asn Lys Gln Tyr Phe Lys Ile Thr Leu Tyr Gly Arg Thr Lys
130                 135                 140

Glu Leu Ser Pro Glu Leu Lys Glu Arg Phe Thr Arg Phe Ala Lys Ser
145                 150                 155                 160

Leu Gly Leu Lys Asp Asn Ile Ile Phe Ser Val Pro Thr Asp Gln
                165                 170                 175

Cys Ile Asp Asn
            180

<210> SEQ ID NO 8
<211> LENGTH: 178
<212> TYPE: PRT
<213> ORGANISM: Rattus norvegicus

<400> SEQUENCE: 8

Gln Asp Ser Thr Gln Asn Leu Ile Pro Ala Pro Leu Ile Ser Val
1               5                   10                  15

Pro Leu Gln Pro Gly Phe Trp Thr Glu Arg Phe Gln Gly Arg Trp Phe
                20                  25                  30

Val Val Gly Leu Ala Ala Asn Ala Val Gln Lys Glu Arg Gln Ser Arg
            35                  40                  45

Phe Thr Met Tyr Ser Thr Ile Tyr Glu Leu Gln Glu Asp Asn Ser Tyr
    50                  55                  60
```

```
Asn Val Thr Ser Ile Leu Val Arg Gly Gln Gly Cys Arg Tyr Trp Ile
 65                  70                  75                  80

Arg Thr Phe Val Pro Ser Ser Arg Pro Gly Gln Phe Thr Leu Gly Asn
                 85                  90                  95

Ile His Ser Tyr Pro Gln Ile Gln Ser Tyr Asp Val Gln Val Ala Asp
            100                 105                 110

Thr Asp Tyr Asp Gln Phe Ala Met Val Phe Phe Gln Lys Thr Ser Glu
        115                 120                 125

Asn Lys Gln Tyr Phe Lys Val Thr Leu Tyr Gly Arg Thr Lys Gly Leu
130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 9
<211> LENGTH: 185
<212> TYPE: PRT
<213> ORGANISM: Ochotona princeps

<400> SEQUENCE: 9

Gln Glu Leu Thr Met Asp Pro Thr Pro Ser Pro Arg Leu Ile Pro Val
 1               5                  10                  15

Pro Ser Leu Arg Lys Ile His Val Gln Lys Asn Phe Gln Ser Asp Gln
                20                  25                  30

Phe Gln Gly Lys Trp Tyr Val Val Gly Leu Ala Gly Asn Asn Ile His
            35                  40                  45

Asn Ser Asp Gln Glu His Gln Gln Met Tyr Ser Thr Thr Tyr Glu Leu
        50                  55                  60

Lys Glu Asp Gly Ser Tyr Asn Val Thr Ser Thr Leu Leu Arg Asn Gln
 65                  70                  75                  80

Gln Cys Asp His Trp Ile Arg Thr Phe Val Pro Gly Ser Lys Leu Gly
                 85                  90                  95

His Phe Asn Leu Gly Asn Ile Lys Ser Tyr Pro Thr Leu Lys Ser Tyr
            100                 105                 110

Leu Ile Arg Val Val Thr Thr Asp Tyr Asn Gln Phe Ala Ile Val Phe
        115                 120                 125

Phe Arg Lys Val Tyr Lys Asn Asn Lys Lys Phe Phe Lys Ile Val Leu
130                 135                 140

Tyr Gly Arg Thr Lys Glu Leu Ser Pro Glu Leu Arg Gly Arg Phe Thr
145                 150                 155                 160

Ser Phe Ala Lys Thr Leu Gly Leu Thr Asp Asn His Ile Val Phe Pro
                165                 170                 175

Ala Pro Ile Gly Gln Cys Ile Asp Asp
            180                 185

<210> SEQ ID NO 10
<211> LENGTH: 178
<212> TYPE: PRT
<213> ORGANISM: Oryctolagus cuniculus

<400> SEQUENCE: 10

Gln Asp Pro Thr Pro Lys Leu Ile Pro Ala Pro Ser Leu Arg Arg Val
 1               5                  10                  15

Pro Leu Gln Arg Asn Phe Gln Asp Glu Gln Phe Gln Gly Lys Trp Tyr
```

```
                20                  25                  30
Val Val Gly Leu Ala Gly Asn Ala Val Gln Lys Arg Glu Glu Gly Gln
            35                  40                  45
Glu Pro Met Tyr Ser Thr Thr Tyr Glu Leu Asn Glu Asp Arg Ser Phe
 50                  55                  60
Asn Val Thr Ser Thr Leu Leu Arg Asp Gln Arg Cys Asp His Trp Ile
 65                  70                  75                  80
Arg Thr Phe Val Pro Thr Ser Arg Pro Gly Gln Tyr Asn Leu Gly Asn
                85                  90                  95
Ile Lys Ser Tyr Pro Gly Val Lys Asn Tyr Ile Val Arg Val Val Ala
            100                 105                 110
Thr Asp Tyr Ser Gln Tyr Ala Met Met Phe Phe Arg Lys Gly Ser Arg
            115                 120                 125
Asn Lys Gln Phe Phe Lys Thr Thr Leu Tyr Gly Arg Thr Lys Glu Leu
            130                 135                 140
Ser Pro Glu Leu Arg Glu Arg Phe Thr Arg Phe Ala Lys Ser Leu Gly
145                 150                 155                 160
Leu Pro Asp Asp Arg Ile Val Phe Pro Thr Pro Ile Asp Gln Cys Ile
                165                 170                 175
Asp Asp

<210> SEQ ID NO 11
<211> LENGTH: 179
<212> TYPE: PRT
<213> ORGANISM: Bos taurus

<400> SEQUENCE: 11

Arg Ser Ser Ser Arg Leu Leu Arg Ala Pro Pro Leu Ser Arg Ile
 1               5                  10                  15
Pro Leu Gln Pro Asn Phe Gln Ala Asp Gln Phe Gln Gly Lys Trp Tyr
            20                  25                  30
Thr Val Gly Val Ala Gly Asn Ala Ile Lys Lys Glu Glu Gln Asp Pro
            35                  40                  45
Leu Lys Met Tyr Ser Ser Asn Tyr Glu Leu Lys Glu Asp Gly Ser Tyr
 50                  55                  60
Asn Val Thr Ser Ile Leu Leu Lys Asp Leu Cys Asp Tyr Trp Ile
 65                  70                  75                  80
Arg Thr Phe Val Pro Ser Ser Gln Pro Gly Gln Phe Thr Leu Gly Asn
                85                  90                  95
Ile Lys Ser Tyr Arg Gly Ile Arg Ser Tyr Thr Val Arg Val Val Asn
            100                 105                 110
Thr Asp Tyr Asn Gln Phe Ala Ile Val Tyr Phe Lys Lys Val Gln Arg
            115                 120                 125
Lys Lys Thr Tyr Phe Lys Ile Thr Leu Tyr Gly Arg Thr Lys Glu Leu
            130                 135                 140
Thr Pro Glu Val Arg Glu Asn Phe Ile Asn Phe Ala Lys Ser Leu Gly
145                 150                 155                 160
Leu Thr Asp Asp His Ile Val Phe Thr Val Pro Ile Asp Arg Cys Ile
                165                 170                 175
Asp Asp Gln

<210> SEQ ID NO 12
<211> LENGTH: 179
<212> TYPE: PRT
<213> ORGANISM: Sus scrofa
```

-continued

<400> SEQUENCE: 12

Gln Gly Thr Ile Pro Asn Trp Ile Pro Ala Pro Pro Leu Ser Lys Val
1               5                   10                  15

Pro Leu Gln Pro Asn Phe Gln Ala Asp Gln Phe Gln Gly Lys Trp Tyr
            20                  25                  30

Val Val Gly Leu Ala Gly Asn Ala Val Lys Lys Glu Glu Gln Gly Arg
        35                  40                  45

Phe Lys Met Tyr Thr Thr Thr Tyr Glu Leu Lys Glu Asp Gly Ser Tyr
    50                  55                  60

Asn Val Ile Ser Thr Leu Leu Arg Gly Gln Leu Cys Asp Asn Trp Ile
65                  70                  75                  80

Arg Thr Phe Val Pro Ser Leu Gln Pro Gly Gln Phe Lys Leu Gly Asp
                85                  90                  95

Ile Lys Lys Tyr Ser Gly Leu Gln Ser Tyr Val Val Arg Val Val Ser
            100                 105                 110

Thr Asn Tyr Ser Gln Phe Ala Ile Val Phe Phe Lys Lys Val Ser Asn
        115                 120                 125

Asn Gln Glu Tyr Phe Lys Thr Thr Leu Tyr Gly Arg Thr Lys Val Leu
    130                 135                 140

Ser Pro Glu Leu Lys Glu Asn Phe Val Arg Phe Ala Lys Ser Leu Gly
145                 150                 155                 160

Leu Ser Asp Asp Asn Ile Ile Phe Pro Val Ala Ile Asp Gln Cys Ile
                165                 170                 175

Asp Gly Gln

<210> SEQ ID NO 13
<211> LENGTH: 179
<212> TYPE: PRT
<213> ORGANISM: Tursiops truncatus

<400> SEQUENCE: 13

Gln Asp Ser Thr Pro Asn Leu Ile Pro Ala Pro Pro Leu Phe Arg Val
1               5                   10                  15

Pro Leu Gln Pro Asn Phe Gln Pro Asp Gln Phe Gln Gly Lys Trp Tyr
            20                  25                  30

Ile Val Gly Leu Ala Gly Asn Ala Phe Lys Lys Glu Lys Gln Gly Gln
        35                  40                  45

Phe Lys Met Tyr Ala Thr Thr Tyr Glu Leu Lys Glu Asp Arg Ser Tyr
    50                  55                  60

Asn Val Thr Ser Ala Leu Leu Arg Asp Glu Arg Cys Asp His Trp Ile
65                  70                  75                  80

Arg Thr Phe Val Pro Ser Ser Arg Pro Gly Gln Phe Thr Leu Gly Asn
                85                  90                  95

Ile Lys Gly Phe Pro Gly Val Gln Ser Tyr Thr Val Arg Val Ala Thr
            100                 105                 110

Thr Asn Tyr Asn Gln Phe Ala Ile Val Tyr Phe Lys Lys Val Tyr Lys
        115                 120                 125

Asn Gln Glu Tyr Phe Lys Thr Thr Leu Tyr Gly Arg Thr Lys Glu Leu
    130                 135                 140

Thr Pro Gln Leu Lys Glu Asn Phe Ile His Phe Ala Lys Ser Leu Gly
145                 150                 155                 160

Leu Thr Asp Glu Tyr Ile Leu Phe Pro Val Pro Ile Asp Lys Cys Ile
                165                 170                 175

Asp Asp Gln

<210> SEQ ID NO 14
<211> LENGTH: 179
<212> TYPE: PRT
<213> ORGANISM: Equus caballus

<400> SEQUENCE: 14

```
Arg Asp Pro Ala Pro Lys Leu Ile Pro Ala Pro Leu Asp Arg Val
1               5                   10                  15

Pro Leu Gln Pro Asp Phe Lys Asp Asp Gln Phe Gln Gly Lys Trp Tyr
                20                  25                  30

Val Val Gly Val Ala Gly Asn Ala Phe Lys Lys Glu Gln Gly Gln
            35                  40                  45

Phe Thr Met Tyr Thr Thr Thr Tyr Glu Leu Lys Glu Asp His Ser Tyr
        50                  55                  60

Asn Val Thr Ser Ile Leu Leu Arg Asp Gln Asn Cys Asp His Trp Ile
65                  70                  75                  80

Arg Thr Phe Ile Pro Ser Ser Gln Pro Gly Gln Phe Asn Leu Gly Asp
                85                  90                  95

Ile Lys Arg Tyr Phe Gly Val Gln Ser Tyr Ile Val Arg Val Ala Asp
            100                 105                 110

Thr Asp Tyr Asn Gln Phe Ala Ile Val Phe Phe Arg Lys Val Tyr Lys
        115                 120                 125

Asn Gln Glu Tyr Phe Lys Thr Thr Leu Tyr Arg Arg Thr Lys Glu Leu
    130                 135                 140

Thr Pro Glu Leu Arg Glu Lys Phe Ile Ser Phe Ala Lys Ser Leu Gly
145                 150                 155                 160

Leu Thr Asp Asp His Ile Ile Phe Pro Val Pro Ile Asp Gln Cys Ile
                165                 170                 175

Asp Glu Glu
```

<210> SEQ ID NO 15
<211> LENGTH: 177
<212> TYPE: PRT
<213> ORGANISM: Microcebus murinus

<400> SEQUENCE: 15

```
Gln Asp Ser Lys Glu Lys Leu Ile Pro Ala Pro Leu Leu Arg Val
1               5                   10                  15

Pro Leu Gln Pro Asp Phe Gln Asp Asp Gln Phe Gln Gly Lys Trp Tyr
                20                  25                  30

Val Val Gly Leu Ala Gly Asn Ala Val Ser Lys Glu Glu Gln Gly Gln
            35                  40                  45

Phe Thr Met Tyr Thr Thr Thr Tyr Glu Leu Lys Asp His Ser Tyr Asn
        50                  55                  60

Val Thr Ser Thr Leu Leu Arg Asn Gly Lys Cys Asp Tyr Trp Ile Arg
65                  70                  75                  80

Thr Phe Val Leu Thr Ser Gln Pro Gly Gln Phe Ala Leu Gly Asn Ile
                85                  90                  95

Asn Arg Tyr Pro Gly Ile Gln Ser Tyr Thr Val Arg Val Val Thr Thr
            100                 105                 110

Asn Tyr Asn Gln Phe Ala Ile Val Phe Phe Lys Lys Val Ser Glu Asn
        115                 120                 125

Lys Glu Tyr Phe Lys Thr Thr Leu Tyr Gly Arg Thr Lys Glu Leu Pro
    130                 135                 140
```

```
Pro Glu Leu Lys Glu Asn Phe Ile Arg Phe Ala Lys Ser Leu Gly Leu
145                 150                 155                 160

Thr Glu Asp His Ile Ile Tyr Pro Val Pro Ile Asp Gln Cys Ile Asp
                165                 170                 175

Asp

<210> SEQ ID NO 16
<211> LENGTH: 179
<212> TYPE: PRT
<213> ORGANISM: Loxodonta africana

<400> SEQUENCE: 16

Gln Thr His Ser Pro Thr Leu Ile Pro Ala Pro Leu Leu Arg Val
1               5                   10                  15

Pro Leu Gln Pro Asp Phe Gln Asp Asp Lys Phe Gln Gly Lys Trp Tyr
                20                  25                  30

Val Ile Gly Leu Ala Gly Asn Ala Val Glu Lys Lys Glu Gln Gly Gln
            35                  40                  45

Phe Lys Met Tyr Thr Thr Thr Tyr Glu Leu Lys Glu Asp Gly Ser Tyr
50                  55                  60

Asn Val Thr Ser Thr Leu Leu Gln Glu Asp Gly Lys Cys Ser Tyr Trp
65                  70                  75                  80

Ile Arg Thr Phe Val Pro Ser Phe Gln Pro Gly Gln Phe Asn Leu Gly
                85                  90                  95

Asn Ile Lys Asn Phe Pro Gly Leu Gln Ser Tyr Thr Val Arg Val Thr
            100                 105                 110

Ala Thr Asn Tyr Asn Gln Phe Ala Ile Val Phe Phe Lys Lys Val Ser
        115                 120                 125

Lys Asn Gly Glu Tyr Phe Lys Thr Thr Leu Tyr Gly Arg Thr Lys Glu
130                 135                 140

Leu Thr Pro Glu Leu Lys Glu Arg Phe Ile Arg Phe Ala Lys Ser Leu
145                 150                 155                 160

Gly Leu Ser Asp His Ile Ile Phe Pro Val Pro Ile Asp Arg Cys Ile
                165                 170                 175

Asp Asp Ala

<210> SEQ ID NO 17
<211> LENGTH: 178
<212> TYPE: PRT
<213> ORGANISM: Peripatopsis capensis

<400> SEQUENCE: 17

Gln Glu Pro Thr Pro Leu Ile Pro Ala Pro Leu Ser Ser Ile Pro
1               5                   10                  15

Leu Lys Pro Asn Phe His Asn Asp Lys Phe Gln Gly Lys Trp Tyr Val
                20                  25                  30

Val Gly Val Ala Gly Asn Ala Ile Thr Lys Glu Lys Asp Pro Ser Leu
            35                  40                  45

Met Tyr Thr Thr Thr Tyr Glu Leu Arg Asp Asp Gly Ser Tyr Asn Val
50                  55                  60

Thr Ser Thr Gln Phe Arg Glu Lys Ile Asn Cys Thr His Trp Thr Arg
65                  70                  75                  80

Thr Phe Val Pro Thr Ser Gln Pro Gly Gln Phe Ser Leu Gly Asn Ile
                85                  90                  95

Asp Lys Tyr Pro His Leu Ser Ser Tyr Thr Val Arg Val Thr Ala Thr
```

```
                    100                 105                 110

Asn Tyr Asn Tyr Phe Ala Ile Val Tyr Phe Lys Lys Val Ser Lys Asn
            115                 120                 125

Gln Glu Tyr Phe Lys Thr Thr Leu Tyr Lys Arg Ile Lys Lys Leu Thr
        130                 135                 140

His Gly Leu Lys Lys His Phe Ile Gln Phe Ala Lys Ser Leu Gly Leu
145                 150                 155                 160

Pro Asp Asn His Ile Thr Phe Leu Val Pro Thr Asp Arg Cys Ile Asp
                165                 170                 175

Asp Ala

<210> SEQ ID NO 18
<211> LENGTH: 178
<212> TYPE: PRT
<213> ORGANISM: Canis lupus familiaris

<400> SEQUENCE: 18

Gln Asp Ser Thr Pro Ser Leu Ile Pro Ala Pro Pro Leu Lys Val
1               5                   10                  15

Pro Leu Gln Pro Asp Phe Gln His Asp Gln Phe Gln Gly Lys Trp Tyr
            20                  25                  30

Val Ile Gly Ile Ala Gly Asn Ile Leu Lys Lys Glu Gly His Gly Gln
        35                  40                  45

Leu Lys Met Tyr Thr Thr Thr Tyr Glu Leu Lys Asp Gln Ser Tyr
    50                  55                  60

Asn Val Thr Ser Thr Leu Leu Arg Asn Glu Arg Cys Asp Tyr Trp Asn
65                  70                  75                  80

Arg Asp Phe Val Pro Ser Phe Gln Pro Gly Gln Phe Ser Leu Gly Asp
                85                  90                  95

Ile Gln Leu Tyr Pro Gly Val Gln Ser Tyr Leu Val Gln Val Val Ala
            100                 105                 110

Thr Asn Tyr Asn Gln Tyr Ala Leu Val Tyr Phe Arg Lys Val Tyr Lys
        115                 120                 125

Ser Gln Glu Tyr Phe Lys Ile Thr Leu Tyr Gly Arg Thr Lys Glu Leu
    130                 135                 140

Pro Leu Glu Leu Lys Lys Glu Phe Ile Arg Phe Ala Lys Ser Ile Gly
145                 150                 155                 160

Leu Thr Glu Asp His Ile Ile Phe Pro Val Pro Ile Asp Gln Cys Ile
                165                 170                 175

Asp Glu

<210> SEQ ID NO 19
<211> LENGTH: 179
<212> TYPE: PRT
<213> ORGANISM: artificial
<220> FEATURE:
<223> OTHER INFORMATION: Homo sapiens Scn with T54C mutation

<400> SEQUENCE: 19

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Cys Ile Tyr Glu Leu Lys Glu Asp Lys Ser Tyr
```

```
                50                  55                  60
Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly

<210> SEQ ID NO 20
<211> LENGTH: 179
<212> TYPE: PRT
<213> ORGANISM: artificial
<220> FEATURE:
<223> OTHER INFORMATION: Homo sapiens Scn with S68C mutation

<400> SEQUENCE: 20

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
                50                  55                  60

Asn Val Thr Cys Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly

<210> SEQ ID NO 21
<211> LENGTH: 179
<212> TYPE: PRT
<213> ORGANISM: artificial
<220> FEATURE:
<223> OTHER INFORMATION: Homo sapiens Scn with T54C and S68C mutations

<400> SEQUENCE: 21
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Cys Ile Tyr Glu Leu Lys Glu Asp Lys Ser Tyr
50                  55                  60

Asn Val Thr Cys Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
            85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly Gly

<210> SEQ ID NO 22
<211> LENGTH: 179
<212> TYPE: PRT
<213> ORGANISM: artificial
<220> FEATURE:
<223> OTHER INFORMATION: Homo sapiens Scn with C87S mutation

<400> SEQUENCE: 22

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
            85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175
```

-continued

Asp Gly Gly

<210> SEQ ID NO 23
<211> LENGTH: 198
<212> TYPE: PRT
<213> ORGANISM: artificial
<220> FEATURE:
<223> OTHER INFORMATION: Homo sapiens Scn with a leader sequence and
      mutations K125A and C87S

<400> SEQUENCE: 23

```
Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Ser Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
130                 135                 140

Ala Val Ser Gln Asn Arg Glu Tyr Phe Ala Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195
```

<210> SEQ ID NO 24
<211> LENGTH: 198
<212> TYPE: PRT
<213> ORGANISM: artificial
<220> FEATURE:
<223> OTHER INFORMATION: Homo sapiens Scn with a leader sequence and
      mutations T54C, S68C, C87S, and K125A

<400> SEQUENCE: 24

```
Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Cys Ile Tyr Glu Leu Lys Glu
65                  70                  75                  80

Asp Lys Ser Tyr Asn Val Thr Cys Val Leu Phe Arg Lys Lys Lys Cys
```

```
                85                  90                  95
Asp Tyr Trp Ile Arg Thr Phe Val Pro Gly Ser Gln Pro Gly Glu Phe
                100                 105                 110

Thr Leu Gly Asn Ile Lys Ser Tyr Pro Gly Leu Thr Ser Tyr Leu Val
                115                 120                 125

Arg Val Val Ser Thr Asn Tyr Asn Gln His Ala Met Val Phe Phe Lys
            130                 135                 140

Ala Val Ser Gln Asn Arg Glu Tyr Phe Ala Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
                180                 185                 190

Asp Gln Cys Ile Asp Gly
                195

<210> SEQ ID NO 25
<211> LENGTH: 446
<212> TYPE: PRT
<213> ORGANISM: artificial
<220> FEATURE:
<223> OTHER INFORMATION: Scn-CD19 fusion protein: Homo sapiens Scn with
      a leader sequence and T54C and C87S mutations; a GGS linker; and
      CD19 scFv sequence

<400> SEQUENCE: 25

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
                20                  25                  30

Leu Ser Lys Val Pro Leu Gln Gln Asn Phe Gln Asp Asn Gln Phe Gln
            35                  40                  45

Gly Lys Trp Tyr Val Val Gly Leu Ala Gly Asn Ala Ile Leu Arg Glu
50                  55                  60

Asp Lys Asp Pro Gln Lys Met Tyr Ala Cys Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Ser Gln Pro Gly Glu Phe
                100                 105                 110

Thr Leu Gly Asn Ile Lys Ser Tyr Pro Gly Leu Thr Ser Tyr Leu Val
            115                 120                 125

Arg Val Val Ser Thr Asn Tyr Asn Gln His Ala Met Val Phe Phe Lys
            130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
                180                 185                 190

Asp Gln Cys Ile Asp Gly Gly Gly Ser Asp Ile Gln Met Thr Gln Thr
            195                 200                 205

Thr Ser Ser Leu Ser Ala Ser Leu Gly Asp Arg Val Thr Ile Ser Cys
            210                 215                 220

Arg Ala Ser Gln Asp Ile Ser Lys Tyr Leu Asn Trp Tyr Gln Gln Lys
225                 230                 235                 240
```

```
Pro Asp Gly Thr Val Lys Leu Leu Ile Tyr His Thr Ser Arg Leu His
                245                 250                 255

Ser Gly Val Pro Ser Arg Phe Ser Gly Ser Gly Ser Gly Thr Asp Tyr
            260                 265                 270

Ser Leu Thr Ile Ser Asn Leu Glu Gln Glu Asp Ile Ala Thr Tyr Phe
        275                 280                 285

Cys Gln Gln Gly Asn Thr Leu Pro Tyr Thr Phe Gly Gly Gly Thr Lys
    290                 295                 300

Leu Glu Ile Thr Gly Ser Thr Ser Gly Ser Gly Lys Pro Gly Ser Gly
305                 310                 315                 320

Glu Gly Ser Thr Lys Gly Glu Val Lys Leu Gln Glu Ser Gly Pro Gly
                325                 330                 335

Leu Val Ala Pro Ser Gln Ser Leu Ser Val Thr Cys Thr Val Ser Gly
            340                 345                 350

Val Ser Leu Pro Asp Tyr Gly Val Ser Trp Ile Arg Gln Pro Pro Arg
        355                 360                 365

Lys Gly Leu Glu Trp Leu Gly Val Ile Trp Gly Ser Glu Thr Thr Tyr
    370                 375                 380

Tyr Asn Ser Ala Leu Lys Ser Arg Leu Thr Ile Ile Lys Asp Asn Ser
385                 390                 395                 400

Lys Ser Gln Val Phe Leu Lys Met Asn Ser Leu Gln Thr Asp Asp Thr
                405                 410                 415

Ala Ile Tyr Tyr Cys Ala Lys His Tyr Tyr Tyr Gly Gly Ser Tyr Ala
            420                 425                 430

Met Asp Tyr Trp Gly Gln Gly Thr Ser Val Thr Val Ser Ser
        435                 440                 445

<210> SEQ ID NO 26
<211> LENGTH: 750
<212> TYPE: PRT
<213> ORGANISM: Homo sapiens

<400> SEQUENCE: 26

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
        130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
```

```
                165                 170                 175
Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
            210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
            290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590
```

-continued

```
Leu Pro Phe Asp Cys Arg Asp Tyr Ala Val Leu Arg Lys Tyr Ala
            595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Glu Thr Leu Ser Glu Val Ala
            740                 745                 750

<210> SEQ ID NO 27
<211> LENGTH: 123
<212> TYPE: PRT
<213> ORGANISM: Homo sapiens

<400> SEQUENCE: 27

Met Lys Ala Val Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ile Leu Ala Leu Leu Pro Ala
            100                 105                 110

Leu Gly Leu Leu Leu Trp Gly Pro Gly Gln Leu
        115                 120

<210> SEQ ID NO 28
<211> LENGTH: 622
<212> TYPE: PRT
<213> ORGANISM: Homo sapiens

<400> SEQUENCE: 28

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45
```

```
Asp Gly Val Leu Ala Asn Pro Pro Asn Ile Ser Ser Leu Ser Pro Arg
     50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Phe Leu Asn Pro
                115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
                195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
                275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
                420                 425                 430

Leu Thr Ala Phe Tyr Pro Gly Tyr Leu Cys Ser Leu Ser Pro Glu Glu
                435                 440                 445

Leu Ser Ser Val Pro Pro Ser Ser Ile Trp Ala Val Arg Pro Gln Asp
450                 455                 460
```

```
Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
            485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
            515                 520                 525

Asp Ala Val Leu Pro Leu Thr Val Ala Glu Val Gln Lys Leu Leu Gly
            530                 535                 540

Pro His Val Glu Gly Leu Lys Ala Glu Arg His Arg Pro Val Arg
545                 550                 555                 560

Asp Trp Ile Leu Arg Gln Arg Gln Asp Leu Asp Thr Leu Gly Leu
            565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
            595                 600                 605

Val Leu Thr Val Leu Ala Leu Leu Ala Ser Thr Leu Ala
            610                 615                 620

<210> SEQ ID NO 29
<211> LENGTH: 556
<212> TYPE: PRT
<213> ORGANISM: Homo sapiens

<400> SEQUENCE: 29

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220
```

-continued

```
Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
            245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe Phe Lys Val
            325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
            405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
            530                 535                 540

Gly Gly Gly Gly Arg Met Gly Thr Trp Ser Thr Arg
545                 550                 555
```

<210> SEQ ID NO 30
<211> LENGTH: 297
<212> TYPE: PRT
<213> ORGANISM: Homo sapiens

<400> SEQUENCE: 30

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
```

```
             35                  40                  45
Ser Lys Thr Leu Gly Ala Val Gln Ile Met Asn Gly Leu Phe His Ile
 50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Ile Met Tyr Ile Ile
                 85                  90                  95

Ser Gly Ser Leu Leu Ala Ala Thr Glu Lys Asn Ser Arg Lys Cys Leu
                100                 105                 110

Val Lys Gly Lys Met Ile Met Asn Ser Leu Ser Leu Phe Ala Ala Ile
                115                 120                 125

Ser Gly Met Ile Leu Ser Ile Met Asp Ile Leu Asn Ile Lys Ile Ser
            130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 31
<211> LENGTH: 937
<212> TYPE: PRT
<213> ORGANISM: Homo sapiens

<400> SEQUENCE: 31

Met His Arg Pro Arg Arg Gly Thr Arg Pro Leu Leu Ala Leu
 1               5                  10                  15

Leu Ala Leu Leu Leu Ala Ala Arg Gly Ala Ala Ala Gln Glu Thr
                 20                  25                  30

Glu Leu Ser Val Ser Ala Glu Leu Val Pro Thr Ser Ser Trp Asn Ile
             35                  40                  45

Ser Ser Glu Leu Asn Lys Asp Ser Tyr Leu Thr Leu Asp Glu Pro Met
 50                  55                  60

Asn Asn Ile Thr Thr Ser Leu Gly Gln Thr Ala Glu Leu His Cys Lys
 65                  70                  75                  80

Val Ser Gly Asn Pro Pro Pro Thr Ile Arg Trp Phe Lys Asn Asp Ala
                 85                  90                  95

Pro Val Val Gln Glu Pro Arg Arg Leu Ser Phe Arg Ser Thr Ile Tyr
                100                 105                 110
```

```
Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
        130                 135                 140

Val Leu Phe Val Lys Phe Gly Pro Pro Thr Ala Ser Pro Gly Tyr
145                 150                 155                 160

Ser Asp Glu Tyr Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
```

```
            530                 535                 540
Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
    930                 935

<210> SEQ ID NO 32
```

```
<211> LENGTH: 168
<212> TYPE: PRT
<213> ORGANISM: Homo sapiens

<400> SEQUENCE: 32

Met Gly His His His His His His His His Ser Ser Gly His
1               5                   10                  15

Ile Glu Gly Arg His Met Arg Arg Val Pro Gly Val Ala Pro Thr Leu
                20                  25                  30

Val Arg Ser Ala Ser Glu Thr Ser Glu Lys Arg Pro Phe Met Cys Ala
            35                  40                  45

Tyr Pro Gly Cys Asn Lys Arg Tyr Phe Lys Leu Ser His Leu Gln Met
        50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 33
<211> LENGTH: 11
<212> TYPE: PRT
<213> ORGANISM: artificial
<220> FEATURE:
<223> OTHER INFORMATION: CDRL1 sequence of variable light chain of human
      or humanized scFv as part of the targeting domain of Scn-metal
      chelator combination targeting ROR1 epitope

<400> SEQUENCE: 33

Ala Ser Gly Phe Asp Phe Ser Ala Tyr Tyr Met
1               5                   10

<210> SEQ ID NO 34
<211> LENGTH: 7
<212> TYPE: PRT
<213> ORGANISM: artificial
<220> FEATURE:
<223> OTHER INFORMATION: CDRL2 sequence of variable light chain of human
      or humanized scFv as part of the targeting domain of Scn-metal
      chelator combination targeting ROR1 epitope

<400> SEQUENCE: 34

Thr Ile Tyr Pro Ser Ser Gly
1               5

<210> SEQ ID NO 35
<211> LENGTH: 9
<212> TYPE: PRT
<213> ORGANISM: artificial
<220> FEATURE:
<223> OTHER INFORMATION: CDRL3 sequence of variable light chain of human
      or humanized scFv as part of the targeting domain of Scn-metal
      chelator combination targeting ROR1 epitope
```

```
<400> SEQUENCE: 35

Ala Asp Arg Ala Thr Tyr Phe Cys Ala
1               5

<210> SEQ ID NO 36
<211> LENGTH: 6
<212> TYPE: PRT
<213> ORGANISM: artificial
<220> FEATURE:
<223> OTHER INFORMATION: CDRH1 sequence of variable heavy chain of human
      or humanized scFv as part of the targeting domain of Scn-metal
      chelator combination targeting ROR1 epitope

<400> SEQUENCE: 36

Asp Thr Ile Asp Trp Tyr
1               5

<210> SEQ ID NO 37
<211> LENGTH: 16
<212> TYPE: PRT
<213> ORGANISM: artificial
<220> FEATURE:
<223> OTHER INFORMATION: CDRH2 sequence of variable heavy chain of human
      or humanized scFv as part of the targeting domain of Scn-metal
      chelator combination targeting ROR1 epitope

<400> SEQUENCE: 37

Val Gln Ser Asp Gly Ser Tyr Thr Lys Arg Pro Gly Val Pro Asp Arg
1               5                   10                  15

<210> SEQ ID NO 38
<211> LENGTH: 8
<212> TYPE: PRT
<213> ORGANISM: artificial
<220> FEATURE:
<223> OTHER INFORMATION: CDRH3 sequence of variable heavy chain of human
      or humanized scFv as part of the targeting domain of Scn-metal
      chelator combination targeting ROR1 epitope

<400> SEQUENCE: 38

Tyr Ile Gly Gly Tyr Val Phe Gly
1               5

<210> SEQ ID NO 39
<211> LENGTH: 11
<212> TYPE: PRT
<213> ORGANISM: artificial
<220> FEATURE:
<223> OTHER INFORMATION: CDRL1 sequence of variable light chain of human
      or humanized scFv as part of the targeting domain of Scn-metal
      chelator combination targeting CD19 epitope

<400> SEQUENCE: 39

Arg Ala Ser Gln Asp Ile Ser Lys Tyr Leu Asn
1               5                   10

<210> SEQ ID NO 40
<211> LENGTH: 7
<212> TYPE: PRT
<213> ORGANISM: artificial
<220> FEATURE:
<223> OTHER INFORMATION: CDRL2 sequence of variable light chain of human
      or humanized scFv as part of the targeting domain of Scn-metal
      chelator combination targeting CD19 epitope

<400> SEQUENCE: 40

Ser Arg Leu His Ser Gly Val
1               5
```

```
<210> SEQ ID NO 41
<211> LENGTH: 9
<212> TYPE: PRT
<213> ORGANISM: artificial
<220> FEATURE:
<223> OTHER INFORMATION: CDRL3 sequence of variable light chain of human
      or humanized scFv as part of the targeting domain of Scn-metal
      chelator combination targeting CD19 epitope

<400> SEQUENCE: 41

Gly Asn Thr Leu Pro Tyr Thr Phe Gly
1               5

<210> SEQ ID NO 42
<211> LENGTH: 5
<212> TYPE: PRT
<213> ORGANISM: artificial
<220> FEATURE:
<223> OTHER INFORMATION: CDRH1 sequence of variable heavy chain of human
      or humanized scFv as part of the targeting domain of Scn-metal
      chelator combination targeting CD19 epitope

<400> SEQUENCE: 42

Asp Tyr Gly Val Ser
1               5

<210> SEQ ID NO 43
<211> LENGTH: 16
<212> TYPE: PRT
<213> ORGANISM: artificial
<220> FEATURE:
<223> OTHER INFORMATION: CDRH2 sequence of variable heavy chain of human
      or humanized scFv as part of the targeting domain of Scn-metal
      chelator combination targeting CD19 epitope

<400> SEQUENCE: 43

Val Thr Trp Gly Ser Glu Thr Thr Tyr Tyr Asn Ser Ala Leu Lys Ser
1               5                   10                  15

<210> SEQ ID NO 44
<211> LENGTH: 7
<212> TYPE: PRT
<213> ORGANISM: artificial
<220> FEATURE:
<223> OTHER INFORMATION: CDRH3 sequence of variable heavy chain of human
      or humanized scFv as part of the targeting domain of Scn-metal
      chelator combination targeting CD19 epitope

<400> SEQUENCE: 44

Tyr Ala Met Asp Tyr Trp Gly
1               5

<210> SEQ ID NO 45
<211> LENGTH: 15
<212> TYPE: PRT
<213> ORGANISM: artificial
<220> FEATURE:
<223> OTHER INFORMATION: Avitag amino acid sequence

<400> SEQUENCE: 45

Gly Leu Asn Asp Ile Phe Glu Ala Gln Lys Ile Glu Trp His Glu
1               5                   10                  15

<210> SEQ ID NO 46
<211> LENGTH: 6
<212> TYPE: PRT
<213> ORGANISM: artificial
```

```
<220> FEATURE:
<223> OTHER INFORMATION: 6xhistidine tag

<400> SEQUENCE: 46

His His His His His His
1               5
```

CHELATING PLATFORM FOR DELIVERY OF RADIONUCLIDES

CROSS-REFERENCE TO RELATED APPLICATIONS

This application claims the benefit of U.S. Provisional Patent Application No. 62/380,885, filed on Aug. 29, 2016, U.S. Provisional Patent Application No. 62/401,687, filed on Sep. 29, 2016, and U.S. Provisional Patent Application No. 62/505,458, filed on May 12, 2017, the entire contents each of which are incorporated herein by reference in their entirety as if fully set forth herein.

STATEMENT OF GOVERNMENT SUPPORT

This invention was made with government support under A1094419 awarded by the National Institutes of Health and DE-AC02-05CH11231 awarded by the Department of Energy. The government has certain rights in the invention.

FIELD OF THE DISCLOSURE

The present disclosure provides siderocalin-metal chelator combinations that bind metallic radioisotopes used in nuclear medicine with high affinity. The high affinity siderocalin-metal chelator combinations include a number of chelator backbone arrangements with functional groups that coordinate with metals. The siderocalin-metal chelator combinations can be used to deliver radionuclides for imaging and therapeutic purposes.

BACKGROUND OF THE DISCLOSURE

Nuclear medicine refers to the diagnosis and/or treatment of conditions by administering radioactive isotopes (radioisotopes or radionuclides) to a subject. For example, nuclear medicine can be used to diagnose various conditions through imaging, such as positron emission topography (PET) imaging. Therapeutic nuclear medicine is often referred to as radiation therapy or radioimmunotherapy (RIT). Examples of conditions that are treated with RIT include various cancers, thyroid diseases, blood disorders, and restenosis following balloon angioplasty and/or stent placement.

Many conditions treated with RIT are associated with uncontrolled or unwanted cell division. When dividing cells are exposed to sufficiently high doses of ionizing radiation, such as in the form of alpha particles, beta particles, or x-ray or gamma radiation, DNA strands break disrupting the normal process of cell division and inhibiting or even stopping cellular growth.

While nuclear medicine offers many effective diagnostic and therapeutic uses, there are drawbacks associated with its use. One drawback is that sites of the body other than the area of diagnostic or therapeutic interest are affected by the radioactivity, often leading to unwanted side effects. This drawback is caused by release of radioactivity before arrival at a site of interest.

Attempts have been made to lessen the release of radioactivity before arrival at a physiological site of interest. In one approach, radionuclides have been attached to chelating agents that are then attached to a targeting ligand that specifically recognizes and attaches to particular cell types. A common example of such a targeting ligand is an antibody. For example, antibodies targeted to tumor-specific cell surface markers or other disease-related markers have been chemically conjugated to potent synthetic chelating agents such as DOTA (1,4,7,10-tetra-azacylcododecane-N,N',N'',N'''-tetraacetic acid) and DTPA (diethylenetriamine pentaacetic acid). These chelating agents have then been charged with radioisotopes of the rare earth elements such as $Y^{3+}$ or $Lu^{3+}$ or similar trivalent metal ions, such as $In^{3+}$ or $Bi^{3+}$. At least two such radionuclide-conjugated antibodies directed against the tumor-specific cell surface marker, CD20, have been approved for use in human patients: Zevalin® (RIT Oncology, LLC, Seattle, Wash.) and Bexxar® (GlaxoSmithKline, LLC, Wilmington, Del.).

U.S. Patent Publication No. 2011/0262353 (Skerra) describes drawbacks of the use of antibody-chelator combinations to deliver radionuclides. Skerra notes long circulation times, leading to reduced site-specific delivery and lowered therapeutic effectiveness and contrast for imaging. Skerra suggests that a solution to this perceived problem would be to couple targeting ligands that are smaller than antibodies to proteins that bind to metal chelators, such as siderocalin (Scn). Scn, also known as Lipocalin-2 or neutrophil gelatinase-associated lipocalin (NGAL), is a member of the lipocalin family of proteins that binds siderophores, a type of small chelator, with very high affinity (in the sub-nanomolar range).

Skerra particularly teaches modifying natural Scn to form Scn "muteins" that bind non-natural ligands. Skerra defines non-natural ligands as any compound which does not bind to native, mature hNGAL under physiological conditions. See, for example, Skerra, paragraph [0021]. Thus, non-natural ligands exclude many, if not all, metal and chelated metal complexes. More particularly, following alteration of the natural Scn protein, the Scn muteins bind non-natural ligands that Scn does not bind with under normal physiological conditions. The alterations to Scn include mutations at one or more of positions 33, 36, 41, 52, 54, 68, 70, 79, 81, 134, 136 and 138. While Skerra's approach increases Scn's ability to bind to targeting ligands that are non-natural Scn binding partners, this approach generates other issues with the targeted delivery of radionuclides described more fully below. Further, even with targeted delivery, the stability of the radioactive complex (chelator and radionuclide) is often not strong enough to sufficiently prevent early release of metallic radioisotopes in unintended areas of the body, creating off-target side effects.

There are other challenges associated with the use of nuclear medicine. For example, one beneficial use of nuclear medicine would be to administer a targeted radioactive imaging complex to ensure that the radioactive complex selectively reaches the physiological site of interest. Once selective delivery is confirmed with the imaging complex, a radioactive therapeutic complex could be administered with confidence in its selective and targeted delivery to the site of interest. In practice, however, such targeted delivery of a therapeutic cannot be confirmed with pre-imaging. This is because of two reasons. First, different radionuclides are used for imaging and therapeutic purposes and there are currently no "universal chelators" that can bind all types of metallic radionuclides. When different chelators must be used for an imaging radionuclide versus a therapeutic radionuclide, the activity of one within the physiological environment is not sufficiently predictive of the activity of the second. Second, currently available chelators do not effectively shield radionuclides from the physiological environment. This means that radionuclides interact with the physiological environment following administration and en route to a site of interest. As a result, radionuclides with different charge states ($^{2+}$, $^{3+}$, $^{4+}$) interact with the physiological environment differently, potentially affecting intended delivery.

Finally, there are significant challenges associated with the efficient manufacturing and use of ionizing radiation in therapeutic and imaging environments.

SUMMARY OF THE DISCLOSURE

The present disclosure provides siderocalin (Scn)-metal chelator combinations that bind metallic radioisotopes used in nuclear medicine (e.g., transition metals, f-elements) with high affinity and effectively shields the metallic radioisotopes from the physiological environment. The high affinity siderocalin-metal chelator combinations include a number of chelator backbone arrangements with functional groups that coordinate with metals. The siderocalin-metal chelator combinations can be used to deliver radionuclides for imaging and therapeutic purposes. These disclosed chelating platforms provide numerous benefits.

First, like Skerra, the disclosed chelating platforms utilize Scn. However, the current disclosure teaches that the muteins described in Skerra, designed to increase binding to non-natural ligands (e.g., targeting ligands) have reduced chelating efficacy. Thus, Scn utilized in the currently disclosed Scn-metal chelator combinations do not include mutations that reduce chelating efficacy. If Scn mutations are used, the mutations maintain or increase, rather than decrease, Scn's chelating efficacy.

Second, the Scn-metal chelator combinations disclosed herein have high affinity, both between the Scn and metal chelator and between the metal chelator and radionuclide. The high affinity between each of these components reduces early release of radioactivity, reducing side effects associated with the use of nuclear medicine.

Third, the current disclosure provides a universal chelating platform that accommodates metallic radioisotopes used in nuclear medicine and effectively shields them from the physiological environment following administration. By accommodating and effectively shielding metallic radioisotopes used in nuclear medicine, the Scn-metal chelator combinations (sometimes referred to as SCCs herein) can be used to administer a targeted radioactive imaging complex to ensure that the radioactive complex selectively reaches the physiological site of interest. Once selective delivery is confirmed with the imaging complex, a radioactive therapeutic complex can be administered, with confidence that the radioactive therapeutic complex will exhibit substantially the same delivery and release kinetics.

The current disclosure also provides a method of separating metal ions. The method can comprise contacting a liquid comprising a plurality of metal ions with a composition as described herein, under conditions sufficient to form a metal ion-composition complex comprising a metal ion of the plurality of metal ions. The method can further comprise separating a first fraction of the mixture enriched for the metal ion-composition complex from a second fraction depleted for the metal ion-composition complex. The first fraction can be enriched for a first metal ion that has a charge that is different from a charge of a second metal ion enriched in the second fraction.

In addition, the current disclosure provides a method of preparing $Bk^{4+}$ from a mixture. The method can comprise contacting a first mixture comprising $Bk^{4+}$ and a trivalent metal ion with a composition as described herein under conditions sufficient to form a complex comprising the trivalent metal ion and the composition. The method can further include separating the complex from the first mixture to generate a second mixture depleted for the trivalent metal ion and chromatographically isolating the $Bk^{4+}$ in the second mixture.

Further, the current disclosure provides a method of reclaiming an actinide from a sample. The method comprises obtaining an aqueous sample comprising, or suspected of comprising, an actinide, contacting the sample with a composition as described herein to generate a mixture under conditions sufficient to form a complex comprising the actinide and the composition, and separating the complex from the mixture.

Many of the described benefits of the SCCs derive from use of the novel chelator and chelator combinations disclosed herein that include a number of chelator backbone arrangements with functional groups that coordinate with metals. The siderocalin-metal chelator combinations can be used to deliver radionuclides for imaging and therapeutic purposes.

Finally, disclosed herein are efficient chelator and SCC manufacturing processes.

BRIEF DESCRIPTION OF THE FIGURES

FIG. 9. Crystallography data collection and refinement statistics.

FIG. 11. Protonation and Eu(III), Zr(IV), and Th(IV) Complex Formation Constants for 3,4,3-LI(CAM)[a] [a]I=0.1 M (KCl), T=25° C. Errors correspond to standard deviations from at least three independent titrations. Protonation and Eu(III), Zr(IV), and Th(IV) complex formation constants previously reported for 3,4,3-LI(1,2-HOPO) are also given for comparison.

FIG. 15. Exemplary sequences of siderocalin orthologs.

FIG. 16. Exemplary sequences of siderocalins that can be used in the chelating platforms disclosed herein.

DETAILED DESCRIPTION

Figure 1:
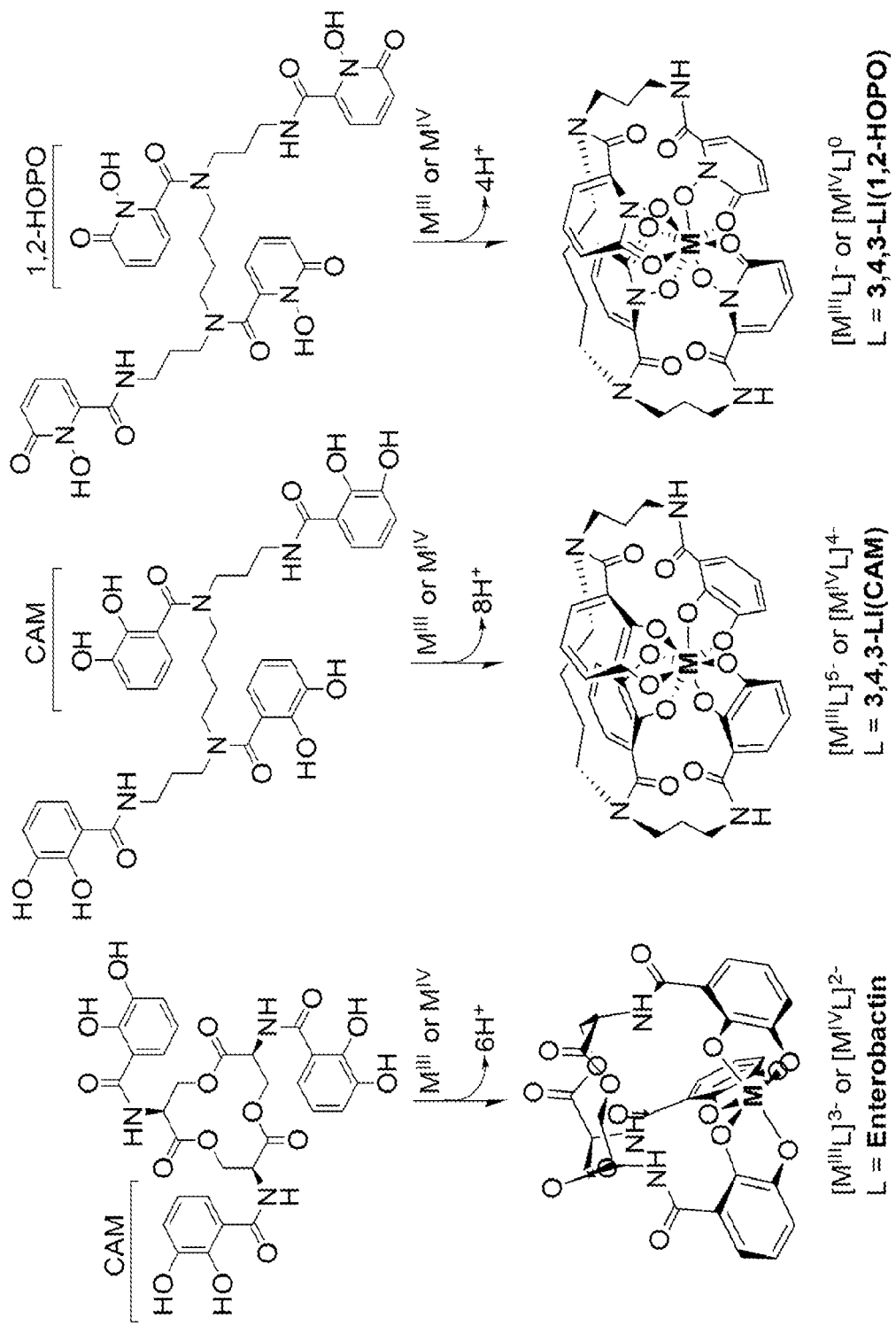
FIG. 1. Complexation of M(III) and M(IV) by the hexadentate siderophore enterobactin or the octadentate synthetic analogs 3,4,3-LI(CAM) or 3,4,3-LI(1,2-HOPO), when deprotonated.

Nuclear medicine refers to the diagnosis and/or treatment of conditions by administering radioactive isotopes (radioisotopes or radionuclides) to a subject. For example, nuclear medicine can be used to diagnose various conditions through the use of imaging, such as positron emission topography (PET) imaging. Therapeutic nuclear medicine is often referred to as radiation therapy or radioimmunotherapy (RIT). Examples of conditions that are treated with RIT include various cancers, thyroid diseases, blood disorders, and restenosis following balloon angioplasty and/or stent placement.

Many conditions treated with RIT are associated with uncontrolled or unwanted cell division. When dividing cells are exposed to sufficiently high doses of ionizing radiation, such as in the form of alpha particles, beta particles, or x-ray or gamma radiation, DNA strands break disrupting the normal process of cell division and inhibiting or even stopping cellular growth.

While nuclear medicine offers many effective diagnostic and therapeutic uses, there are drawbacks associated with its use. One drawback is that sites of the body other than the area of diagnostic or therapeutic interest are affected by the radioactivity, often leading to unwanted side effects. This drawback is caused by release of radioactivity before arrival at a site of interest.

Attempts have been made to lessen the release of radioactivity before arrival at a physiological site of interest. In one approach, radionuclides have been attached to chelating agents that are then attached to a targeting ligand that specifically recognizes and attaches to particular cell types. A common example of such a targeting ligand is an antibody. For example, antibodies targeted to tumor-specific cell surface markers or other disease-related markers have been chemically conjugated to potent synthetic chelating agents such as DOTA (1,4,7,10-tetra-azacylcododecane-N,N',N'',N'''-tetraacetic acid) and DTPA (diethylenetriamine pentaacetic acid). These chelating agents have then been charged with radioisotopes of the rare earth elements such as $Y^{3+}$ or $Lu^{3+}$ or similar trivalent metal ions, such as $In^{3+}$ or $Bi^{3+}$. At least two such radionuclide-conjugated antibodies directed against the tumor-specific cell surface marker, CD20, have been approved for use in human patients: Zevalin® (RIT Oncology, LLC, Seattle, Wash.) and Bexxar® (GlaxoSmithKline, LLC, Wilmington, Del.).

U.S. Patent Publication No. 2011/0262353 (Skerra) describes drawbacks of the use of antibody-chelator combinations to deliver radionuclides. Skerra notes long circulation times, leading to reduced site-specific delivery and lowered therapeutic effectiveness and contrast for imaging. Skerra suggests that a solution to this perceived problem would be to couple targeting ligands that are smaller than antibodies to proteins that bind to metal chelators, such as siderocalin (Scn). Scn, also known as Lipocalin-2 or neutrophil gelatinase-associated lipocalin, is a member of the lipocalin family of proteins that binds siderophores, a type of small chelator, with very high affinity (in the sub-nanomolar range).

Skerra particularly teaches modifying natural Scn to form Scn "muteins" that bind non-natural Scn ligands. Skerra defines non-natural ligands as any compound which does not bind to native, mature hNGAL under physiological conditions. See, for example, Skerra, paragraph [0021]. Thus, non-natural ligands exclude many, if not all, metal and chelated metal complexes. More particularly, following alteration of the natural Scn protein, the Scn muteins bind non-natural ligands that Scn does not bind with under normal physiological conditions. The alterations to Scn include mutations at one or more of positions 33, 36, 41, 52, 54, 68, 70, 79, 81, 134, 136 and 138. While Skerra's approach increases Scn's ability to bind to targeting ligands that are non-natural Scn binding partners, this approach generates other issues with the targeted delivery of radionuclides described more fully below. Further, even with targeted delivery, the stability of the radioactive complex (chelator and radionuclide) is often not strong enough to sufficiently prevent early release of metallic radioisotopes in unintended areas of the body, creating off-target side effects.

There are other challenges associated with the use of nuclear medicine. For example, one beneficial use of nuclear medicine would be to administer a targeted radioactive imaging complex to ensure that the radioactive complex selectively reaches the physiological site of interest. Once selective delivery is confirmed with the imaging complex, a radioactive therapeutic complex could be administered. In practice, however, such targeted delivery of a therapeutic cannot be confirmed with pre-imaging. This is because of two reasons. First, different radionuclides are used for imaging and therapeutic purposes and there are currently no "universal chelators" that can bind all types of metallic radionuclides. When different chelators must be used for an imaging radionuclide versus a therapeutic radionuclide, the activity of one within the physiological environment is not sufficiently predictive of the activity of the second. Second, currently available chelators do not effectively shield radionuclides from the physiological environment. This means that radionuclides interact with the physiological environment following administration and en route to a site of interest. As a result, radionuclides with different charge states ($2+$, $3+$, $4+$) interact with the physiological environment differently, potentially affecting intended delivery.

Finally, there are significant challenges associated with the efficient manufacturing and use of ionizing radiation in therapeutic and imaging environments.

The present disclosure provides siderocalin (Scn)-metal chelator combinations that bind metallic radioisotopes used in nuclear medicine with high affinity and effectively shield the metallic radioisotopes from the physiological environment. The high affinity siderocalin-metal chelator combinations include a number of backbone arrangements with functional groups that coordinate with metals. The siderocalin-metal chelator combinations can be used to deliver radionuclides for imaging and therapeutic purposes. These disclosed chelating platforms provide numerous benefits.

First, like Skerra, the disclosed chelating platforms utilize Scn. However, the current disclosure teaches that the muteins described in Skerra, designed to increase binding to non-natural ligands (e.g., targeting ligands) have reduced chelating efficacy. Thus, Scn utilized in the currently disclosed Scn-metal chelator combinations do not include mutations that reduce chelating efficacy. If Scn mutations are used, the mutations maintain or increase, rather than decrease, Scn's chelating efficacy.

Second, the Scn-metal chelator combinations disclosed herein have high affinity, both between the Scn and metal chelator and between the metal chelator and radionuclide. The high affinity between each of these components reduces early release of radioactivity, reducing side effects associated with the use of nuclear medicine.

Third, in particular embodiments, the current disclosure provides a universal chelating platform that accommodates metallic radioisotopes used in nuclear medicine and effectively shields them from the physiological environment following administration. As is understood by one of ordinary skill in the art, effective shielding can be confirmed by thermodynamic and kinetic assays. By accommodating and effectively shielding metallic radioisotopes used in nuclear medicine, the Scn-metal chelator combinations (sometimes referred to as SCCs herein) can be used to administer a targeted radioactive imaging complex to ensure that the radioactive complex selectively reaches the physiological site of interest. Once selective delivery is confirmed with the imaging complex, a radioactive therapeutic complex can be administered, with confidence that the radioactive therapeutic complex will exhibit substantially the same delivery and release kinetics.

Many of the described benefits of the Scn-metal chelator combinations derive from use of the novel chelator and chelator combinations disclosed herein that include a number of backbone arrangements with functional groups that coordinate with metals. Finally, disclosed herein are chelator and SCC manufacturing processes.

Aspects of the disclosure are now described in more detail.

Lipocalins/Siderocalin. Lipocalins are extracellular ligand-binding proteins that are found in a variety of organisms from bacteria to humans. Lipocalins possess many different functions, such as the binding and transport of small hydrophobic molecules, nutrient transport, cell growth regulation, modulation of the immune response, inflammation, and prostaglandin synthesis. Lipocalins have a deep ligand-binding pocket, which allows for high-affinity ligand interactions. Ligands that bind lipocalin can become deeply buried within the protein, and can therefore be shielded from the physiological environment.

Siderocalin (Scn), also known as Lipocalin-2 or neutrophil gelatinase-associated lipocalin, is a member of the lipocalin family that binds siderophores, a type of small chelator, with very high affinity (in the sub-nanomolar range). Siderophores secreted by microbes can steal iron from host organisms by binding tightly to iron and delivering the iron to the microbe. Scn secreted by host organisms can prevent iron-pirating by microbes, by sequestering siderophores and preventing their delivery back to the microbe. Therefore, high affinity binding to chelators is a natural function of Scn.

Scn also has an exceptionally stable protein structure, and therefore is an ideal binding partner for fusion proteins, as the stability of the Scn domain can impart stability on the whole fusion protein. Additionally, Scn naturally contains a secretion signal, so Scn can be a useful fusion partner for of a variety of peptides, proteins, and protein domains, including when extracellular expression is desired. Further, Scn possesses a single N-linked glycosylation site, which is involved in correct processing in the ER before secretion. Another advantage is that human Scn can be used, reducing stimulation of immune responses against it in human diagnostic and/or therapeutic uses. Making minimal (e.g., 3 or less or 2 or less) mutations to the Scn can also minimize the likelihood of immune response stimulation. For all of these reasons, Scn was chosen as the chelator binding protein for the chelating platforms disclosed herein.

In particular embodiments, Scn refers to a natural Scn sequence that retains its natural specificity for its chelator binding partners, such as carboxymycobactin and enterochelin. Retaining natural specificity means that there is no statistically significant difference in binding affinity when assessed under comparable conditions. In particular embodiments, Scn particularly refers to the human ortholog of Scn (SWISS-PROT Data Bank Accession Number P80188), which has 178 amino acids and a molecular weight of 20,547 Da (FIG. 15; SEQ ID NO: 1, which is P80188 with the first 20 amino acids deleted). In particular embodiments, Scn can refer to the ortholog expressed by another species, such as the mouse ortholog (FIG. 15; SEQ ID NO: 7, which is SWISS-PROT Data Bank Accession Number P11672 with the first 20 amino acids deleted), or the rat ortholog (FIG. 15; SEQ ID NO: 8, which is SWISS-PROT Data Bank Accession Number P30152 with the first 20 amino acids deleted). For additional orthologs, see FIG. 15; SEQ ID NOs. 2-6 and 9-18) and Correnti & Strong, (2013) "Iron Sequestration in Immunity" In Metals in Cells, Encyclopedia of Inorganic and Bioinorganic Chemistry. (Culcotta & Scott, eds.) John Wiley & Sons, pp. 349-59.

In particular embodiments, Scn refers to an Scn sequence that can include mutations, so long as the mutations do not significantly affect Scn's natural specificity for its chelator binding partners, such as carboxymycobactin and enterochelin. Human Scn residues that are important for binding to siderophores include (referring to SEQ ID NO: 1): 52, 54, 68, 70, 79, 81, 100, 106, 123, 125, 132, 133, 134, 138, and 141. Holmes, et al., Structure 2005, 13, 29-41. In particular embodiments, Scns disclosed herein exclude mutations at one or more of residues: 52, 54, 68, 70, 79, 81, 100, 106, 123, 125, 132, 133, 134, 138, and 141 of SEQ ID NO: 1. In particular embodiments, Scns disclosed herein exclude mutations at 2 or more, 3 or more, 4 or more, 5 or more, 6 or more, 7 or more, 8 or more, 9 or more, 10 or more, 11 or more, 12 or more, 13 or more, 14 or more or 15 or more of residues: 52, 54, 68, 70, 79, 81, 100, 106, 123, 125, 132, 133, 134, 138, and 141 of SEQ ID NO: 1. In particular embodiments, Scns disclosed herein exclude mutations at residues: 52, 54, 68, 70, 79, 81, 100, 106, 123, 125, 132, 133, 134, 138, and 141 of SEQ ID NO: 1.

Figure 2:
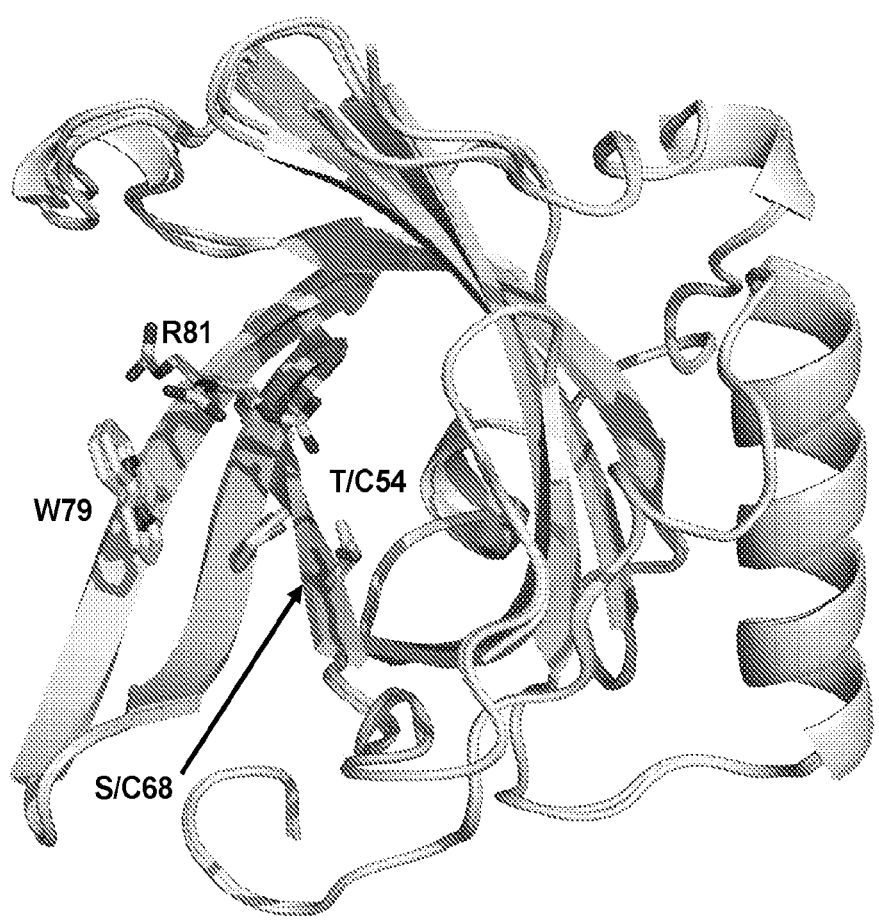
FIG. 2. A superposition of the structures of wild-type, human siderocalin and two mutants: T54C and S68C. Structures were determined by x-ray crystallography as described in the Crystallography section of the Materials and Methods. Siderocalin structures are shown as cartoon ribbons, highlighting the conservation of overall structure despite mutagenesis. The side-chains of four residues are highlighted in licorice-stick representations: T/C54, S/C68, W79, and R81.

In particular embodiments, Scns can include mutations that improve its ability to bind to chelators. For example, mutations at residues 54 and/or 68 can stabilize Scn interaction with chelators by providing a "chelator trap". In particular embodiments, chelator traps can be created by providing a cysteine at residues 54 and/or 68 to introduce a thiol moiety. FIG. 2. shows the superposition of the structures of wild-type, human Scn and two mutants: T54C and S68C. Scn structures are shown as cartoon ribbons, highlighting the conservation of overall structure despite mutagenesis. The side-chains of four residues are highlighted in licorice-stick representations: T/C54, S/C68, W79, and R81. W79 and R81 are the most mobile side-chains in the ligand binding site, and are observed in different rotamers in different structures. The side-chains at positions 54 and 68 show that replacing the wild-type residues with cysteine does not affect the local structure of the ligand binding site, conserving wild-type ligand specificity. The crystal structures of the mutants, protected deep in the ligand binding site, also show that these cysteines, protected deep in the ligand binding site, remain reduced, available for conjugation.

In particular embodiments, at least one of the amino acids of Scn may be substituted for a non-native amino acid to achieve a different benefit. For example, a C87S mutation in Scn can prevent dimerization and can yield pure monomeric fusion protein. Goetz, et al., Molecular Cell 2002, 10, 1033-43. In additional embodiments, mutations can be generated that enable interactions with non-native ligands, so long as the mutations do not reduce chelator binding affinity. FIG. 16 depicts Scn of SEQ ID NO: 1 altered to include: a T54C mutation (SEQ ID NO: 19); a S68C mutation (SEQ ID NO: 20); T54C and S68C mutations (SEQ ID NO: 21); a C87S mutation (SEQ ID NO: 22); a leader sequence, K125A and C87S mutations (SEQ ID NO: 23); a leader sequence, T54C, S68C, C87S, and K125A mutations (SEQ ID NO: 24); and a leader sequence, T54C and C87S mutations, a GSS linker, and a CD19 scFV (SEQ ID NO: 25). In particular embodiments, any combination of mutations depicted in FIG. 16 can be used. Additional potential alternations to Scn that can be used are described in the Section of this application related to Methods of Protein Expression.

Chelators. Chelators are molecules that can bind metals. Chelators can include organic molecules that covalently bond with a metal. As used herein, a covalent bond describes the sharing of one or more pairs of electrons between atoms. In some instances, chelators are agents that remove excess metal from an environment. Previous metal chelators that have been joined to proteins for the purpose of loading the chelator with a radioisotope are described in U.S. Pat. Nos. 4,454,106; 4,472,509; 4,831,175; 5,246,692; 5,250,285; 5,514,363; 5,837,218; 5,891,418; 5,922,302; 6,180,082; 6,183,721; and 6,203,775.

In particular embodiments, chelators can include a number of metal coordinating atoms that bond with a metal. The metal coordinating atoms can bond with metals having cations with a +1 charge. The metal coordinating atoms can also bond with metals having cations with a +2 charge. Additionally, the metal coordinating atoms can bond with metals having cations with a +3 charge. Further, the metal coordination atoms can bond with metals having cations with a +4 charge. The chelators described herein can, in some cases, include siderophores.

In particular embodiments, the metal coordinating atoms of the chelators described herein can be included in one or more functional groups of the chelators. In some examples, the metal coordinating atoms of the chelators can be included in one or more catecholate (CAM) groups. A CAM group can include at least a phenyl ring substituted by hydroxyl groups on adjacent carbon atoms. According to some illustrative embodiments, a CAM group can include:

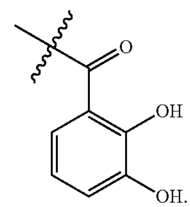 [SMILES: *C(=O)c1cccc(O)c1O]

In particular embodiments, the metal coordinating atoms of the chelators can be included in one or more hydroxymate (HA) groups. According to some embodiments, a HA group can include:

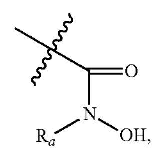

where $R_a$ can include H or an alkyl group including no greater than 5 carbon atoms. For example, $R_a$ can include a methyl group, an ethyl group, a propyl group, an isopropyl group, a butyl group, a sec-butyl group, an iso-butyl group, a tert-butyl group, a pentyl group, a tert-pentyl group, a neopentyl group, or an iso-pentyl group.

In particular embodiments, the metal coordinating atoms of the chelators can be included in one or more hydroxypyridinone (HOPO) groups. A HOPO group can include a pyridinone ring substituted by a hydroxyl group on the N atom. In some cases, a HOPO group can include a 1,2-HOPO group. According to some illustrative embodiments, a 1,2-HOPO group can include:

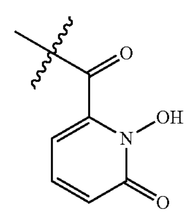 [SMILES: *C(=O)c1cccc(=O)n1O]

The metal coordinating atoms of the chelators can be included in combinations of two or more of one or more CAM groups, one or more HA groups, or one or more HOPO groups. In illustrative examples, the metal coordinating atoms of the chelators can be included in one or more CAM groups and one or more HA groups. In other illustrative examples, the metal coordinating atoms of the chelators can be included in one or more CAM groups and one or more HOPO groups. In additional illustrative examples, the metal coordinating atoms of the chelators can be included in one or more HA groups and one or more HOPO groups. In further illustrative examples, the metal coordinating atoms of the chelators can be included in one or more HA groups, one or more CAM groups, and one or more HOPO groups.

The chelators can include a number of functional groups having metal coordinating atoms with the functional groups being bonded to a linear scaffold or a branched scaffold. The functional groups and/or substituents described herein may be substituted or unsubstituted. Substituted functional groups and/or substituents can be substituted by one or more hydroxyl groups, one or more alkyl groups having no greater than 10 carbon atoms, one or more amine groups, one of more thiol groups, one or more ester groups, or combinations thereof.

The scaffold can include one or more amine groups. An amine group can include a nitrogen atom bonded to three substituents. In particular embodiments, an amine group can include a nitrogen atom bonded at least one carbon atom of substituent. In various embodiments, an amine group can include a nitrogen atom bonded to at least a first carbon atom of a first substituent and a second carbon atom of a second substituent. In further embodiments, an amine group can include a nitrogen atom bonded to a first carbon atom of a first substituent, a second carbon atom of a second substituent and a third carbon atom of a third substituent. In certain embodiments, an amine group can include a nitrogen atom bonded to one or more hydrogen atoms.

In some embodiments, the scaffold can include one or more amide groups. An amide group can include a nitrogen atom bonded to a carbonyl group and two additional substituents. In various examples, an amide group can include a nitrogen atom bonded to a carbonyl group and a carbon atom of a first additional substituent. In other examples, an amide group can include a nitrogen atom bonded to a carbonyl group and a first carbon atom of a first additional substituent and a second carbon atom of a second additional substituent.

In particular embodiments, the scaffold can include one or more amine groups and one or more amide groups. The scaffold can include one or more carbon-based chains bonded between amine groups, a carbon-based chain bonded between amide groups, or one or more carbon-based chains bonded between a combination of one or more amine groups and one or more amide groups. The carbon-based chains can include at least one carbon atom, at least 2 carbon atoms, at least 3 carbon atoms, at least 4 carbon atoms, or at least 5 carbon atoms. In addition, the carbon-based chains can include no greater than 10 carbon atoms, no greater than 9 carbon atoms, no greater than 8 carbon atoms, no greater than 7 carbon atoms, or no greater than 6 carbon atoms. In various embodiments, the carbon-based chains can include from 1 carbon atom to 10 carbon atoms, from 2 carbon atoms to 7 carbon atoms, or from 3 carbon atoms to 6 carbon atoms. In illustrative embodiments, the carbon-based chains can include alkane chains having carbon-carbon single bonds. In some cases, the carbon-based chains can include alkene chains having at least one carbon-carbon double bond. The carbon-based chains can be substituted or unsubstituted.

In particular embodiments, compositions that function as chelators for radionuclides can have the following structure, referred to herein as Structure I:

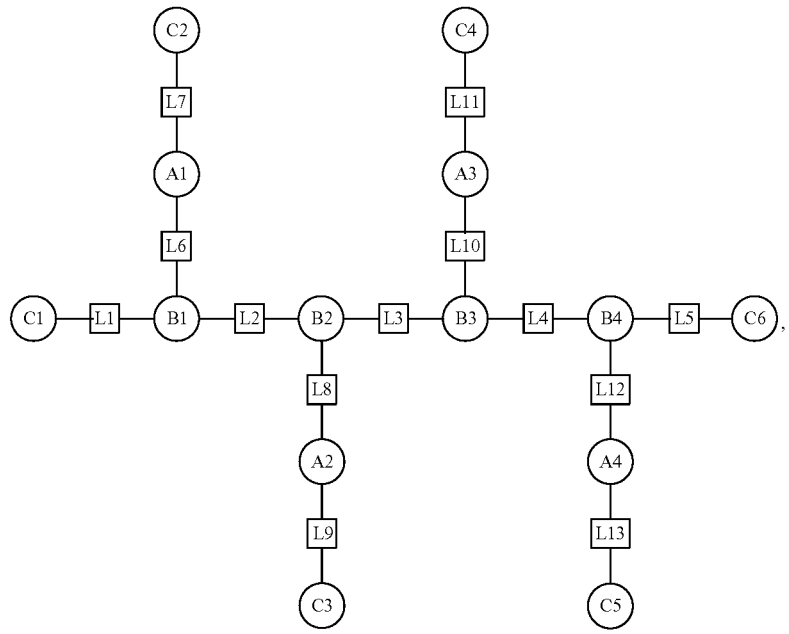

In some examples, A1, A2, A3, and A4 can, individually, include a CAM group, a HOPO group, or a HA group. Additionally, B1, B2, B3, and B4 can, individually, include an amide group or an amine group. Further, at least one of C1, C2, C3, C4, C5, or C6 can, individually, include SH, C(=O)OH, or $NH_2$. Also, in various examples, at least another one of C1, C2, C3, C4, C5, or C6 can be optional. In particular examples, at least one of L1, L2, L3, L4, L5, L6, L7, L8, L9, L10, L11, L12, or L13 can, individually, include H, an alkyl group having no greater than 10 carbon atoms, an alkylamino group having no greater than 10 carbon atoms and no greater than 2 nitrogen atoms; an alkyl ether group having no greater than 10 carbon atoms, a hydroxy ester group, or an alkyl ester group having no greater than 10 carbon atoms. In certain examples, at least one of L1, L5, L6, L7, L8, L9, L10, L11, L12, or L13 can be optional.

In illustrative examples, at least another one of L2, L3, or L4, can, individually, include an amine group or an amide group. In additional illustrative examples, L1, C1, L7, C2, L9, C3, L11, C4, and L13, C5 can be absent, L5 can include an alkyl group having no greater than 5 carbon atoms, and C6 can include SH, C(=O)OH, or $NH_2$. In further illustrative examples, L2, L3, L4, L6, L8, L10, and L12 can, individually, include an alkyl group having no greater than 5 carbon atoms. Also, A1 can include a CAM group or a 1,2-HOPO group; A2 can include a HA group, A3 can include a HA group, and A4 can include a CAM group, a 1,2-HOPO group, or a HA group. In other illustrative examples, at least one of L2, L3, or L4 includes an alkylamino group.

In various illustrative examples, B1, B2, and B3 can, individually, include an amide group and B4 can include an amino group, L2 and L3 can include an amino group, and L4 can include an alky group having no greater than 5 carbon atoms. Additionally, C1, C2, C3, C4, C5, L1, A1, A2, A3, L1, L6, L7, L8, L9, L10, L11, L12, and L13 can be absent; A4 can include a CAM group, a 1,2-HOPO group, or a HA group; and L5 can include an alkyl group having no greater than 5 carbon atoms.

In certain illustrative examples, B1, B2, and B3 can include an amide group and B4 can include an amide group; L2 and L3 can, individually, include an amino group; and L4 includes an alky group having no greater than 5 carbon atoms. Further, C1, C2, C3, C4, C5, A1, A2, A3, L1, L6, L7, L8, L9, L10, L11, and L13 can be absent, L12 can include an amino group, L5 can include an ether group having no greater than 10 carbon atoms, and A4 can include a CAM group, a 1,2-HOPO group, or a HA group.

In particular illustrative examples, C1, C2, C5, C6, L1, L2, L3, L4, L5, L7, L13, B2, and B4 can be absent; B1 and B3 can, individually, include an amide group; L6, L8, L10, and L12 can, individually, include an amino group, A1, A2, A3, and A4 can, individually, include a CAM group, a 1,2-HOPO group, or a HA group; and L9 and L11 can, individually, include an alkyl group having no greater than 5 carbon atoms.

In particular embodiments, compositions that function as chelators for radionuclides can have the following structure, referred to herein as Structure II:

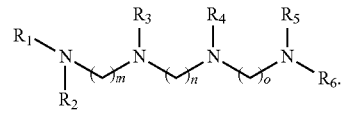

$R_1$, $R_2$, $R_3$, $R_4$, and $R_5$ can, individually, include H, an alkyl group having from 1 to 10 carbon atoms, a CAM group, a HA group, or a 1,2-HOPO group. $R_6$ can include H, an alkyl group having from 1 to 10 carbon atoms, or an alkyl group having from 1 to 10 carbon atoms and substituted by at least one of SH, $NH_2$, or C(=O)OH. m can be from 1 to 6; n can be from 1 to 6; and o can be from 1 to 6. In particular embodiments, at least one of $R_1$, $R_2$, $R_3$, $R_4$, or $R_5$ can, individually, include a CAM group, a HA group, or a 1,2-HOPO group. In various embodiments, Structure II can include a linear, spermine-based backbone.

In particular embodiments, compositions that function as chelators for radionuclides can have the following structure, referred to herein as Structure III:

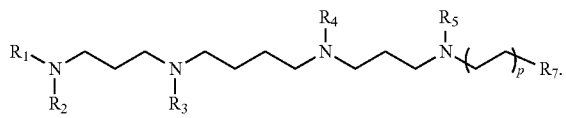

At least one of $R_1$, $R_3$, $R_4$, or $R_5$ can, individually, include a CAM group, a HA group, or a 1,2-HOPO group. Optionally, another one of $R_1$, $R_3$, $R_4$, or $R_5$ can, individually, include H, OH, or an alkyl group having from 1 to 10 carbon atoms. $R_2$ can include H, OH, or an alkyl group including from 1 to 5 carbon atoms. p can be from 0 to 4. $R_7$ can include SH, C(=O)OH, or $NH_2$. In illustrative embodiments, $R_1$ can include a CAM group or a 1,2-HOPO group, $R_3$ and $R_4$ can, individually, include a HA group, and $R_5$ can include a CAM group, a 1,2-HOPO group, or a HA group.

In particular embodiments, compositions that function as chelators for radionuclides can have the following structure, referred to herein as Structure IV:

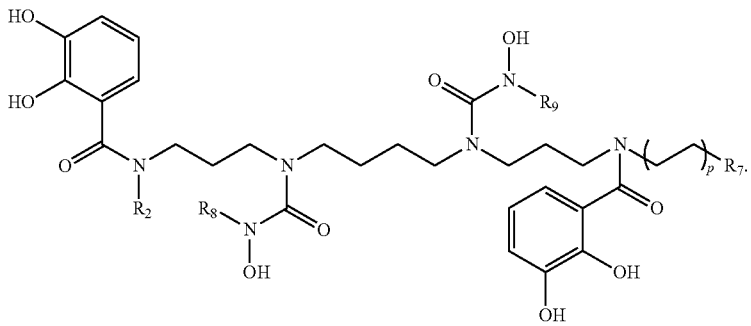

$R_7$ can include SH, $NH_2$, or C(=O)OH. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure V:

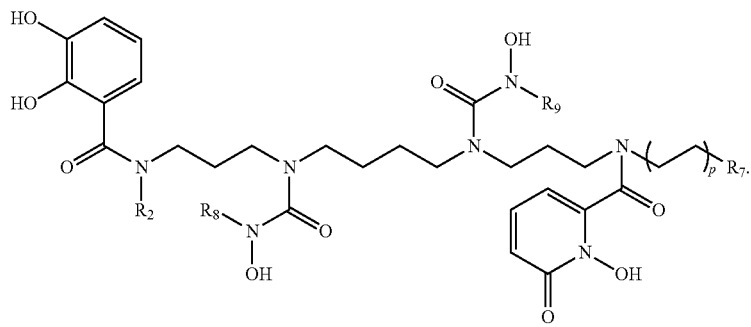

15

$R_7$ can include SH, $NH_2$, or C(=O)OH. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure VI:

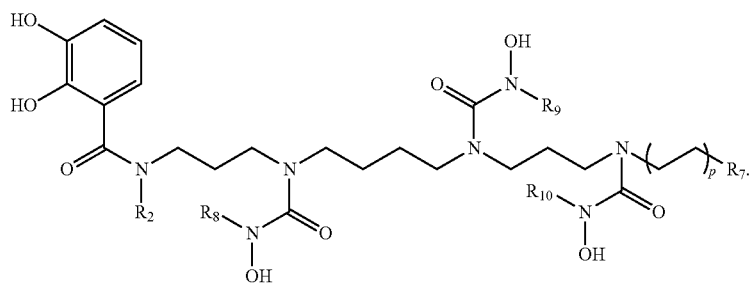

40

$R_7$ can include SH, $NH_2$, or C(=O)OH. $R_2$, $R_8$, $R_9$, and $R_{10}$ can, individually, include H, OH, or an alkyl group including from 1 to 5 carbon atoms. p can be from 0 to 4.

In particular embodiments, compositions that function as chelators for radionuclides can have the following structure, referred to herein as Structure VII:

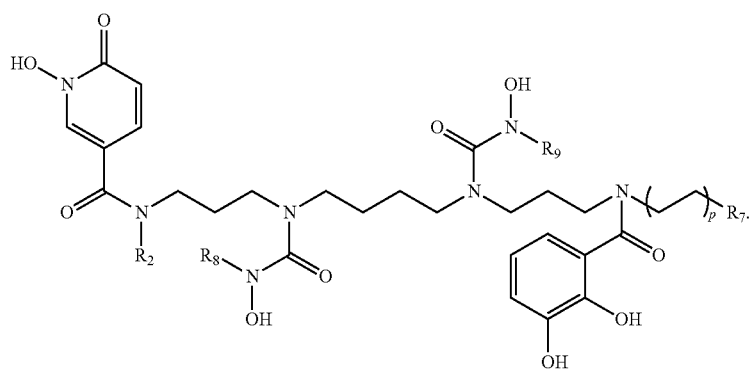

$R_7$ can include SH, $NH_2$, or C(=O)OH. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure VIII:

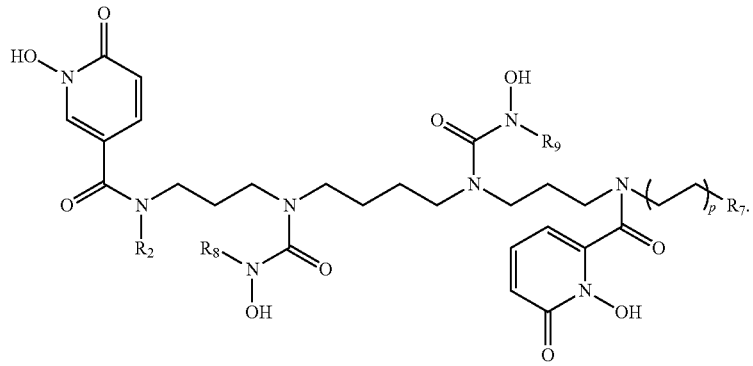

$R_7$ can include SH, $NH_2$, or C(=O)OH. $R_2$, $R_8$, and $R_9$ can, individually, include H, OH, or an alkyl group including from 1 to 5 carbon atoms. p can be from 0 to 4.

In particular embodiments, compositions that function as chelators for radionuclides can have the following structure, referred to herein as Structure IX:

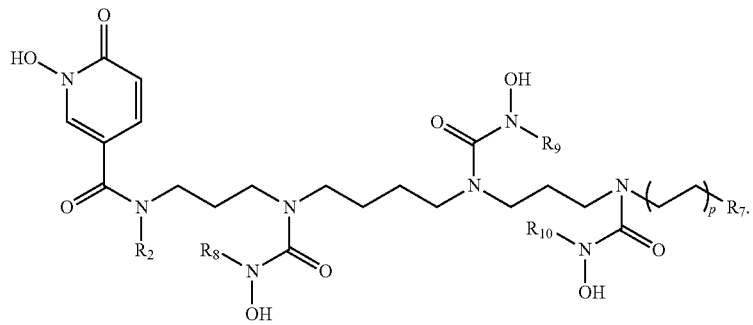

$R_7$ can include SH, $NH_2$, or C(=O)OH. $R_2$, $R_8$, $R_9$, and $R_{10}$ can, individually, include H, OH, or an alkyl group including from 1 to 5 carbon atoms. p can be from 0 to 4.

In particular embodiments, compositions that function as chelators for radionuclides can have the following structure, referred to herein as Structure X:

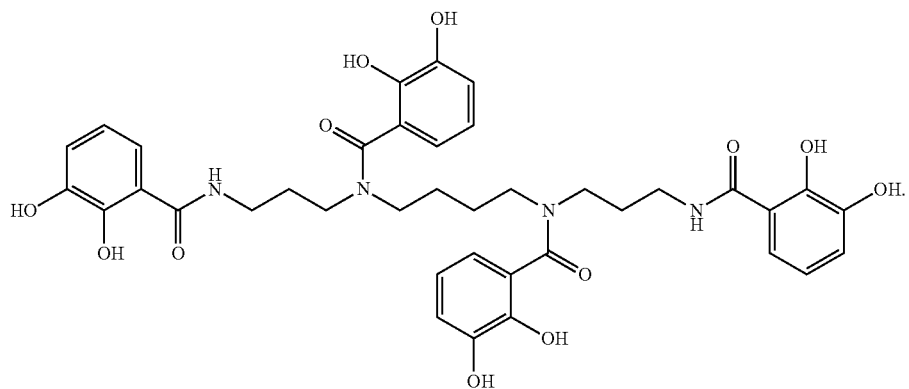 [SMILES: O=C(NCCCN(CCCCN(CCCNC(=O)c1cccc(O)c1O)C(=O)c1cccc(O)c1O)C(=O)c1cccc(O)c1O)c1cccc(O)c1O]

In particular embodiments, compositions that function as chelators for radionuclides can have the following structure, referred to herein as Structure XI:

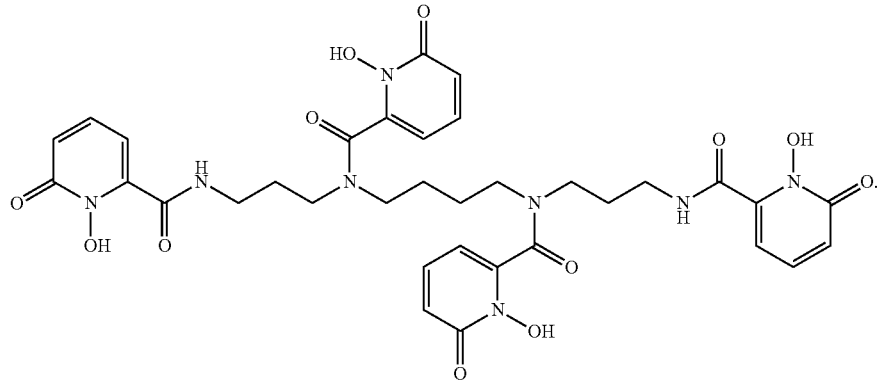 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

In particular embodiments, compositions can have a branched backbone rather than the linear, spermine-based backbone of Structures III-XI. In particular embodiments, compositions that function as chelators for radionuclides can have the following structure, referred to herein as Structure XII:

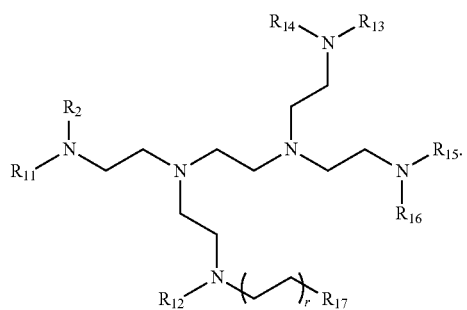

At least one of $R_{11}$, $R_{12}$, $R_{13}$, or $R_{15}$, can, individually, include a CAM group, a HA group, or a 1,2-HOPO group. Optionally, at least another one of $R_{11}$, $R_{12}$, $R_{13}$, or $R_{15}$ can, individually, include H, OH, or an alkyl group having from 1 to 10 carbon atoms. $R_{17}$ can include SH, $NH_2$, or C(=O)OH. r can be from 0 to 6. $R_2$, $R_{14}$, and $R_{16}$ can, individually, include H, OH, or an alkyl group having from 1 to 10 carbon atoms. In illustrative embodiments, $R_{11}$ can include a CAM group or a 1,2-HOPO group, $R_{12}$ and $R_{15}$ can, individually, include a HA group, and $R_{13}$ can include a CAM group, a 1,2-HOPO group, or a HA group.

In particular embodiments, compositions that function as chelators for radionuclides can have the following structure, referred to herein as Structure XIII:

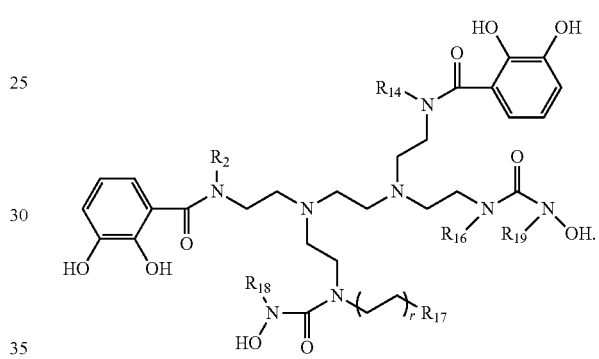

$R_2$, $R_{14}$, $R_{16}$, $R_{18}$, and $R_{19}$ can, individually, include H, OH, or an alkyl group having from 1 to 10 carbon atoms. $R_{17}$ can include SH, $NH_2$, or C(=O)OH. r can be from 0 to 4.

In particular embodiments, compositions that function as chelators for radionuclides can have the following structure, referred to herein as Structure XIV:

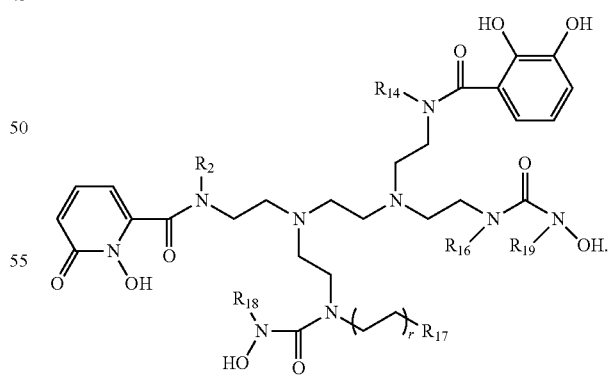

$R_2$, $R_{14}$, $R_{16}$, $R_{18}$, and $R_{19}$ can, individually, include H, OH, or an alkyl group having from 1 to 10 carbon atoms. $R_{17}$ can include SH, $NH_2$, or C(=O)OH. r can be from 0 to 4.

In particular embodiments, compositions that function as chelators for radionuclides can have the following structure, referred to herein as Structure XV:

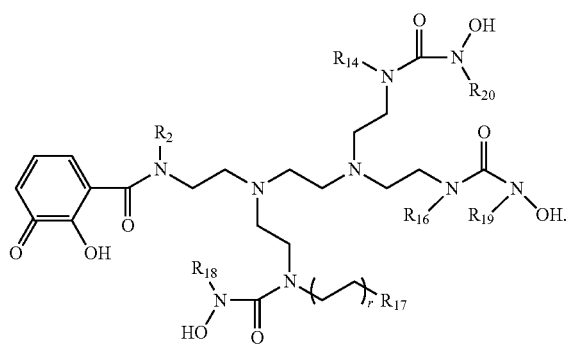

$R_2$, $R_{14}$, $R_{16}$, $R_{18}$, $R_{19}$, and $R_{20}$ can, individually, include H, OH, or an alkyl group having from 1 to 10 carbon atoms. $R_{17}$ can include SH, NH$_2$, or C(=O)OH. r can be from 0 to 4.

In particular embodiments, compositions that function as chelators for radionuclides can have the following structure, referred to herein as Structure XVI:

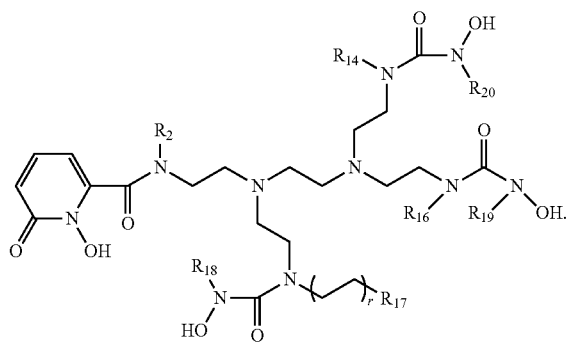

$R_2$, $R_{14}$, $R_{16}$, $R_{18}$, $R_{19}$, and $R_{20}$ can, individually, include H, OH, or an alkyl group having from 1 to 10 carbon atoms. $R_{17}$ can include SH, NH$_2$, or C(=O)OH. r can be from 0 to 4.

In particular embodiments, compositions that function as chelators for radionuclides can have the following structure, referred to herein as Structure XVII:

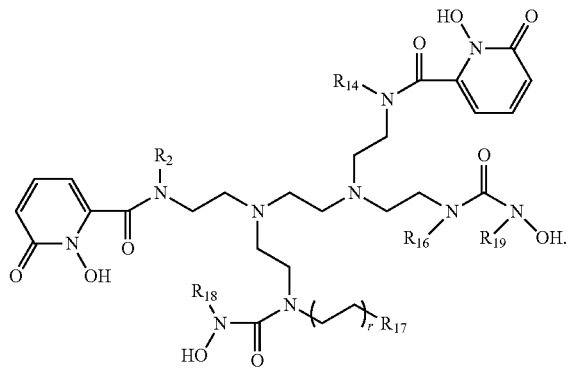

$R_2$, $R_{14}$, $R_{16}$, $R_{18}$, and $R_{19}$ can, individually, include H, OH, or an alkyl group having from 1 to 10 carbon atoms. $R_{17}$ can include SH, NH$_2$, or C(=O)OH. r can be from 0 to 4.

In particular embodiments, compositions that function as chelators for radionuclides can have the following structure, referred to herein as Structure XVIII:

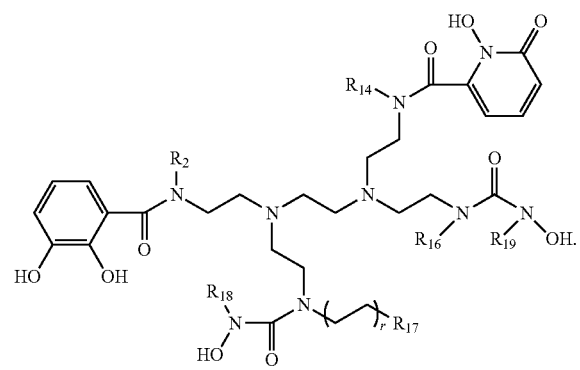

$R_2$, $R_{14}$, $R_{16}$, $R_{18}$, and $R_{19}$ can include H, OH, or an alkyl group having from 1 to 10 carbon atoms. $R_{17}$ can, individually, include SH, NH$_2$, or C(=O)OH. r can be from 0 to 4.

In particular embodiments, compositions can have a backbone that includes a number of amide groups and a number of amine groups. In some embodiments, the backbone of compositions that function as chelators for radionuclides can be based on Desferrioxamine B. In particular embodiments, compositions that function as chelators can have the following structure, referred to herein as Structure XIX:

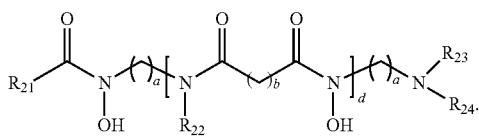

$R_{21}$ and $R_{22}$ can include H, OH, or an alkyl group having from 1 to 10 carbon atoms. $R_{23}$ can include H, OH, an alkyl group having from 1 to 10 carbon atoms, or (CH$_2$)$_e$R$_a$, where R$_a$ is SH, C(=O)OH, or NH$_2$ and e is from 1 to 10. $R_{24}$ can include a substituent that includes a CAM group, a 1,2-HOPO group, or a HA group. Optionally, $R_{24}$ can include SH, C(=O)OH, or NH$_2$. a, b, and c can include from 1 to 10 and d can include from 1 to 4.

In particular embodiments, compositions that function as chelators for radionuclides can have the following structure, referred to herein as Structure XX:

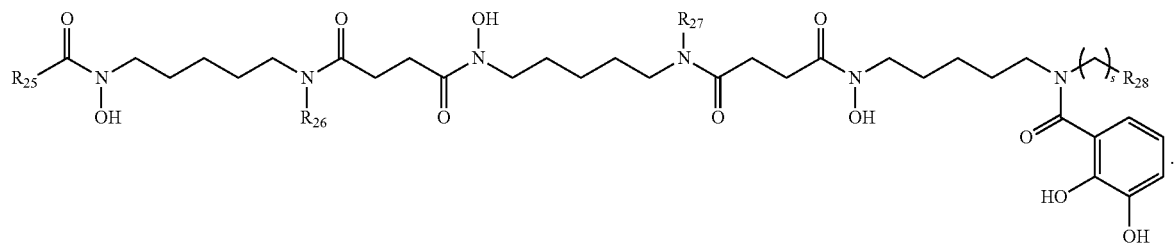

$R_{25}$, $R_{26}$, and $R_{27}$ can, individually, include H, OH, or an alkyl group having from 1 to 10 carbon atoms. $R_{28}$ can include H, an alkyl group having from 1 to 5 carbon atoms, SH, $NH_2$, or $C(=O)OH$. s can be from 0 to 4.

In particular embodiments, compositions that function as chelators for radionuclides can have the following structure, referred to herein as Structure XXI:

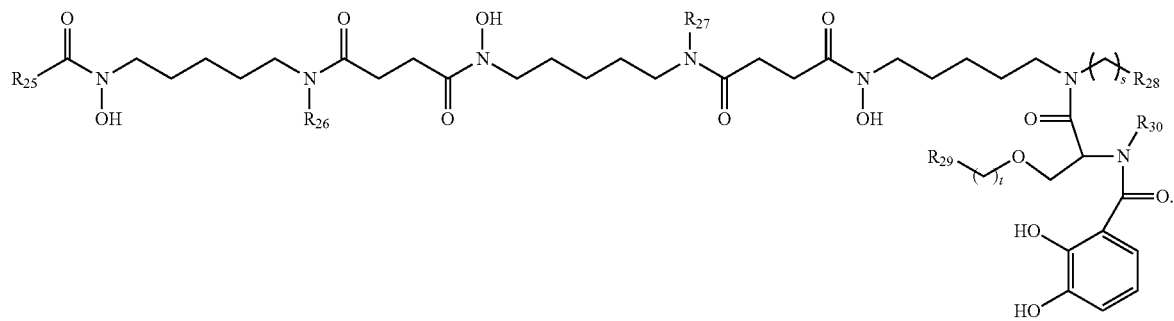

$R_{25}$, $R_{26}$, $R_{27}$, and $R_{30}$ can, individually, include H, OH, or an alkyl group having from 1 to 10 carbon atoms. $R_{28}$ and $R_{29}$ can, individually, include H, an alkyl group having from 1 to 5 carbon atoms, SH, $NH_2$, or $C(=O)OH$. s can be from 0 to 4. t can be from 0 to 4.

In particular embodiments, compositions that function as chelators for radionuclides can have the following structure, referred to herein as Structure XXII:

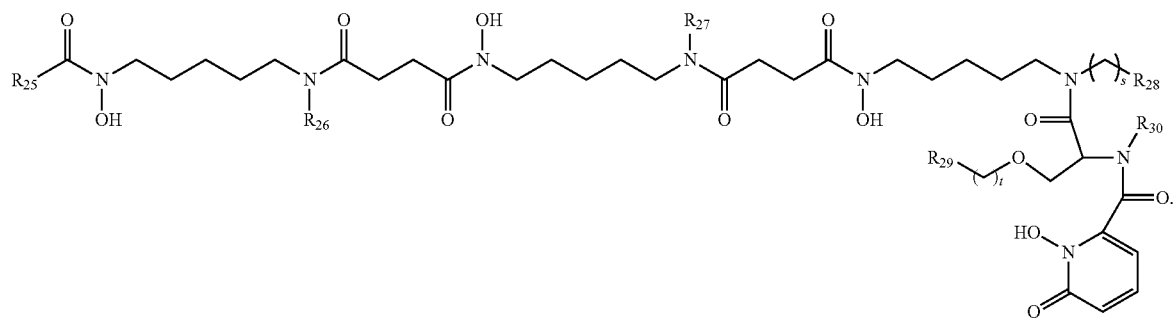

$R_{25}$, $R_{26}$, $R_{27}$, and $R_{30}$ can, individually, include H, OH, or an alkyl group having from 1 to 10 carbon atoms. $R_{28}$ and $R_{29}$ can, individually, include H, an alkyl group having from 1 to 5 carbon atoms, SH, $NH_2$, or $C(=O)OH$. s can be from 0 to 4. t can be from 0 to 4.

In particular embodiments, compositions that function as chelators for radionuclides can have the following structure, referred to herein as Structure XXIII:

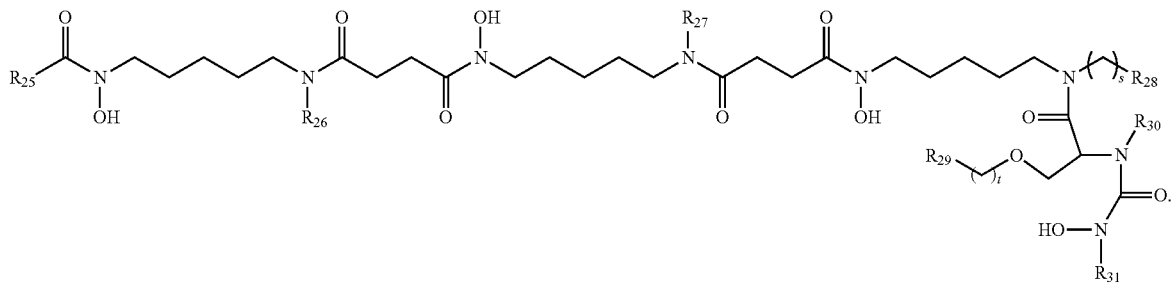

$R_{25}$, $R_{26}$, $R_{27}$, $R_{30}$, and $R_{31}$ can, individually, include H, OH, or an alkyl group having from 1 to 10 carbon atoms. $R_{28}$ and $R_{29}$ can, individually, include H, an alkyl group having from 1 to 5 carbon atoms, SH, $NH_2$, or C(=O)OH. s can be from 0 to 4. t can be from 0 to 4.

In particular embodiments, compositions that function as chelators for radionuclides can have the following structure, referred to herein as Structure XXIV:

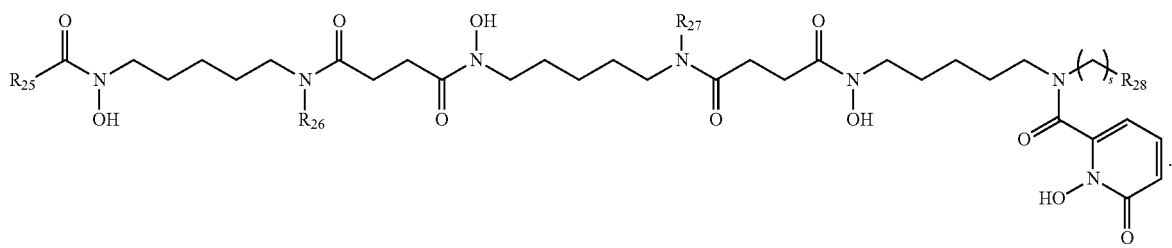

$R_{25}$, $R_{26}$, and $R_{27}$ can, individually, include H, OH, or an alkyl group having from 1 to 10 carbon atoms. $R_{28}$ can include H, an alkyl group having from 1 to 5 carbon atoms, SH, $NH_2$, or C(=O)OH. s can be from 0 to 4.

In particular embodiments, compositions that function as chelators for radionuclides can have the following structure, referred to herein as Structure XXV:

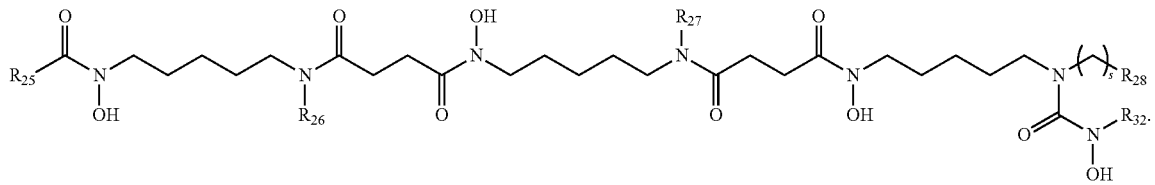

$R_{25}$, $R_{26}$, $R_{27}$, and $R_{32}$ can, individually, include H, OH, or an alkyl group having from 1 to 10 carbon atoms. $R_{28}$ can include H, an alkyl group having from 1 to 5 carbon atoms, SH, $NH_2$, or C(=O)OH. s can be from 0 to 4.

In particular embodiments, compositions can have an amide-based backbone. In particular embodiments, compositions that function as chelators can have the following structure, referred to herein as Structure XXVI:

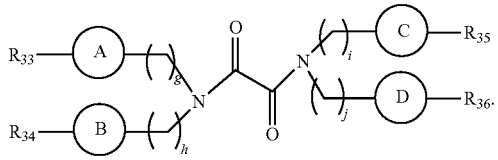

A, B, C, and D can, individually, include one or more amide groups, one or more amine groups, or an alkyl group having from 1 to 10 carbon atoms. $R_{33}$, $R_{34}$, $R_{35}$, and $R_{36}$ can, individually, include a CAM group, a 1,2-HOPO group, or a HA group. g, h, i, and j can, individually, be from 1 to 10.

In particular embodiments, compositions that function as chelators for radionuclides can have the following structure, referred to herein as Structure XXVII:

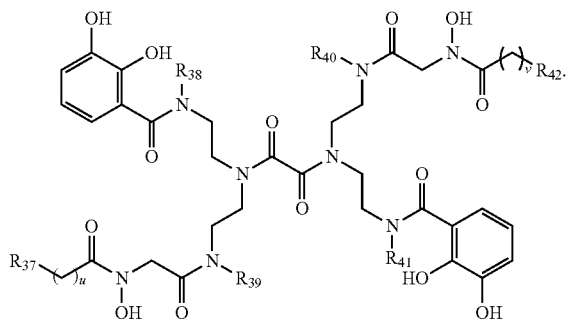

$R_{37}$ and $R_{42}$ can, individually, include H, an alkyl group having from 1 to 5 carbon atoms, SH, C(=O)OH, or $NH_2$. $R_{38}$, $R_{39}$, $R_{40}$, and $R_{41}$ can, individually, include H, OH, or an alkyl group having from 1 to 5 carbon atoms. u and v can, individually, be from 0 to 5.

In particular embodiments, compositions that function as chelators for radionuclides can have the following structure, referred to herein as Structure XXVIII:

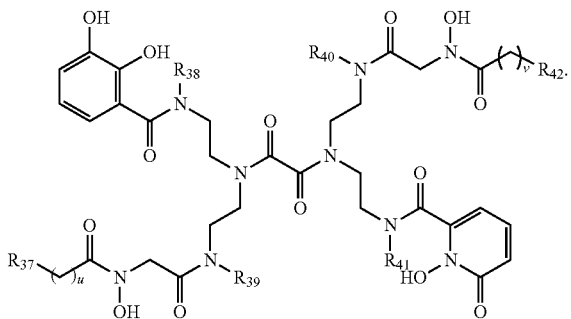

$R_{37}$ and $R_{42}$ can, individually, include H, an alkyl group having from 1 to 5 carbon atoms, SH, C(=O)OH, or $NH_2$. $R_{38}$, $R_{39}$, $R_{40}$, and $R_{41}$ can, individually, include H, OH, or an alkyl group having from 1 to 5 carbon atoms. u and v can, individually, be from 0 to 5.

In particular embodiments, compositions that function as chelators for radionuclides can have the following structure, referred to herein as Structure XXIX:

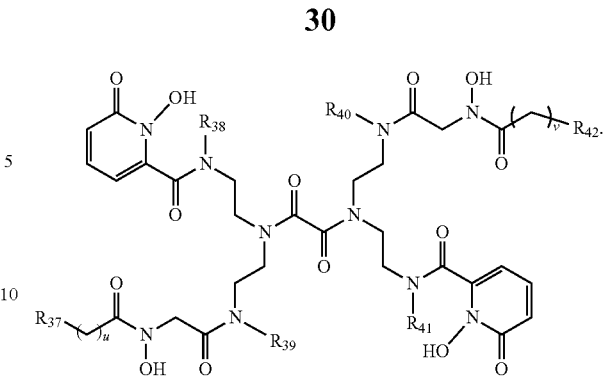

$R_{37}$ and $R_{42}$ can, individually, include H, an alkyl group having from 1 to 5 carbon atoms, SH, C(=O)OH, or $NH_2$. $R_{38}$, $R_{39}$, $R_{40}$, and $R_{41}$ can, individually, include H, OH, or an alkyl group having from 1 to 5 carbon atoms. u and v can, individually, be from 0 to 5.

The chelators can bind to a protein. In particular embodiments, the chelators can bind to siderocalin. In some embodiments, the chelators can bind to a dye. For example, the chelators can bind to a fluorophore. Additionally, the chelators can bind to both a protein and a dye. In various embodiments, the chelators can bind to a metal to form a chelator-metal complex that can also bind to siderocalin. The metal can include a radionuclide.

The chelators and/or the chelator-metal complex can have an equilibrium dissociation constant with siderocalin of no greater than 100 nanomolar (nM), no greater than 90 nM, no greater than 80 nM, no greater than 70 nM, no greater than 60 nM, no greater than 50 nM, no greater than 45 nM, no greater than 40 nM, no greater than 35 nM, no greater than 30 nM, no greater than 25 nM, no greater than 20 nM, or no greater than 15 nM. In addition, the chelators can have an equilibrium dissociation constant with siderocalin of at least 0.1 nM, at least 0.5 nM, at least 0.8 nM, at least 1 nM, at least 1.5 nM, at least 2 nM, at least 3 nM, at least 5 nM, at least 8 nM, at least 10 nM, or at least 12 nM. It will be appreciated that the equilibrium dissociation constant between a chelator and siderocalin can be within a range between any of the values noted above. In illustrative examples, the equilibrium dissociation constant between a chelator and siderocalin can be from 0.1 nM to 50 nM. In other illustrative examples, the equilibrium dissociation constant between a chelator and siderocalin can be from 1 nM to 40 nM. In additional illustrative examples, the equilibrium dissociation constant between a chelator and siderocalin can be from 0.8 nM to 10 nM. In further illustrative examples, the equilibrium dissociation constant between a chelator and siderocalin can be from 0.5 nM to 5 nM.

In particular embodiments, a composition E can be bound to a dye, a protein, or both a dye and a protein. Additionally, the composition E can be bound to one or more CAM groups, one or more 1,2-HOPO groups, one or more HA groups, or a combination thereof. In some embodiments, the composition E can be bound to the one or more CAM groups, the one or more 1,2-HOPO groups, or the one or more HA groups through an amide linkage. In particular embodiments, the composition E can include a number of carbon atoms, a number of nitrogen atoms, and a number of oxygen atoms. In illustrative embodiments, the composition E can include from 4 to 40 carbon atoms, from 1 to 20 nitrogen atoms, and from 1 to 15 oxygen atoms.

In various embodiments, the composition E can include from 1 to 20 carbon atoms, from 1 to 8 nitrogen atoms, and from 1 to 5 oxygen atoms. In some illustrative examples, a composition according to embodiments herein can include the following structure, referred to herein as Structure XXXI:

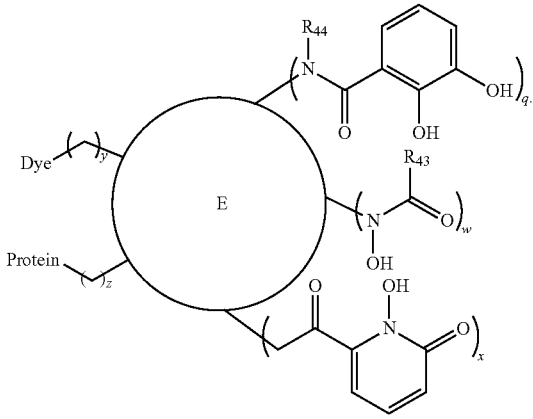

$R_{43}$ and $R_{44}$ can, individually, include H or an alkyl group from 1 to 5 carbon atoms. q can be from 0 to 4, w can be from 0 to 4, and x can be from 0 to 4. In some embodiments, at least one of q, w, or x is 1. Additionally, y and z can, individually, be from 0 to 4. In various embodiments, the dye and/or the protein can be bound to E via an SH group, an amide group, or a carboxyl group. In particular embodiments, one or more groups included in the structures described herein can bind to a protein and/or a dye. In illustrative examples, $R_6$, $R_7$, $R_{17}$, $R_{23}$, $R_{28}$, $R_{29}$, $R_{37}$, $R_{42}$, or combinations thereof, can, individually, bind to a protein and/or a dye.

In particular embodiments, the composition E can be bound to one or more amino acids of the protein. For example, the composition E can be bound to one or more lysine residues of siderocalin, such as K125 and/or K134. In other examples, the composition E can be bound to one or more amino acids of the protein that have been modified. To illustrate, siderocalin can be modified such that T54 and S68 are modified to cysteine residues. In these situations, the composition E can be bound to at least one of the modified $Scn^{T54C}$ or $Scn^{S68C}$ mutations.

Radionuclides. The Scn-chelator combinations (SCCs) disclosed herein are charged with radionuclides for use in nuclear medicine. Radionuclides that are chemically compatible with the SCCs should be chosen. Chemically compatible means that the radionuclide, in its elemental form or ionic form should not be so reactive that it changes the structure or function of any component of SCCs in a way that impairs achievement of an intended purpose.

Criteria for choosing radionuclides for a particular use in nuclear medicine can include the type and energy of radioactive decay product yielded by the radioisotope; the half-life of decay; chemical properties of the atom or ion; and the biological and/or toxicological properties of the atom or ion.

The decay product(s) yielded by the decay of a radionuclide (also referred to as a radioisotope) should be capable of interacting with cells in such a way as to inhibit or interfere with biological processes necessary for cellular replication, or that cause the cell to undergo apoptosis. In particular embodiments, the decay product(s) should be of sufficiently high energy, and sufficiently low mass such that they, whether particles or photons, reach and penetrate the nuclei of unwanted cells. Usually, the energy is not so high that the decay product(s) reach tissues far away from unwanted cells, or reach persons in close proximity to a patient. However, there may be circumstances wherein high energy and highly penetrative decay products are desirable. In particular embodiments, particularly useful radionuclides are those that decay with the emission of alpha particles, beta particles, gamma rays, positrons, x-rays, or Auger electrons. In particular embodiments, particularly useful radionuclides decay with the emission of alpha particles.

Radionuclides with different half-lives can be chosen based on the length of time desirable for irradiation of unwanted cells. Usually, a half-life of decay is not chosen if it is too short and thus, not sufficiently effective to arrest the growth of unwanted cells. Likewise, a half-life of decay that is too long is not chosen, thus avoiding the persistence of radiation at a high level after such time that unwanted cells are substantially or completely growth inhibited. In this manner, deleterious side effects of radiation are minimized. In particular embodiments, isotopes that decay with half-lives of 3 hours to 300 days are selected. Such isotopes can decay to negligible levels in 1 day to 4 years.

Examples of radioisotopes useful in nuclear medicine include $^{225}Ac$, $^{226}Ac$, $^{228}Ac$, $^{105}Ag$, $^{106}mAg$, $^{110}mAg$, $^{111}Ag$, $^{112}Ag$, $^{113}Ag$, $^{239}Am$, $^{240}Am$, $^{242}Am$, $^{244}Am$, $^{37}Ar$, $^{71}As$, $^{72}As$, $^{73}As$, $^{74}As$, $^{76}As$, $^{77}As$, $^{209}At$, $^{210}At$, $^{191}Au$, $^{192}Au$, $^{193}Au$, $^{194}Au$, $^{195}Au$, $^{196}Au$, $^{196m2}Au$, $^{198}Au$, $^{198}mAu$, $^{199}Au$, $^{200}mAu$, $^{128}Ba$, $^{131}Ba$, $^{133}mBa$, $^{135}mBa$, $^{140}Ba$, $^{7}Be$, $^{203}Bi$, $^{204}Bi$, $^{205}Bi$, $^{206}Bi$, $^{210}Bi$, $^{212}Bi$, $^{243}Bk$, $^{244}Bk$, $^{245}Bk$, $^{246}Bk$, $^{248}mBk$, $^{250}Bk$, $^{76}Br$, $^{77}Br$, $^{80}mBr$, $^{82}Br$, $^{11}C$, $^{14}C$, $^{45}Ca$, $^{47}Ca$, $^{107}Cd$, $^{115}Cd$, $^{115}mCd$, $^{117}mCd$, $^{132}Ce$, $^{133}mCe$, $^{134}Ce$, $^{135}Ce$, $^{137}Ce$, $^{137}mCe$, $^{139}Ce$, $^{141}Ce$, $^{143}Ce$, $^{144}Ce$, $^{246}Cf$, $^{247}Cf$, $^{253}Cf$, $^{254}Cf$, $^{240}Cm$, $^{241}Cm$, $^{242}Cm$, $^{252}Cm$, $^{55}Co$, $^{56}Co$, $^{57}Co$, $^{58}Co$, $^{58}mCo$, $^{60}Co$, $^{48}Cr$, $^{51}Cr$, $^{127}Cs$, $^{129}Cs$, $^{131}Cs$, $^{132}Cs$, $^{136}Cs$, $^{137}Cs$, $^{61}Cu$, $^{62}Cu$, $^{64}Cu$, $^{67}Cu$, $^{153}Dy$, $^{155}Dy$, $^{157}Dy$, $^{159}Dy$, $^{165}Dy$, $^{166}Dy$, $^{160}Er$, $^{161}Er$, $^{165}Er$, $^{169}Er$, $^{171}Er$, $^{172}Er$, $^{250}Es$, $^{251}Es$, $^{253}Es$, $^{254}Es$, $^{254}mEs$, $^{255}Es$, $^{256}mEs$, $^{145}Eu$, $^{146}Eu$, $^{147}Eu$, $^{148}Eu$, $^{149}Eu$, $^{150}mEu$, $^{152}mEu$, $^{156}Eu$, $^{157}Eu$, $^{52}Fe$, $^{59}Fe$, $^{251}Fm$, $^{252}Fm$, $^{253}Fm$, $^{254}Fm$, $^{255}Fm$, $^{257}Fm$, $^{66}Ga$, $^{67}Ga$, $^{68}Ga$, $^{72}Ga$, $^{73}Ga$, $^{146}Gd$, $^{147}Gd$, $^{149}Gd$, $^{151}Gd$, $^{153}Gd$, $^{159}Gd$, $^{68}Ge$, $^{69}Ge$, $^{71}Ge$, $^{77}Ge$, $^{170}Hf$, $^{171}Hf$, $^{173}Hf$, $^{175}Hf$, $^{179m2}Hf$, $^{180}mHf$, $^{181}Hf$, $^{184}Hf$, $^{192}Hg$, $^{193}Hg$, $^{193}mHg$, $^{195}Hg$, $^{195}mHg$, $^{197}Hg$, $^{197}mHg$, $^{203}Hg$, $^{160}mHo$, $^{166}Ho$, $^{167}Ho$, $^{123}I$, $^{124}I$, $^{126}I$, $^{130}I$, $^{132}I$, $^{133}I$, $^{135}I$, $^{109}In$, $^{110}In$, $^{111}In$, $^{114}mIn$, $^{115}mIn$, $^{184}Ir$, $^{185}Ir$, $^{186}Ir$, $^{187}Ir$, $^{188}Ir$, $^{189}Ir$, $^{190}Ir$, $^{190m2}Ir$, $^{192}Ir$, $^{193}mIr$, $^{194}Ir$, $^{194m2}Ir$, $^{195}mIr$, $^{42}K$, $^{43}K$, $^{76}Kr$, $^{79}Kr$, $^{81}mKr$, $^{85}mKr$, $^{132}La$, $^{133}La$, $^{135}La$, $^{140}La$, $^{141}La$, $^{262}Lr$, $^{169}Lu$, $^{170}Lu$, $^{171}Lu$, $^{172}Lu$, $^{174}mLu$, $^{176}mLu$, $^{177}Lu$, $^{177}mLu$, $^{179}Lu$, $^{257}Md$, $^{258}Md$, $^{260}Md$, $^{28}Mg$, $^{52}Mn$, $^{90}Mo$, $^{93}mMo$, $^{99}Mo$, $^{13}N$, $^{24}Na$, $^{90}Nb$, $^{91}mNb$, $^{92}mNb$, $^{95}Nb$, $^{95}mNb$, $^{96}Nb$, $^{138}Nd$, $^{139}mNd$, $^{140}Nd$, $^{147}Nd$, $^{56}Ni$, $^{57}Ni$, $^{66}Ni$, $^{234}Np$, $^{236}mNp$, $^{238}Np$, $^{239}Np$, $^{15}O$, $^{182}Os$, $^{183}Os$, $^{183}mOs$, $^{185}Os$, $^{189}mOs$, $^{191}Os$, $^{191}mOs$, $^{193}Os$, $^{32}P$, $^{33}P$, $^{228}Pa$, $^{229}Pa$, $^{230}Pa$, $^{232}Pa$, $^{233}Pa$, $^{234}Pa$, $^{200}Pb$, $^{201}Pb$, $^{202}mPb$, $^{203}Pb$, $^{209}Pb$, $^{212}Pb$, $^{100}Pd$, $^{101}Pd$, $^{103}Pd$, $^{109}Pd$, $^{111}mPd$, $^{112}Pd$, $^{143}Pm$, $^{148}Pm$, $^{148}mPm$, $^{149}Pm$, $^{151}Pm$, $^{204}Po$, $^{206}Po$, $^{207}Po$, $^{210}Po$, $^{139}Pr$, $^{142}Pr$, $^{143}Pr$, $^{145}Pr$, $^{188}Pt$, $^{189}Pt$, $^{191}Pt$, $^{193}mPt$, $^{195}mPt$, $^{197}Pt$, $^{200}Pt$, $^{202}Pt$, $^{234}Pu$, $^{237}Pu$, $^{243}Pu$, $^{245}Pu$, $^{246}Pu$, $^{247}Pu$, $^{223}Ra$, $^{224}Ra$, $^{225}Ra$, $^{81}Rb$, $^{82}Rb$, $^{82}mRb$, $^{83}Rb$, $^{84}Rb$, $^{86}Rb$, $^{181}Re$, $^{182}Re$, $^{182}mRe$, $^{183}Re$, $^{184}Re$, $^{184}mRe$, $^{186}Re$, $^{188}Re$, $^{189}Re$, $^{190}mRe$, $^{99}Rh$, $^{99}mRh$, $^{100}Rh$, $^{101}mRh$, $^{102}Rh$, $^{103}mRh$, $^{105}Rh$, $^{211}Rn$, $^{222}Rn$, $^{97}Ru$, $^{103}Ru$, $^{105}Ru$, $^{35}S$, $^{118}mSb$, $^{119}Sb$, $^{120}Sb$, $^{120}mSb$, $^{122}Sb$, $^{124}Sb$, $^{126}Sb$, $^{127}Sb$, $^{128}Sb$, $^{129}Sb$, $^{43}Sc$, $^{44}Sc$, $^{44}mSc$, $^{46}Sc$, $^{47}Sc$, $^{48}Sc$, $^{72}Se$, $^{73}Se$, $^{75}Se$, $^{153}Sm$, $^{156}Sm$, $^{110}Sn$, $^{113}Sn$, $^{117}mSn$, $^{119}mSn$, $^{121}Sn$, $^{123}Sn$, $^{125}Sn$, $^{82}Sr$, $^{83}Sr$, $^{85}Sr$, $^{89}Sr$, $^{91}Sr$, $^{173}Ta$, $^{175}Ta$, $^{176}Ta$, $^{177}Ta$, $^{180}Ta$, $^{182}Ta$, $^{183}Ta$, $^{184}$Ta, $^{149}$Tb, $^{150}$Tb, $^{151}$Tb, $^{152}$Tb, $^{153}$Tb, $^{154}$Tb, $^{154}$mTb, $^{154}$m2Tb, $^{155}$Tb, $^{156}$Tb, $^{156}$mTb, $^{156}$m2Tb, $^{160}$Tb, $^{161}$Tb, $^{94}$Tc, $^{95}$Tc, $^{95}$mTc, $^{96}$Tc, $^{97}$mTc, $^{99}$mTc, $^{118}$Te, $^{119}$Te, $^{119}$mTe, $^{121}$Te, $^{121}$mTe, $^{123}$mTe, $^{125}$mTe, $^{127}$Te, $^{127}$mTe, $^{129}$mTe, $^{131}$mTe, $^{132}$Te, $^{227}$Th, $^{231}$Th, $^{234}$Th, $^{45}$Ti, $^{198}$Tl, $^{199}$Tl, $^{200}$Tl, $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W, $^{181}$W, $^{185}$W, $^{187}$W, $^{188}$W, $^{122}$Xe, $^{125}$Xe, $^{127}$Xe, $^{129}$mXe, $^{131}$mXe, $^{133}$Xe, $^{133}$mXe, $^{135}$Xe, $^{85}$mY, $^{86}$Y, $^{87}$Y, $^{87}$mY, $^{88}$Y, $^{90}$Y, $^{90}$mY, $^{91}$Y, $^{92}$Y, $^{93}$Y, $^{166}$Yb, $^{169}$Yb, $^{175}$Yb, $^{62}$Zn, $^{65}$Zn, $^{69}$mZn, $^{71}$mZn, $^{72}$Zn, $^{86}$Zr, $^{88}$Zr, $^{89}$Zr, $^{95}$Zr, and $^{97}$Zr.

It can be helpful to classify cytotoxic radionuclides into groups, for example, metals (e.g., $^{90}$Y, $^{67}$Cu, $^{213}$Bi, $^{212}$Bi), and transitional elements (e.g., $^{186}$Re). Further, examples of pure β-emitters include $^{67}$Cu and $^{90}$Y; and examples of α-emitters include $^{213}$Bi. β-emitters that emit γ-radiation include $^{177}$Lu and $^{186}$Re, while Auger emitters and radionuclides that decay by internal conversion include $^{67}$Ga.

In particular embodiments, SCCs can be charged with radionuclides that are useful for imaging methods, such as PET imaging. An example of a radionuclide that is useful for PET imaging includes $^{89}$Zr. $^{89}$Zr has a half-life of 3 days and forms the daughter isotope $^{89}$Y.

In particular embodiments, SCCs can be charged with radionuclides that are useful for radiation therapy. Examples of radionuclides that are useful for radiation therapy include $^{225}$Ac and $^{227}$Th. $^{225}$Ac is a radionuclide with the half-life of ten days. As $^{225}$Ac decays the daughter isotopes $^{221}$Fr, $^{213}$Bi, and $^{209}$Pb are formed. $^{227}$Th has a half-life of 19 days, and forms the daughter isotope $^{223}$Ra.

As indicated, radionuclides can decay to form daughter isotopes. In particular embodiments, the SCCs disclosed herein retain daughter isotopes. For example, when an SCC is charged with $^{227}$Th, $^{223}$Ra daughter isotopes can be produced. In these embodiments, the $^{223}$Ra daughter isotope can be retained in the SCC longer than in classical chelating constructs due to encapsulation within the protein calyx. As is understood by one of ordinary skill in the art, such longer retention may be characterized by kinetic assays.

As will be appreciated by one of ordinary skill in the art, more than one radioisotope may be chosen and used in particular nuclear medicine indications. Thus, embodiments can include a single species of radioisotope, two species of radioisotopes, or a population of a plurality of species of radioisotopes combined in various proportions. In this manner the useful properties of different radioisotopes can be combined. For example, a single radioisotope decays at a linear rate. By combining radioisotopes of different half-lives, it is possible to create a non-linear decay rate.

Targeting Domains. In particular embodiments, SCCs disclosed herein include a targeting domain. Targeting domains can direct charged SCCs to imaging or therapeutic areas of interest. In particular embodiments, the targeting domains direct the SCC to a region of the body that will be imaged using nuclear medicine diagnostic techniques. In particular embodiments, the targeting domains direct the SCC to a cell type that is targeted for radiotherapy.

In particular embodiments, targeting domains can be derived from whole proteins or protein fragments with an affinity for particular tissues and/or cell types of interest. In particular embodiments, targeting domains can be derived from whole antibodies or binding fragments of an antibody, e.g., Fv, Fab, Fab', F(ab')$_2$, Fc, and single chain Fv fragments (scFvs) or any biologically effective fragments of an immunoglobulin that bind specifically to, for example, a cancer antigen epitope. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Targeting domains from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects. Targeting domains can particularly include any peptide that specifically binds a selected unwanted cell epitope. Sources of targeting domains include antibody variable regions from various species (which can be in the form of antibodies, sFvs, scFvs, Fabs, scFv-based grababody, or soluble VH domain or domain antibodies). These antibodies can form antigen-binding regions using only a heavy chain variable region, i.e., these functional antibodies are homodimers of heavy chains only (referred to as "heavy chain antibodies") (Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008).

Phage display libraries of partially or fully synthetic antibodies are available and can be screened for an antibody or fragment thereof that can bind a selected epitope. For example, targeting domains may be identified by screening a Fab phage library for Fab fragments that specifically bind to a target of interest (see Hoet et al., Nat. Biotechnol. 23:344, 2005). Phage display libraries of human antibodies are also available. Additionally, traditional strategies for hybridoma development using a target of interest as an immunogen in convenient systems (e.g., mice, HuMAb Mouse®, TC Mouse™, KM-Mouse®, llamas, chicken, rats, hamsters, rabbits, etc.) can be used to develop targeting domains. In particular embodiments, antibodies specifically bind to selected epitopes expressed by targeted cells and do not cross react with nonspecific components or unrelated targets. Once identified, the amino acid sequence or polynucleotide sequence coding for the antibody can be isolated and/or determined.

An alternative source of targeting domains includes sequences that encode random peptide libraries or sequences that encode an engineered diversity of amino acids in loop regions of alternative non-antibody scaffolds, such as scTCR (see, e.g., Lake et al., Int. Immunol. 11:745, 1999; Maynard et al., J. Immunol. Methods 306:51, 2005; U.S. Pat. No. 8,361,794), mAb$^2$ or Fcab™ (see, e.g., PCT Patent Application Publication Nos. WO 2007/098934; WO 2006/072620), affibody, avimers, fynomers, cytotoxic T-lymphocyte associated protein-4 (Weidle et al., Cancer Gen. Proteo. 10:155, 2013), or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Pluckthun, Curr. Opin. Biotechnol. 22:849, 2011).

In particular embodiments, an antibody fragment is used as the targeting domain of a SCC. An "antibody fragment" denotes a portion of a complete or full length antibody that retains the ability to bind to an epitope. Examples of antibody fragments include Fv, scFv, Fab, Fab', Fab'-SH, F(ab')$_2$; diabodies; and linear antibodies.

A single chain variable fragment (scFv) is a fusion protein of the variable regions of the heavy and light chains of immunoglobulins connected with a short linker peptide. Fv fragments include the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including VL, VH, CL and CH1 domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011))) can also be used. Antibody fragments can also include isolated CDRs. For a review of antibody fragments, see Hudson, et al., Nat. Med. 9 (2003) 129-134.

Antibody fragments can be made by various techniques, including proteolytic digestion of an intact antibody as well as production by recombinant host-cells (e.g. *E. coli* or phage), as described herein. Antibody fragments can be screened for their binding properties in the same manner as intact antibodies.

In particular embodiments, targeting domains can also include a natural receptor or ligand for an epitope. For example, if a target for binding includes PD-L1, the binding domain can include PD-1 (including, e.g., a PD-1/antiCD3 fusion). One example of a receptor fusion for binding is Enbrel® (Immunex). Natural receptors or ligands can also be modified to enhance binding. For example, betalacept is a modified version of abatacept.

Binding can also be enhanced through increasing avidity. Any screening method known in the art can be used to identify increased avidity to an antigen epitope.

As used herein, an epitope denotes the binding site on a protein target bound by a corresponding targeting domain. The targeting domain either binds to a linear epitope, (e.g., an epitope including a stretch of 5 to 12 consecutive amino acids), or the targeting domains binds to a three-dimensional structure formed by the spatial arrangement of several short stretches of the protein target. Three-dimensional epitopes recognized by a targeting domain, e.g. by the epitope recognition site or paratope of an antibody or antibody fragment, can be thought of as three-dimensional surface features of an epitope molecule. These features fit precisely (in)to the corresponding binding site of the targeting domains and thereby binding between the targeting domains and its target protein is facilitated.

"Bind" means that the targeting domain associates with its target epitope with a dissociation constant (1(D) of $10^{-8}$ M or less, in one embodiment of from $10^{-5}$ M to $10^{-13}$ M, in one embodiment of from $10^{-5}$ M to $10^{-10}$ M, in one embodiment of from $10^{-5}$ M to $10^{-7}$ M, in one embodiment of from $10^{-8}$ M to $10^{-13}$ M, or in one embodiment of from $10^{-9}$ M to $10^{-13}$ M. The term can be further used to indicate that the targeting domains does not bind to other biomolecules present, (e.g., it binds to other biomolecules with a dissociation constant (KD) of $10^{-4}$ M or more, in one embodiment of from $10^{-4}$ M to 1 M.

In particular embodiments, targeting domains of SCCs can be designed to target cancer cell antigens. Cancer cell antigens are preferentially expressed by cancer cells. "Preferentially expressed" means that a cancer cell antigen is found at higher levels on cancer cells as compared to other cell types. The difference in expression level is significant enough that, within sound medical judgment, administration of therapeutics selectively targeting the cancer cells based on the presence of the cancer antigen outweighs the risk of collateral killing of other non-cancer cells that may also express the marker to a lesser degree. In some instances, a cancer antigen is only expressed by the targeted cancer cell type. In other instances, the cancer antigen is expressed on the targeted cancer cell type at least 25%, 35%, 45%, 55%, 65%, 75%, 85%, 95%, 96%, 97%, 98%, 99%, or 100% more than on non-targeted cells.

The following table provides examples of particular cancer antigens that can be targeted by SCCs.

| Targeted Cancer | Cancer Antigens |
| --- | --- |
| Leukemia/Lymphoma | CD19, CD20, CD22, ROR1, CD33, WT-1 |
| Multiple Myeloma | B-cell maturation antigen (BCMA) |
| Prostate Cancer | PSMA, WT1, Prostate Stem Cell antigen (PSCA), SV40 T |
| Breast Cancer | HER2, ERBB2, ROR1 |
| Stem Cell Cancer | CD133 |
| Ovarian Cancer | L1-CAM, extracellular domain of MUC16 (MUC-CD), folate binding protein (folate receptor), Lewis Y, ROR1, mesothelin, WT-1 |
| Mesothelioma | mesothelin |
| Renal Cell Carcinoma | carboxy-anhydrase-IX (CAIX); |
| Melanoma | GD2 |
| Pancreatic Cancer | mesothelin, CEA, CD24, ROR1 |
| Lung Cancer | ROR1 |

In more particular examples, cancer cell antigens include:

| Cancer Antigen | Sequence |
| --- | --- |
| PSMA | MWNLLHETDSAVATARRPRWLCAGALVLAGGFFLL GFLFGWFIKSSNEATNITPKHNMKAFLDELKAENI KKFLYNFTQIPHLAGTEQNFQLAKQIQSQWKEFGL DSVELAHYDVLLSYPNKTHPNYISIINEDGNEIFN TSLFEPPPPGYENVSDIVPPFSAFSPQGMPEGDLV YVNYARTEDFFKLERDMKINCSGKIVIARYGKVFR GNKVKNAQLAGAKGVILYSDPADYFAPGVKSYPDG WNLPGGGVQRGNILNLNGAGDPLTPGYPANEYAYR RGIAEAVGLPSIPVHPIGYYDAQKLLEKMGGSAPP DSSWRGSLKVPYNVGPGFTGNFSTQKVKMHIHSTN EVTRIYNVIGTLRGAVEPDRYVILGGHRDSWVFGG IDPQSGAAVVHEIVRSFGTLKKEGWRPRRTILFAS WDAEEFGLLGSTEWAEENSRLLQERGVAYINADSS IEGNYTLRVDCTPLMYSLVHNLTKELKSPDEGFEG KSLYESWTKKSPSPEFSGMPRISKLGSGNDFEVFF QRLGIASGRARYTKNWETNKFSGYPLYHSVYETYE LVEKFYDPMFKYHLTVAQVRGGMVFELANSIVLPF DCRDYAVVLRKYADKIYSISMKHPQEMKTYSVSFD SLFSAVKNFTEIASKFSERLQDFDKSNPIVLRMMN DQLMFLERAFIDPLGLPDRPFYRHVIYAPSSHNKY AGESFPGIYDALFDIESKVDPSKAWGEVKRQIYVA AFTVQAAAETLSEVA (SEQ ID NO: 26) |
| PSCA | MKAVLLALLMAGLALQPGTALLCYSCKAQVSNEDC LQVENCTQLGEQCWTARIRAVGLLTVISKGCSLNC VDDSQDYYVGKKNITCCDTDLCNASGAHALQPAAA ILALLPALGLLLWGPGQL (SEQ ID NO: 27) |
| Mesothelin | MALPTARPLLGSCGTPALGSLLFLLFSLGWVQPSR TLAGETGQEAAPLDGVLANPPNISSLSPRQLLGFP |

| Cancer Antigen | Sequence |
|---|---|
| | CAEVSGLSTERVRELAVALAQKNVKLSTEQLRCLA HRLSEPPEDLDALPLDLLLFLNPDAFSGPQACTHF FSRITKANVDLLPRGAPERQRLLPAALACWGVRGS LLSEADVRALGGLACDLPGRFVAESAEVLLPRLVS CPGPLDQDQQEAARAALQGGGPPYGPPSTWSVSTM DALRGLLPVLGQPIIRSIPQGIVAAWRQRSSRDPS WRQPERTILRPRFRREVEKTACPSGKKAREIDESL IFYKKWELEACVDAALLATQMDRVNAIPFTYEQLD VLKHKLDELYPQGYPESVIQHLGYLFLKMSPEDIR KWNVTSLETLKALLEVNKGHEMSPQVATLIDRFVK GRGQLDKDTLDTLTAFYPGYLCSLSPEELSSVPPS SIWAVRPQDLDTCDPRQLDVLYPKARLAFQNMNGS EYFVKIQSFLGGAPTEDLKALSQQNVSMDLATFMK LRTDAVLPLTVAEVQKLLGPHVEGLKAEERHRPVR DWILRQRQDDLDTLGLGLQGGIPNGYLVLDLSVQE ALSGTPCLLGPGPVLTVLALLLASTLA (SEQ ID NO: 28) |
| CD19 | MPPPRLLFFLLFLTPMEVRPEEPLVVKVEEGDNAV LQCLKGTSDGPTQQLTWSRESPLKPFLKLSLGLPG LGIHMRPLASWLFIFNVSQQMGGFYLCQPGPPSEK AWQPGWTVNVEGSGELFRWNVSDLGGLGCGLKNRS SEGPSSPSGKLMSPKLYVWAKDRPEIWEGEPPCVP PRDSLNQSLSQDLTMAPGSTLWLSCGVPPDSVSRG PLSWTHVHPKGPKSLLSLELKDDRPARDMWVMETG LLLPRATAQDAGKYYCHRGNLTMSFHLEITARPVL WHWLLRTGGWKVSAVTLAYLIFCLCSLVGILHLQR ALVLRRKRKRMTDPTRRFFKVTPPPGSGPQNQYGN VLSLPTPTSGLGRAQRWAAGLGGTAPSYGNPSSDV QADGALGSRSPPGVGPEEEEGEGYEEPDSEEDSEF YENDSNLGQDQLSQDGSGYENPEDEPLGPEDEDSF SNAESYENEDEELTQPVARTMDFLSPHGSAWDPSR EATSLGSQSYEDMRGILYAAPQLRSIRGQPGPNHE EDADSYENMDNPDGPDPAWGGGRMGTWSTR (SEQ ID NO: 29) |
| CD20 | MTTPRNSVNGTFPAEPMKGPIAMQSGPKPLFRRMS SLVGPTQSFFMRESKTLGAVQIMNGLFHIALGGLL MIPAGIYAPICVTVWYPLWGGIMYIISGSLLAATE KNSRKCLVKGKMIMNSLSLFAAISGMILSIMDILN IKISHFLKMESLNFIRAHTPYINIYNCEPANPSEK NSPSTQYCYSIQSLFLGILSVMLIFAFFQELVIAG IVENEWKRTCSRPKSNIVLLSAEEKKEQTIEIKEE VVGLTETSSQPKNEEDIEIIPIQEEEEEETENFP EPPQDQESSPIENDSSP (SEQ ID NO: 30) |
| ROR1 | MHRPRRRGTRPPLLALLAALLLAARGAAAQETELS VSAELVPTSSWNISSELNKDSYLTLDEPMNNITTS LGQTAELHCKVSGNPPPTIRWFKNDAPVVQEPRRL SFRSTIYGSRLRIRNLDTTDTGYFQCVATNGKEVV SSTGVLFVKFGPPPTASPGYSDEYEEDGFCQPYRG IACARFIGNRTVYMESLHMQGEIENQITAAFTMIG TSSHLSDKCSQFAIPSLCHYAFPYCDETSSVPKPR DLCRDECEILENVLCQTEYIFARSNPMILMRLKLP NCEDLPQPESPEAANCIRIGIPMADPINKNHKCYN STGVDYRGTVSVTKSGRQCQPWNSQYPHTHTFTAL RFPELNGGHSYCRNPGNQKEAPWCFTLDENFKSDL CDIPACDSKDSKEKNKMEILYILVPSVAIPLAIAL LFFFICVCRNNQKSSSAPVQRQPKHVRGQNVEMSM LNAYKPKSKAKELPLSAVRFMEELGECAFGKIYKG HLYLPGMDHAQLVAIKTLKDYNNPQQWTEFQQEAS LMAELHHPNIVCLLGAVTQEQPVCMLFEYINQGDL HEFLIMRSPHSDVGCSSDEDGTVKSSLDHGDFLHI AIQIAAGMEYLSSHFFVHKDLAARNILIGEQLHVK ISDLGLSREIYSADYYRVQSKSLLPIRWMPPEAIM YGKFSSDSDIWSFGVVLWEIFSFGLQPYYGFSNQE VIEMVRKRQLLPCSEDCPPRMYSLMTECWNEIPSR RPRFKDIHVRLRSWEGLSSHTSSTTPSGGNATTQT TSLSASPVSNLSNPRYPNYMFPSQGITPQGQIAGF IGPPIPQNQRFIPINGYPIPPGYAAFPAAHYQPTG PPRVIQHCPPPKSRSPSSASGSTSTGHVTSLPSSG SNQEANIPLLPHMSIPNHPGGMGITVFGNKSQKPY KIDSKQASLLGDANIHGHTESMISAEL (SEQ ID NO: 31) |
| WT1 | MGHHHHHHHHHHSSGHIEGRHMRRVPGVAPTLVRS ASETSEKRPFMCAYPGCNKRYFKLSHLQMHSRKHT GEKPYQCDFKDCERRFFRSDQLKRHQRRHTGVKPF QCKTCQRKFSRSDHLKTHTRTHTGEKPFSCRWPSC QKKFARSDELVRHHNMHQRNMTKLQLAL (SEQ ID NO: 32) |

In particular embodiments, the targeting domains of the SCC targets a ROR1 epitope. In particular embodiments, the targeting domains of the SCC is a human or humanized scFv including a variable light chain including a CDRL1 sequence of ASGFDFSAYYM (SEQ ID NO: 33), CDRL2 sequence of TIYPSSG (SEQ ID NO: 34), and a CDRL3 sequence of ADRATYFCA (SEQ ID NO: 35). In particular embodiments, the targeting domain of the SCC is a human or humanized scFv including a variable heavy chain including CDRH1 sequence of DTIDWY (SEQ ID NO: 36), CDRH2 sequence of VQSDGSYTKRPGVPDR (SEQ ID NO: 37), and a CDRH3 sequence of YIGGYVFG (SEQ ID NO: 38). A number of antibodies specific for ROR1 are known to those of skill in the art and can be readily characterized for sequence, epitope binding, and affinity.

In a particular embodiment, the targeting domain of the SCC binds to a CD19 epitope. In particular embodiments, the targeting domain of the SCC is a single chain Fv fragment (scFv) that includes VH and VL regions specific for CD19. In certain embodiments, the $V_H$ and $V_L$ regions are human. Exemplary $V_H$ and $V_L$ regions include the segments of anti-CD19 specific monoclonal antibody FMC63. In particular embodiments, the scFV is a human or humanized and includes a variable light chain including a CDRL1 sequence of RASQDISKYLN (SEQ ID NO: 39), CDRL2 sequence of SRLHSGV (SEQ ID NO: 40), and a CDRL3 sequence of GNTLPYTFG (SEQ ID NO: 41). In other embodiments, the scFV is a human or humanized ScFv including a variable heavy chain including CDRH1 sequence of DYGVS (SEQ ID NO: 42), CDRH2 sequence of VTWGSETTYYNSALKS (SEQ ID NO: 43), and a CDRH3 sequence of YAMDYWG (SEQ ID NO: 44). Other CD19-targeting antibodies such as SJ25C1 and HD37 are known. (SJ25C1: Bejcek et al. Cancer Res 2005, PMID 7538901; HD37: Pezutto et al. JI 1987, PMID 2437199).

In particular embodiments, the targeting domain of the SCC targets a PSMA epitope. A number of antibodies specific for PSMA are known to those of skill in the art and can be readily characterized for sequence, epitope binding, and affinity. Targeting domains can also include anti-Mesothelin ligands (associated with treating ovarian cancer, pancreatic cancer, and mesothelioma). As will be understood by one of ordinary skill in the art, the targeting domains can bind any number of epitopes on the cancer antigens disclosed herein (among others).

Rituxan (Rituximab, Genentech) targets CD20 for CD20-positive non-Hodgkin's lymphoma and Arzerra (Ofatumumab, Novartis), targets a different epitope of CD20. Herceptin can also be used.

Proteins disclosed herein include variants. Variants of proteins disclosed herein include proteins having one or more amino acid additions, deletions, stop positions, or substitutions, as compared to a protein disclosed herein. To qualify as a variant, the altered protein must provide an equivalent or improved intended effect as compared to a reference protein provided elsewhere herein. Equivalent means not statistically significantly different. Improved means higher affinity binding.

An amino acid substitution can be a conservative or a non-conservative substitution. Variants of proteins disclosed herein can include those having one or more conservative amino acid substitutions. A conservative substitution involves a substitution found in one of the following conservative substitutions groups: Group 1: alanine (Ala or A), glycine (Gly or G), Ser, Thr; Group 2: aspartic acid (Asp or D), E; Group 3: asparagine (Asn or N), glutamine (Gln or Q); Group 4: Arg, lysine (Lys or K), histidine (His or H); Group 5: Ile, leucine (Leu or L), methionine (Met or M), valine (Val or V); and Group 6: F, Tyr, W.

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, G, A, V, L, and I. Other groups containing amino acids that are considered conservative substitutions for one another include: sulfur-containing:M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W. Additional information is found in Creighton (1984) Proteins, W.H. Freeman and Company.

Variants of proteins disclosed herein also include sequences with at least 70% sequence identity, at least 80% sequence identity, at least 85% sequence, at least 90% sequence identity, at least 95% sequence identity, at least 96% sequence identity, at least 97% sequence identity, at least 98% sequence identity, or at least 99% sequence identity to a protein disclosed herein. More particularly, variants of the proteins disclosed herein include proteins that share: 70% sequence identity with any of e.g., SEQ ID NO: 1-46; 80% sequence identity with any of e.g., SEQ ID NO: 1-46; 81% sequence identity with any of e.g., SEQ ID NO: 1-46; 82% sequence identity with any of e.g., SEQ ID NO: 1-46; 83% sequence identity with any of e.g., SEQ ID NO: 1-46; 84% sequence identity with any of e.g., SEQ ID NO: 1-46; 85% sequence identity with any of e.g., SEQ ID NO: 1-46; 86% sequence identity with any of e.g., SEQ ID NO: 1-46; 87% sequence identity with any of e.g., SEQ ID NO: 1-46; 88% sequence identity with any of e.g., SEQ ID NO: 1-46; 89% sequence identity with any of e.g., SEQ ID NO: 1-46; 90% sequence identity with any of e.g., SEQ ID NO: 1-1-46; 91% sequence identity with any of e.g., SEQ ID NO: 1-46; 92% sequence identity with any of e.g., SEQ ID NO: 1-46; 93% sequence identity with any of e.g., SEQ ID NO: 1-46; 94% sequence identity with any of e.g., SEQ ID NO: 1-46; 95% sequence identity with any of e.g., SEQ ID NO: 1-46; 96% sequence identity with any of e.g., SEQ ID NO: 1-46; 97% sequence identity with any of e.g., SEQ ID NO: 1-46; 98% sequence identity with any of e.g., SEQ ID NO: 1-46; or 99% sequence identity with any of e.g., SEQ ID NO: 1-46.

% sequence identity refers to a relationship between two or more sequences, as determined by comparing the sequences. In the art, identity also means the degree of sequence relatedness between sequences as determined by the match between strings of such sequences. Identity (often referred to as similarity) can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the default values of the program referenced. Default values mean any set of values or parameters which originally load with the software when first initialized.

D-substituted analogs include protein disclosed herein having one more L-amino acids substituted with one or more D-amino acids. The D-amino acid can be the same amino acid type as that found in the reference sequence or can be a different amino acid. Accordingly, D-analogs can also be variants.

While exemplary sequences are provided herein, sequence information provided by public databases can be used to identify additional related and relevant protein sequences and associated nucleic acid sequences encoding such proteins.

Methods of Protein Production. Embodiments disclosed herein utilize siderocalin (Scn), in particular embodiments, in combination or as a fusion with a targeting domain. In particular embodiments, proteins disclosed herein are formed using the Daedalus expression system as described in Pechman et al., Am J Physiol 294: R1234-R1239, 2008. The Daedalus system utilizes inclusion of minimized ubiquitous chromatin opening elements in transduction vectors to reduce or prevent genomic silencing and to help maintain the stability of decigram levels of expression. This system can bypass tedious and time-consuming steps of other protein production methods by employing the secretion pathway of serum-free adapted human suspension cell lines, such as 293 Freestyle. Using optimized lentiviral vectors, yields of 20-100 mg/l of correctly folded and post-translationally modified, endotoxin-free protein of up to 70 kDa in size, can be achieved in conventional, small-scale (100 ml) culture.

In particular embodiments, the amount of peptide obtained can be between 10 mg/L and 200 mg/L, between 50 mg/L and 200 mg/L, between 100 mg/L and 200 mg/L, and between 150 mg/L and 200 mg/L. At these yields, most proteins can be purified using a single size-exclusion chromatography step, immediately appropriate for use in structural, biophysical or therapeutic applications. Bandaranayake et al., Nucleic Acids Res., 2011 (November); 39(21). In some instances, purification by chromatography may not be needed due to the purity of manufacture according the methods described herein. Further, Scn when loaded with siderophores and iron, has a deep red color that can aid in chromatography or other purification steps.

Particular embodiments utilize DNA constructs (e.g., chimeric genes, expression cassettes, expression vectors, recombination vectors, etc.) including a nucleic acid sequence encoding the protein or proteins of interest operatively linked to appropriate regulatory sequences. Such DNA constructs are not naturally-occurring DNA molecules and are useful for introducing DNA into host-cells to express selected proteins of interest.

Operatively linked refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis et al., Molecular Cloning: A Laboratory Manual, Cold Spring Harbor, N.Y., 1982; and Sambrook et al., Molecular Cloning: A Laboratory Manual, Cold Spring Harbor, N.Y., 1989.

Expression control sequences are DNA sequences involved in any way in the control of transcription or translation. Suitable expression control sequences and methods of making and using them are well known in the art. Expression control sequences generally include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts et al., Proc. Natl. Acad. Sci. USA, 76:760-764, 1979.

The promoter may include, or be modified to include, one or more enhancer elements. In particular embodiments, the promoter will include a plurality of enhancer elements. Promoters containing enhancer elements can provide for higher levels of transcription as compared to promoters that do not include them.

For efficient expression, the coding sequences can be operatively linked to a 3' untranslated sequence. In particular embodiments, the 3' untranslated sequence can include a transcription termination sequence and a polyadenylation sequence. The 3' untranslated region can be obtained, for example, from the flanking regions of genes.

In particular embodiments, a 5' untranslated leader sequence can also be employed. The 5' untranslated leader sequence is the portion of an mRNA that extends from the 5' CAP site to the translation initiation codon.

In particular embodiments, a "hisavi" tag can be added to the N-terminus or C-terminus of a gene by the addition of nucleotides coding for the Avitag amino acid sequence, GLNDIFEAQKIEWHE (SEQ ID NO: 45), as well as the 6×histidine tag coding sequence, HHHHHH (SEQ ID NO: 46). The Avitag avidity tag can be biotinylated by a biotin ligase to allow for biotin-avidin or biotin-streptavidin based interactions for protein purification, as well as for immunobiology (such as immunoblotting or immunofluorescence) using anti-biotin antibodies. The 6×histidine tag allows for protein purification using Ni-2+ affinity chromatography.

In particular embodiments, expressed fusion proteins can include or be encoded by an IgK starter sequence, a sFLAG, a HIS, and a TEV. In certain embodiments, the fusion protein includes the following construct: IgK SP-sFLAG-HIS-siderocalin-TEV-peptide. In some embodiments, the fusion protein is generated by direct fusion of each subunit to the adjacent subunits. In certain embodiments, the composition further includes a linker sequence between the targeting domain and the Scn protein.

Nucleic acid sequences encoding proteins disclosed herein can be derived by those of ordinary skill in the art. Nucleic acid sequences can also include one or more of various sequence polymorphisms, mutations, and/or sequence variants. In particular embodiments, the sequence polymorphisms, mutations, and/or sequence variants do not affect the function of the encoded protein. The sequences can also include degenerate codons of a native sequence or sequences that may be introduced to provide codon preference.

In some aspects, the DNA constructs can be introduced by transfection, a technique that involves introduction of foreign DNA into the nucleus of eukaryotic cells. In some aspects, the proteins can be synthesized by transient transfection (DNA does not integrate with the genome of the eukaryotic cells, but the genes are expressed for 24-96 hours). Various methods can be used to introduce the foreign DNA into the host-cells, and transfection can be achieved by chemical-based means including by the calcium phosphate, by dendrimers, by liposomes, and by the use of cationic polymers. Non-chemical methods of transfection include electroporation, sono-poration, optical transfection, protoplast fusion, impalefection, and hydrodynamic delivery. In some embodiments, transfection can be achieved by particle-based methods including gene gun where the DNA construct is coupled to a nanoparticle of an inert solid which is then "shot" directly into the target-cell's nucleus. Other particle-based transfection methods include magnet assisted transfection and impalefection.

Methods of Synthesizing Chelators. In some embodiments, compositions of chelators described herein can be synthesized using techniques that are simpler and less harsh than conventional techniques. In particular, the use of dichlorophenylmethane improves the synthesis of natural siderophores and analogs, such as 3,4,3-LI(CAM), by minimizing the use of harsh, toxic substances in the synthesis of siderophores and siderophore-like ligands. Additionally, the reaction conditions are improved when dichlorophenylmethane is used in the synthesis of siderophores and siderophore-like ligands.

Methods of Making Siderocalin-Chelator Combinations. In particular embodiments, SCCs can be made by contacting Scn or Scn-targeting domain fusion protiens with chelators and allowing complexes between the two molecules to form.

Methods of Making Radionuclides. Radioisotopes can be obtained in solution in water or other polar fluid in elemental form (i.e., uncharged) or ionic form. As appreciated by the skilled artisan, when in ionic form, radioisotopes may occur in various different valence states, as anions, or as cations, depending upon the particular radioisotope being considered.

Methods of Charging Chelators with Radionuclides. In particular embodiments, chelators can be charged with radionuclides by contacting the chelators with metallic radioisotopes and allowing complexes between the two molecules to form.

Methods of Making Siderocalin-Chelator-Radionuclide Complexes. In particular embodiments, SCC-metal complexes can be made by contacting SCCs with metallic radioisotopes and allowing complexes between the molecules to form. In other embodiments, SCC-metal complexes can be made by contacting chelator-metal combinations with siderocalins and allowing complexes between the molecules to form.

Formulations. The various forms of Scn-chelator combinations (SCCs) and charged SCCs described herein, are referred to herein as active ingredients. Active ingredients also include prodrugs, salts, analogs, and/or derivatives of SCCs, charged SCCs, or portions of SCCs or charged SCCs.

A prodrug includes an active ingredient which is converted into a therapeutically active or more therapeutically active compound after administration, such as by cleavage of a protein.

A pharmaceutically acceptable salt includes any salt that retains the activity of the active ingredient and is acceptable for pharmaceutical use. A pharmaceutically acceptable salt also refers to any salt which may form in vivo as a result of administration of an acid, another salt, or a prodrug which is converted into an acid or salt. Suitable pharmaceutically acceptable acid addition salts can be prepared from an inorganic acid or an organic acid. Examples of inorganic acids include hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine, arginine and procaine.

The term analog (also structural analog or chemical analog) is used to refer to a compound that is structurally similar to another compound but differs with respect to a certain component, such as an atom, a functional group, or a substructure. The term derivative refers to a compound that is obtained from a similar compound or a precursor compound by a chemical reaction. As used herein, analogs and derivatives retain the therapeutic effectiveness of the parent compound (i.e., there is no statistically significant difference in therapeutic activity according to an imaging assay or assessment of clinical improvement) or have improved therapeutic effectiveness as defined elsewhere herein.

Active ingredients are formulated into compositions for administration to subjects. Compositions include at least one active ingredient and at least one pharmaceutically acceptable carrier. In particular embodiments, compositions include active ingredients of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent for use as a pharmaceutically acceptable carrier is EDTA. Other chelating agents disclosed herein may also be used.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the active ingredient or helps to prevent denaturation or adherence to the container wall. Typical stabilizers can include polyhydric sugar alcohols; amino acids, such as R, K, G, Q, N, H, A, ornithine, L-leucine, 2-F, E, and T; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on active ingredient weight.

In particular embodiments, the compositions disclosed herein can be formulated for administration by injection (e.g., intravenous injection). Compositions can also be formulated for administration by, for example, inhalation, infusion, perfusion, lavage, or ingestion. The compositions disclosed herein can be further be formulated for intradermal, intraarterial, intranodal, intralymphatic, intraperitoneal, intralesional, intraprostatic, intravaginal, intrarectal, topical, intrathecal, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intramuscular, intravesicular, and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use. Particular embodiments are formulated for intravenous or intramuscular administration.

For oral administration, the compositions can be formulated as tablets, pills, dragees, capsules, liquids, gels, syrups, slurries, suspensions and the like. Compositions can be formulated as an aerosol for inhalation. In one embodiment, the aerosol is provided as part of an anhydrous, liquid or dry powder inhaler. Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. Additionally, compositions can be formulated as sustained-release systems utilizing semipermeable matrices of solid polymers containing at least one active ingredient.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Kits. Also disclosed herein are kits including one or more containers including one or more of the active ingredients, compositions, Scn proteins, chelators, and/or radionuclides described herein. In various embodiments, the kits may include one or more containers containing one or more portions of active ingredients and/or compositions to be used in combination with other portions of the active ingredients and/or compositions described herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the methods disclosed herein. In various embodiments, the kit may include instructions regarding preparation of the active ingredients and/or compositions for administration; administration of the active ingredients and/or compositions; appropriate reference levels to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. The instructions may be in English and/or in any national or regional language. In various embodiments, possible side effects and contraindications to further use of components of the kit based on a subject's symptoms can be included.

In various embodiments, the kits described herein include some or all of the necessary medical supplies needed to use the kit effectively, thereby eliminating the need to locate and gather such medical supplies. Such medical supplies can include syringes, ampules, tubing, facemasks, protective clothing, a needleless fluid transfer device, an injection cap, sponges, sterile adhesive strips, Chloraprep, gloves, and the like. Variations in contents of any of the kits described herein can be made. Particular kits provide materials to administer compositions through intravenous administration.

Methods of Use. Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with therapeutic compositions disclosed herein. Treating subjects includes delivering therapeutically effective amounts. Therapeutically effective amounts include those that provide effective amounts and therapeutic treatments.

An "effective amount" is the amount of a composition necessary to result in a desired physiological change in the subject. Effective amounts are often administered for research purposes. Effective amounts disclosed herein can cause a statistically-significant effect in an animal model assessing a use of nuclear medicine.

A "therapeutic treatment" can include a treatment administered to a subject in need of imaging. The subject can be in need of imaging to aid in diagnosis; to locate a position for a therapeutic intervention; to assess the functioning of a body part; and/or to assess the presence or absence of a condition. The effectiveness of a therapeutic imaging treatment can be confirmed based on the capture of an image sufficient for its intended purpose.

Exemplary types of imaging that utilize nuclear medicine include: positron emission tomography (PET), single photon emission computed tomography, radioisotope renography, and scintigraphy.

A "therapeutic treatment" can also include a treatment administered to a subject with a condition. The therapeutic treatment reduces, controls, or eliminates the condition or a symptom associated with the condition. Conditions treated with nuclear medicine include those associated with the proliferation of unwanted cells.

In particular embodiments, therapeutic treatments reduce cellular proliferation. Cellular proliferation refers to the process of cellular division, either through mitosis or meiosis, whereby increased cell numbers result. In particular embodiments, therapeutic treatments reduce cellular growth. Cellular growth refers both to an increase in cell mass or size, as well as cellular physiological processes necessary to support a cell's life.

Particular conditions that can be treated include various cancers, thyroid diseases (e.g., hyperthyroidism or thyrotoxicosis), blood disorders (e.g., Polycythemia vera, an excess of red blood cells produced in the bone marrow), and cellular proliferation in blood vessels following balloon angioplasty and/or stent placement (known as restenosis).

The effectiveness of a therapeutic treatment can be confirmed based on a beneficial change related to the condition following the treatment.

In the context of cancers, therapeutic treatments can decrease the number of cancer cells, decrease the number of metastases, decrease tumor volume, increase life expectancy, induce chemo- or radiosensitivity in cancer cells, inhibit angiogenesis near cancer cells, inhibit cancer cell proliferation, inhibit tumor growth, prevent or reduce metastases, prolong a subject's life, reduce cancer-associated pain, and/or reduce relapse or re-occurrence of cancer following treatment. In particular embodiments, therapeutic treatments reduce, delay, or prevent further metastasis from occurring.

For hyperthyroidism or thyrotoxicosis, therapeutic treatments can aid in the return of thyroid secreted hormones, such as T3 and T4, to more normal levels. These hormones can be measured from patient blood samples. In particular embodiments, a therapeutic treatment returns serum levels of T3 and/or T4 to within a normal range (80-180 ng/dl and 4.6-12 µg/dl, respectively).

For Polycythemia vera, therapeutic treatments can aid in the return of red blood cell counts to more normal levels. In particular embodiments, a therapeutic treatment returns the red blood cell count to within a normal range (4.7 to 6.1 million cells/µl).

For restenosis, therapeutic treatments can include the placement of radionuclides in the region of a vessel where a stent was placed or balloon angioplasty was performed, in order to inhibit the narrowing of the vessel due to proliferation of blood vessel cells. Treatment for restenosis can be deemed effective if normal blood flow through the affected blood vessel is restored. One test that can be used to diagnose improper blood flow is a stress test, which involves physical exercise while blood pressure and heart rate are measured. A normal stress test result means that the patient was able to exercise for a normal length of time and at a normal intensity level for their age and gender. Another test that can be performed to diagnose improper blood flow is a CT or MRI angiogram, which involves placement of a dye into the bloodstream and imaging of blood vessels. If restenosis treatment is effective, the CT or MRI angiogram will reveal normal blood flow through the affected vessel.

As indicated previously, particular uses of the chelating platforms disclosed herein include in imaging and treatment in the same subject.

The actual dose amount administered to a particular subject can be determined by a physician, veterinarian, or researcher taking into account parameters such as physical and physiological factors including body weight; severity of condition; previous or concurrent therapeutic interventions; idiopathy of the subject; and route of administration.

In particular embodiments, the total dose of absorbed radiation may include 10-3 grays (Gy), 10-2 Gy, 10-1 Gy, 1 Gy, 5 Gy, 10 Gy, 25 Gy, 50 Gy, 75 Gy, 100 Gy, 200 Gy, 300 Gy, 400 Gy, 500 Gy, 600 Gy, 700 Gy, 800 Gy, 900 Gy, or 1000 Gy.

Doses of absorbed radiation can be achieved by delivering an appropriate amount of a composition. Exemplary amounts of compositions can include 0.05 mg/kg to 5.0 mg/kg administered to a subject per day in one or more doses. For certain indications, the total daily dose can be 0.05 mg/kg to 3.0 mg/kg administered intravenously to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of composition using 60-minute QD, BID, or TID intravenous infusion dosing. Additional useful doses can often range from 0.1 to 5 µg/kg or from 0.5 to 1 µg/kg. In other examples, a dose can include 1 µg/kg, 20 µg/kg, 40 µg/kg, 60 µg/kg, 80 µg/kg, 100 µg/kg, 200 µg/kg, 350 µg/kg, 500 µg/kg, 700 µg/kg, 0.1 to 5 mg/kg, or from 0.5 to 1 mg/kg. In other examples, a dose can include 1 mg/kg, 10 mg/kg, 20 mg/kg, 40 mg/kg, 60 mg/kg, 80 mg/kg, 100 mg/kg, 200 mg/kg, 400 mg/kg, 500 mg/kg, 700 mg/kg, 750 mg/kg, 1000 mg/kg, or more.

Therapeutically effective amounts can be achieved by administering single or multiple doses during the course of an imaging or treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

Provided herein are methods for the separation or purification of metal ions. Currently available methods for the separation and purification of metal ions are either hydrometallurgical processes (liquid-liquid extraction, precipitation, electrodeposition, etc.) or analytical techniques (high performance liquid chromatography, ion chromatography, impregnated resins, capillary electrophoresis, mass spectrometry, etc.). The hydrometallurgical processes usually allow one to process important quantities of materials, are operated at ambient or low pressure but require harsh chemical conditions and multiple steps in order to reach the desire purity. Their recovery yield also rarely reaches 100%.

In contrast, the analytical techniques convey very little quantities, are operated at very high pressure (such as in HPLC methods) or very low pressure and high temperature (as in mass spectrometry techniques) and they are difficult, if not impossible, to scale-up for industrial applications. Both hydrometallurgical and analytical methods also often require the use of organic solvents either hydrosoluble or hydrophobic. The new strategy provided herein can be fast, efficient, scalable and operable at room temperature, ambient pressure and in fully aqueous solvent.

Experimental results showed that the siderocalin protein is able to bind various charged metal complexes through electrostatic interactions. While siderocalin binds tightly to negatively charged complexes, it doesn't bind to neutral complexes due to a lack of electrostatic interactions. The general strategy provided is to use siderocalin (or variants thereof or other proteins) as a platform for the separation of metal ions owing to the formation of high-molecular species (Protein-composition (e.g., ligand) metal adduct) versus low-molecular weight species (composition (e.g., ligand)-metal complex that is not recognized by the protein).

The low-molecular weight composition (e.g., ligand) can be tuned to match the charge of the metal ions to separate. For instance, the complex of zirconium ion ($Zr^{4+}$) with $[3,4,3-LI(1,2-HOPO)]^{4-}$ is neutral ($[Zr(IV)L]^0$) and therefore it is not recognized by siderocalin. In contrast, the complex of europium ion ($Eu^{3+}$) with $[3,4,3-LI(1,2-HOPO)]^{4-}$ possesses one negative charge ($[Eu(III)L]^-$) and it is recognized and tightly bound by siderocalin. In this example, $Zr^{4+}$ and $Eu^{3+}$ ions can therefore be separated.

In some embodiments, the separation of ions is based on the formation of high-molecular weight versus low-molecular weight species. The protein-composition (e.g., ligand) system therefore acts as a sorting device at a molecular level. The separation in itself between the low-molecular weight species and the macromolecular entities can be based on various fundamental leverages like differences in size, mass, polarity, solubility, etc. Hence, the separation of the metal-composition (e.g., ligand)-protein adducts from the low-molecular weight species can potentially be performed by various techniques such as (among others) size exclusion chromatography, cut-off filter filtration, solid-liquid extraction using solid supports grafted with the protein or the protein-composition (e.g., ligand) adduct, tangential filtration, ultra-, micro- or nano-filtration and liquid-liquid extraction. Experimental examples and details for the separation of different metal ions are provided herein.

Some embodiments provided herein can be used for the separation of actinides. In some embodiments, the methods provided herein can be used for sequestering and separation of radioactive elements. In some embodiments, the protein siderocalin displays a range of affinities with different actinide and lanthanide complexes of natural and synthetic compositions (e.g., ligands) that can allow new separation approaches.

As noted above, siderocalin (Scn) is an iron-transport protein that also binds actinide elements (such as thorium, plutonium, americium, and curium). In some embodiments, this discovery can be applied as a molecular mechanism through which radioactive elements can be probed and remediated from a contaminated environment.

In some embodiments, provided herein are methods and compositions for the separation of metal ions of differing charges from one another. In some embodiments, $M^{3+}$ ions can be separated from $M^{4+}$ ions, using a system comprising the composition (e.g., ligand), such as 3,4,3-LI(1,2-HOPO) and the protein siderocalin (or other protein that selectively binds to a charged (or uncharged) complex). In some embodiments, provided herein are separation processes for $M^{4+}$ ions, based on the use of 3,4,3-LI(1,2-HOPO). That is, the resulting complex of metal+composition (e.g., ligand) is either bound, or not, by a larger molecular weight protein. The fact that the metal composition (e.g., ligand) complex is either bound or not to the larger molecular weight protein allows one to separate the metal via separating the larger protein. In some embodiments, the binding of the composition (e.g., ligand) to the metal allows one to create either a charged complex or a neutral complex (depending upon the combined charge of the ligand and metal), which in turn is selectively bound (or not) by the protein (e.g., siderocalin). In some embodiments, methods and compositions are provided for separation between $Bk^{4+}$ and other $M^{3+}$ metals.

The applications of the invention are numerous, going from water purification to nuclear waste treatment and also portable analysis, production of radiation sources, etc. The process can selectively remove (or enrich) one charged species over a different charge species. Typical examples of metal ions separation include, among others, the separation of plutonium ($Pu^{4+}$) from adjacent actinide elements ($Am^{3+}$, $Cm^{3+}$, $Cf^{3+}$), the separation of thorium ($Th^{4+}$) from actinium ($Ac^{3+}$) or scandium ($Sc^{3+}$), the separation of zirconium ($Zr^{4+}$) from yttrium ($Y^{3+}$), the separation of tin ($Sn^{4+}$) from indium ($In^{3+}$), the separation of cerium ($Ce^{4+}$) from other lanthanides ($Ln^{3+}$) and the separation of berkelium ($Bk^{4+}$) form other actinides ($Cf^{3+}$, $Cm^{3+}$, $Am^{3+}$). The methods and compositions provided herein can be used in a variety of settings, including, without limitation, for: 1) the mining industry, 2) the nuclear industry, 3) pharmaceutical isotope production industry, and/or 4) the chemical industry developing separation supports.

In some embodiments, one can scale the process such that it allows for versatile separation of different metal ions under soft conditions (aqueous environments, ambient pressure and temperature, high yields, separation material recovery for numerous separation cycles, etc.). Based on the experimental results presented herein, one can employ such processes through standard engineering techniques.

As noted above, experimental results have shown that a protein (B. E. Allred, P. B. Rupert, S. S. Gauny, D. D. An, C. Y. Ralston, M. Sturzbecher-Hoehne, R. K. Strong, and R. J. Abergel, "Siderocalin-mediated recognition, sensitization, and cellular uptake of actinides," Proc. Natl. Acad. Sci., vol. 112, no. 33, pp. 10342-10347, August 2015), called siderocalin, is able to bind various charged metal complexes. The metal complexes have the general formula $[ML]^{n-}$ and siderocalin is able to bind these complexes due to electrostatic interactions. The final adduct "metal-ligand-protein" is referred hereafter as "Scn[ML]" (Scn standing for siderocalin, M for metal and L for ligand, such as one of the compositions provided herein). The protein recognizes the metal complexes of the synthetic ligands $[3,4,3\text{-LI}(1,2\text{-HOPO})]^{4-}$ or $[3,4,3\text{-LI-CAM}]^{8-}$ (shown below).

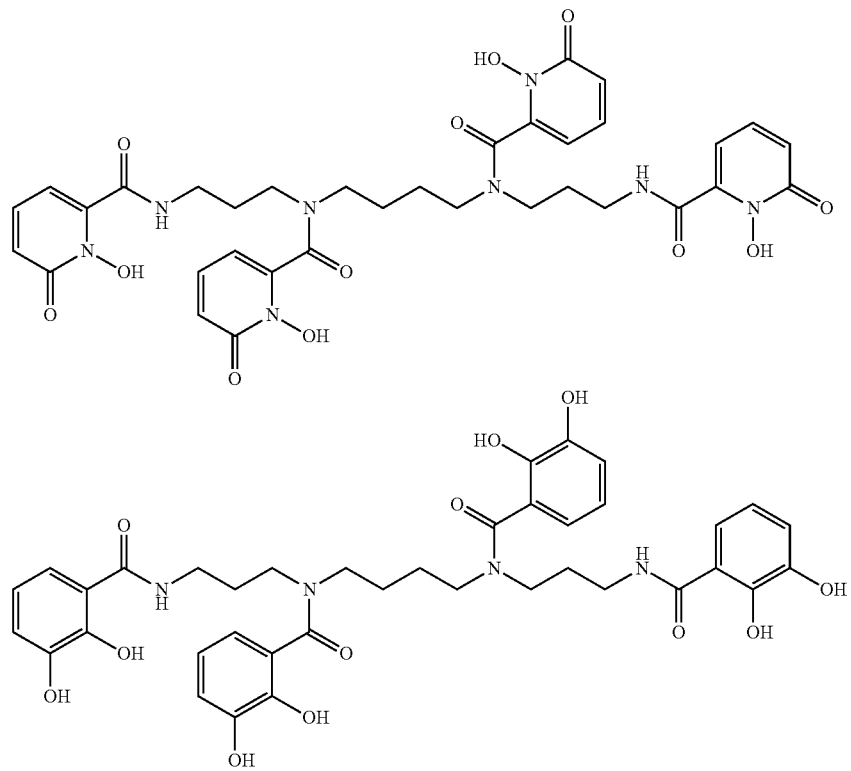

Formulas for 3,4,3-LI(1,2-HOPO) (top) and 3,4,3-LI-CAM (bottom).

While siderocalin binds tightly to the negatively charged complexes, it doesn't bind to the neutral complexes due to a lack of electrostatic interactions. In some embodiments provided herein, the general strategy is to use siderocalin (or other proteins) as a platform for the separation of metal ions owing to the formation of high-molecular species versus low-molecular weight species. The discrimination between two or more ions can be due to fundamentally different processes, some embodiments of which are summarized in FIG. 17.

Figure 17:
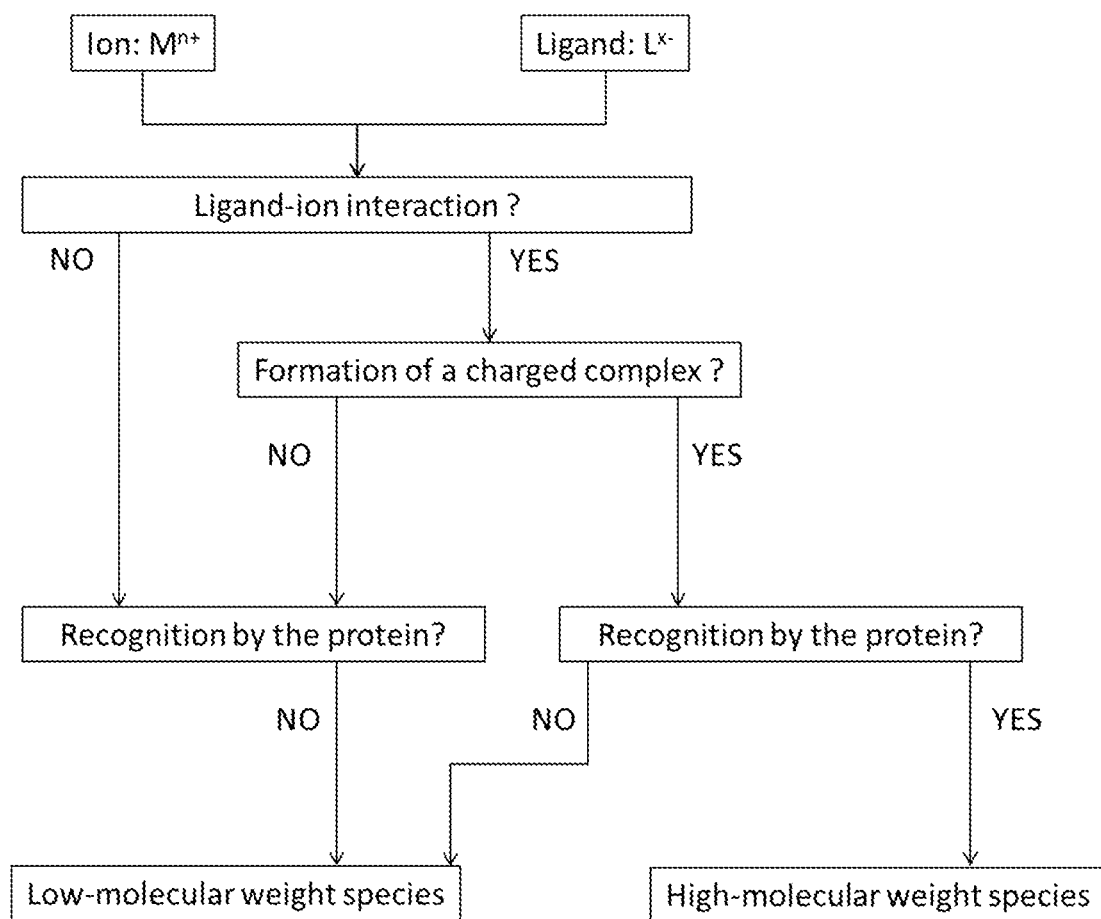
FIG. 17 is a flow chart of some embodiments of the processes leading to the formation of a low-molecular weight species or high-molecular weight species.

FIG. 17 is a flow chart of some embodiments of the processes leading to the formation of a low-molecular weight species or high-molecular weight species. This separated arrangement provides the ability to separate various species. A metal ion of interest (to either enrich or remove) is combined with a composition (e.g., ligand) (having the opposite charge). Where there is an interaction between the two, to form a complex, the complex can either be uncharged (resulting in no recognition or adequate binding by the protein (such as siderocalin), or charged, which in turn can be recognized by the protein (bound by it) resulting in the metal being associated with the higher molecular weight species or not recognized by the protein (resulting in the metal being in the low-molecular weight species. Thus, in some embodiments, selection of the metal can occur or go through one or more of the steps outlined in FIG. 17. In some embodiments, selection is based upon formation of a charged complex and then selection of the higher molecular weight species over the lower molecular weight species (to obtain the metal). In some embodiments, when the metal to be selected results in a neutral complex, then the selection is such that the composition (e.g., ligand) binds to the metal, resulting in a neutral complex, which is then obtained by selecting the low-molecular weight species from the sample. In some embodiments, selection occurs by a charged complex being generated and the protein recognizing the complex (and one collects the high-molecular weight species).

In some embodiments, the low-molecular weight composition (e.g., ligand) can be tuned to match the charge of the metal ions to separate. For instance, the complex of zirconium ion ($Zr^{4+}$) with [3,4,3-LI(1,2-HOPO)]$^{4-}$ is neutral ([Zr(IV)L]$^0$) and therefore it is not recognized by siderocalin. In contrast, the complex of europium ion ($Eu^{3+}$) with [3,4,3-LI(1,2-HOPO)]$^{4-}$ possesses one negative charge ([Eu(III)L]$^-$) and it is recognized and tightly bound by siderocalin. Thus, $Zr^{4+}$ and $Eu^{3+}$ ions (or other ions with similar charge differences) can therefore be separated.

The applications of the invention are numerous, going from water purification to nuclear waste treatment and also portable analysis, production of radiation sources, etc. Examples of metal ions separation would include (but are not limited to), the separation of plutonium ($Pu^{4+}$) from adjacent actinide elements ($Am^{3+}$, $Cm^{3+}$, $Cf^{3+}$), the separation of thorium ($Th^{4+}$) from actinium ($Ac^{3+}$) or scandium ($Sc^{3+}$), the separation of zirconium ($Zr^{4+}$) from yttrium ($Y^{3+}$), the separation of tin ($Sn^{4+}$) from indium ($In^{3+}$), the separation of cerium ($Ce^{4+}$) from other lanthanides ($Ln^{3+}$) and the separation of berkelium ($Bk^{4+}$) form other actinides ($Cf^{3+}$, $Cm^{3+}$, $Am^{3+}$). In some embodiments, any first metal can be separated from a second metal as long as there is a difference in charge between the first metal and the second metal. In some embodiments, the first metal can be separated from two, three, four, five or more other metals, as long as the first metal differs in charge from the other metals.

In some embodiments, the methods provided herein can be performed at room temperature, and/or ambient temperature, and/or in a one-step process, and/or under mild chemical conditions (e.g., fully aqueous solvent, pH 7.4). In some embodiments, there are no volatile elements in the processing. In some embodiments, there are volatile elements in the processing.

In some embodiments, separation can be achieved between any two metals that differ in charge, including those above, below in the examples, and/or any of the following pairs $Ac^{3+}/Th^{4+}$, $Bk^{4+}/Cf^{3+}$, $M^{4+}/M^{3+}$, and $M^{4+}/M^{2+}$.

In some embodiments, the enrichment/purification method can comprise contacting a liquid comprising a plurality of metal ions with a composition as described herein, under conditions sufficient to form a metal ion-composition complex comprising a metal ion of the plurality of metal ions. The method can further comprise separating a first fraction of the mixture enriched for the metal ion-composition complex from a second fraction depleted for the metal ion-composition complex, wherein the first fraction is enriched for a first metal ion that has a charge that is different from a charge of a second metal ion enriched in the second fraction.

In some embodiments, the method isolates $Bk^{4+}$ from a mixture. The method can comprise contacting a first mixture comprising $Bk^{4+}$ and a trivalent metal ion with a composition as described herein under conditions sufficient to form a complex comprising the trivalent metal ion and the composition. The method can further include separating the complex from the first mixture to generate a second mixture depleted for the trivalent metal ion and chromatographically isolating the $Bk^{4+}$ in the second mixture.

In some embodiments, the method reclaims an actinide from a sample. The method comprises obtaining an aqueous sample comprising, or suspected of comprising, an actinide, contacting the sample with a composition as described herein to generate a mixture under conditions sufficient to form a complex comprising the actinide and the composition; and separating the complex from the mixture.

In some embodiments, separating is based on molecular weight. In some embodiments, the separating comprises size-exclusion chromatography or affinity chromatography.

In some embodiments, a first fraction is enriched for a trivalent metal ion or a divalent metal ion, and a second fraction is enriched for a tetravalent metal ion. In some embodiments, a first fraction is enriched for a metal ion selected from the group consisting of: actinides, lanthanides, $Ac^{3+}$, $Sc^{3+}$, $Y^{3+}$, and $In^{3+}$. In some embodiments, a second fraction is enriched for a metal ion selected from the group consisting of: $Pu^{4+}$, $Np^{4+}$, $Th^{4+}$, $Zr^{4+}$, $Sn^{4+}$, $Ce^{4+}$, and $Bk^{4+}$. In some embodiments, a first fraction is enriched for a metal ion selected from the group consisting of $Am^{3+}$, $Cm^{3+}$, $Bk^{3+}$ and $Cf^{3+}$, and a second fraction comprises $Pu^{4+}$. In some embodiments, a first fraction is enriched for $Ac^{3+}$ and/or $Sc^{3+}$, and a second fraction is enriched for $Th^{4+}$. In some embodiments, a first fraction is enriched for $Eu^{3+}$ or $Y^{3+}$, and a second fraction is enriched for $Zr^{4+}$. In some embodiments, a first fraction is enriched for $In^{3+}$, and a second fraction is enriched for $Sn^{4+}$. In some embodiments, a first fraction is enriched for a lanthanide, and a second fraction is enriched for $Ce^{4+}$. In some embodiments, a first fraction is enriched for $Tm^{3+}$. In some embodiments, a first fraction is enriched for an actinide, and a second fraction is enriched for $Bk^{4+}$. In some embodiments, a first fraction is enriched for a metal ion selected from the group consisting of $Am^{3+}$, $Cm^{3+}$, and $Cf^{3+}$.

In some embodiments, a first mixture further comprises one or more actinides selected from the group consisting of: $Cm^{3+}$, $Am^{3+}$, $Cf^{3+}$, $Th^{4+}$, $Np^{4+}$, $Pu^{4+}$, and $Ce^{4+}$. In some embodiments, a mixture is prepared by neutron irradiation of Pu, Am or Cm. In some embodiments, the composition comprises a hydroxypyridonate ligand. In some embodiments, the composition comprises 3,4,3-LI(1,2-HOPO).

In some embodiments, the actinide comprises $Am^{3+}$ and/or $Cm^{3+}$.

In some embodiments, the sample is derived from a river, ocean, lake, soil, or industrial run off. In some embodiments, the sample is an industrial sample. In some embodiments, the composition comprises a hydroxypyridonate ligand. In some embodiments, the composition comprises 3,4,3-LI(1,2-HOPO).

Figure 26:
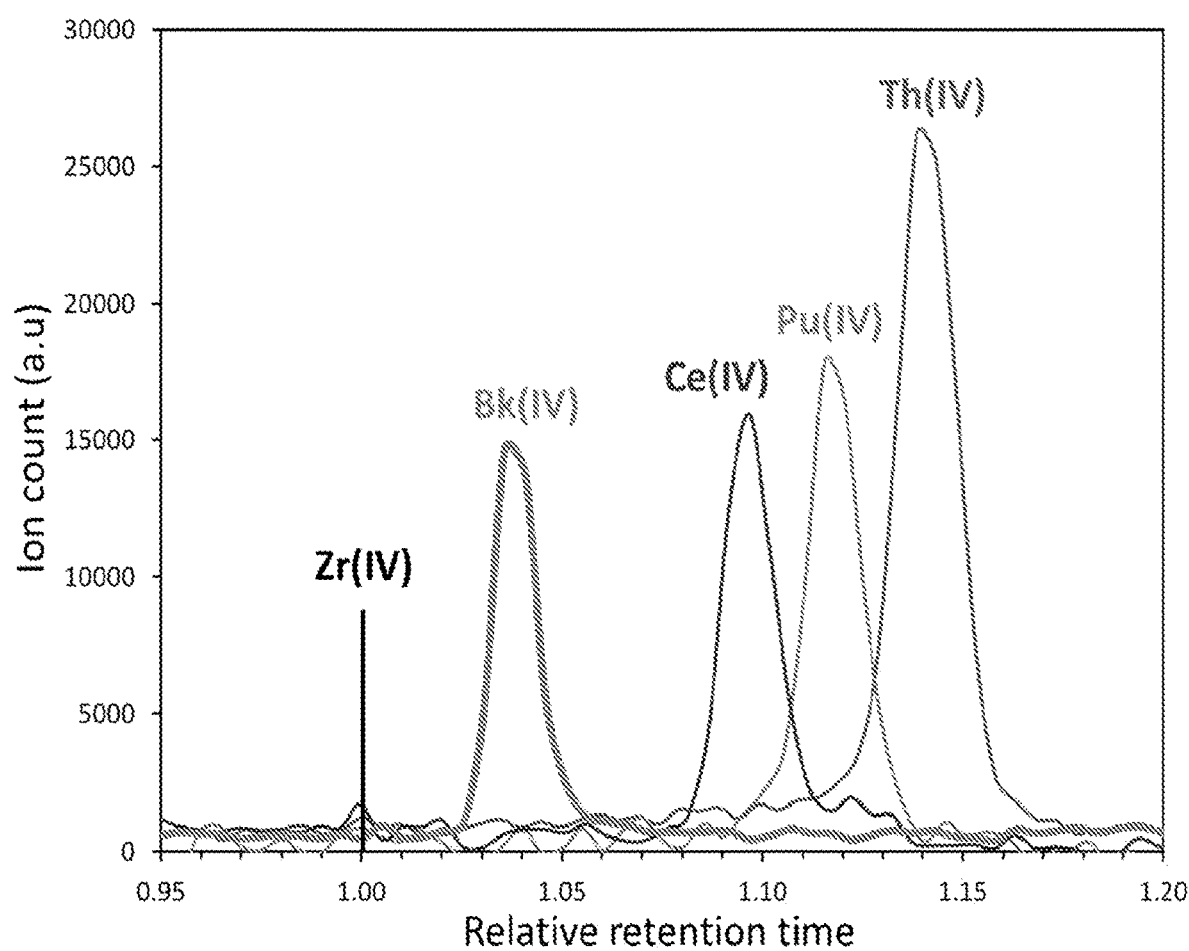
FIG. 26 depicts the relative chromatographic retention of $[Ce^{IV}3,4,3-LI(1,2-HOPO)]$, $[^{232}Th^{IV}3,4,3-LI(1,2-HOPO)]$, $[^{242}Pu^{IV}3,4,3-LI(1,2-HOPO)]$, and $[^{249}Bk^{IV}3,4,3-LI(1,2-HOPO)]$, relative to $[Zr^{IV}3,4,3-LI(1,2-HOPO)]$, on an XDB-C18 column. Detection achieved by mass spectrometry (m/z=859, 909, 1001, 1011, 1018 for Zr, Ce, Th, Pu, Bk, respectively).

Current processes to separate Bk from Am, Cm, Cf, and fission products after its production by neutron irradiation of Pu, Am, or Cm targets, necessitate numerous steps and use strong oxidizers such as sodium bromate to segregate Bk(IV) from the non-tetravalent ions. The non-recognition of [Bk$^{IV}$3,4,3-LI(1,2-HOPO)] by Scn suggests innovative procedures to separate Bk from M(III) ions could involve passing a 3,4,3-LI(1,2-HOPO) solution of the irradiated mixture through a Scn-containing medium, followed by size-exclusion discrimination. However, the separation of Bk(IV) from other M(IV) ions potentially present during Bk production, namely Ce, Th and Pu, also present a challenge. In current production-purification processes, the Ce—Bk pair is difficult due to the almost-identical redox properties of the two elements, which has led to complicated solvent extraction or ion exchange techniques. FIG. 26 displays the relative retention of various M(IV) complexes of 3,4,3-LI (1,2-HOPO) on a classical C18 LC column. The retention time of the Bk complex falls between those of Zr(IV) and Ce(IV), trending with the ionic radii of the metals, when octa-coordinated (0.84, 0.93, and 0.97 pm for Zr$^{4+}$, Bk$^{4+}$ and Ce$^{4+}$ respectively). Without actual optimization, [Bk$^{IV}$3,4,3-LI(1,2-HOPO)] was easily discriminated from its Ce, Th and Pu analogs. Hence, a two-step separation process is sufficient for separating Bk from all other Ln and An ions, with step 1 sequestering 3$^+$ ions based on Scn selectivity towards [M$^{III}$3,4,3-LI(1,2-HOPO)]$^-$ complexes, and step 2 separating Bk from 4$^+$ ions under classical chromatography. This entire procedure is mono-phasic, operated at room temperature and does not require any liquid-liquid extraction step or introduce additional non-volatile elements.

In some embodiments, further separation of metals with the same valence or oxidation state (such as M4+ from M4+, M3+ from M3+ or M2+ from M2+) can be achieved through classical liquid chromatography, as the complexes formed between the metal and ligands described in the invention (including 3,4,3-LI(1,2-HOPO)) exhibit different retention times on standard chromatographic columns (see FIG. 26).

EXEMPLARY EMBODIMENTS

1. A method of treating a subject in need thereof comprising administering to the subject a therapeutically effective amount of a composition including a structure

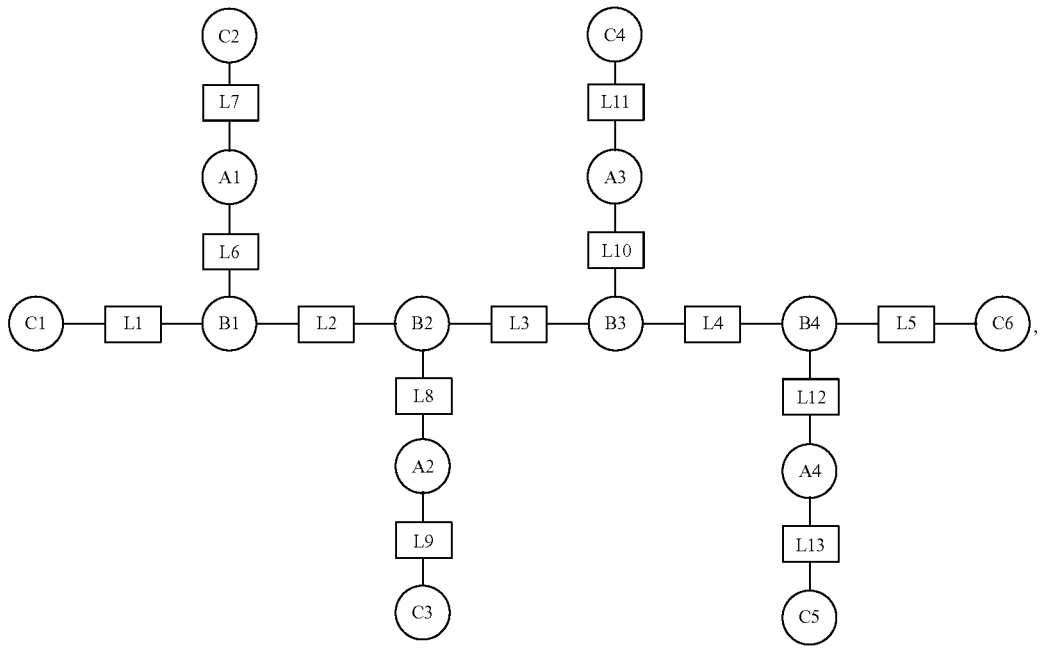

wherein:
(i) A1, A2, A3, and A4, individually, include a CAM group, a 1,2-HOPO group, or a HA group;
(ii) B1, B2, B3, and B4, individually, include an amide group or an amine group;
(iii) at least one of C1, C2, C3, C4, C5, or C6, individually, include SH, C(=O)OH, or NH$_2$;
(iv) at least another one of C1, C2, C3, C4, C5, or C6 is optional;
(v) at least one of L1, L2, L3, L4, L5, L6, L7, L8, L9, L10, L11, L12, or L13, individually, include H, an alkyl group having no greater than 10 carbon atoms, an alkylamino group having no greater than 10 carbon atoms and no greater than 2 nitrogen atoms; an alkyl ether group having no greater than 10 carbon atoms, a hydroxy ester group, or an alkyl ester group having no greater than 10 carbon atoms; and
(vi) at least one of L1, L5, L6, L7, L8, L9, L10, L11, L12, or L13 is optional;
wherein the structure of the composition is bound to a siderocalin and a metal, thereby treating the subject.

2. A method of embodiment 1, wherein at least another one of L2, L3, or L4, individually, include an amine group or an amide group.

3. A method of embodiment 1 or embodiment 2, wherein L1, C1, L7, C2, L9, C3, L11, C4, and L13, C5 are absent, L5 includes an unsubstituted alkyl group having no greater than 5 carbon atoms, and C6 includes SH, C(=O)OH, or NH$_2$.

4. A method of embodiment 3, wherein L2, L3, L4, L6, L8, L10, and L12, individually, include an unsubstituted alkyl group having no greater than 5 carbon atoms.

5. A method of embodiment 4, wherein A1 includes a CAM group or a HOPO group; A2 includes a HA group, A3 includes a HA group, and A4 includes a CAM group, a HOPO group, or a HA group.

6. A method of any one of embodiments 1-5, wherein at least one of L2, L3, or L4, individually, include an alkylamino group.

7. A method of embodiment 1, wherein B1, B2, and B3, individually, include an amide group and B4 includes an amino group, L2 and L3 include an amino group, and L4 includes an alky group having no greater than 5 carbon atoms 8. A method of embodiment 7, wherein:
C1, C2, C3, C4, C5, L1, A1, A2, A3, L1, L6, L7, L8, L9, L10, L11, L12, and L13 are absent,
A4 includes a CAM group, a HOPO group, or a HA group; and
L5 includes an alkyl group having no greater than 5 carbon atoms.

9. A method of embodiment 1, wherein B1, B2, and B3, individually, include an amide group and B4 includes an amide group, L2 and L3, individually, include an amino group, and L4 includes an alky group having no greater than 5 carbon atoms.

10. A method of embodiment 9, wherein C1, C2, C3, C4, C5, A1, A2, A3, L1, L6, L7, L8, L9, L10, L11, and L13 are absent, L12 includes an amino group, L5 includes an ether group having no greater than 10 carbon atoms, and A4 includes a CAM group, a HOPO group, or a HA group.

11. A method of embodiment 1, wherein C1, C2, C5, C6, L1, L2, L3, L4, L5, L7, L13, B2, and B4 are absent, B1 and B3, individually, include an amide group, L6, L8, L10, and L12, individually, include an amino group, A1, A2, A3, and A4, individually, include a CAM group, a HOPO group, or a HA group, L9 and L11, individually, include an alkyl group having no greater than 5 carbon atoms.

12. A method of treating a subject in need thereof comprising administering to the subject a therapeutically effective amount of a composition including a structure:

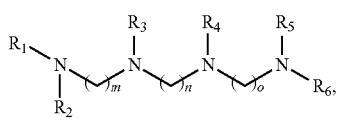

wherein:
at least one of $R_1$, $R_2$, $R_3$, $R_4$, and $R_5$, individually, include a CAM group, a HA group, or a 1,2-HOPO group;
at least another one of $R_1$, $R_2$, $R_3$, $R_4$, and $R_5$, individually, include H or an alkyl group having from 1 to 10 carbon atoms;
$R_6$ includes (i) H, (ii) an alkyl group having from 1 to 10 carbon atoms, or (iii) an alkyl group having from 1 to 10 carbon atoms and substituted by at least one of SH, $NH_2$, or $C(=O)OH$;
m can be from 1 to 6;
n can be from 1 to 6;
o can be from 1 to 6;

wherein the structure of the composition is bound to a siderocalin and a metal, thereby treating the subject.

13. A method of embodiment 12, including a structure:

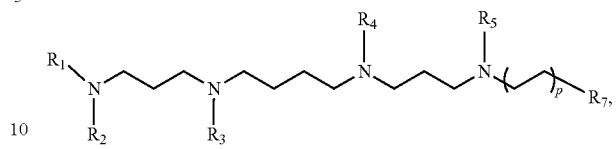

wherein:
at least one of $R_1$, $R_3$, $R_4$, or $R_5$ $R_1$, $R_2$, $R_3$, $R_4$, and $R_5$, individually, include a CAM group, a HA group, or a 1,2-HOPO group;
optionally, another one of $R_1$, $R_3$, $R_4$, or $R_5$ $R_1$, $R_2$, $R_3$, $R_4$, and $R_5$, individually, include H or an alkyl group having from 1 to 10 carbon atoms;
$R_2$ includes H or an alkyl group including from 1 to 5 carbon atoms;
$R_7$ includes SH, $C(=O)OH$, or $NH_2$; and
p is from 0 to 4.

14. A method of embodiment 13, wherein:
$R_1$ includes a CAM group or a 1,2-HOPO group;
$R_3$ and $R_4$, individually, include a HA group; and
$R_5$ includes a CAM group, a 1,2-HOPO group, or a HA group.

15. A method of embodiment 12, including a structure:

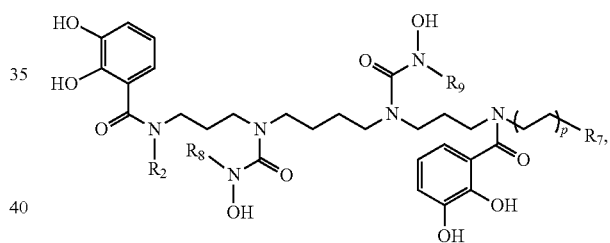

wherein:
$R_7$ includes SH, $NH_2$, or $C(=O)OH$;
$R_2$, $R_8$, and $R_9$, individually, include H, OH, or an alkyl group including from 1 to 5 carbon atoms; and
p is from 0 to 4.

16. A method of embodiment 12, including a structure:

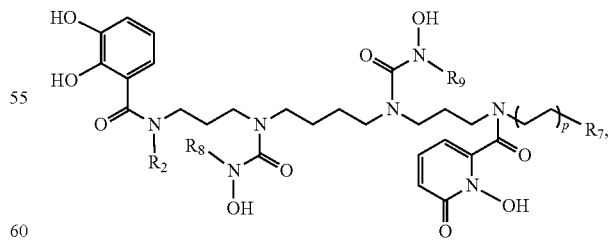

wherein:
$R_7$ includes SH, $NH_2$, or $C(=O)OH$;
$R_2$, $R_8$, and $R_9$, individually, include H, OH, or an alkyl group including from 1 to 5 carbon atoms; and
p is from 0 to 4.

17. A method of embodiment 12, including a structure:

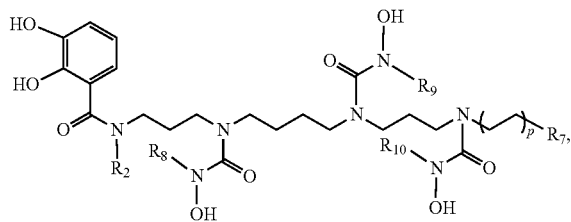

wherein:
R$_7$ includes SH, NH$_2$, or C(=O)OH;
R$_2$, R$_8$, R$_9$, and R$_{10}$, individually, include H, OH, or an alkyl group including from 1 to 5 carbon atoms; and
p is from 0 to 4.

18. A method of embodiment 12, including a structure:

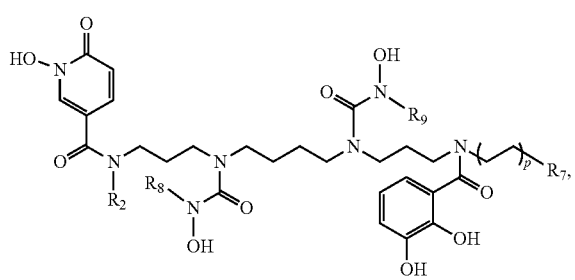

wherein:
R$_7$ includes SH, NH$_2$, or C(=O)OH;
R$_2$, R$_8$, and R$_9$, individually, include H, OH, or an alkyl group including from 1 to 5 carbon atoms; and
p is from 0 to 4.

19. A method of embodiment 12, including a structure:

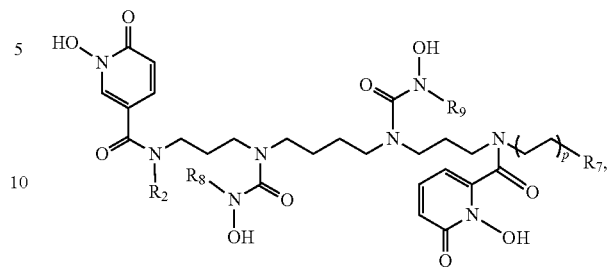

wherein:
R$_7$ includes SH, NH$_2$, or C(=O)OH;
R$_2$, R$_8$, and R$_9$, individually, include H, OH, or an alkyl group including from 1 to 5 carbon atoms; and
p is from 0 to 4.

20. A method of embodiment 12, including a structure:

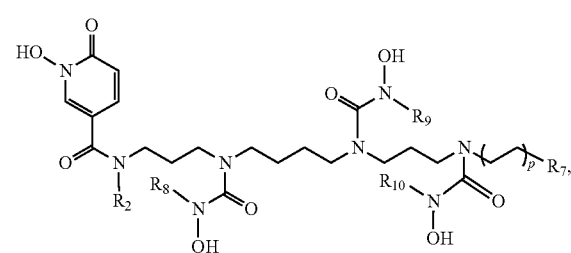

wherein:
R$_7$ includes SH, NH$_2$, or C(=O)OH;
R$_2$, R$_8$, R$_9$, and R$_{10}$, individually, include H, OH, or an alkyl group including from 1 to 5 carbon atoms; and
p is from 0 to 4.

21. A method of embodiment 12, including a structure:

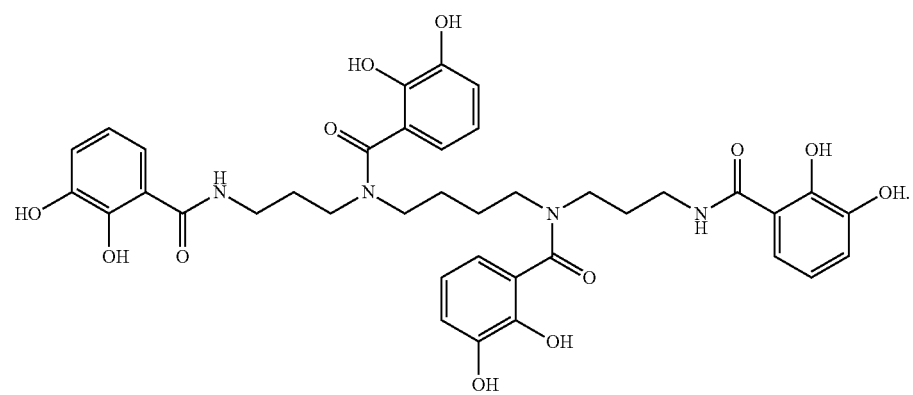 [SMILES: O=C(NCCCN(CCCCN(CCCNC(=O)c1cccc(O)c1O)C(=O)c1cccc(O)c1O)C(=O)c1cccc(O)c1O)c1cccc(O)c1O]

22. A method of embodiment 12, including a structure:

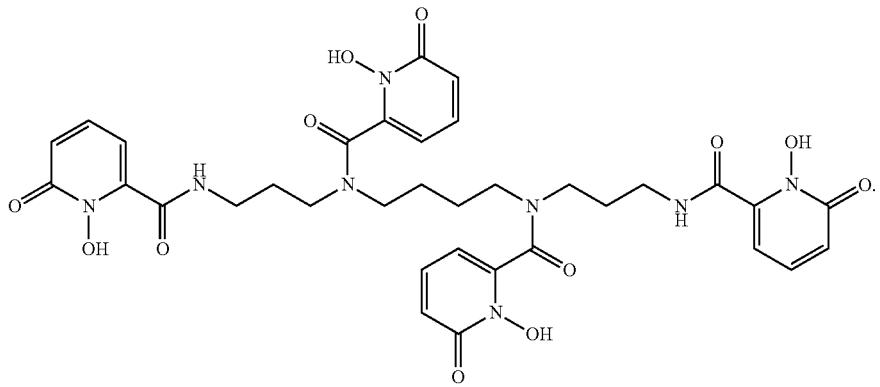 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

23. A method of treating a subject in need thereof comprising administering to the subject a therapeutically effective amount of a composition including a structure:

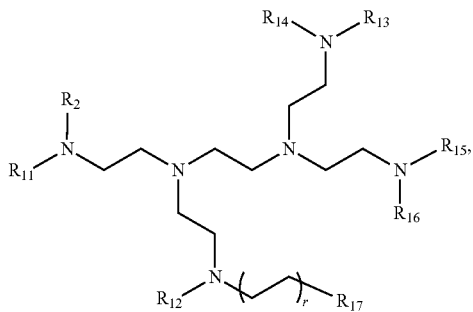

wherein:
at least one of $R_{11}$, $R_{12}$, $R_{13}$, or $R_{15}$, individually, include a CAM group, a HA group, or a 1,2-HOPO group;
optionally, at least another one of $R_{11}$, $R_{12}$, $R_{13}$, or $R_{15}$, individually, include H, OH, or an alkyl group having from 1 to 10 carbon atoms;
$R_{17}$ includes SH, $NH_2$, or C(=O)OH;
$R_2$, $R_{14}$, and $R_{16}$, individually, include H, OH, or an alkyl group having from 1 to 10 carbon atoms; and
r can be from 0 to 6
wherein the structure of the composition is bound to a siderocalin and a metal, thereby treating the subject.

24. A method of embodiment 23, wherein:
$R_{11}$ includes a CAM group or a 1,2-HOPO group;
$R_{12}$ and $R_{15}$, individually, include a HA group; and
$R_{13}$ includes a CAM group, a 1,2-HOPO group, or a HA group.

25. A method of embodiment 23, including a structure:

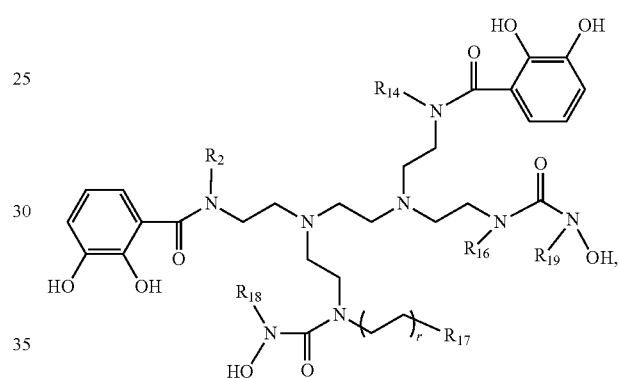

wherein:
$R_2$, $R_{14}$, $R_{16}$, $R_{18}$, and $R_{19}$, individually, include H, OH, or an alkyl group having from 1 to 10 carbon atoms;
$R_{17}$ includes SH, $NH_2$, or C(=O)OH; and
r can be from 0 to 4.

26. A method of embodiment 23, including a structure:

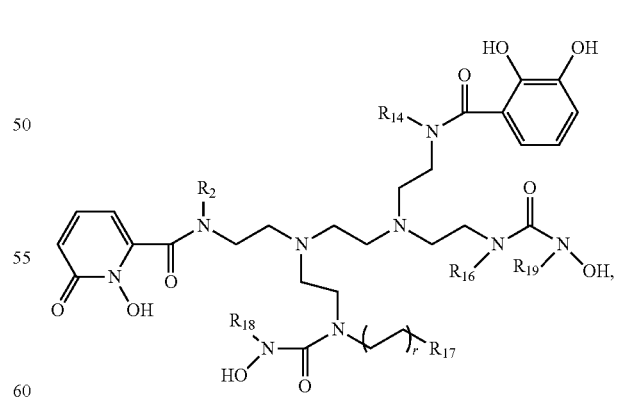

wherein
$R_2$, $R_{14}$, $R_{16}$, $R_{18}$, and $R_{19}$, individually, include H, OH, or an alkyl group having from 1 to 10 carbon atoms;
$R_{17}$ includes SH, $NH_2$, or C(=O)OH; and
r is from 0 to 4.

27. A method of embodiment 23, including a structure:

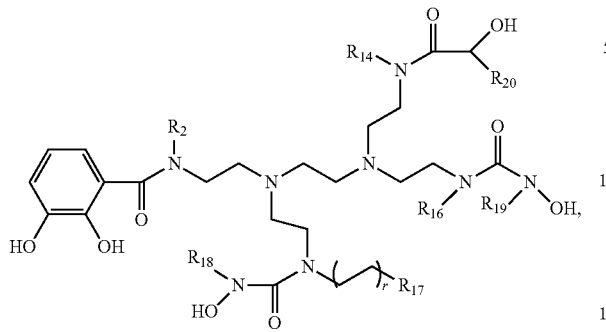

wherein:
$R_2$, $R_{14}$, $R_{16}$, $R_{18}$, $R_{19}$, and $R_{20}$, individually, include H, OH, or an alkyl group having from 1 to 10 carbon atoms;
$R_{17}$ includes SH, $NH_2$, or $C(=O)OH$; and
r can be from 0 to 4.

28. A method of embodiment 23, including a structure:

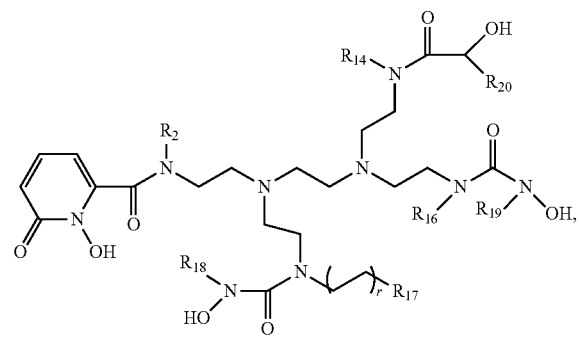

wherein:
$R_2$, $R_{14}$, $R_{16}$, $R_{18}$, $R_{19}$, and $R_{20}$, individually, include H, OH, or an alkyl group having from 1 to 10 carbon atoms;
$R_{17}$ includes SH, $NH_2$, or $C(=O)OH$; and
r can be from 0 to 4.

29. A method of embodiment 23, including a structure:

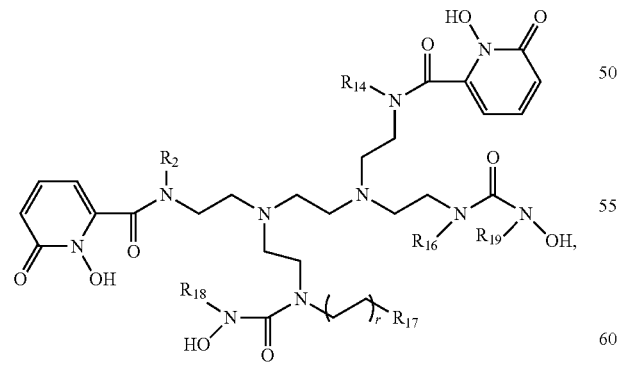

wherein:
$R_2$, $R_{14}$, $R_{16}$, $R_{18}$, and $R_{19}$, individually, include H, OH, or an alkyl group having from 1 to 10 carbon atoms;
$R_{17}$ includes SH, $NH_2$, or $C(=O)OH$; and
r is from 0 to 4.

30. A method of embodiment 23, including a structure:

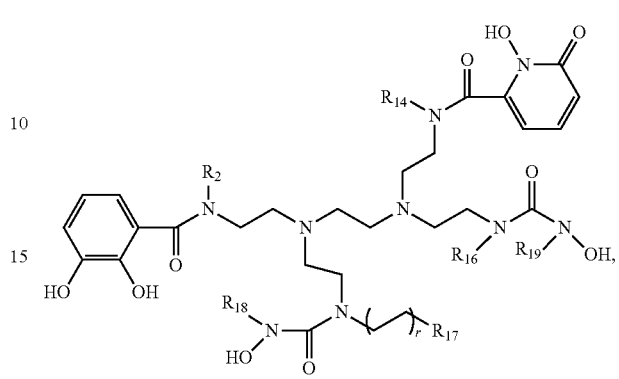

wherein:
$R_2$, $R_{14}$, $R_{16}$, $R_{18}$, and $R_{19}$, individually, include H, OH, or an alkyl group having from 1 to 10 carbon atoms;
$R_{17}$ includes SH, $NH_2$, or $C(=O)OH$;
r is from 0 to 4.

31. A method of treating a subject in need thereof comprising administering to the subject a therapeutically effective amount of a composition including a structure:

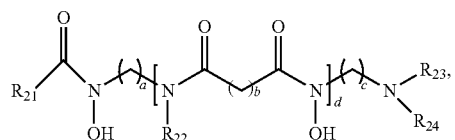

wherein:
$R_{21}$ and $R_{22}$, individually, include H, OH, or an alkyl group having from 1 to 10 carbon atoms;
$R_{23}$ includes H, OH, an alkyl group having from 1 to 10 carbon atoms, or $(CH_2)_e R_a$,
where $R_a$ is SH, $C(=O)OH$, or $NH_2$;
$R_{24}$ includes a substituent having a CAM group, a 1,2-HOPO group, or a HA group;
a, b, and c, individually, are from 1 to 10;
d is from 1 to 4; and
e is from 1 to 10;
wherein the structure of the composition is bound to a siderocalin and a metal, thereby treating the subject.

32. A method of embodiment 31, wherein $R_{24}$ includes a substituent having SH, $C(=O)OH$, or $NH_2$.

33. A method of embodiment 31, including a structure:

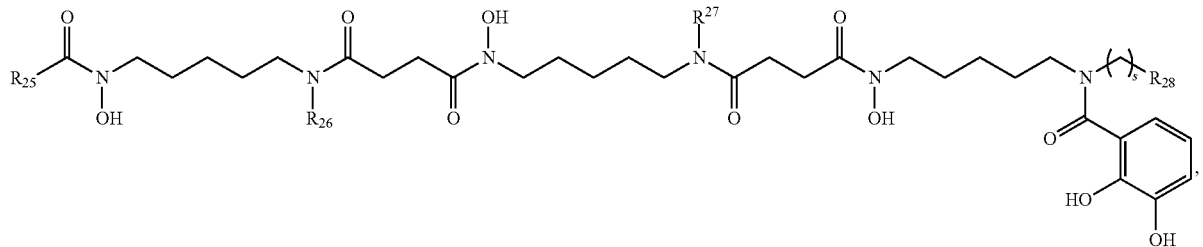

wherein:
$R_{25}$, $R_{26}$, and $R_{27}$, individually, include H, OH, or an alkyl group having from 1 to 10 carbon atoms;
$R_{28}$ includes H, an alkyl group having from 1 to 5 carbon atoms, SH, $NH_2$, or $C(=O)OH$; and
s is from 0 to 4.

34. A method of embodiment 31, including a structure:

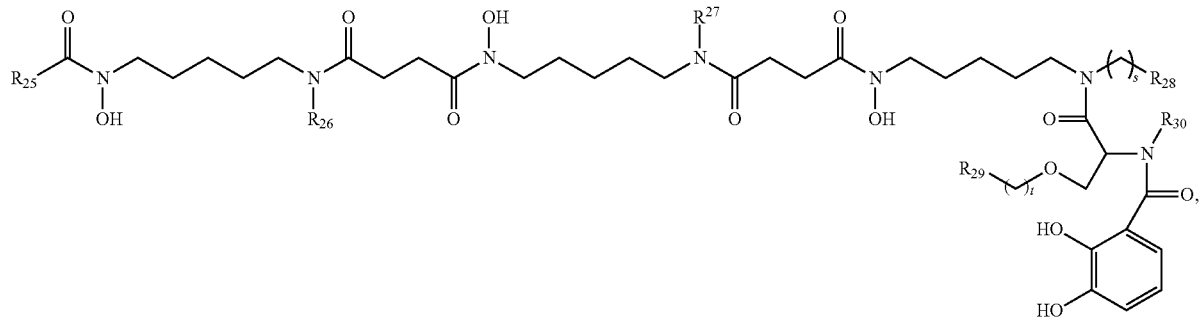

wherein:
$R_{25}$, $R_{26}$, $R_{27}$, and $R_{30}$, individually, include H, OH, or an alkyl group having from 1 to 10 carbon atoms;
$R_{28}$ and $R_{29}$, individually, include H, an alkyl group having from 1 to 5 carbon atoms, SH, $NH_2$, or $C(=O)OH$;
s is from 0 to 4; and
t is from 0 to 4.

35. A method of embodiment 31, including a structure:

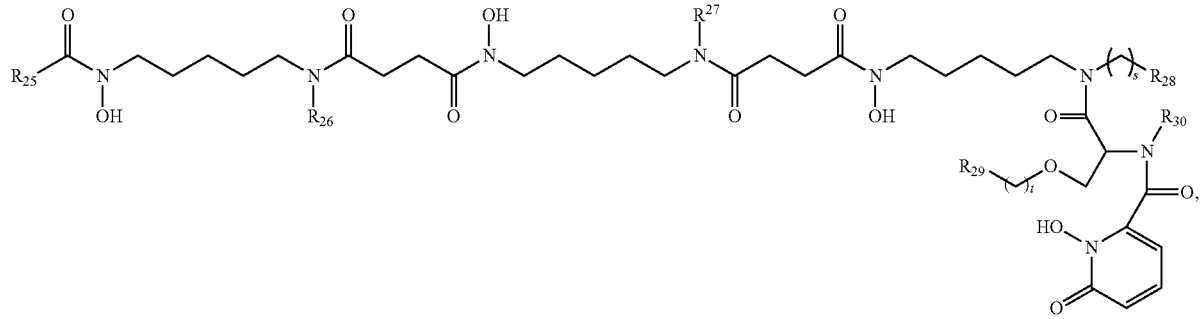

wherein:
$R_{25}$, $R_{26}$, $R_{27}$, and $R_{30}$, individually, include H, OH, or an alkyl group having from 1 to 10 carbon atoms;
$R_{28}$ and $R_{29}$, individually, include H, an alkyl group having from 1 to 5 carbon atoms, SH, $NH_2$, or $C(=O)OH$;
s is from 0 to 4; and
t is from 0 to 4.

36. A method of embodiment 31, including a structure:

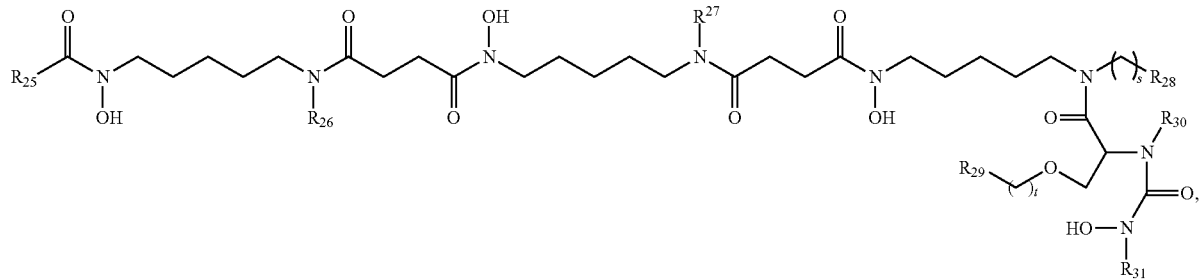

wherein:
$R_{25}$, $R_{26}$, $R_{27}$, $R_{30}$, and $R_{31}$, individually, include H, OH, or an alkyl group having from 1 to 10 carbon atoms;
$R_{28}$ and $R_{29}$, individually, include H, an alkyl group having from 1 to 5 carbon atoms, SH, $NH_2$, or $C(=O)OH$;
s is from 0 to 4; and
t is from 0 to 4.

37. A method of embodiment 31, including a structure:

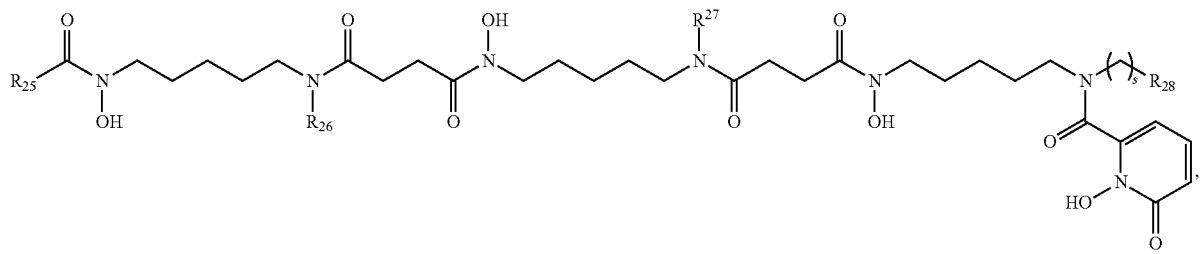

wherein
$R_{25}$, $R_{26}$, and $R_{27}$, individually, include H, OH, or an alkyl group having from 1 to 10 carbon atoms;
$R_{28}$ includes H, an alkyl group having from 1 to 5 carbon atoms, SH, $NH_2$, or $C(=O)OH$; and
s is from 0 to 4.

38. A method of embodiment 31, including a structure:

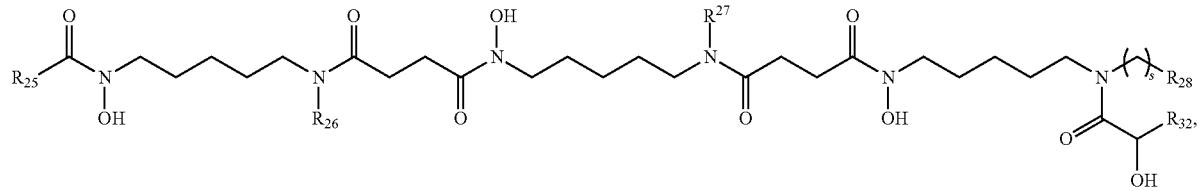

wherein:
$R_{25}$, $R_{26}$, $R_{27}$, and $R_{32}$, individually, include H, OH, or an alkyl group having from 1 to 10 carbon atoms;
$R_{28}$ includes H, an alkyl group having from 1 to 5 carbon atoms, SH, $NH_2$, or $C(=O)OH$; and
s is from 0 to 4.

39. A method of treating a subject in need thereof comprising administering to the subject a therapeutically effective amount of a composition including a structure:

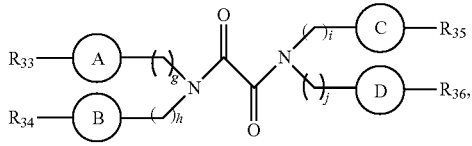

wherein:
A, B, C, and D, individually, include one or more amide groups, one or more amine groups, or an alkyl group having from 1 to 10 carbon atoms;
$R_{33}$, $R_{34}$, $R_{35}$, and $R_{36}$, individually, include a CAM group, a 1,2-HOPO group, or a HA group; and
g, h, i, and j, individually, are from 1 to 10;
wherein the structure of the composition is bound to a siderocalin and a metal, thereby treating the subject.

40. A method of embodiment 39, including a structure:

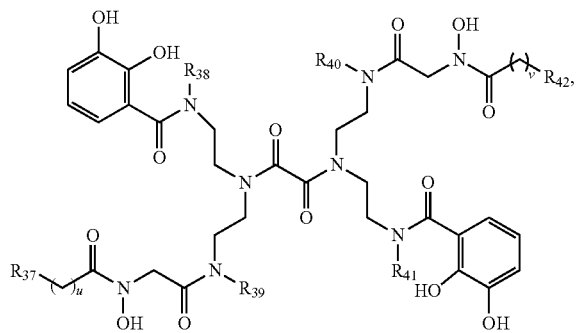

wherein:
$R_{37}$ and $R_{42}$, individually, include H, an alkyl group having from 1 to 5 carbon atoms, SH, C(=O)OH, or $NH_2$;
$R_{38}$, $R_{39}$, $R_{40}$, and $R_{41}$, individually, include H, OH, or an alkyl group having from 1 to 5 carbon atoms; and
u and v, individually, are from 0 to 5.

41. A method of embodiment 39, including a structure:

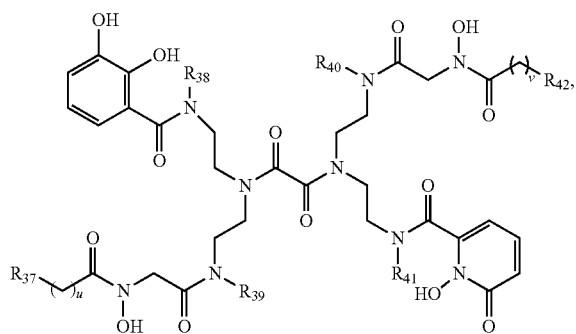

wherein:
$R_{37}$ and $R_{42}$, individually, include H, an alkyl group having from 1 to 5 carbon atoms, SH, C(=O)OH, or $NH_2$;
$R_{38}$, $R_{39}$, $R_{40}$, and $R_{41}$, individually, include H, OH, or an alkyl group having from 1 to 5 carbon atoms; and
u and v, individually, are from 0 to 5.

42. A method of embodiment 39, including a structure:

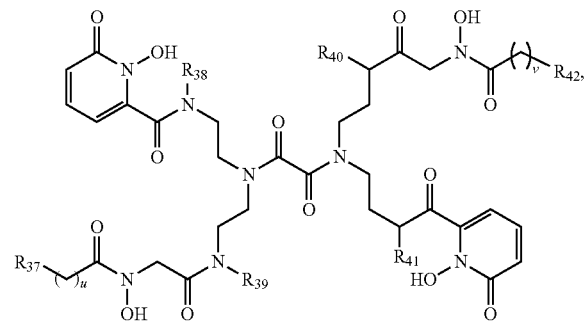

wherein:
$R_{37}$ and $R_{42}$, individually, include H, an alkyl group having from 1 to 5 carbon atoms, SH, C(=O)OH, or $NH_2$;
$R_{38}$, $R_{39}$, $R_{40}$, and $R_{41}$, individually, include H, OH, or an alkyl group having from 1 to 5 carbon atoms; and
u and v, individually, are from 0 to 5.

43. A method of any one of embodiments 1-42, wherein the siderocalin includes any of SEQ ID NOs: 1-25.

44. A method of any one of embodiments 1-43, wherein the composition is bound to:
position K125 of siderocalin;
position K134 of siderocalin, or
both position K125 and position K134 of siderocalin.

45. A method of any one of embodiments 1-44, wherein the metal is a radionuclide.

46. A method of embodiment 45, wherein the radionuclide includes $^{225}Ac$, $^{226}Ac$, $^{228}Ac$, $^{105}Ag$, $^{106}mAg$, $^{110}mAg$, $^{111}Ag$, $^{112}Ag$, $^{113}Ag$, $^{239}Am$, $^{240}Am$, $^{242}Am$, $^{244}Am$, $^{37}Ar$, $^{71}As$, $^{72}As$, $^{73}As$, $^{74}As$, $^{76}As$, $^{77}As$, $^{209}At$, $^{210}At$, $^{191}Au$, $^{192}Au$, $^{193}Au$, $^{194}Au$, $^{195}Au$, $^{196}Au$, $^{196}m^2Au$, $^{198}Au$, $^{198}mAu$, $^{199}Au$, $^{200}mAu$, $^{128}Ba$, $^{131}Ba$, $^{133}mBa$, $^{135}mBa$, $^{140}Ba$, $^{7}Be$, $^{203}Bi$, $^{204}Bi$, $^{205}Bi$, $^{206}Bi$, $^{210}Bi$, $^{212}Bi$, $^{243}Bk$, $^{244}Bk$, $^{245}Bk$, $^{246}Bk$, $^{248}mBk$, $^{250}Bk$, $^{76}Br$, $^{77}Br$, $^{80}mBr$, $^{82}Br$, $^{11}C$, $^{14}C$, $^{45}Ca$, $^{47}Ca$, $^{107}Cd$, $^{115}Cd$, $^{115}mCd$, $^{117}mCd$, $^{132}Ce$, $^{133}mCe$, $^{134}Ce$, $^{135}Ce$, $^{137}Ce$, $^{137}mCe$, $^{139}Ce$, $^{141}Ce$, $^{143}Ce$, $^{144}Ce$, $^{246}Cf$, $^{247}Cf$, $^{253}Cf$, $^{254}Cf$, $^{240}Cm$, $^{241}Cm$, $^{242}Cm$, $^{252}Cm$, $^{55}Co$, $^{56}Co$, $^{57}Co$, $^{58}Co$, $^{58}mCo$, $^{60}Co$, $^{48}Cr$, $^{51}Cr$, $^{127}Cs$, $^{129}Cs$, $^{131}Cs$, $^{132}Cs$, $^{136}Cs$, $^{137}Cs$, $^{61}Cu$, $^{62}Cu$, $^{64}Cu$, $^{67}Cu$, $^{153}Dy$, $^{155}Dy$, $^{157}Dy$, $^{159}Dy$, $^{165}Dy$, $^{166}Dy$, $^{160}Er$, $^{161}Er$, $^{165}Er$, $^{169}Er$, $^{171}Er$, $^{172}Er$, $^{250}Es$, $^{251}Es$, $^{253}Es$, $^{254}Es$, $^{254}mEs$, $^{255}Es$, $^{256}mEs$, $^{145}Eu$, $^{146}Eu$, $^{147}Eu$, $^{148}Eu$, $^{149}Eu$, $^{150}mEu$, $^{152}mEu$, $^{156}Eu$, $^{157}Eu$, $^{52}Fe$, $^{59}Fe$, $^{251}Fm$, $^{252}Fm$, $^{253}Fm$, $^{254}Fm$, $^{255}Fm$, $^{257}Fm$, $^{66}Ga$, $^{67}Ga$, $^{68}Ga$, $^{72}Ga$, $^{73}Ga$, $^{146}Gd$, $^{147}Gd$, $^{149}Gd$, $^{151}Gd$, $^{153}Gd$, $^{159}Gd$, $^{68}Ge$, $^{69}Ge$, $^{71}Ge$, $^{77}Ge$, $^{170}Hf$, $^{171}Hf$, $^{173}Hf$, $^{175}Hf$, $^{179}m^2Hf$, $^{180}mHf$, $^{181}Hf$, $^{184}Hf$, $^{192}Hg$, $^{193}Hg$, $^{193}mHg$, $^{195}Hg$, $^{195}mHg$, $^{197}Hg$, $^{197}mHg$, $^{203}Hg$, $^{160}mHo$, $^{166}Ho$, $^{167}Ho$, $^{123}I$, $^{124}I$, $^{126}I$, $^{130}I$, $^{132}I$, $^{133}I$, $^{135}I$, $^{109}In$, $^{110}In$, $^{111}In$, $^{114}mIn$, $^{115}mIn$, $^{184}Ir$, $^{185}Ir$, $^{186}Ir$, $^{187}Ir$, $^{188}Ir$, $^{189}Ir$, $^{190}Ir$, $^{190}m^2Ir$, $^{192}Ir$, $^{193}mIr$, $^{194}Ir$, $^{194}m^2Ir$, $^{195}mIr$, $^{42}K$, $^{43}K$, $^{76}Kr$, $^{79}Kr$, $^{81}mKr$, $^{85}mKr$, $^{132}La$, $^{133}La$, $^{135}La$, $^{140}La$, $^{141}La$, $^{262}Lr$, $^{169}Lu$, $^{170}Lu$, $^{171}Lu$, $^{172}Lu$, $^{174}mLu$, $^{176}mLu$, $^{177}Lu$, $^{177}mLu$, $^{179}Lu$, $^{257}Md$, $^{258}Md$, $^{260}Md$, $^{28}Mg$, $^{52}Mn$, $^{90}Mo$, $^{93}mMo$, $^{99}Mo$, $^{13}N$, $^{24}Na$, $^{90}Nb$, $^{91}mNb$, $^{92}mNb$, $^{95}Nb$, $^{95}mNb$, $^{96}Nb$, $^{138}Nd$, $^{139}mNd$, $^{140}Nd$, $^{147}Nd$, $^{56}Ni$, $^{57}Ni$, $^{66}Ni$, $^{234}Np$, $^{236}mNp$, $^{238}Np$, $^{239}Np$, $^{15}O$, $^{182}Os$, $^{183}Os$, $^{183}mOs$, $^{185}Os$, $^{189}mOs$, $^{191}Os$, $^{191}mOs$, $^{193}$Os, $^{32}$P, $^{33}$P, $^{228}$Pa, $^{229}$Pa, $^{230}$Pa, $^{232}$Pa, $^{233}$Pa, $^{234}$Pa, $^{200}$Pb, $^{201}$Pb, $^{202}$mPb, $^{203}$Pb, $^{209}$Pb, $^{212}$Pb, $^{100}$Pd, $^{101}$Pd, $^{103}$Pd, $^{109}$Pd, $^{111}$mPd, $^{112}$Pd, $^{143}$Pm, $^{148}$Pm, $^{148}$mPm, $^{149}$Pm, $^{151}$Pm, $^{204}$Po, $^{206}$Po, $^{207}$Po, $^{210}$Po, $^{139}$Pr, $^{142}$Pr, $^{143}$Pr, $^{145}$Pr, $^{188}$Pt, $^{189}$Pt, $^{191}$Pt, $^{193}$mPt, $^{195}$mPt, $^{197}$Pt, $^{200}$Pt, $^{202}$Pt, $^{234}$Pu, $^{237}$Pu, $^{243}$Pu, $^{245}$Pu, $^{246}$Pu, $^{247}$Pu, $^{223}$Ra, $^{224}$Ra, $^{225}$Ra, $^{81}$Rb, $^{82}$Rb, $^{82}$mRb, $^{83}$Rb, $^{84}$Rb, $^{86}$Rb, $^{181}$Re, $^{182}$Re, $^{182}$mRe, $^{183}$Re, $^{184}$Re, $^{184}$mRe, $^{186}$Re, $^{188}$Re, $^{189}$Re, $^{190}$mRe, $^{99}$Rh, $^{99}$mRh, $^{100}$Rh, $^{101}$mRh, $^{102}$Rh, $^{103}$mRh, $^{105}$Rh, $^{211}$Rn, $^{222}$Rn, $^{97}$Ru, $^{103}$Ru, $^{105}$Ru, $^{35}$S, $^{118}$mSb, $^{119}$Sb, $^{120}$Sb, $^{120}$mSb, $^{122}$Sb, $^{124}$Sb, $^{126}$Sb, $^{127}$Sb, $^{128}$Sb, $^{129}$Sb, $^{43}$Sc, $^{44}$Sc, $^{44}$mSc, $^{46}$Sc, $^{47}$Sc, $^{48}$Sc, $^{72}$Se, $^{73}$Se, $^{75}$Se, $^{153}$Sm, $^{156}$Sm, $^{110}$Sn, $^{113}$Sn, $^{117}$mSn, $^{119}$mSn, $^{121}$Sn, $^{123}$Sn, $^{125}$Sn, $^{82}$Sr, $^{83}$Sr, $^{85}$Sr, $^{89}$Sr, $^{91}$Sr, $^{173}$Ta, $^{175}$Ta, $^{176}$Ta, $^{177}$Ta, $^{180}$Ta, $^{182}$Ta, $^{183}$Ta, $^{184}$Ta, $^{149}$Tb, $^{150}$Tb, $^{151}$Tb, $^{152}$Tb, $^{153}$Tb, $^{154}$Tb, $^{154}$mTb, $^{154}$m²Tb, $^{155}$Tb, $^{156}$Tb, $^{156}$mTb, $^{156}$m²Tb, $^{160}$Tb, $^{161}$Tb, $^{94}$Tc, $^{95}$Tc, $^{95}$mTc, $^{96}$Tc, $^{97}$mTc, $^{99}$mTc, $^{118}$Te, $^{119}$Te, $^{119}$mTe, $^{121}$Te, $^{121}$mTe, $^{123}$mTe, $^{125}$mTe, $^{127}$Te, $^{127}$mTe, $^{129}$mTe, $^{131}$mTe, $^{132}$Te, $^{227}$Th, $^{231}$Th, $^{234}$Th, $^{45}$Ti, $^{198}$Tl, $^{199}$Tl, $^{200}$Tl, $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W, $^{181}$W, $^{185}$W, $^{187}$W, $^{188}$W, $^{122}$Xe, $^{125}$Xe, $^{127}$Xe, $^{129}$mXe, $^{131}$mXe, $^{133}$Xe, $^{133}$mXe, $^{135}$Xe, $^{85}$mY, $^{86}$Y, $^{87}$Y, $^{87}$mY, $^{88}$Y, $^{90}$Y, $^{90}$mY, $^{91}$Y, $^{92}$Y, $^{93}$Y, $^{166}$Yb, $^{169}$Yb, $^{175}$Yb, $^{62}$Zn, $^{65}$Zn, $^{69}$mZn, $^{71}$mZn, $^{72}$Zn, $^{86}$Zr, $^{88}$Zr, $^{89}$Zr, $^{95}$Zr, and/or $^{97}$Zr.

47. A method of embodiment 45, wherein the radionuclide includes $^{90}$Y, $^{67}$Cu, $^{213}$Bi, $^{212}$Bi, $^{186}$Re, $^{67}$Cu $^{90}$Y, $^{213}$Bi, $^{177}$Lu, $^{186}$Re, and/or $^{67}$Ga.

48. A method of embodiment 45, wherein the radionuclide includes $^{89}$Zr, $^{225}$Ac, and/or $^{227}$Th.

49. A method of any one of embodiments 45-48, wherein the metal includes a daughter isotope of a radionuclide.

50. A method of embodiment 49, wherein the daughter isotope of the radionuclide includes $^{89}$Y, $^{18}$O, $^{221}$Fr, $^{213}$Bi, and/or $^{209}$Pb.

51. A method of any of embodiments 1-50, wherein the treating provides imaging to aid in diagnosis; to locate a position for a therapeutic intervention; to assess the functioning of a body part; and/or to assess the presence or absence of a condition.

52. A method of embodiment 51, wherein the imaging is through positron emission tomography (PET), single photon emission computed tomography, radioisotope renography, or scintigraphy 53. A method of any of embodiments 1-52, wherein the treating reduces cellular proliferation.

54. A method of embodiment 53, wherein the cellular proliferation is due to cancer, a thyroid disease, a blood disorder, and/or restenosis.

55. A method of embodiment 54, wherein the cancer is adrenal cancer, bladder cancer, blood cancer, bone cancer, brain cancer, breast cancer, carcinoma, cervical cancer, colon cancer, colorectal cancer, corpus uterine cancer, ear, nose and throat (ENT) cancer, endometrial cancer, esophageal cancer, gastrointestinal cancer, head and neck cancer, Hodgkin's disease cancer, intestinal cancer, kidney cancer, larynx cancer, leukemia, liver cancer, lymph node cancer, lymphoma, lung cancer, melanoma, mesothelioma, myeloma, nasopharynx cancer, neuroblastoma, non-Hodgkin's lymphoma, oral cancer, ovarian cancer, pancreatic cancer, penile cancer, pharynx cancer, prostate cancer, rectal cancer, sarcomcancer, seminomcancer, skin cancer, stomach cancer, teratomcancer, testicular cancer, thyroid cancer, uterine cancer, vaginal cancer, vascular tumor cancer, and/or cancer from metastases thereof.

56. A method of embodiment 54, wherein the thyroid disease is hyperthyroidism or thyrotoxicosis.

57. A method of embodiment 54, wherein the blood disorder is Polycythemia vera.

58. A method of embodiment 54, wherein the restenosis follows balloon angioplasty and/or stent placement.

59. A composition including a mutated siderocalin with position 54 modified from threonine to cysteine, position 68 modified from serine to cysteine, or both position 54 modified from threonine to cysteine and position 68 modified from serine to cysteine.

60. A composition of embodiment 59, wherein the mutated siderocalin is bound to any of the structures included in embodiments 1-42 at least at position 54, position 68, or both position 54 and position 68.

61. A method of treating a subject in need thereof comprising administering a therapeutically effective amount of a composition of embodiments 59 or 60 to the subject thereby treating the subject.

62. A method of synthesizing a siderophore including at least one SH substituent using dichlorodiphenylmethane.

63. A kit including one or more compositions including the structure included in any of embodiments 1-42, one or more siderocalins, and/or one or more metals.

64. A kit of embodiment 54, wherein the one or more siderocalins include any of SEQ ID NOs. 1-25.

65. A kit of embodiment 54 or 55, wherein the metal is a radionuclide.

66. A kit of embodiment 56 wherein the metal is a radionuclide of any of embodiments 46-50.

67. A method including performing imaging and treatment of a condition in a same subject using the same combination of a siderocalin, a chelator, and a metal in the imaging and the treatment of the subject.

68. A method of embodiment 67, wherein the chelator comprises the structure included in any of embodiments 1-42.

69. A method of embodiment 67 or 68, wherein the siderocalin includes one of SEQ ID NOs. 1-25.

70. A method of embodiment 67 or 68 wherein the siderocalin is a mutated siderocalin with position 54 modified from threonine to cysteine, position 68 modified from serine to cysteine, or both position 54 modified from threonine to cysteine and position 68 modified from serine to cysteine.

71. A method of embodiment 70, wherein the mutated siderocalin is bound to the chelator at least at position 54, position 68, or both position 54 and position 68.

72. A method of any of embodiments 67-71, wherein the metal is a radionuclide.

73. A method of any of embodiments 67-71, wherein the metal is a radionuclide of embodiment 46.

74. A method of any of embodiments 67-71 wherein the metal is a radionuclide selected from $^{90}$Y, $^{67}$Cu, $^{213}$Bi, $^{212}$Bi, $^{186}$Re, $^{67}$Cu $^{90}$Y, $^{213}$Bi, $^{177}$Lu, $^{186}$Re, and $^{67}$Ga.

75. A method of any of embodiments 67-71 wherein the metal is a radionuclide selected from $^{89}$Zr, $^{225}$Ac, and $^{227}$Th.

76. A composition having a structure including:

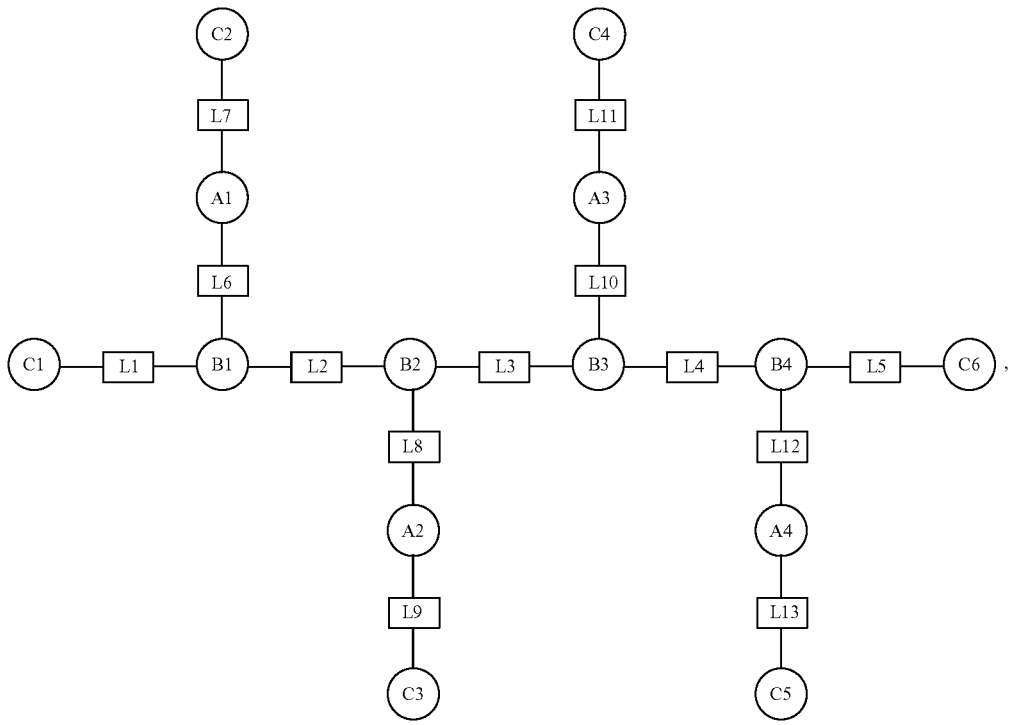

wherein:
(i) A1, A2, A3, and A4, individually, include a CAM group, a 1,2-HOPO group, or a HA group;
(ii) B1, B2, B3, and B4, individually, include an amide group or an amine group;
(iii) at least one of C1, C2, C3, C4, C5, or C6, individually, include SH;
(iv) at least another one of C1, C2, C3, C4, C5, or C6 is optional and, individually, includes C(=O)OH or $NH_2$;
(v) at least one of L1, L2, L3, L4, L5, L6, L7, L8, L9, L10, L11, L12, or L13, individually, include H, an alkyl group having no greater than 10 carbon atoms, an alkylamino group having no greater than 10 carbon atoms and no greater than 2 nitrogen atoms; an alkyl ether group having no greater than 10 carbon atoms, a hydroxy ester group, or an alkyl ester group having no greater than 10 carbon atoms; and
(vi) at least one of L1, L5, L6, L7, L8, L9, L10, L11, L12, or L13 is optional.

77. A composition of embodiment 76, wherein at least another one of L2, L3, or L4, individually, include an amine group or an amide group.

78. A composition of embodiment 76 or embodiment 77, wherein L1, C1, L7, C2, L9, C3, L11, C4, and L13, C5 are absent, L5 includes an unsubstituted alkyl group having no greater than 5 carbon atoms, and C6 includes SH, C(=O)OH, or $NH_2$.

79. A composition of embodiment 78, wherein L2, L3, L4, L6, L8, L10, and L12, individually, include an unsubstituted alkyl group having no greater than 5 carbon atoms.

80. A composition of embodiment 79, wherein A1 includes a CAM group or a HOPO group; A2 includes a HA group, A3 includes a HA group, and A4 includes a CAM group, a HOPO group, or a HA group.

81. A composition of any one of embodiments 76-80, wherein at least one of L2, L3, or L4, individually, include an alkylamino group.

82. A composition of embodiment 76, wherein B1, B2, and B3, individually, include an amide group and B4 includes an amino group, L2 and L3 include an amino group, and L4 includes an alky group having no greater than 5 carbon atoms 83. A composition of embodiment 82, wherein:

C1, C2, C3, C4, C5, L1, A1, A2, A3, L1, L6, L7, L8, L9, L10, L11, L12, and L13 are absent, A4 includes a CAM group, a HOPO group, or a HA group; and L5 includes an alkyl group having no greater than 5 carbon atoms.

84. A composition of embodiment 76, wherein B1, B2, and B3, individually, include an amide group and B4 includes an amide group, L2 and L3, individually, include an amino group, and L4 includes an alky group having no greater than 5 carbon atoms.

85. A composition of embodiment 84, wherein C1, C2, C3, C4, C5, A1, A2, A3, L1, L6, L7, L8, L9, L10, L11, and L13 are absent, L12 includes an amino group, L5 includes an ether group having no greater than 10 carbon atoms, and A4 includes a CAM group, a HOPO group, or a HA group.

86. A composition of embodiment 85, wherein C1, C2, C5, C6, L1, L2, L3, L4, L5, L7, L13, B2, and B4 are absent, B1 and B3, individually, include an amide group, L6, L8, L10, and L12, individually, include an amino group, A1, A2, A3, and A4, individually, include a CAM group, a HOPO group, or a HA group, L9 and L11, individually, include an alkyl group having no greater than 5 carbon atoms.

87. A composition, including a structure:

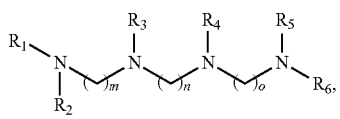

wherein:
at least one of $R_1$, $R_2$, $R_3$, $R_4$, and $R_5$, individually, include a CAM group, a HA group, or a 1,2-HOPO group;
at least another one of $R_1$, $R_2$, $R_3$, $R_4$, and $R_5$, individually, include H or an alkyl group having from 1 to 10 carbon atoms;
$R_6$ includes an alkyl group having from 1 to 10 carbon atoms and substituted by SH;
m can be from 1 to 6;
n can be from 1 to 6;
o can be from 1 to 6.

88. A composition of embodiment 87, including a structure:

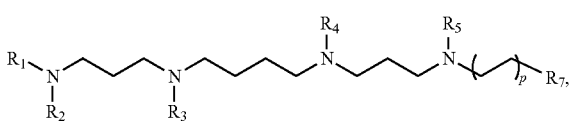

wherein:
at least one of $R_1$, $R_3$, $R_4$, or $R_5$ $R_1$, $R_2$, $R_3$, $R_4$, and $R_5$, individually, include a CAM group, a HA group, or a 1,2-HOPO group;
optionally, another one of $R_1$, $R_3$, $R_4$, or $R_5$ $R_1$, $R_2$, $R_3$, $R_4$, and $R_5$, individually, include H or an alkyl group having from 1 to 10 carbon atoms;
$R_2$ includes H or an alkyl group including from 1 to 5 carbon atoms;
$R_7$ includes SH; and
p is from 0 to 4.

89. A composition of embodiment 88, wherein:
$R_1$ includes a CAM group or a 1,2-HOPO group;
$R_3$ and $R_4$, individually, include a HA group; and
$R_5$ includes a CAM group, a 1,2-HOPO group, or a HA group.

90. A composition of embodiment 87, including a structure:

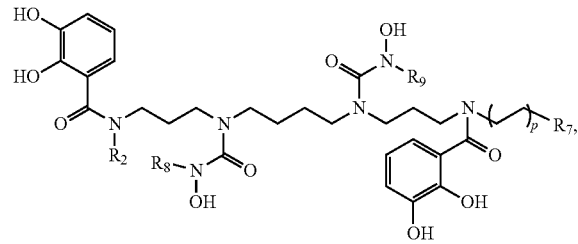

wherein:
$R_7$ includes SH;
$R_2$, $R_8$, and $R_9$, individually, include H, OH, or an alkyl group including from 1 to 5 carbon atoms; and
p is from 0 to 4.

91. A composition of embodiment 87, including a structure:

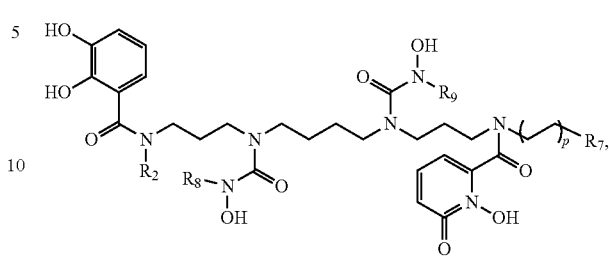

wherein:
$R_7$ includes SH;
$R_2$, $R_8$, and $R_9$, individually, include H, OH, or an alkyl group including from 1 to 5 carbon atoms; and
p is from 0 to 4.

92. A composition of embodiment 87, including a structure:

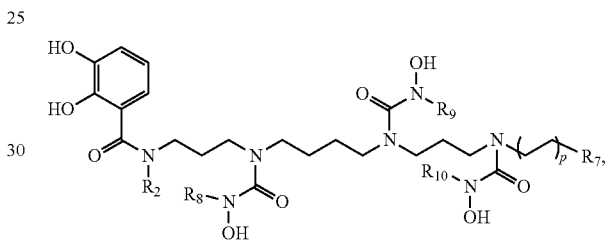

wherein:
$R_7$ includes SH;
$R_2$, $R_8$, $R_9$, and $R_{10}$, individually, include H, OH, or an alkyl group including from 1 to 5 carbon atoms; and
p is from 0 to 4.

93. A composition of embodiment 87, including a structure:

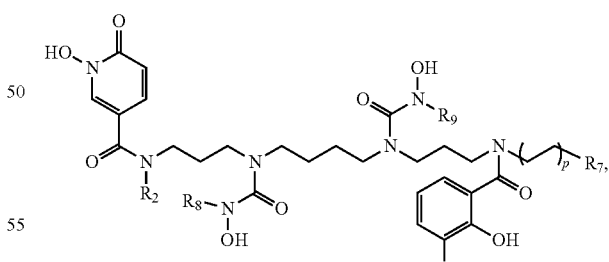

wherein:
$R_7$ includes SH;
$R_2$, $R_8$, and $R_9$, individually, include H, OH, or an alkyl group including from 1 to 5 carbon atoms; and
p is from 0 to 4.

94. A composition of embodiment 87, including a structure:

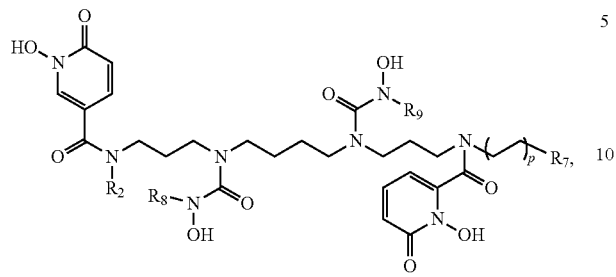

wherein:
$R_7$ includes SH;
$R_2$, $R_8$, and $R_9$, individually, include H, OH, or an alkyl group including from 1 to 5 carbon atoms; and
p is from 0 to 4.

95. A composition of embodiment 87, including a structure:

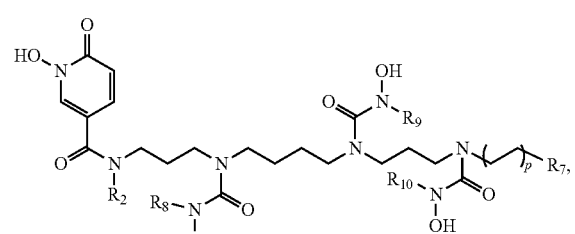

wherein:
$R_7$ includes SH;
$R_2$, $R_8$, $R_9$, and $R_{10}$, individually, include H, OH, or an alkyl group including from 1 to 5 carbon atoms; and
p is from 0 to 4.

96. A composition, including a structure:

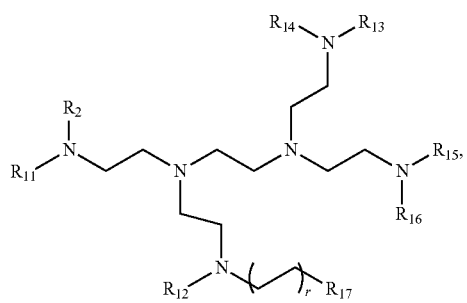

wherein:
at least one of $R_{11}$, $R_{12}$, $R_{13}$, or $R_{15}$, individually, include a CAM group, a HA group, or a 1,2-HOPO group;
optionally, at least another one of $R_{11}$, $R_{12}$, $R_{13}$, or $R_{15}$, individually, include H, OH, or an alkyl group having from 1 to 10 carbon atoms;
$R_{17}$ includes SH;
$R_2$, $R_{14}$, and $R_{16}$, individually, include H, OH, or an alkyl group having from 1 to 10 carbon atoms; and
r can be from 0 to 6.

97. A composition of embodiment 96, wherein:
$R_{11}$ includes a CAM group or a 1,2-HOPO group;
$R_{12}$ and $R_{15}$, individually, include a HA group; and
$R_{13}$ includes a CAM group, a 1,2-HOPO group, or a HA group.

98. A composition of embodiment 96, including a structure:

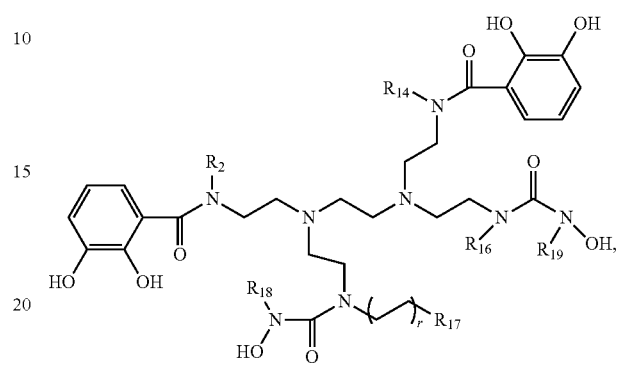

wherein:
$R_2$, $R_{14}$, $R_{16}$, $R_{18}$, and $R_{19}$, individually, include H, OH, or an alkyl group having from 1 to 10 carbon atoms; and
r can be from 0 to 4.

99. A composition of embodiment 96, including a structure:

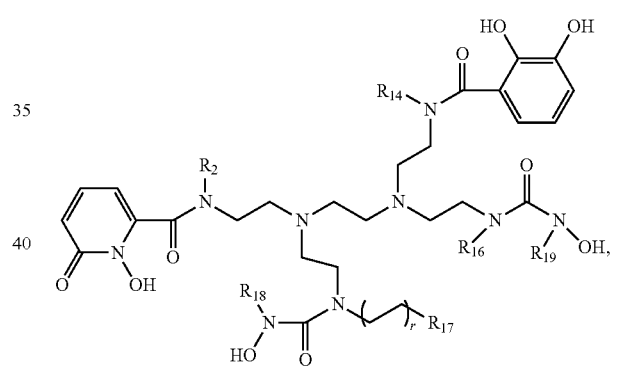

wherein
$R_2$, $R_{14}$, $R_{16}$, $R_{18}$, and $R_{19}$, individually, include H, OH, or an alkyl group having from 1 to 10 carbon atoms; and
r is from 0 to 4.

100. A composition of embodiment 96, including a structure:

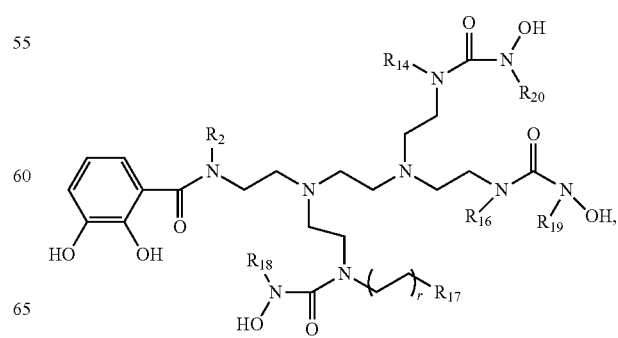

wherein:
$R_2$, $R_{14}$, $R_{16}$, $R_{18}$, $R_{19}$, and $R_{20}$, individually, include H, OH, or an alkyl group having from 1 to 10 carbon atoms; and
r can be from 0 to 4.

101. A composition of embodiment 96, including a structure:

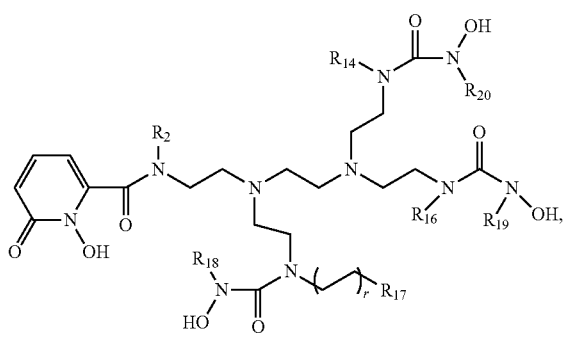

wherein:
$R_2$, $R_{14}$, $R_{16}$, $R_{18}$, $R_{19}$, and $R_{20}$, individually, include H, OH, or an alkyl group having from 1 to 10 carbon atoms; and
r can be from 0 to 4.

102. A composition of embodiment 96, including a structure:

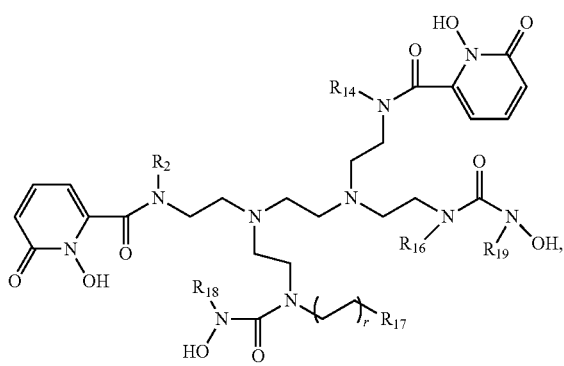

wherein:
$R_2$, $R_{14}$, $R_{16}$, $R_{18}$, and $R_{19}$, individually, include H, OH, or an alkyl group having from 1 to 10 carbon atoms; and
r is from 0 to 4.

103. A composition of embodiment 96, including a structure:

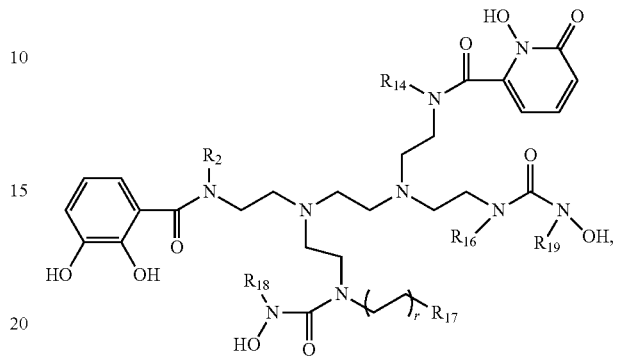

wherein:
$R_2$, $R_{14}$, $R_{16}$, $R_{18}$, and $R_{19}$, individually, include H, OH, or an alkyl group having from 1 to 10 carbon atoms;
r is from 0 to 4.

104. A composition, including a structure:

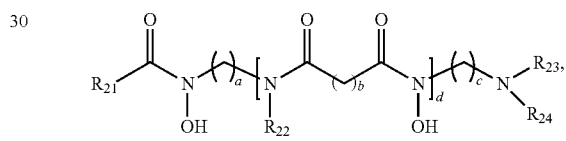

wherein:
$R_{21}$ and $R_{22}$, individually, include H, OH, or an alkyl group having from 1 to 10 carbon atoms;
$R_{23}$ includes H, OH, an alkyl group having from 1 to 10 carbon atoms, or $(CH_2)_e R_a$, where $R_a$ is SH;
$R_{24}$ includes a substituent having a CAM group, a 1,2-HOPO group, or a HA group;
a, b, and c, individually, are from 1 to 10;
d is from 1 to 4; and
e is from 1 to 10.

105. A composition of embodiment 104, wherein $R_{24}$ includes a substituent having SH, C(=O)OH, or $NH_2$.

106. A composition of embodiment 104, including a structure:

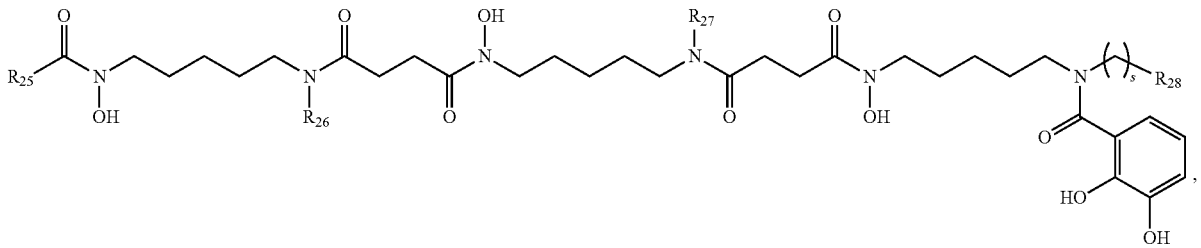

wherein:
$R_{25}$, $R_{26}$, and $R_{27}$, individually, include H, OH, or an alkyl group having from 1 to 10 carbon atoms;
$R_{28}$ includes SH; and
s is from 0 to 4.

107. A composition of embodiment 104, including a structure:

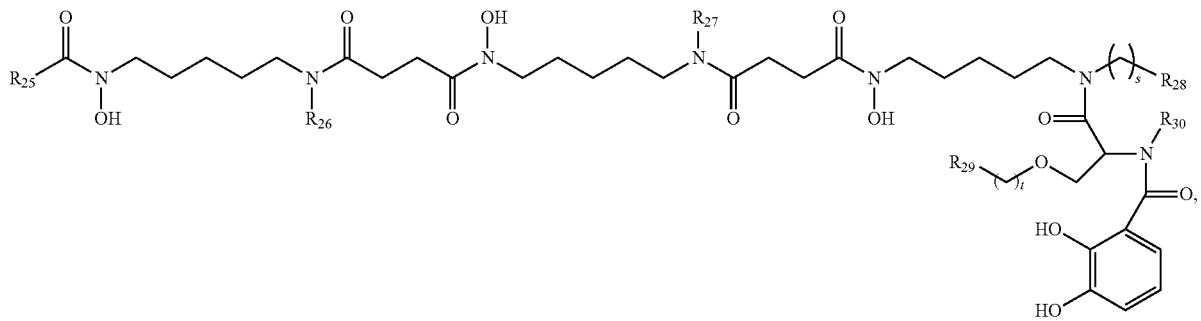

wherein:
$R_{25}$, $R_{26}$, $R_{27}$, and $R_{30}$, individually, include H, OH, or an alkyl group having from 1 to 10 carbon atoms;
at least one of $R_{28}$ or $R_{29}$, individually, includes SH and the other of $R_{28}$ or $R_{29}$ includes H, an alkyl group having from 1 to 5 carbon atoms, SH, $NH_2$, or $C(=O)OH$;
s is from 0 to 4; and
t is from 0 to 4.

108. A composition of embodiment 104, including a structure:

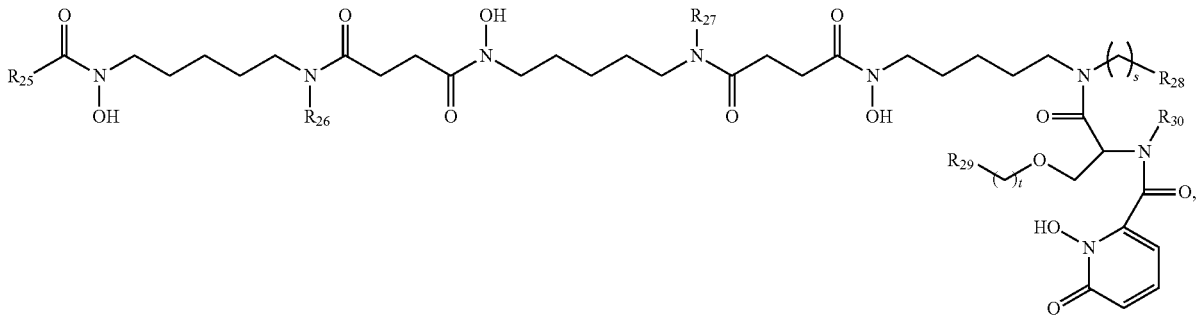

wherein:
$R_{25}$, $R_{26}$, $R_{27}$, and $R_{30}$, individually, include H, OH, or an alkyl group having from 1 to 10 carbon atoms;
at least one of $R_{28}$ or $R_{29}$, individually, includes SH and the other of $R_{28}$ or $R_{29}$ includes H, an alkyl group having from 1 to 5 carbon atoms, SH, $NH_2$, or $C(=O)OH$;
s is from 0 to 4; and
t is from 0 to 4.

109. A composition of embodiment 104, including a structure:

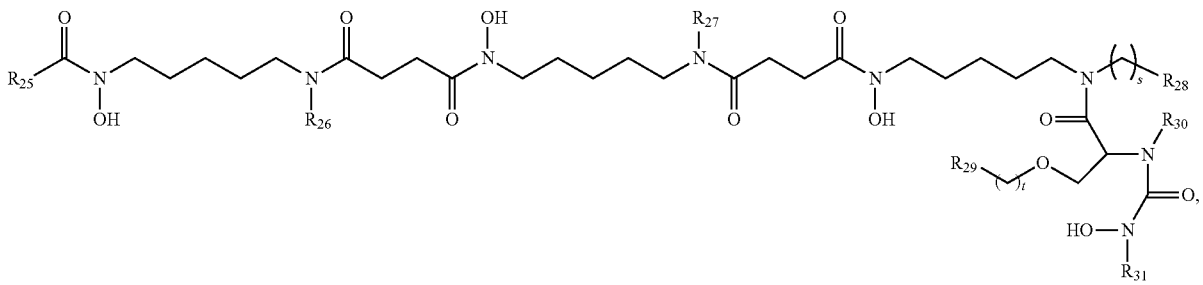

wherein:
R$_{25}$, R$_{26}$, R$_{27}$, R$_{30}$, and R$_{31}$, individually, include H, OH, or an alkyl group having from 1 to 10 carbon atoms;
at least one of R$_{28}$ or R$_{29}$, individually, includes SH and the other of R$_{28}$ or R$_{29}$ includes H, an alkyl group having from 1 to 5 carbon atoms, SH, NH$_2$, or C(=O)OH;
s is from 0 to 4; and
t is from 0 to 4.

110. A composition of embodiment 104, including a structure:

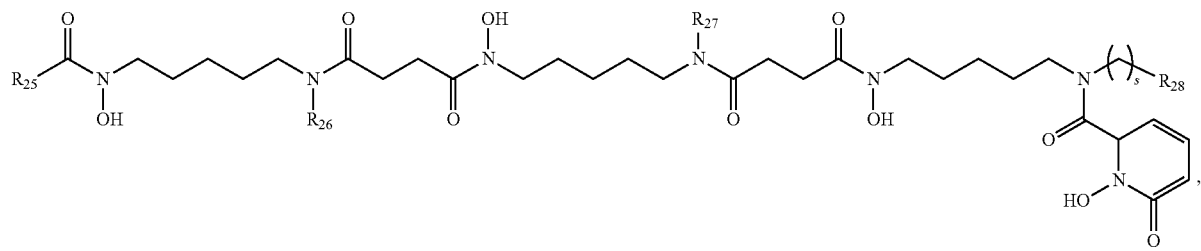

wherein
R$_{25}$, R$_{26}$, and R$_{27}$, individually, include H, OH, or an alkyl group having from 1 to 10 carbon atoms;
R$_{28}$ includes SH; and
s is from 0 to 4.

111. A composition of embodiment 104, including a structure:

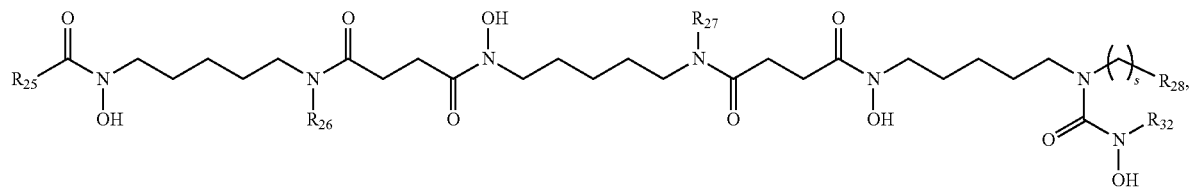

wherein:
R$_{25}$, R$_{26}$, R$_{27}$, and R$_{32}$, individually, include H, OH, or an alkyl group having from 1 to 10 carbon atoms;
R$_{28}$ includes SH; and
s is from 0 to 4.

112. A composition, including a structure:

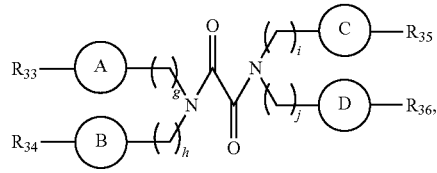

wherein:
A, B, C, and D, individually, include one or more amide groups, one or more amine groups, or an alkyl group having from 1 to 10 carbon atoms;
R$_{33}$, R$_{34}$, R$_{35}$, and R$_{36}$, individually, include a CAM group, a 1,2-HOPO group, or a HA group and at least one of R$_{33}$, R$_{34}$, R$_{35}$, or R$_{36}$ are substituted by SH; and
g, h, i, and j, individually, are from 1 to 10.

113. A composition of embodiment 112, including a structure:

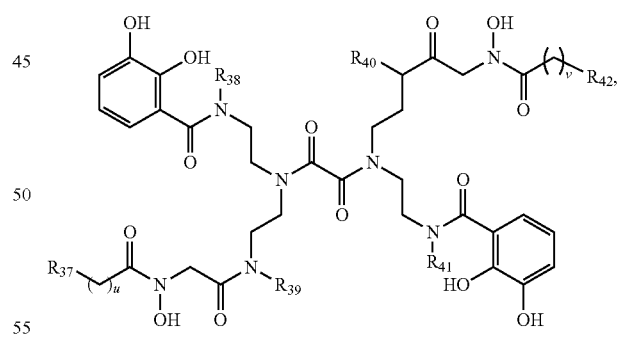

wherein:
at least one of R$_{37}$ or R$_{42}$, individually, includes SH and the other of R$_{37}$ or R$_{42}$ includes H, an alkyl group having from 1 to 5 carbon atoms, SH, C(=O)OH, or NH$_2$;
R$_{38}$, R$_{39}$, R$_{40}$, and R$_{41}$, individually, include H, OH, or an alkyl group having from 1 to 5 carbon atoms; and
u and v, individually, are from 0 to 5.

114. A composition of embodiment 112, including a structure:

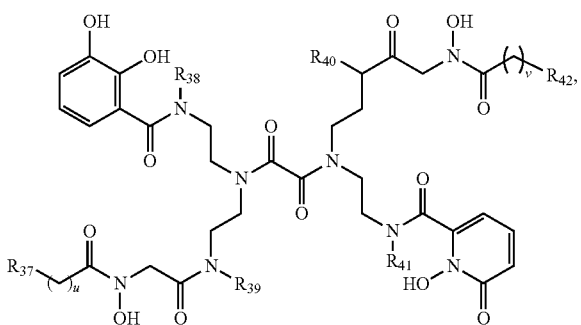

wherein:
at least one of $R_{37}$ or $R_{42}$, individually, includes SH and the other of $R_{37}$ or $R_{42}$ includes H, an alkyl group having from 1 to 5 carbon atoms, SH, C(=O)OH, or $NH_2$;
$R_{38}$, $R_{39}$, $R_{40}$, and $R_{41}$, individually, include H, OH, or an alkyl group having from 1 to 5 carbon atoms; and
u and v, individually, are from 0 to 5.

115. A composition of embodiment 112, including a structure:

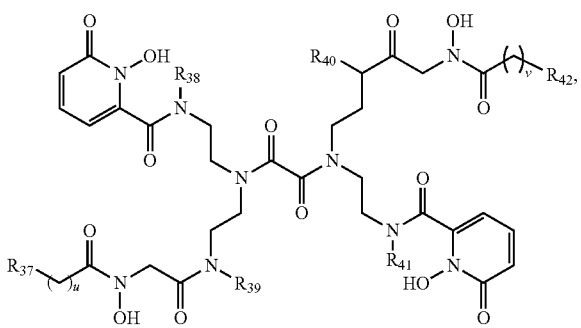

wherein:
at least one of $R_{37}$ or $R_{42}$, individually, includes SH and the other of $R_{37}$ or $R_{42}$ includes H, an alkyl group having from 1 to 5 carbon atoms, SH, C(=O)OH, or $NH_2$;
$R_{38}$, $R_{39}$, $R_{40}$, and $R_{41}$, individually, include H, OH, or an alkyl group having from 1 to 5 carbon atoms; and
u and v, individually, are from 0 to 5.

116. A method of separating metal ions, comprising:
contacting a liquid comprising a plurality of metal ions with a composition having the structure included in any one of embodiments 1-42, under conditions sufficient to form a metal ion-composition complex comprising a metal ion of the plurality of metal ions; and separating a first fraction of the mixture enriched for the metal ion-composition complex from a second fraction depleted for the metal ion-composition complex, wherein the first fraction is enriched for a first metal ion that has a charge that is different from a charge of a second metal ion enriched in the second fraction.

117. The method of embodiment 116, wherein the separating is based on molecular weight.

118. The method of embodiment 116 or 117, wherein the separating comprises size-exclusion chromatography or affinity chromatography.

119. The method of any one of embodiments 116-118, wherein:

a) the first fraction is enriched for a trivalent metal ion or a divalent metal ion, and the second fraction is enriched for a tetravalent metal ion;
b) the first fraction is enriched for a metal ion selected from the group consisting of: actinides, lanthanides, $Ac^{3+}$, $Sc^{3+}$, $Y^{3+}$, and $In^{3+}$;
c) the second fraction is enriched for a metal ion selected from the group consisting of: $Pu^{4+}$, $Np^{4+}$, $Th^{4+}$, $Zr^{4+}$, $Sn^{4+}$, $Ce^{4+}$, and $Bk^{4+}$;
d) the first fraction is enriched for a metal ion selected from the group consisting of $Am^{3+}$, $Cm^{3+}$, $Bk^{3+}$ and $Cf^{3+}$, and the second fraction comprises $Pu^{4+}$;
e) the first fraction is enriched for $Ac^{3+}$ and/or $Sc^{3+}$, and the second fraction is enriched for $Th^{4+}$;
f) the first fraction is enriched for $Eu^{3+}$ or $Y^{3+}$, and the second fraction is enriched for $Zr^{4+}$;
g) the first fraction is enriched for $In^{3+}$, and the second fraction is enriched for $Sn^{4+}$;
h) the first fraction is enriched for a lanthanide, and the second fraction is enriched for $Ce^{4+}$;
i) the first fraction is enriched for $Tm^{3+}$;
j) the first fraction is enriched for an actinide, and the second fraction is enriched for $Bk^{4+}$; or
k) the first fraction is enriched for a metal ion selected from the group consisting of $Am^{3+}$, $Cm^{3+}$, and $Cf^{3+}$.

120. A method of preparing $Bk^{4+}$ from a mixture, comprising:
contacting a first mixture comprising $Bk^{4+}$ and a trivalent metal ion with a composition having a structure included in of any one of embodiments 1-42 under conditions sufficient to form a complex comprising the trivalent metal ion and the composition having the structure included in any one of embodiments 1-42;
separating the complex from the first mixture to generate a second mixture depleted for the trivalent metal ion; and
chromatographically isolating the $Bk^{4+}$ in the second mixture.

121. The method of embodiment 120, wherein:
a) the first mixture further comprises one or more actinides selected from the group consisting of: $Cm^{3+}$, $Am^{3+}$, $Cf^{3+}$, $Th^{4+}$, $Np^{4+}$, $Pu^{4+}$, and $Ce^{4+}$;
b) the first mixture is prepared by neutron irradiation of Pu, Am or Cm;
c) the composition comprises a hydroxypyridonate ligand; or
d) the composition comprises 3,4,3-LI(1,2-HOPO)

122. A method of reclaiming an actinide from a sample, the method comprising: obtaining an aqueous sample comprising, or suspected of comprising, an actinide; contacting the sample with a composition having a structure included in any one of embodiments 1-42 to generate a mixture under conditions sufficient to form a complex comprising the actinide and the composition; and separating the complex from the mixture.

123. The method of embodiment 122, wherein:
a) the actinide comprises $Am^{3+}$ and/or $Cm^{3+}$;
b) the sample is derived from a river, ocean, lake, soil, or industrial run off;
c) the sample is an industrial sample;
d) the composition comprises a hydroxypyridonate ligand; or
e) the composition comprises 3,4,3-LI(1,2-HOPO).

Experimental Examples

Example 1. Tightening the Recognition of Tetravalent Zr and Th Complexes by the Siderophore-Binding Mammalian Protein Siderocalin for Theranostic Applications Introduction. Targeted alpha therapy (TAT), or radioimmunotherapy that uses α-particle emitting nuclides, is a promising treatment for small metastatic tumors and other localized diseases. Owing to α-particles' short path length, much of the decay energy may be deposited into target areas while mitigating damage to surrounding tissue (Mulford, et al., *Journal of Nuclear Medicine*, 46 (1 suppl), 199S-204S, 2005). A number of radionuclides that emit single α particles, including $^{213}$Bi and $^{212}$Pb, are currently under investigation (Kim & Brechbiel, *Tumor Biol.*, 33: 573-590, 2012). A growing subset of the field includes in vivo α-generator radionuclides $^{225}$Ac, $^{223}$Ra, and $^{227}$Th, isotopes that emit multiple a particles in their decay chains and dramatically increase the potential delivered dose (McDevitt, et al., *Science*, 2001, 294 (5546): 1537-1540). This principle was recently exploited in the development of Alpharadin, $^{223}$RaCl$_2$, a drug for bone metastases (Liepe & Alpharadin, *Curr Opin Investig Drugs*, 2009, 10 (12): 1346-1358). While Alpharadin relies on the natural propensity of $^{223}$Ra for bone, other specifically targeted α-radiation delivery strategies use constructs formed with a chelating agent to complex metallic α-emitters and a cancer site targeting vector (i.e., targeting ligand) (Kim & Brechbiel, *Tumor Biol.*, 33: 573-590, 2012). Though sound in theory, these designs have been slow to appear in the clinic, with only scarce examples of promising α-generator immunoconjugates, such as the lintuzumab conjugate $^{225}$Ac-HuM195 for myeloid leukemia treatment (Ravandi, et al., *Blood*, 2013, 122 (21): 1460-1460) and $^{227}$Th-DOTA-trastuzumab for treating HER-2 positive breast and ovarian cancer (Heyerdahl, et al., *PloS one*, 2012, 7 (8): e42345). There are many reasons for this slow development; inadequate chelation being one of the major limitations, together with poor retention of the α-emitters and their respective daughter products at the target site.

The $^{225}$Ac and $^{227}$Th radioisotopes are members of the actinide (An) series of elements. They display high coordination numbers and are best chelated by high denticity chelators that contain hard donor atoms, such as the multidentate hydroxypyridinone-based (HOPO) compounds, workhorse chelators for in vivo actinide decorporation (Bunin, et al., *Rad. Res.* 2013, 179: 171-182). The chelator 3,4,3-LI(1,2-HOPO) is an octadentate, tetraprotic compound including 4 bidentate 1,2-HOPO metal binding units attached onto a spermine ("3,4,3-LI") scaffold (FIG. 1), which was recently modified to enable monoclonal antibody attachment and form a bioconjugate chelator that displayed great properties for positron emission tomography (PET) when bound to $^{89}$Zr (Deri, et al., *Bioconjugate Chemistry*, 2015, 26 (12): 2579-2591; Deri, et al., *J. Med. Chem.*, 2014, 57 (11): 4849-4860). Although successful, such modifications necessitate extensive synthetic procedures with fairly low yields (Deri, et al., *Bioconjugate Chemistry*, 2015, 26 (12): 2579-2591), which prompted investigation of alternate routes to link therapeutic and imaging radionuclides to targeting ligands.

The mammalian protein, the siderophore-binding siderocalin (Scn), binds lanthanide (Ln) and An ions pre-complexed with a suitable ligand in solution with very high affinity (Allred, et al., *PNAS*, 2015, 112 (33): 10342-10347). Although the ferric complex of the hexadentate catecholate enterobactin ([Fe$^{III}$(Ent)]$^{3-}$) is Scn's native ligand (Clifton, et al., *Biometals*, 2009, 22 (4): 557-564), Scn's sterically hindered binding pocket was shown to bind Ln and An complexes of Ent (FIG. 1) (Allred, et al., *PNAS*, 2015, 112 (33): 10342-10347). More surprisingly, the protein could also accommodate the much stronger Ln and An complexes formed with the octadentate synthetic analog 3,4,3-LI(1,2-HOPO) (Allred, et al., *PNAS*, 2015, 112 (33): 10342-10347). Building on this work, one can envision using the Scn-ligand-metal system as a radionuclide binder for TAT as well as a reporter ligand for concurrent diagnostics. The advantage of using a protein-mediated binding system is two-fold: potentially tighter binding to nuclides of interest and retention of daughter products within the macromolecular construct, as well as easier conjugation to targeting ligands by using well-established biochemical methods. The aforementioned $^{225}$Ac$^{3+}$ and $^{227}$Th$^{4+}$ show promise in radioimmunotherapy, while $^{89}$Zr$^{4+}$ is useful as a PET tracer; all of these metals may be captured by the Scn-ligand system. Formed upon deprotonotation of the 1,2-HOPO units (FIG. 1), overall negative 3,4,3-LI(1,2-HOPO) complexes of Ln$^{3+}$ and An$^{3+}$ are tightly bound by Scn, but formally neutral 3,4,3-LI(1,2-HOPO) complexes of 4$^+$ metals interact weakly (Allred, et al., *PNAS*, 2015, 112 (33): 10342-10347). The difference in binding originates from insufficient electrostatic interaction between the metal-chelator complex and Scn. In order to restore complex binding by Scn, a ligand of high denticity that binds both 3$^+$ and 4$^+$ metals, forms overall negatively charged complexes, and does not cause steric clashes in Scn's tight binding pocket should be used. This Example aimed to address the inability of the Scn-3,4,3-LI (1,2-HOPO) system to bind 4$^+$ ions by exploring more suitable chelators.

Materials and Methods. Caution. $^{232}$Th, $^{238}$Pu, $^{242}$Pu, $^{243}$Am, and $^{248}$Cm are hazardous radionuclides with high specific activities that should only be manipulated in specifically designated facilities in accordance with appropriate safety controls.

General Considerations. Chemicals were obtained from commercial suppliers and were used as received. The siderophore Ent was provided by Prof. K. N. Raymond (Department of Chemistry, University of California at Berkeley). The LnCl$_3$.nH$_2$O lanthanide salts utilized were of the highest purity available (>99.9%). Stock solutions of $^{232}$Th (IV) and Zr(IV) were prepared from $^{232}$ThCl$_4$.8H$_2$O (Baker & Adamson, ACS grade) and ZrCl$_4$ (Sigma-Aldrich, 99.99%), respectively. A stock of $^{238}$Pu(IV) was purchased as $^{238}$Pu(NO$_3$)$_4$ in 4 M HNO$_3$ from Eckert & Ziegler (lot 118521). $^{242}$Pu was received from Oak Ridge National Laboratory as PuO2 (lot Pu-242-327 A, 99.93 wt % of metal $^{242}$Pu) and a stock solution of $^{242}$Pu(IV) was prepared as described previously (Ravandi, et al., *Blood*, 2013, 122 (21): 1460-1460). The $^{242}$Pu isotope was used for in vitro binding experiments whereas $^{238}$Pu was used in biodistribution studies. Aliquots of acidified stocks of carrier-free $^{243}$Am and $^{248}$Cm (95.78% $^{248}$Cm, 4.12% $^{246}$Cm, 0.06% $^{245}$Cm, 0.02% $^{244}$Cm/$^{247}$Cm isotopic distribution by atom percentage) from Lawrence Berkeley National Laboratory were used. All solutions were prepared using deionized water purified by a Millipore Milli-Q reverse osmosis cartridge system, and special care was taken to adjust the pH with concentrated HCl, H$_2$SO$_4$, KOH, or NaOH when needed. Measurements were conducted at room temperature unless otherwise noted. $^1$H NMR spectra were recorded on Bruker instruments; $^{13}$C NMR spectra were recorded on Bruker instruments with tetramethylsilane as an internal reference.

SilicaFlash G60 (particle size 60-200 μm) was used for flash column chromatography. LC-MS was performed on an Agilent LC/MS system including an Agilent 1200 binary LC pump, a temperature-controlled autosampler, a PDA UV detector, and a 6530 Accurate Mass Q-TOF mass spectrometer (Wilmington, Del., USA). The mass spectrometer was equipped with a JetStream® ESI probe operating at atmospheric pressure. The ESI source parameter settings were: mass range m/z 100-1000, gas temperature 350° C., gas flow 10 L/min, nebulizer 50 psi, sheath gas temperature 400° C., sheath gas flow 12 L/min, capillary voltage (Vcap) 3500 V, nozzle voltage 500 V, fragmentor 200 V, skimmer 65 V, octopole RF (OCT 1 RF Vpp) 750 V. Reverse phase preparatory HPLC was performed on a Varian ProStar system with a Vydac C18 column. High-resolution mass spectra were acquired using a Waters Xevo G2 QT of mass spectrometer. Absorption spectra were recorded on a Varian Cary G5 double beam absorption spectrometer or a NanoDrop 2000C, using quartz cells of 10 and 2 mm path lengths, respectively.

Methyl 2,3-dihydroxybenzoate (2). A stirred suspension of 1 (8.06 g, 52.3 mmol) in 100 mL of MeOH was treated with 2.00 ml of concentrated sulfuric acid. The suspension warmed and clarified 2 minutes after the addition. The reaction was equipped with a reflux condenser and was heated to 65° C. overnight. The next morning the conversion was verified by LC-MS and the volatiles were removed under reduced pressure. The crude was partitioned between $H_2O$ (100 mL) and ethyl acetate (100 mL) and the aqueous layer was extracted with ethyl acetate (3×50 mL). The organic extracts were combined, dried over $MgSO_4$, and concentrated under reduced pressure. The crude was passed through a plug of silica using 10% ethyl acetate in hexanes as eluent. The eluent was concentrated under reduced pressure and dried under high vacuum for 2 hours to yield 2 (7.66 g, 45.6 mmol, 88%) as a white solid, the spectral properties of which matched previous reports (Weitl, et al., *J. Am. Chem. Soc.*, 1980, 102 (7): 2289-2293).

Methyl 2,2-diphenylbenzo[d][1,3]dioxole-4-carboxylate (3). Precursor 2 (5.00 g, 29.7 mmol) was mixed with dichlorodiphenylmethane (8.56 mL, 44.6 mol) under an argon atmosphere; the resulting suspension was stirred and heated to 160° C. for 1 hour. The mixture was allowed to cool to room temperature and was diluted with 100 mL of ethyl acetate. The solution was washed with sat. $NaHCO_3$ (30 mL), brine (30 mL), dried over $MgSO_4$, and then concentrated under reduced pressure. The ensuing greyish oil was dissolved in 30 mL of hot MeOH (65° C.) and was slowly cooled to 5° C., which resulted in the formation of white crystals. The crystals were a mixture of 3 and benzophenone that could not be easily separated; the crude product was used as is for the subsequent step.

2,2-diphenylbenzo[d][1,3]dioxole-4-carboxylic acid (4). The mixture from the previous step was dissolved in 100 mL of THF and was treated with 100 mL of 0.9 M LiOH. The emulsion was rapidly stirred and heated to reflux for 5 hours. Conversion was verified by LC-MS and the reaction was cooled to room temperature. The solution was neutralized with 10% v/v aqueous acetic acid and was extracted with ethyl acetate (3×50 mL). The organic extracts were combined, dried over $MgSO_4$, and concentrated under reduced pressure. The crude was chromatographed using 25% ethyl acetate in hexanes as eluent. Volatiles were then removed under reduced pressure followed by high vacuum to yield 4 (7.6 g, 24.06 mmol, 81% over 2 steps) as a white solid, the spectral properties of which matched previous reports (Weitl, et al., *J. Am. Chem. Soc.*, 1980, 102 (7): 2289-2293).

Figure 3A:
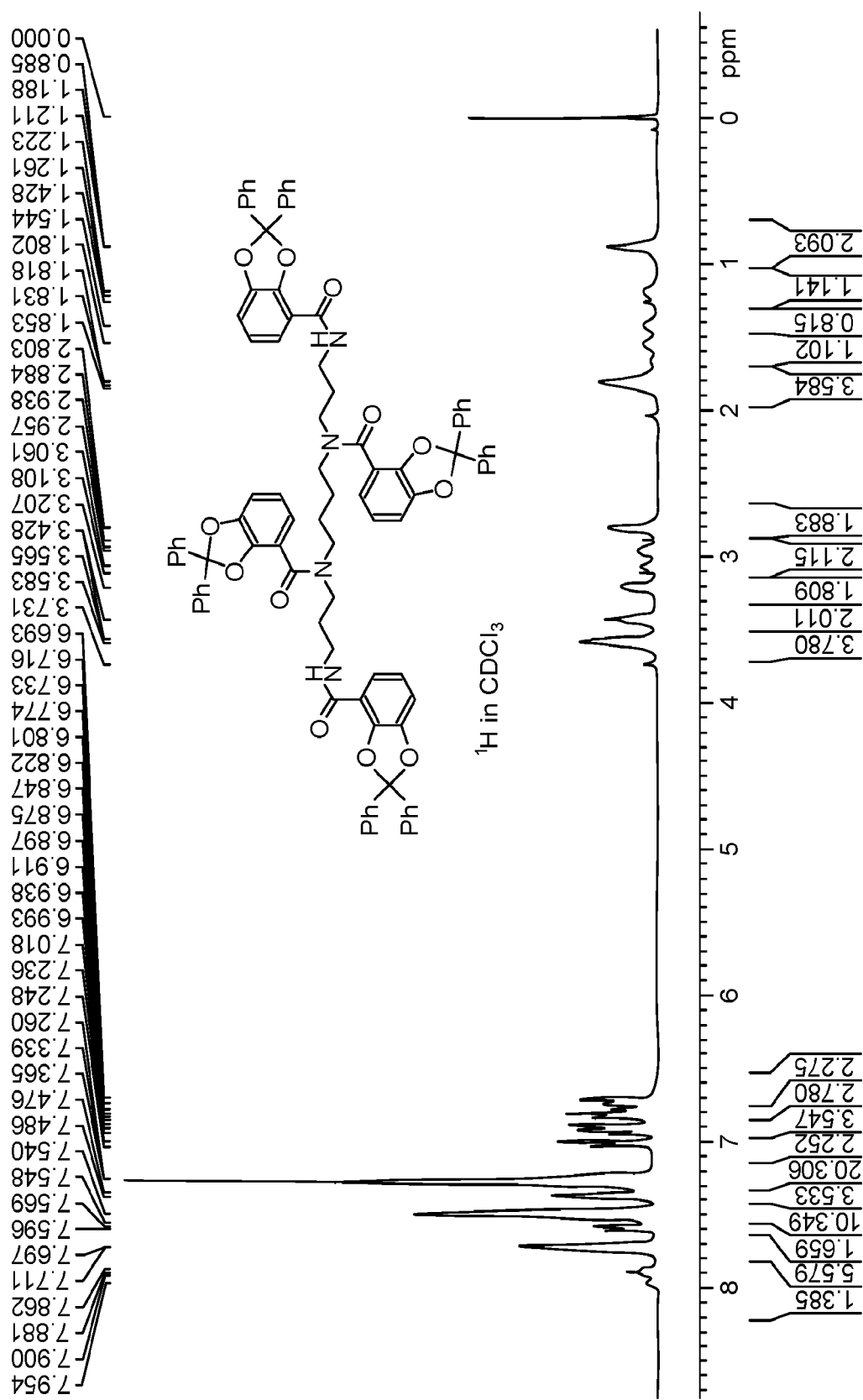
FIGS. 3A and 3B. 3,4,3-LI(2,2-diphenylbenzo[d][1,3]-2, 3-catecholamide) (5)—NMR Spectra.
Figure 3B:
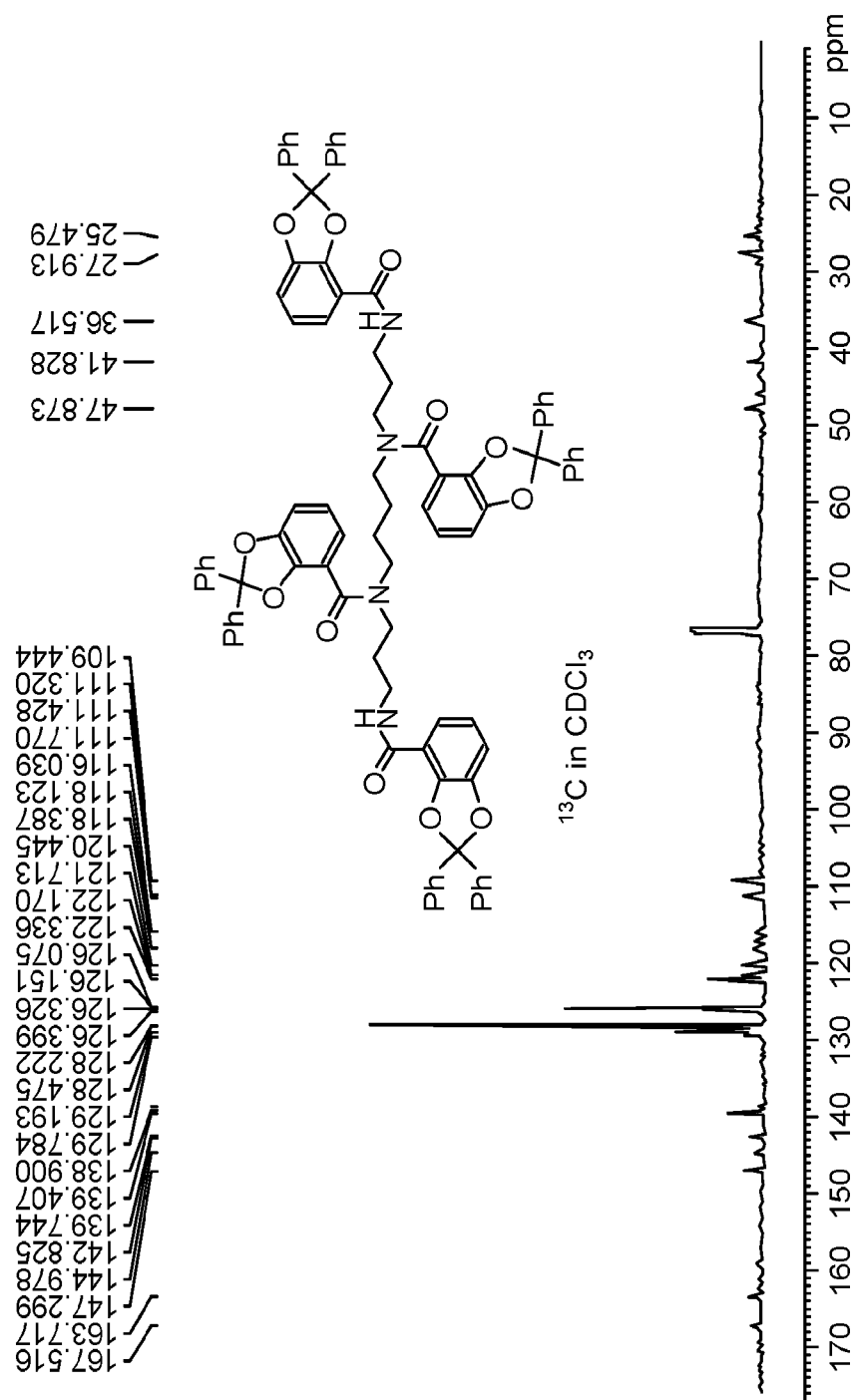
Figure 4A:
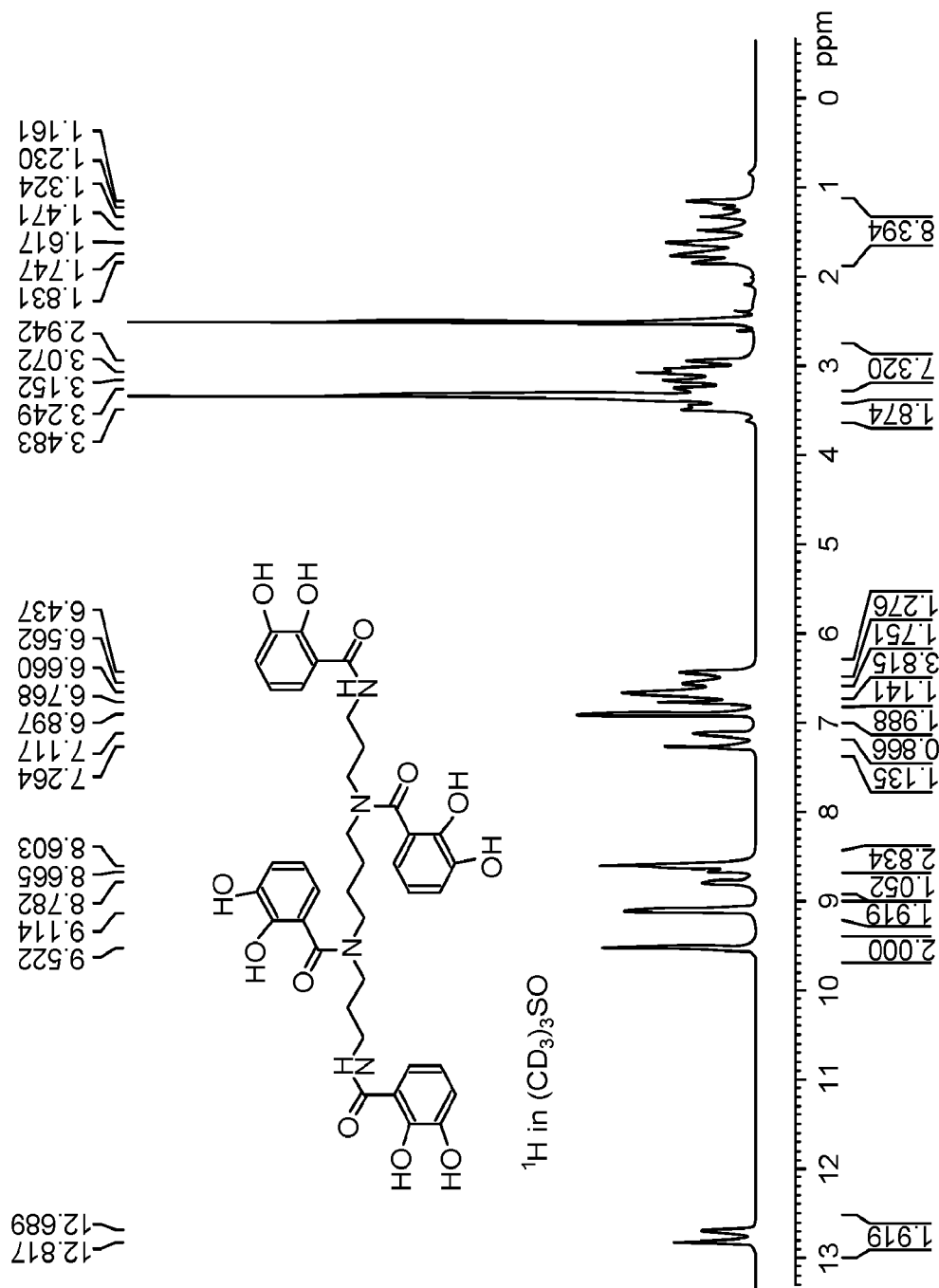
FIGS. 4A and 4B. 3,4,3-LI(CAM) (6)—NMR Spectra.
Figure 4B:
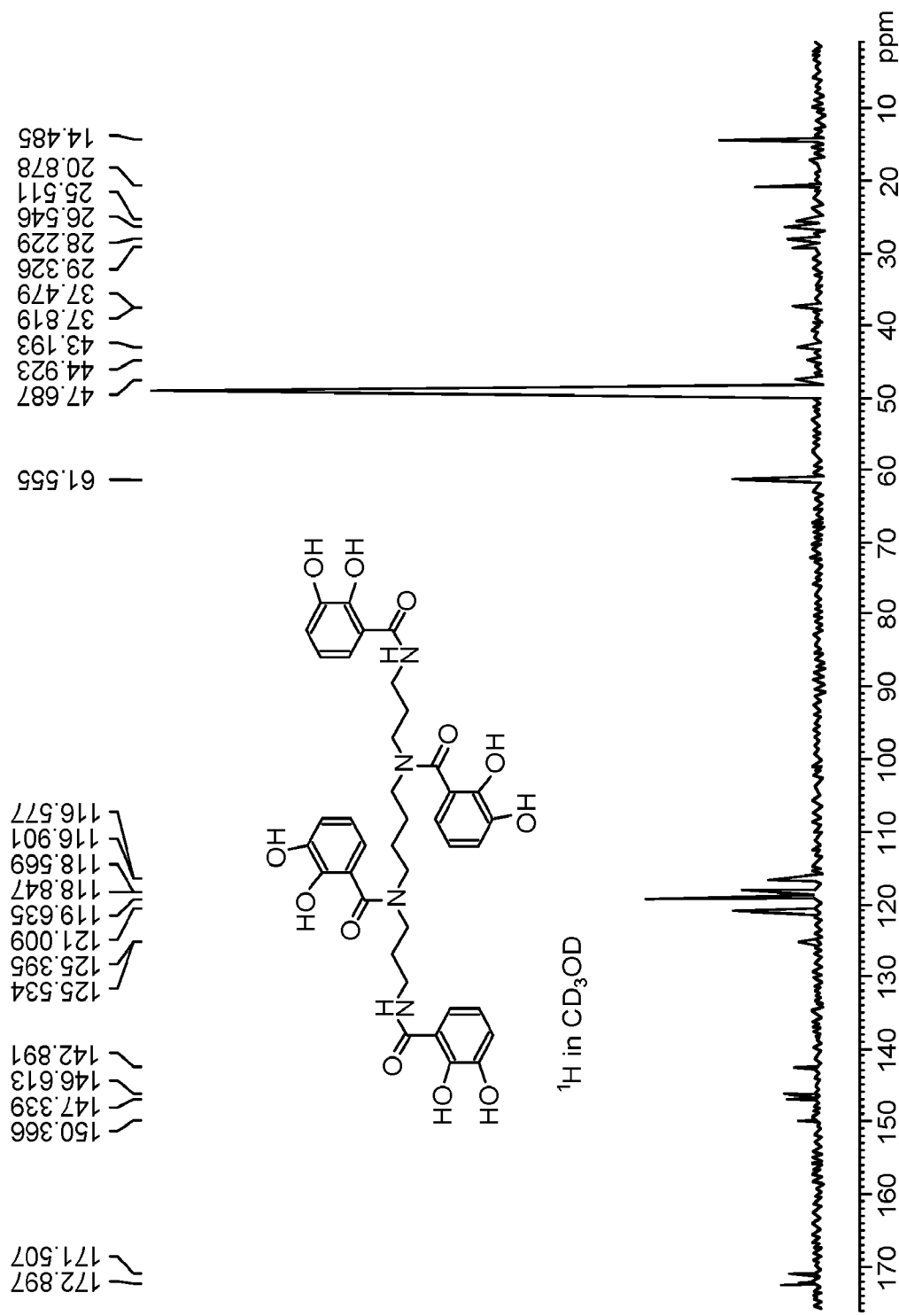

3,4,3-LI(2,2-diphenylbenzo[d][1,3]-2,3-catecholamide) (5). Precursor 4 (746 mg, 2.33 mmol) was suspended in 10 mL of dry toluene under an argon atmosphere and was treated with oxalyl chloride (220 μL, 2.55 mmol). Catalytic N,N-dimethylformamide was added and the suspension was heated to 40° C. The solution was stirred until the evolution of gas ceased and was concentrated on the manifold vacuum at the same temperature. The resulting brown oil was dissolved in 10 mL of dry THF. In a separate container a solution of spermine (118 mg, 0.583 mmol), triethylamine (356 μL, 2.56 mmol), and THF (5 mL) was prepared. The solutions were combined and heated to 50° C. overnight in a sealed flask. The following day the reaction was filtered and concentrated under reduced pressure. The resulting crude oil was chromatographed using 3% MeOH in $CH_2Cl_2$ as eluent. The volatiles were then removed under reduced pressure and dried under vacuum, yielding 5 as a white foam (641 mg, 0.457 mmol, 78% yield). $^1$H NMR (300 MHz, $CDCl_3$) δ7.88 (1H, t, J=5.7 Hz), 7.66-7.76 (6H, br t), 7.60 (1H, br s), 7.57 (1H, br s), 7.43-7.53 (10H, br s), 7.33-7.40 (4H, br s), 7.19-7.31 (20H, br s), 7.01 (2H, d, J=7.6 Hz), 6.91 (4H, dd, J=12.1 Hz, 8.0 Hz), 6.80 (2H, br s), 6.72 (2H, br s), 3.85 (4H, br s), 3.43 (2H br s), 3.21 (2H, br s), 3.06 (1H, br s), 2.96 (1H, br s), 2.80 (2H, br s), 1.81 (4H, br s), 1.54 (1H, br s), 1.43 (1H, br s), 1.19 (1H, br s), 0.89 (2H, br s). $^{13}$C NMR (75 MHz, $CDCl_3$) δ 167.5, 163.7, 147.3, 147.1, 145.0, 142.8, 139.7, 139.4, 138.9, 129.7, 129.2, 128.4, 128.3, 126.4, 126.3, 126.1, 126.0, 122.3, 122.2, 121.7, 120.4, 118.4, 118.1, 116.0, 111.8, 111.4, 111.3, 109.4, 47.9, 41.8, 36.5, 27.9, 25.5 (FIG. 3).

Figure 5:
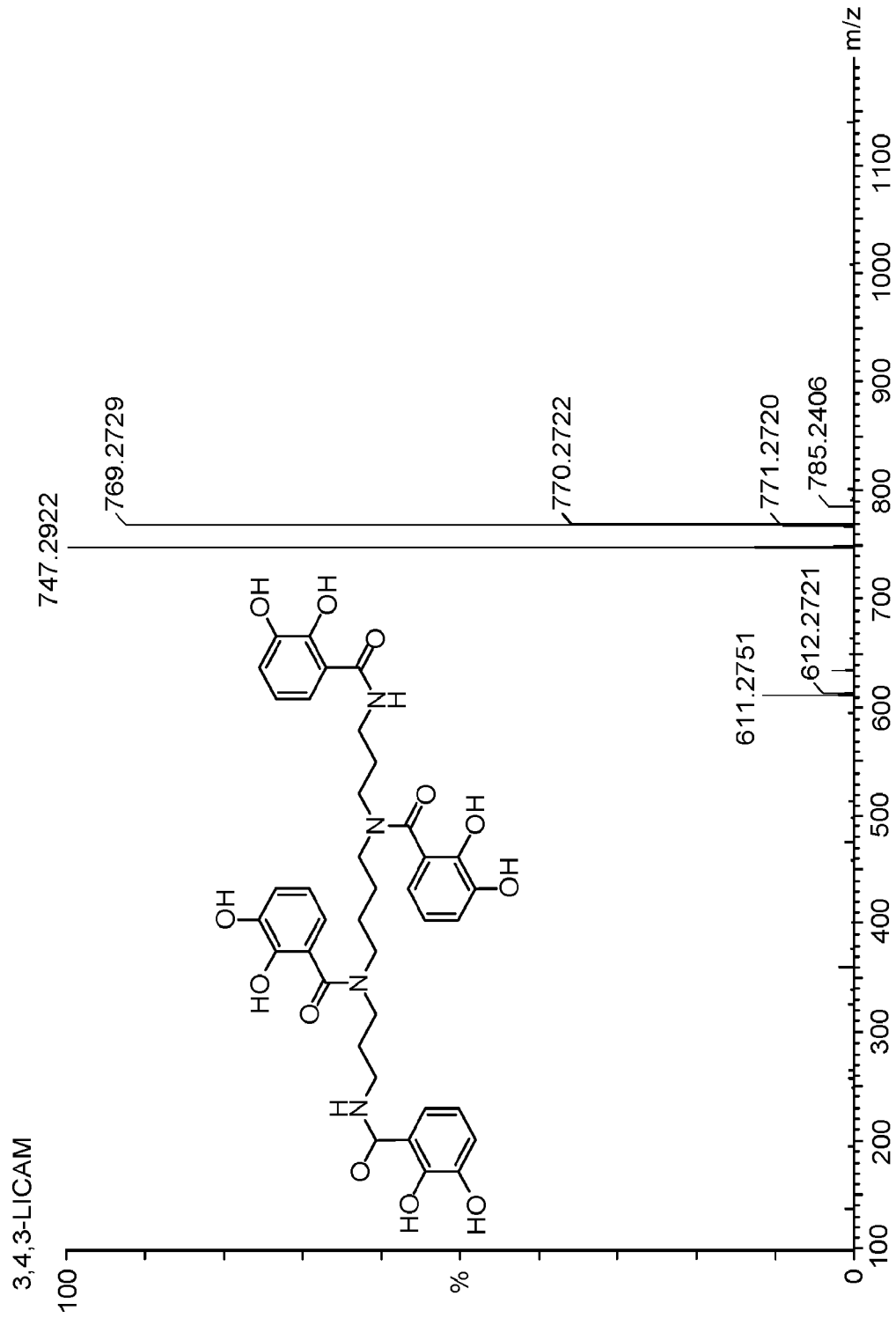
FIG. 5. 3,4,3-LI(CAM) (6)—Mass Spectrum, Positive Mode.

3,4,3-LI(CAM) (6). The protected chelator 5 (411 mg, 2.93×10$^{-4}$ mol) was dissolved in a mixture of 5 mL acetic acid, 0.5 mL $H_2O$, and 0.1 mL concentrated HCl. The solution was stirred in a sealed container at 60° C. overnight. The next day the conversion was confirmed by LC-MS and the volatiles were removed under vacuum. A portion of the crude was purified using reverse-phase prep-HPLC using at 10-50% MeOH in $H_2O$+0.1% trifluoroacetic acid as eluent. The solvent was removed on a Genevac centrifugal evaporator followed by lyophilization of residual $H_2O$. CAM was obtained as a pure white powder (90% yield). $^1$H NMR (600 MHz, DMSO-$d_6$) δ12.82 (1H, br s), 12.69 (1H, br s), 9.52 (2H, br s), 9.11 (2H, br s), 8.78 (1H, br s), 8.60 (3H, br s), 7.26 (1H, br s), 7.12 (1H, br s), 6.90 (2H, br s), 6.77 (1H, br s), 6.66 (4H, br s), 6.56 (2H, br s), 6.44 (1H, br s), 2.88-3.52 (12H, overlapping aliphatic signals), 1.16-1.83 (8H, overlapping aliphatic signals); $^{13}$C NMR (125 MHz, MeOD-$d_4$) δ172.9, 171.5, 150.4, 147.3, 146.6, 125.6, 125.4, 121.0, 119.6, 119.1, 118.8, 118.6, 116.9, 116.6, 47.7, 44.9, 43.2, 37.8, 37.5, 29.3, 28.2, 26.5, 25.5 (FIG. 3). MS-ESI (m/z) [M+H] Calcd for $C_{38}H_{43}N_4O_{12}$, 747.2878; found 747.2922 and [M−H] Calcd. for $C_{38}H_{41}N_4O_{12}$, 745.2721; found 745.2774 (FIG. 5).

Another pathway for synthesizing a chelator that includes a carboxyl group for binding with another compound, such as a protein or a dye, can include:

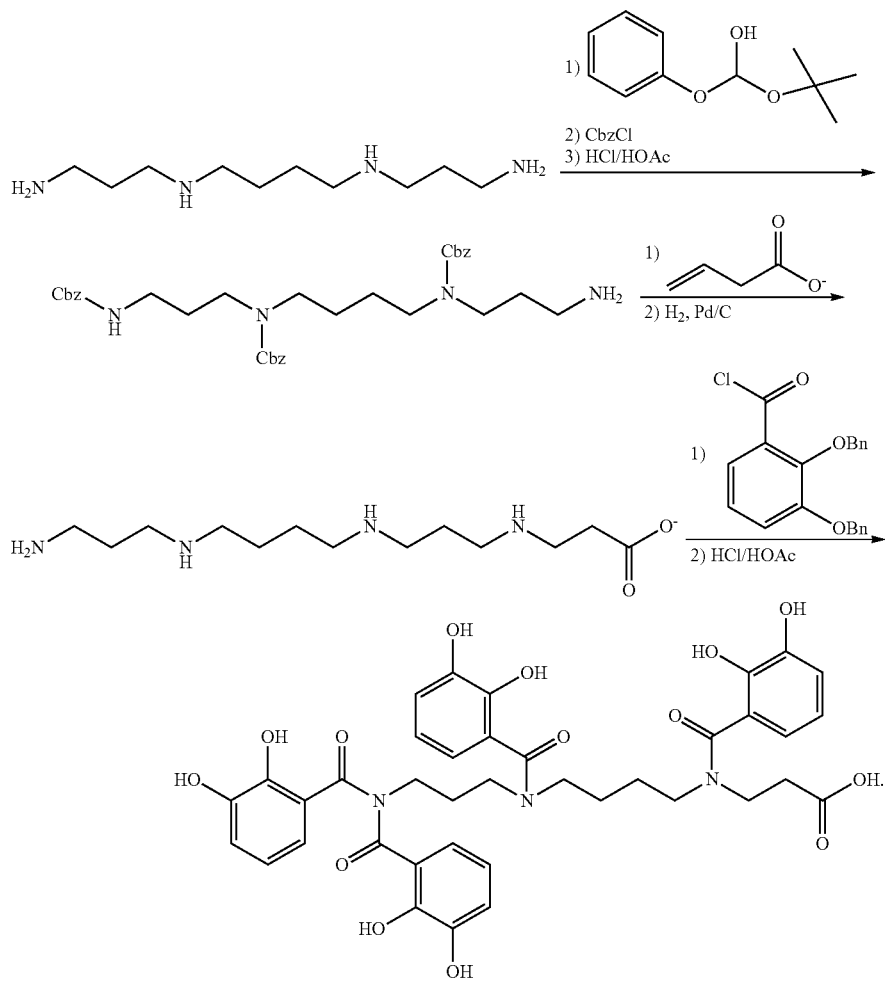

Metal, Chelator, and Protein Working Solutions. The trivalent lanthanide Ln(III) working solutions were prepared in standardized 0.1 M HCl. A Zr(IV) stock solution was prepared by dissolving $ZrCl_4$ in 3.0 M $H_2SO_4$, to prevent hydrolysis. The metal salt $ZrCl_4$ was handled and stored in a glovebox kept under inert atmosphere. The Zr(IV) stock solution was standardized against EDTA, with xylene orange as the indicator (Welcher, F. J. *The analytical uses of ethylenediamine tetraacetic acid;* 1958). A Th(IV) stock solution was prepared in 0.1 M $H_2SO_4$. Stock solutions (4 mM) of Ent, and 3,4,3-LI(CAM) were prepared by direct dissolution of a weighed portion of chelator in DMSO and aliquots were removed prior to each set of experiments. Recombinant human Scn was prepared as previously described (Goetz, et al., *Molecular cell,* 2002, 10 (5): 1033-1043).

Solution Thermodynamics. All titrant solutions were degassed by boiling for 1 h while being purged under Ar. Carbonate-free 0.1 M KOH was prepared from concentrate (J. T Baker Dilut-It) and was standardized by titrating against 0.1 M potassium hydrogen phthalate (99.95%, Sigma Aldrich). Solutions of 0.1 M HCl were similarly prepared and were standardized by titrating against TRIS (99.9%, J. T. Baker). The glass electrode (Metrohm-Micro Combi-response to [H+]) used for the pH measurements was calibrated at 25.0° C. and at an ionic strength of 0.1 M (KCl) before each potentiometric or spectrophotometric titration. The calibration data were analyzed using the program GLEE (Gans & O'Sullivan, *Talanta,* 2000, 51 (1): 33-37) to refine for the E° and slope. All thermodynamic measurements were conducted at 25.0° C., in 0.1 M KCl supporting electrolyte under positive Ar gas pressure. The automated titration system was controlled by an 867 pH Module (Metrohm). Two-milliliter Dosino 800 burets (Metrohm) dosed the titrant (0.1 M KOH or 0.1 M HCl) into the thermostated titration vessel (5-90 mL). UV-visible spectra were acquired with an Ocean Optics USB4000-UV-vis spectrometer equipped with a TP-300 dip probe (Ocean Optics; path length of 10 mm), fiber optics and a DH-2000 light source (deuterium and halogen lamps). The fully automated titration system and the UV-vis spectrophotometer were coordinated by LBNL titration system, a computer program developed in house.

Figure 6A:
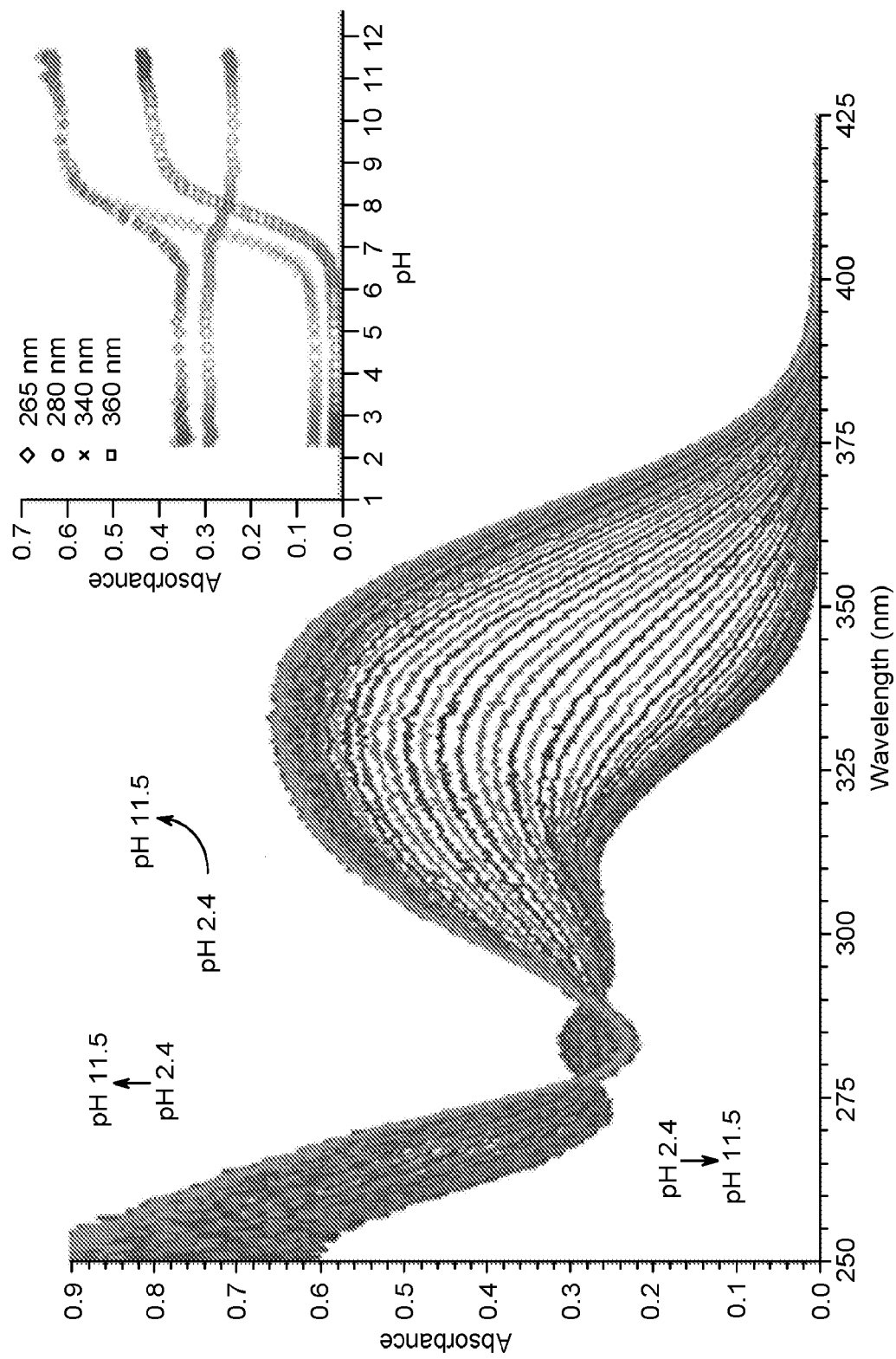
FIGS. 6A and 6B. (6A) Example of spectrophotometric competition titration of Th(IV)-CAM complexes. Starting conditions: 50 μM 3,4,3-LI(CAM), 50 μM Th(IV), 112 μM DTPA, 3 mM CHES, 3 mM TRIS, 3 mM MES, 10 mM HCl. I=0.1 M (KCl). T=25° C. 130 spectra measured between pH 2.4 and 11.5. Path length=10 mm. Spectra corrected for dilution. Inset: Change in absorbance 360 nm (squares), 340 nm (crosses), 280 nm (circles) and 265 nm (diamonds) as a function of pH. (6B) Speciation diagram of the 3,4,3-LI (CAM) ligand in the presence of Th(IV). [Th]=[CAM]=10 μM. T=25° C., I=0.1 M. Species: $CAMH_8$, $CAMH_7^-$, $[CAMHTh]^{3-}$ and $[CAMTh]^{4-}$. Calculations performed with Hyss software.
Figure 6B:
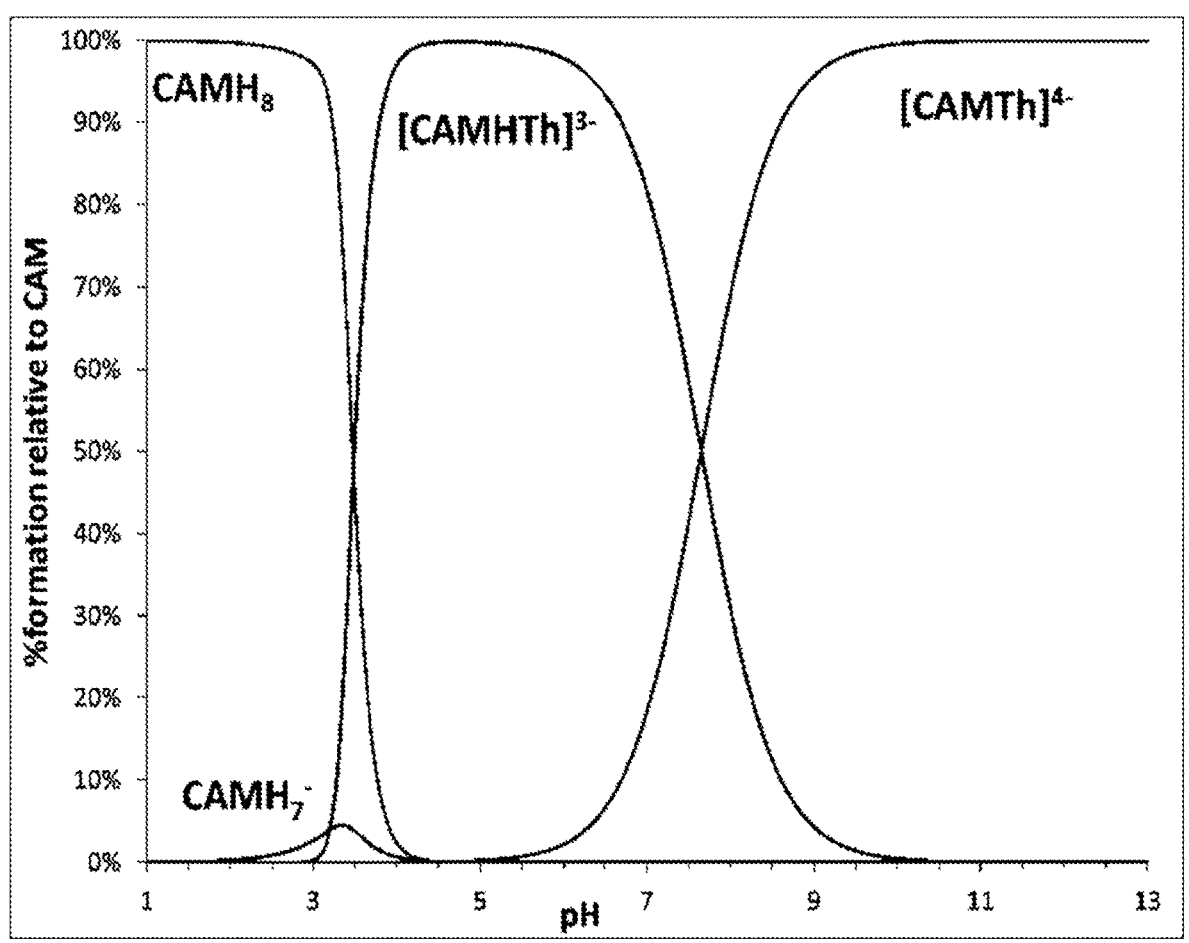
Figure 7A:
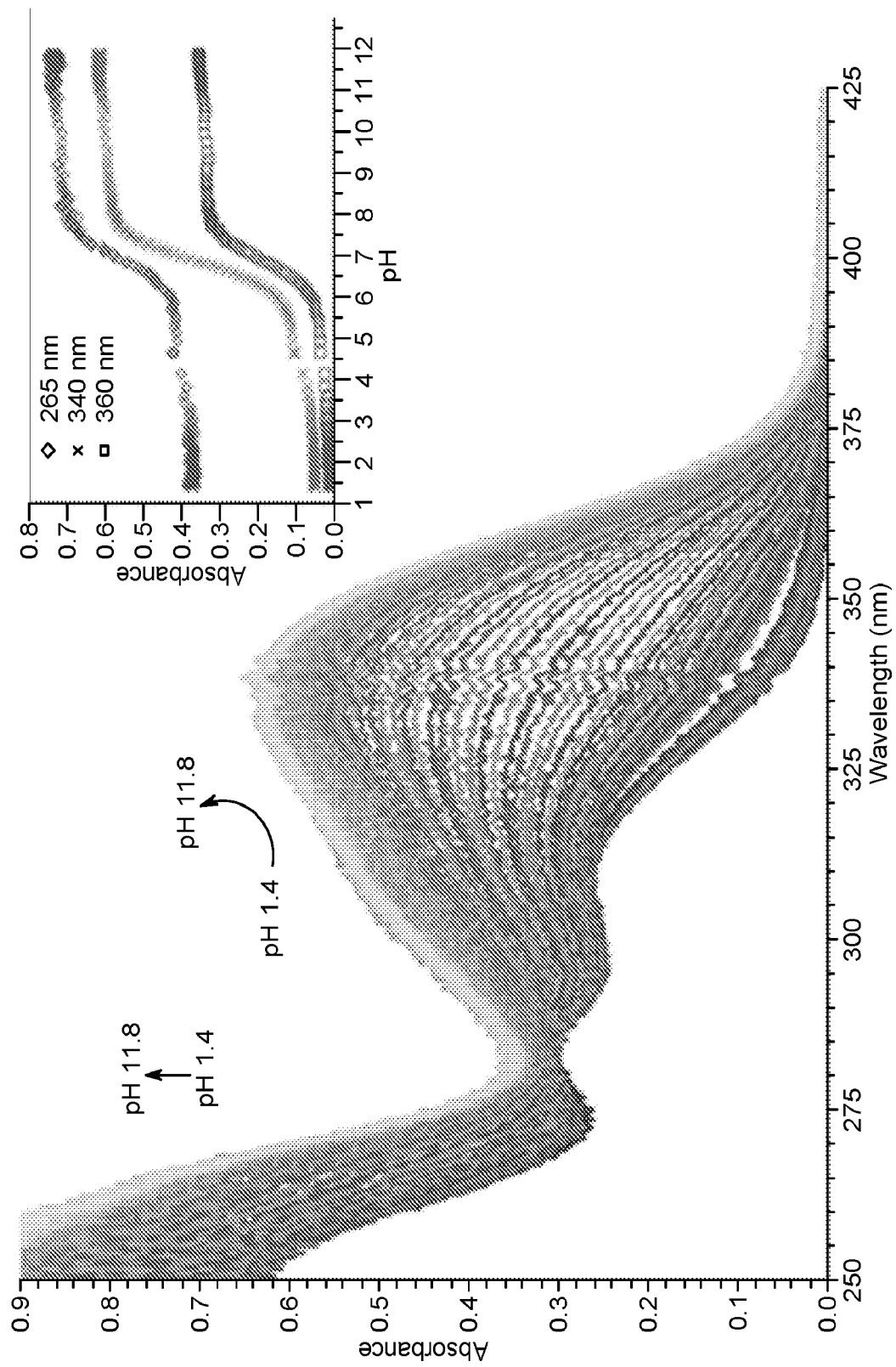
FIGS. 7A and 7B. (7A) Example of spectrophotometric competition titration of Zr(IV)-CAM complexes. Starting conditions: 50 μM 3,4,3-LI(CAM), 50 μM Zr(IV), 56 μM DTPA, 5 mM CHES, 5 mM TRIS, 5 mM MES, 45 mM HCl. I=0.1 M (KCl). T=25° C. 230 spectra measured between pH 1.4 and 11.8. Path length=10 mm. Spectra corrected for dilution. Inset: Change in absorbance 360 nm (squares), 340 nm (crosses) and 265 nm (diamonds) as a function of pH. (7B) Speciation diagram of the 3,4,3-LI(CAM) ligand in the presence of Zr(IV). [Zr]=[CAM]=10 μM. T=25° C., I=0.1 M. Species: $CAMH_8$, $CAMH_7^-$, $[CAMHZr]^{3-}$ and $[CAMZr]^{4-}$. Calculations performed with Hyss software.
Figure 7B:
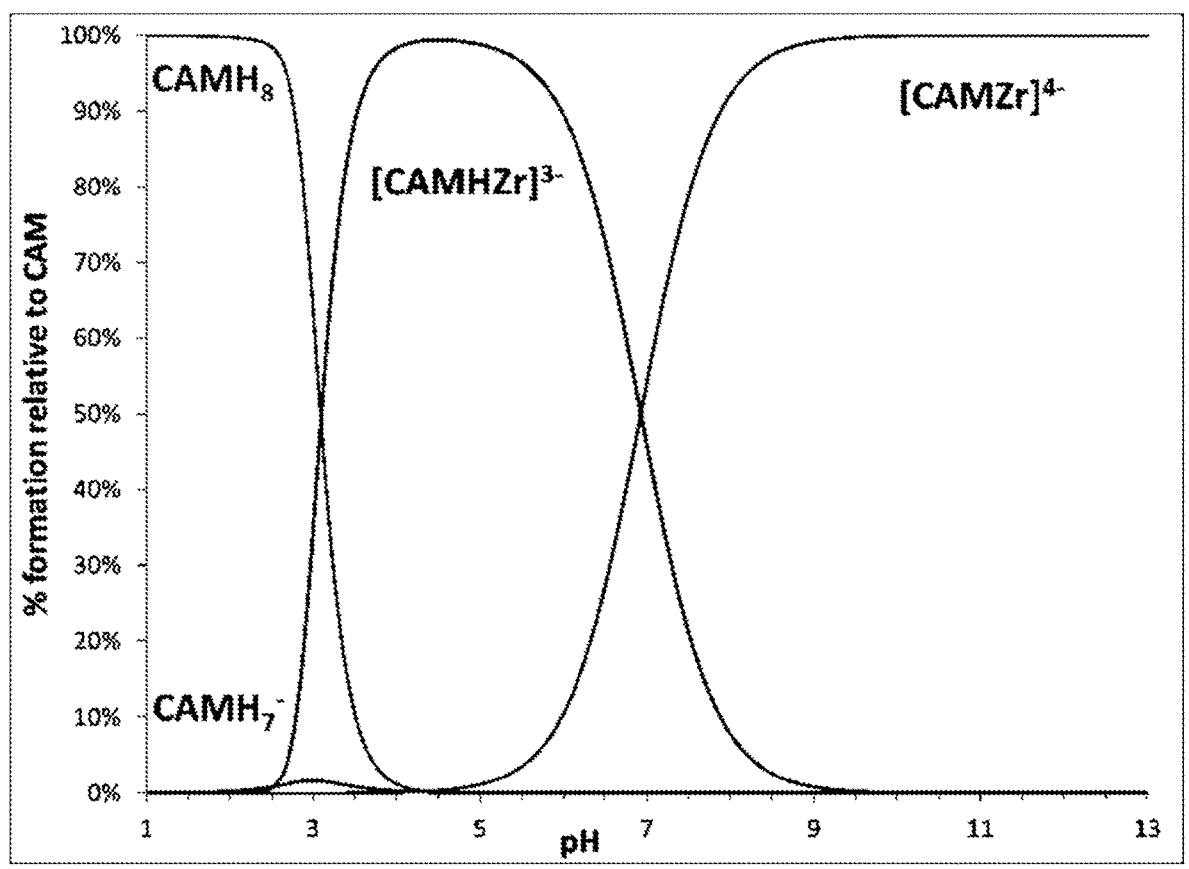
Figure 8A:
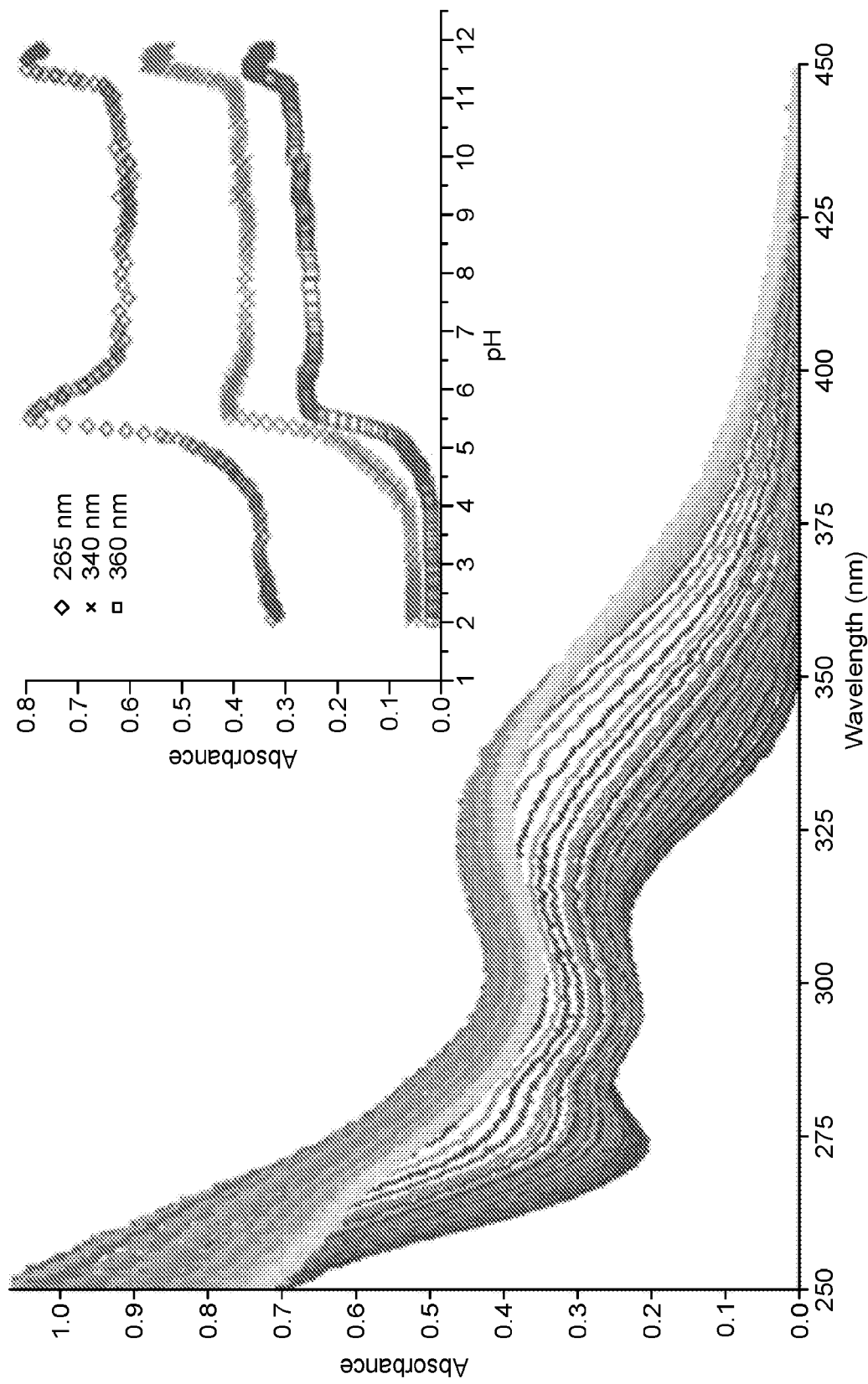
FIGS. 8A and 8B. (8A) Example of spectrophotometric competition titration of Eu(III)-CAM complexes. Starting conditions: 50 μM 3,4,3-LI(CAM), 50 μM Eu(IV), 10 mM CHES, 10 mM MES, 10 mM acetic acid, 10 mM HCl. I=0.1 M (KCl). T=25° C. 215 spectra measured between pH 2.0 and 11.9. Path length=10 mm. Spectra corrected for dilution. Inset: Change in absorbance 360 nm (squares), 340 nm (crosses) and 265 nm (diamonds) as a function of pH. (8B) Speciation diagram of the 3,4,3-LI(CAM) ligand in the presence of Eu(III). [Eu]=[CAM]=10 μM. T=25° C., I=0.1 M. Species: $CAMH_8$, $CAMH_7^-$, $CAMH_6^{2-}$, $[CAMH_2Eu]^{3-}$, $[CAMHEu]^{4-}$ and $[CAMEu]^{5-}$. Calculations performed with Hyss software.
Figure 8B:
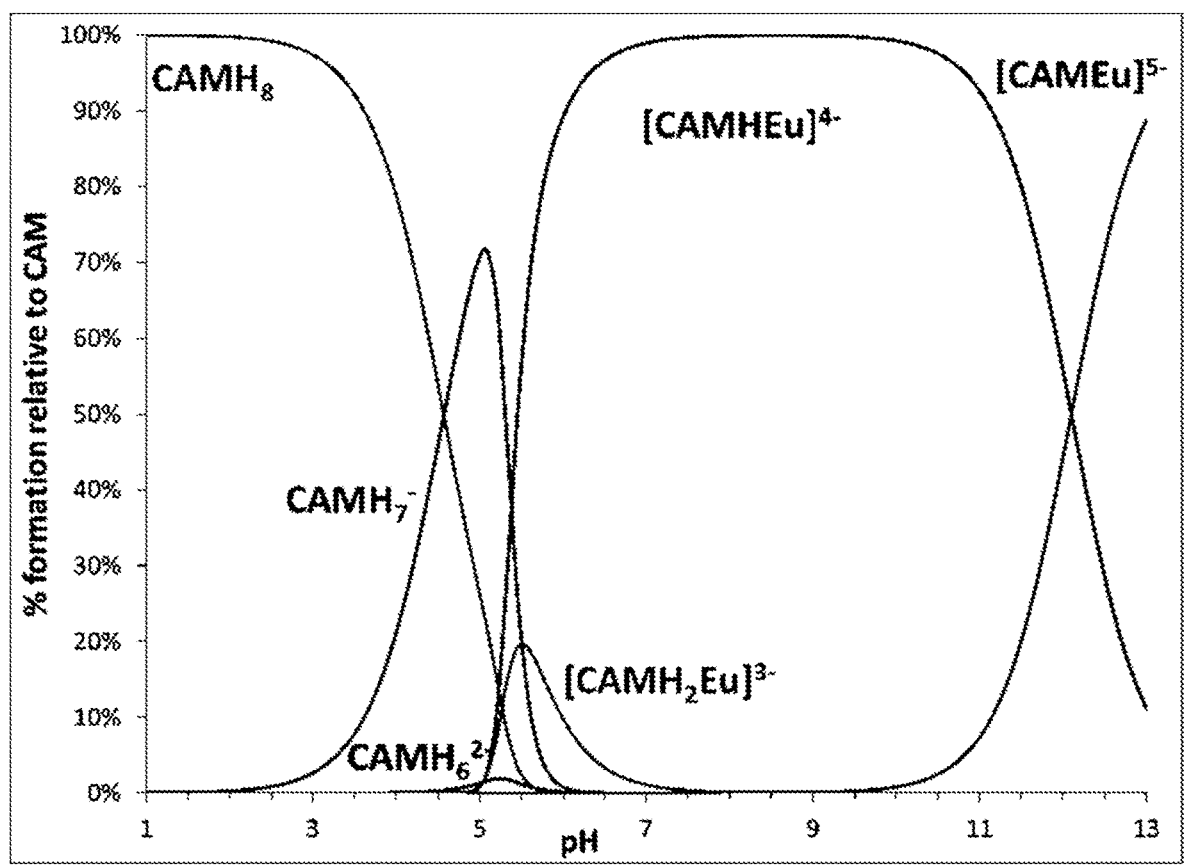

Incremental Spectrophotometric Titrations. This method was used to determine the protonation constants of 3,4,3-LI(CAM) as well as the stability constants of its complexes formed with Eu(III), Zr(IV) and $^{232}$Th(IV). The experimental titration setup is similar to previously described systems (Sturzbecher-Hoehne, et al., *Radiochimica Acta.,* 2013, 101 (6): 359-366). For the 3,4,3-LI(CAM) protonation (and Eu(III)-3,4,3-LI(CAM) complexes), titrations were performed with an initial concentration of 50 μM of 3,4,3-LI (CAM) (and 50 µM of Eu(III)) resulting in absorbance values included between 0 and 1.0 throughout the titration. Typically, 9 mL of a sample containing 3,4,3-LI(CAM) (and Eu(III)) and the supporting electrolyte (KCl/HCl) were incrementally perturbed by addition of 0.025 mL of carbonate-free 0.1 M KOH followed by a time delay of 80 s. Buffering of the solution was ensured by the addition of 10 mM of HEPES, 10 mM of CHES and 10 mM of MES. Between 130 and 250 data points were collected per titration, each data point including a pH measurement and a UV-Vis spectrum (250-450 nm) over the pH range 1.5 to 12.0. All spectra were corrected for dilution before data fitting. The entire procedure (electrode calibrate, titration and data treatment) was performed independently five times for the protonation constants and four times for the Eu(III)-3,4,3-LI(CAM) complexes. For the Zr(IV) and Th(IV) complexes, titrations were performed similarly but in the presence of DTPA to avoid the formation of metal hydroxides at low pH, before the uptake by 3,4,3-LI(CAM). For each metal, three titrations were performed independently in the presence of 1.1 to 40 equivalents of DTPA. Examples of titrations are displayed in the Supporting Information (FIGS. 5-7).

Data Treatment. Thermodynamic constants and spectral deconvolution were refined using the nonlinear least-squares fitting program HypSpec (Gans, et al., *Talanta*, 1996, 43 (10): 1739-1753). All equilibrium constants were defined as cumulative formation constants, $\beta_{mlh}$ according to Equation (1), where the metal and chelator are designated as M and L, respectively. All metal and chelator concentrations were held at estimated values determined from the volume of standardized stock solutions. All species formed with 3,4,3-LI(CAM) were considered to have significant absorbance to be observed in the UV-vis spectra and were therefore included in the refinement process. The refinements of the overall formation constants β included in each case with previously determined chelator protonation constants and the metal hydrolysis products, whose equilibrium constants were fixed to the literature values (Smith, et al., NIST standard reference database 46. NIST Critically selected stability constants of metal complexes database ver 2004, 2) The speciation diagrams were calculated using the modeling program Hyss (Alderighi, et al., *Coordination Chemistry Reviews*, 1999, 184 (1): 311-318). Errors on log $\beta_{Mlh}$ and $pK_a$ values presented in this Example correspond to the standard deviation observed over the n replicates (n=3 to 5) of the entire procedure (electrode calibrate, titration and data treatment).

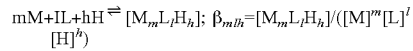

Fluorescence Quenching Binding Assay. Equimolar amounts of metal and chelator were used to constitute metal-chelator solutions (2 µM, pH 7.4, 5% DMSO) in Tris-buffered saline (TBS). Then, a solution of recombinant wild-type Scn (50 nM, 3 mL, 10 µg/mL ubiquitin, TBS pH 7.4, 5% DMSO) was titrated with the metal-chelator solution. Fluorescence quenching of Scn was measured after each titrant addition on a HORIBA Jobin Yvon IBH FluoroLog-3 spectrofluorimeter, with 3 nm slit band-pass, using the characteristic excitation and emission wavelengths $\lambda_{exc}$=280 and $\lambda_{em}$=320-360 nm. The intrinsic fluorescence in proteins is generally attributed to tryptophan residues; two residues W31 and W79 are found in the proximity of the Scn binding site. Fluorescence values were corrected for dilution upon addition of titrant. Fluorescence data were analyzed by nonlinear regression analysis of fluorescence response versus chelator concentration using a one-site binding model as described elsewhere. Allred, et al., *PNAS*, 2015, 112 (33): 10342-10347) The $K_d$ values are the results of at least three independent titrations were determined according to Equation (2). Control experiments were performed with $[Fe^{III}(Ent)]^{3-}$ to ensure the stability of the protein under experimental conditions.

Crystallography. For crystallization, 1 mM solutions of equimolar metal/chelator complexes (prepared as above) were mixed in a 2:1 molar ratio with Scn, which was then buffer-exchanged into 25 mM PIPES (pH=7.0), 150 mM NaCl, 1 mM EDTA, and 0.01% w/w NaN$_3$, and concentrated to 10 mg/ml protein. Diffraction-quality crystals were grown by vapor diffusion from drops containing 1 µl of ternary metal-chelator-protein complex plus 1 µl of well solution (50 mM NaCl, 200 mM Li$_2$SO$_4$, 100 mM NaOAc (pH=4.3-4.5), 1.2-1.4 M (NH$_4$)$_2$SO$_4$). Crystals were cryo-preserved by transfer to 50 mM NaCl, 200 mM Li$_2$SO$_4$, 100 mM NaOAc (pH=4.3-4.5), 1.2 M (NH$_4$)$_2$SO$_4$, and 20% v/v glycerol. Diffraction data were collected on beamline 5.0.2 at the Advanced Light Source (ALS, Berkeley, Calif.). Diffraction data were integrated and scaled with HKL-2000 (Otwinowski & Minor, Processing of X-ray Diffraction Data Collected in Oscillation Mode. In Methods in Enzymology, Carter, C. W., Jr.; Sweet, R. M., Eds. Academic Press: New York, 1997; Vol. 276, pp 307-326). Initial phases were determined by rigid body positional refinement with Refmac (Murshudov, et al., *Acta Crystallogr D Biol Crystallogr*, 1997, 53: 240-255) using 3FW5.pdb as a starting structure, or molecular replacement with MolRep (Vagin & Teplyakov, MOLREP: an automated program for molecular replacement. *J. Appl. Cryst.*, 1997, 30, 1022-1025) using 3FW5.pdb as a search model. Structures were refined through iterative rounds of positional refinement using Refmac (Murshudov, et al., *Acta Crystallogr D Biol Crystallogr*, 1997, 53: 240-255) alternating with model building using COOT, 30 followed by a final round of TLS refinement 31 Residues or side-chains that did not exhibit clear electron density in $2F_{obs}-F_{calc}$ Fourier syntheses when contoured at 0.7σ were removed or truncated to the Cβ atom. The quality of the final model was assessed using ProCheck (Laskowski, et al., *J. Appl. Cryst.*, 1993, 26: 283-291) and Molprobity (Davis, et al., *Nucleic Acids Res.*, 2007, 35: W375-383). Crystallographic statistics are reported in FIG. 9. Final models have been deposited in the PDB (Berman, et al., *Nucleic Acids Res.*, 2000, 28 (1), 235-242).

In Vivo Biodistribution Assay. All procedures and protocols used in the presented in vivo studies were reviewed and approved by the Institutional Animal Care and Use Committee at Lawrence Berkeley National Laboratory and performed in AAALAC accredited facilities. The animals used were adult female CD-1 mice (180±7 days old, 40.8±5.8 g). Solutions of $^{238}$Pu complexed by 3,4,3-LI(CAM) and Scn: 3,4,3-LI(CAM) were prepared in situ at molar ratios protein:ligand:$^{238}$Pu of 0:100:1 and 100:100:1, respectively by mixing and incubating the appropriate quantities of $^{238}$Pu (NO$_3$)$_4$, ligand, and protein in phosphate-buffered saline (PBS) to reach a $^{238}$Pu concentration of 12 ng L−1. Protein solutions were washed thrice with PBS using 10 kDa molecular weight cut-off membrane-based centrifugal filters, and all solutions were filter-sterilized (0.22 µm) prior to injection. Under isoflurane anesthesia, groups of three normally fed mice were injected intravenously with 0.2 mL of a complex solution (370 Bq per mouse). After injection of the $^{238}$Pu tracer, mice were weighed, identified, and housed in groups of three in plastic stock cages lined with a 0.5 cm layer of highly absorbent low-ash pelleted cellulose bedding (Alpha-dri) for separation of urine and feces. Mice were given water and food ad libitum and euthanized at 4, 24, or 48 h after tracer injection. All experiments using $^{238}$Pu tracers were managed as metabolic balance studies, in which tissues and excreta were analyzed for $^{238}$Pu by liquid scintillation counting on a Perkin Elmer Packard Tri-Carb model B4430. The methods of sample collection, preparation, radioactivity measurements, and data reduction have been published previously (Sturzbecher-Hoehne, et al., *Dalton Transactions,* 2011, 40 (33): 8340-8346: Kullgren, et al., *Toxicology mechanisms and methods,* 2013, 23 (1), 18-26; Durbin, et al., *Health physics* 2000, 78 (5): 511-521). Those methods provide quantitative measurements of radioactivity in biological samples; material recoveries averaged 99% of the amount injected in these experiments.

Figure 10:
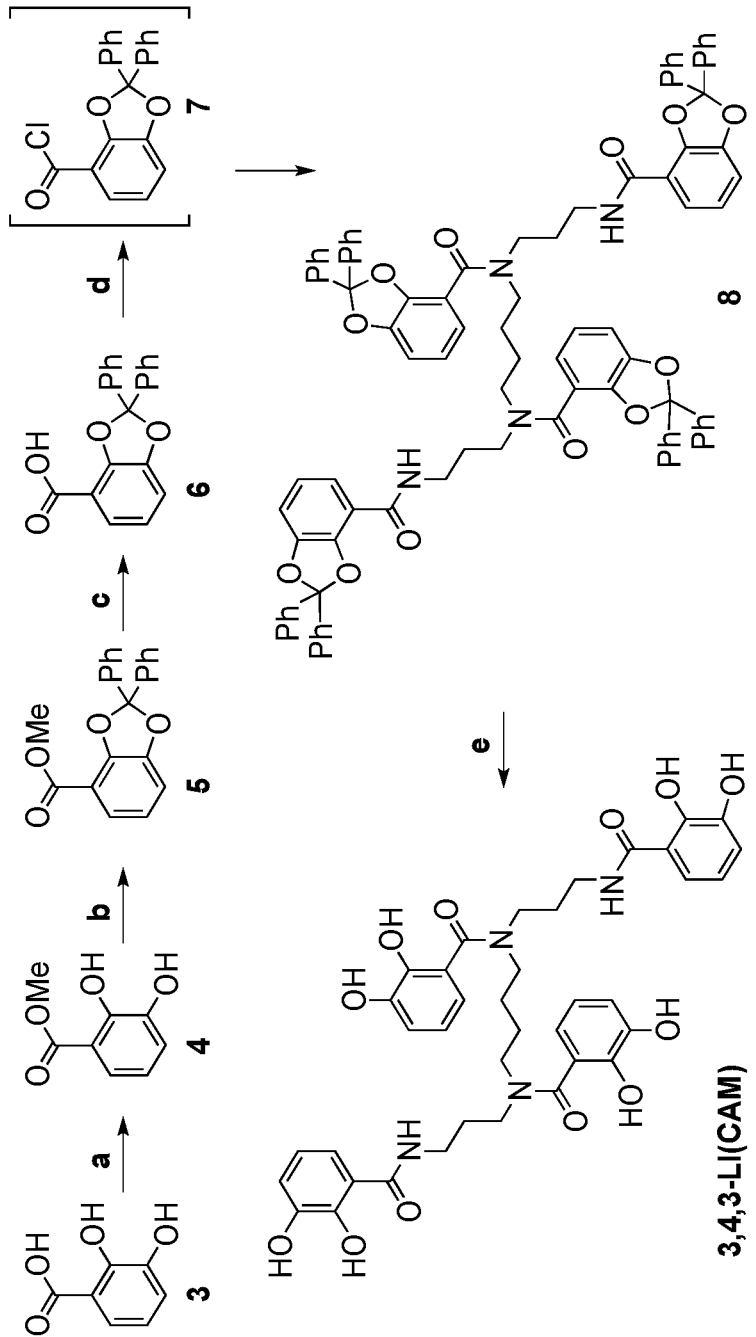
FIG. 10. Synthesis of 3,4,3-LI(CAM). (A) $H_2SO_4$, MeOH, 65° C., 16 h (88%). (B) dichlorodiphenylmethane, 160° C., 1 h. (C) 50/50 THF/$H_2O$, reflux 5 h (81% over 2 steps). (D) $(COCl)_2$, toluene, cat. DMF; then spermine, $Et_3N$, THF, 50° C., O/N (78%). (E) AcOH/$H_2O$+conc. HCl, 16 h (90%).
Figure 12A:
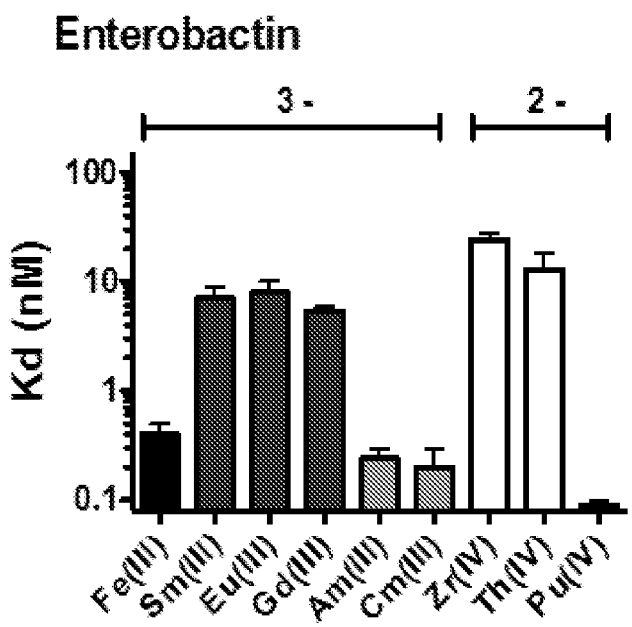
FIGS. 12A and 12D. Scn dissociation constants determined from fluorescence quenching analyses for M(III) and M(IV) complexes formed with Ent (12A, top left), 3,4,3-LI (1,2-HOPO) (12B, top right), or 3,4,3-LI(CAM) (12C, bottom left), and crystal pictures for the Scn adducts formed with the Zr(IV) (12D, bottom middle) and Th(IV) (12E, bottom right) complexes of 3,4,3-LI(CAM). The charges of the discussed metal complexes vary from 0 to −4 at pH 7.4 and are indicated above each bar; asterisks indicate that no binding was observed. Ent and 3,4,3-LI(1,2-HOPO) data are plotted based on previously reported values (Allred, et al., PNAS, 2015, 112 (33): 10342-10347), except for the Zr complex $K_d$ values that were determined in this work; the affinity observed with the ferric complex of Ent is shown for reference, as it is the native Scn ligand.
Figure 12B:
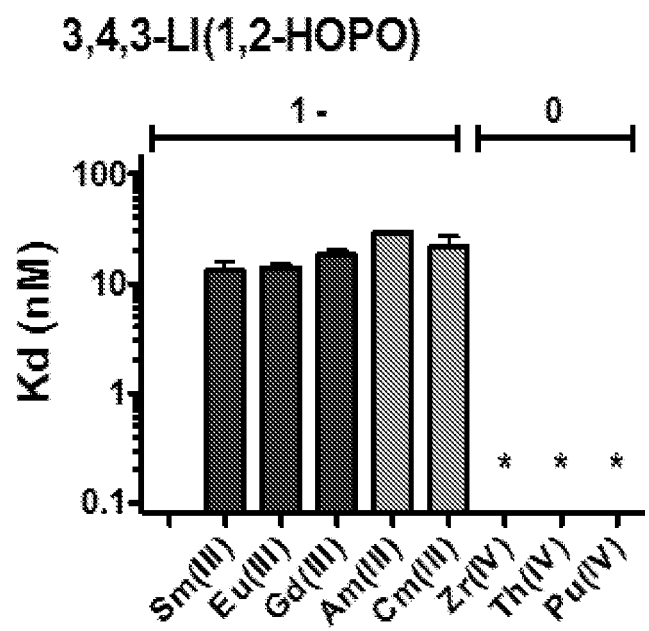
Figure 12C:
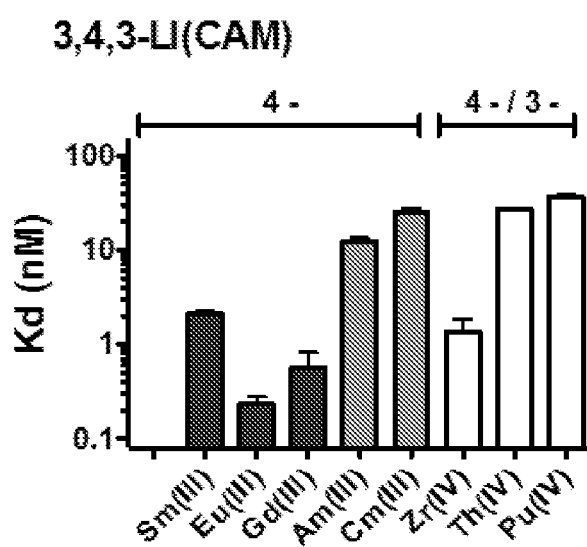
Figure 12D:
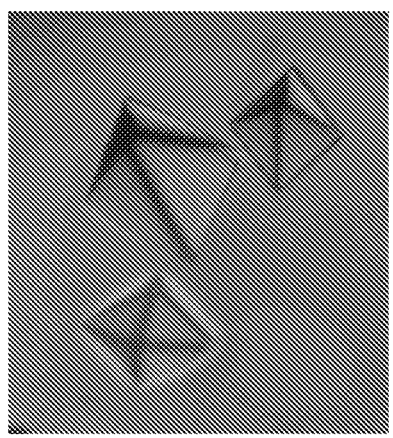
Figure 12E:
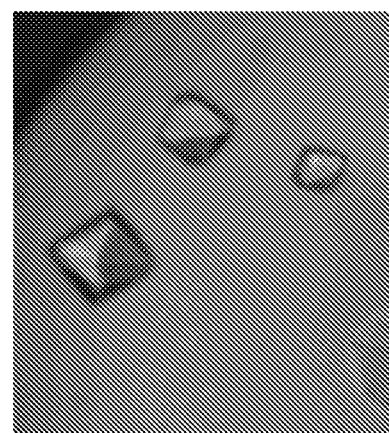

Results & Discussion. Synthesis of Octadentate Ligand 3,4,3-LI(CAM). Since electrostatic interactions between Scn and Ln/An complexes play a key role in binding, chelators that would form overall negative complexes with both 3+ and 4+ metals were explored. Although Scn exhibits a broad, degenerate recognition mechanism for native siderophores, previous studies probing the extent of Scn binding to synthetic siderophore analogs showed that the Scn binding site allows only limited changes to its ligands (Abergel, et al., *J Am Chem Soc,* 2006, 128 (34): 10998-10999; Holmes, et al., *Structure,* 2005, 13 (1) 29-41). Thus, the simplest way to correct the binding would be to employ chelators with similar structural features. Occam's razor was followed by using 3,4,3-LI(CAM), a known compound first prepared by Raymond and coworkers for plutonium decorporation (Weitl, et al., *J Am Chem Soc,* 1980, 102 (7): 2289-2293). This octadentate ligand leverages grafting of catecholamide (CAM) moieties found in microbial siderophores on the spermine scaffold to form a hybrid version of Ent and 3,4,3-LI(1,2-HOPO) that should (i) display increased complex stability over Ent due to its higher denticity and (ii) bear more negative charges than 3,4,3-LI (1,2-HOPO) due to CAM units requiring further deprotonation for metal binding (FIG. 1). 3,4,3-LI(CAM) was synthesized from readily available building blocks using a process developed in-house (FIG. 10). The new preparation moves away from using harsh reaction conditions by using the protected diphenylmethylene acetal derivative (5), which greatly simplifies purification of the final product.

Affinity of 3,4,3-LI(CAM) Toward 3+ and 4+ Metals. A comprehensive solution thermodynamic analysis was performed to characterize the affinity of 3,4,3-LI(CAM) for trivalent and tetravalent metals and the effect of substituting 1,2-HOPO for CAM binding units on the octadentate spermine scaffold. The protonation constants of 3,4,3-LI(CAM) were determined by spectrophotometric titrations, and eight protonation equilibria were assigned to sequential removal of two protons from each of the four CAM units (FIG. 11). Previous studies of Ent and other CAM-containing synthetic analogs established that the protonation constants ($pK_{a1}$-$pK_{a4}$) of the meta-hydroxyl oxygen atoms are well separated from the ortho-hydroxyl oxygen atoms ($pK_{a5}$-$pK_{a8}$) (Loomis & Raymond, *Inorganic Chemistry,* 1991, 30 (5): 906-911). The last four $pK_a$ values are most relevant to metal binding as moieties corresponding to these values have to be deprotonated at physiological pH in order to bind the metal ions. The overall acidity of 3,4,3-LI(CAM) can be defined as $\Sigma pK_{a5-8}=45.4$ versus 3,4,3-LI(1,2-HOPO)'s 21.2 (Abergel, et al., *Inorganic chemistry* 2009, 48 (23): 10868-10870) with lower values representing higher acidity. 3,4,3-LI(CAM) is therefore less prone to bind hard Lewis acids at low pH than its 1,2-HOPO analog, due to competition between metal uptake and protonation of the CAM moieties.

Incremental spectrophotometric titrations were then carried out to determine the formation of $Eu^{III}$, $Zr^{IV}$ or $Th^{IV}$ complexes with 3,4,3-LI(CAM). Because of the very short half-life of $^{225}$Ac and the scarce availability of the longer-lived $^{227}$Ac, $Eu^{III}$ was used here as a non-radioactive Ln surrogate for $Ac^{III}$. Based on previous solution thermodynamic studies of $Ln^{III}$ complexes of 3,4,3-LI(1,2-HOPO) and other common polyaminocarboxylate chelators,15 it is reasonable to expect similar stability constants for $Eu^{III}$ and $Ac^{III}$ complexes of 3,4,3-LI(CAM). The CAM octadentate chelator showed a very high affinity for both 3+ and 4+ ions (FIG. 11). The stability constants of $[Eu-3,4,3-LI(CAM)]^{5-}$, $[Th-3,4,3-LI(CAM)]^{4-}$ and $[Zr-3,4,3-LI(CAM)]^{4-}$ are several orders of magnitude higher than those of their 1,2-HOPO counterparts, with log β110 values of 29.7, 47.7 and 57.3, respectively. Consequently, 3,4,3-LI(CAM) is one of the strongest chelators ever reported for the chelation of both trivalent and tetravalent f-elements. For comparison, a cyclic octadentate terephthalamide derivative was recently designed to bind Th4+ in vivo and showed an unprecedented affinity for Th4+ with a log β110 (ThL4−) value of 53.7 (Pham, et al., *J. Am. Chem. Soc.,* 2014, 136 (25): 9106-9115). To inspect the pH dependency of metal complex formation, speciation diagrams were calculated for 3,4,3-LI (CAM) in the presence of 1 equivalent of Eu(III), Zr(IV) or Th(IV) (FIGS. 5-7). Both Zr(IV) and Th(IV) complexes start forming at around pH 3, with the mono and fully deprotonated species, $[M^{IV}LH]^{3-}$ and $[M^{IV}L]^{4-,}$ being predominant at physiological pH (7.4). This behavior departs from that of 3,4,3-LI(1,2-HOPO), with which 4+ metal complexes are formed even under very acidic conditions (pH<0) (Deblonde, et al., *Inorganic chemistry,* 2013, 52 (15); 8805-8811; Sturzbecher-Hoehne, et al., *Inorganic chemistry,* 2015, 54 (7): 3462-3468). For Eu(III), complexation by 3,4,3-LI(CAM) starts at pH 5 and the mono-protonated complex, $[Eu^{III}LH]^{4-}$, is the only species present at pH 7.4. Similar to what is observed with 4+ metals, the pH at which $Eu(III)^{-3}$,4,3-LI(CAM) complexes start forming is higher than in the case of $Eu(III)^{-3}$,4,3-LI(1,2-HOPO) species that already appear at pH 1 under those same conditions (Abergel, et al., *Inorganic chemistry,* 2009, 48 (23): 10868-10870). However, it is important to note the multiple negative charges of the 3,4,3-LI(CAM) complexes with 3+ and 4+ metals complexes under physiologically relevant conditions ($[M^{III}LH]^{4-}$, $[M^{IV}LH]^{3-}$ and $[M^{IV}L]^{4-}$), which are now capable of forming electrostatic interactions with the Scn protein. This represents a large advantage over 3,4,3-LI(1,2-HOPO), for which the complexes with $M^{III}$ at pH 7.4 have only one negative charge and are neutral in the case of $M^{IV}$ ions.

Scn Recognition of 3,4,3-LI(CAM)-Metal Complexes. As described in several previous reports (Allred, et al., *PNAS,* 2015, 112 (33): 10342-10347; Abergel, et al., *J Am Chem Soc,* 2006, 128 (34): 10998-10999; Abergel, et al., *PNAS* 2006, 103 (49): 18499-18503), the affinity of Scn for chelators or metal-chelator complexes is quantified by monitoring protein fluorescence quenching upon ligand or complex binding. The equilibrium dissociation constant of Scn for the apo form of the chelator 3,4,3-LI(CAM), $K_d=1.2\pm0.4$ nM, is nearly identical to that determined for the native siderophore apo-Ent,11a indicating that the addition of a fourth CAM unit does not affect chelator recognition by the protein. Subsequent determination of $K_d$ values for various metal complexes of 3,4,3-LI(CAM) ($M^{III}$=Sm, Eu, Gd, $^{243}$Am, or $^{248}$Cm, and $M^{IV}$=Zr, $^{232}$Th, or $^{242}$PU) confirm tight binding to the protein, independent of the metal valence, with values well below 40 nM (FIG. 12). As hypothesized, these data demonstrate a large difference in protein recognition between the 3,4,3-LI(CAM) and 3,4,3-LI(1,2-HOPO) complexes of tetravalent metals. Use of the biprotic CAM units in lieu of the monoprotic 1,2-HOPO moieties led to the formation of negatively charged complexes, enabling electrostatic interactions with the protein trilobal calyx. In addition, while the addition of a fourth CAM metal-binding group in the octadentate 3,4,3-LI(CAM) was important for increased stability of the metal-ligand complexes at pH 7.4, it did not prevent the high Scn affinities initially observed with hexa-coordinated Ent complexes. Interestingly, some subtle differences were observed with the recognition patterns: for similarly charged complexes, weaker binding was observed with actinide complexes (AmIII, $Cm^{III}$, $Th^{IV}$, and $Pu^{IV}$) as compared to corresponding lanthanide or d-block metal complexes ($Sm^{III}$, $Eu^{III}$, $Gd^{III}$, $Zr^{IV}$) in the case of 3,4,3-LI(CAM). The opposite trend had been noted with Ent complexes of $M^{III}$ metals9 and was confirmed here with $Zr^{IV}$, while no significant differences are discernable with 3,4,3-LI(1,2-HOPO).

Figure 13A:
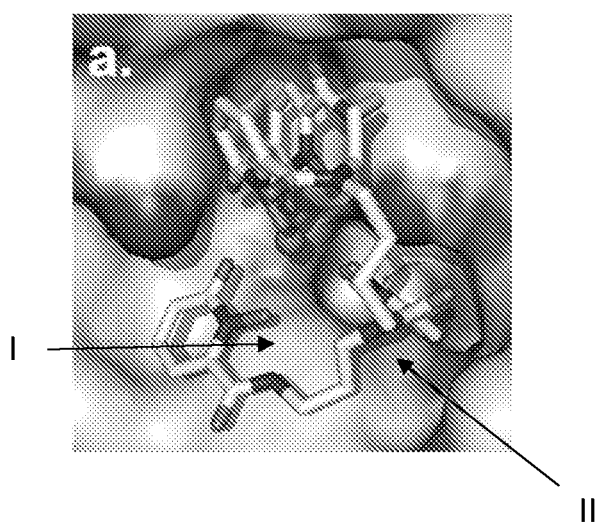
FIGS. 13A-13E. Crystallographic analyses of the binding of $^{232}$Th-3,4,3-LI(CAM) and Zr-3,4,3-LI(CAM) by Scn. (13A) A molecular surface representation of the calyx of Scn is colored by atom type (C: light gray, O: medium gray, N: dark grey), with the $^{243}$Am-3,4,3-LI(1,2-HOPO) complex shown in a licorice-stick representation, also shaded by atom type. The metal ion is shown as a small sphere, in the center of the FIG. Surface contributed by the side-chains of W79 and R81 are shaded areas I and II, respectively. Two prominent dark grey-tipped protuberances sticking into the calyx correspond to the side-chains of K125 and K134, which bracket the crucial binding pocket in the calyx. (13B) A view into the Scn calyx of the $^{232}$Th-3,4,3-LI(CAM) complex structure, shown as in (13A). In this structure, the side-chain of W79 is disordered, indicated by the dashed circle, due to sampling of multiple rotamers in the complex, allowing much more of the surface of R81 to be seen. Only one substituent CAM group and the actinide (sphere in the center of the FIG) are ordered and visualized in the complex crystal structure, as had been seen in previous hexadentate CAM/actinide/Scn structure [Allred et al., Proceedings of the National Academy of Sciences 2015, 112 (33), 10342-10347]. The one ordered CAM moiety sits in the key binding pocket defined by the side-chains of K125 and K134. (13C) A view into the Scn calyx of the Zr-3,4,3-LI(CAM) complex structure, shown as in (13A) and (13B). In this structure, the side-chains of W79 and R81 have repositioned to accommodate this ligand. Like the $^{232}$Th structure, only one substituent CAM group and the Zr atom (sphere in the center of the FIG) are ordered. (13D) A view perpendicular to that in (13A), (13B), and (13C) highlights the differential packing of the CAM or HOPO substituents in the key binding pocket. Other atoms in the chelator have been removed for clarity, and the molecular surface has been rendered partially transparent. Metal and carbon atoms have been re-shaded to indicate the complex: $^{243}$Am-3,4,3-LI(1,2-HOPO), $^{232}$Th-3, 4,3-LI(CAM), and Zr-3,4,3-LI(CAM) (13E). The side-chains of W79 and R81 and the connecting protein backbone have been isolated and superimposed from the three complexes, they are shown in a licorice-stick representation, shaded as in (13D). This view highlights the different rotamers selected in the different complexes, the only element of conformational flexibility in the extremely rigid Scn calyx.
Figure 13B:
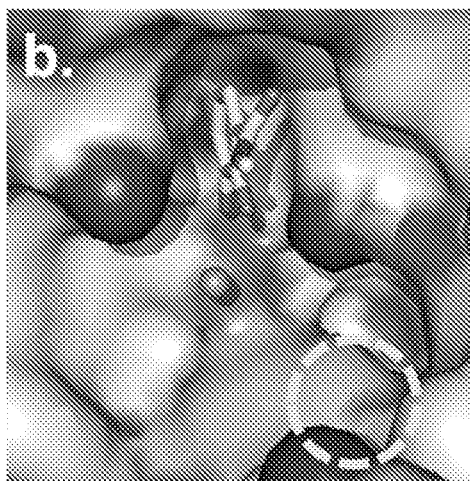
Figure 13C:
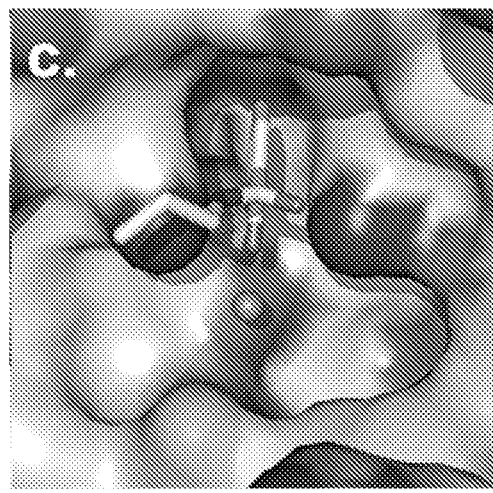
Figure 13D:
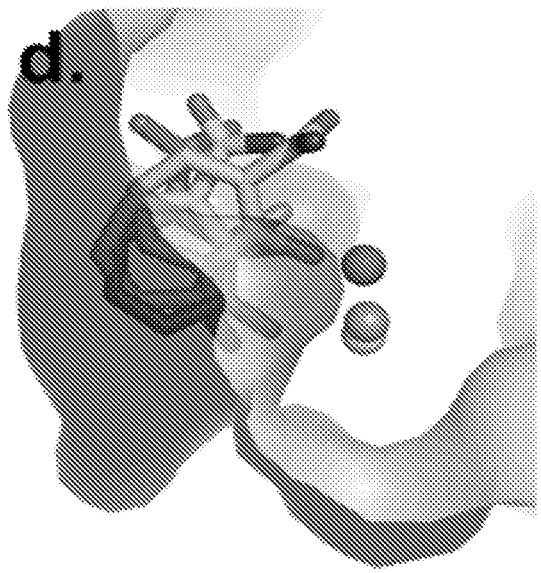
Figure 13E:
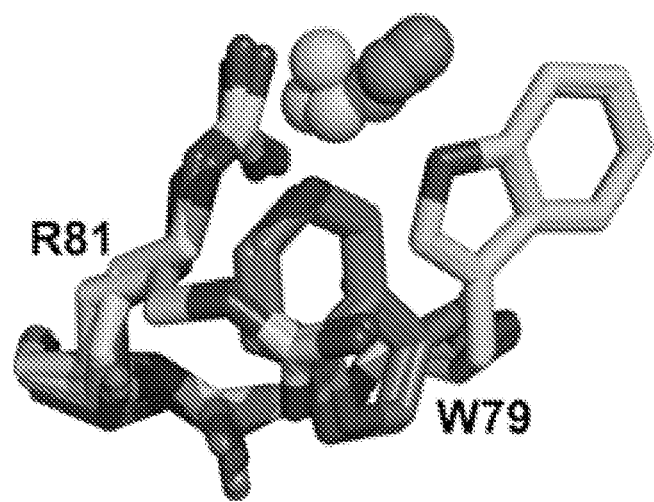

Structural Characterization of Scn-CAM adducts. X-ray crystallography was used as previously described9 to determine the structures of the Scn adducts formed with the $^{232}$Th-3,4,3-LI(CAM) and Zr-3,4,3-LI(CAM) complexes (FIG. 9). As expected, and as observed in previous Scn complex structures (eg., with $^{243}$Am-3,4,3-LI(1,2-HOPO)) (Allred, et al., PNAS, 2015, 112 (33): 10342-10347), the compounds bound in the deeply-recessed trilobal binding site, or calyx, of Scn (FIGS. 13A, 13B, and 13C). As in previous structures of Scn bound to CAM-bearing ligands with An ions, only one CAM substituent is ordered in the crystal structures along with the bound metal, Zr or Th. This was likely the result of the remainder of the chelator sampling multiple conformations between molecules in the crystal, but clearly confirmed binding of chelator and metal in both adducts. The CAM substituent bound in the key binding pocket in the Scn calyx, between the side-chains of two bracketing lysine residues (K125 and K134; FIG. 3D). The structure of the Scn calyx is highly conserved with prior structures, reflecting its rigidity, with the side-chains of two residues, W79 and R81, the only elements flexing to accommodate different chelators (FIG. 13E). In prior Ent or Ent analog chelator/actinide structures (Allred, et al., PNAS, 2015, 112 (33): 10342-10347), where two of the three CAM groups are also disordered, the side-chain of W79 adopted an unusual rotamer, flipping inwards towards the metal to contribute a cation-π interaction. However, in these structures, this side-chain adopts more conventional orientations, either sampling multiple rotamers, rendering it disordered in the crystallographic analysis (in the Zr complex), or lying against the calyx wall in the Th complex. Apart from these two side-chains, the overall impression conveyed by these and previous results is that the chelator flexes and distorts to fit in an essentially rigid and unyielding calyx.

Figure 14:
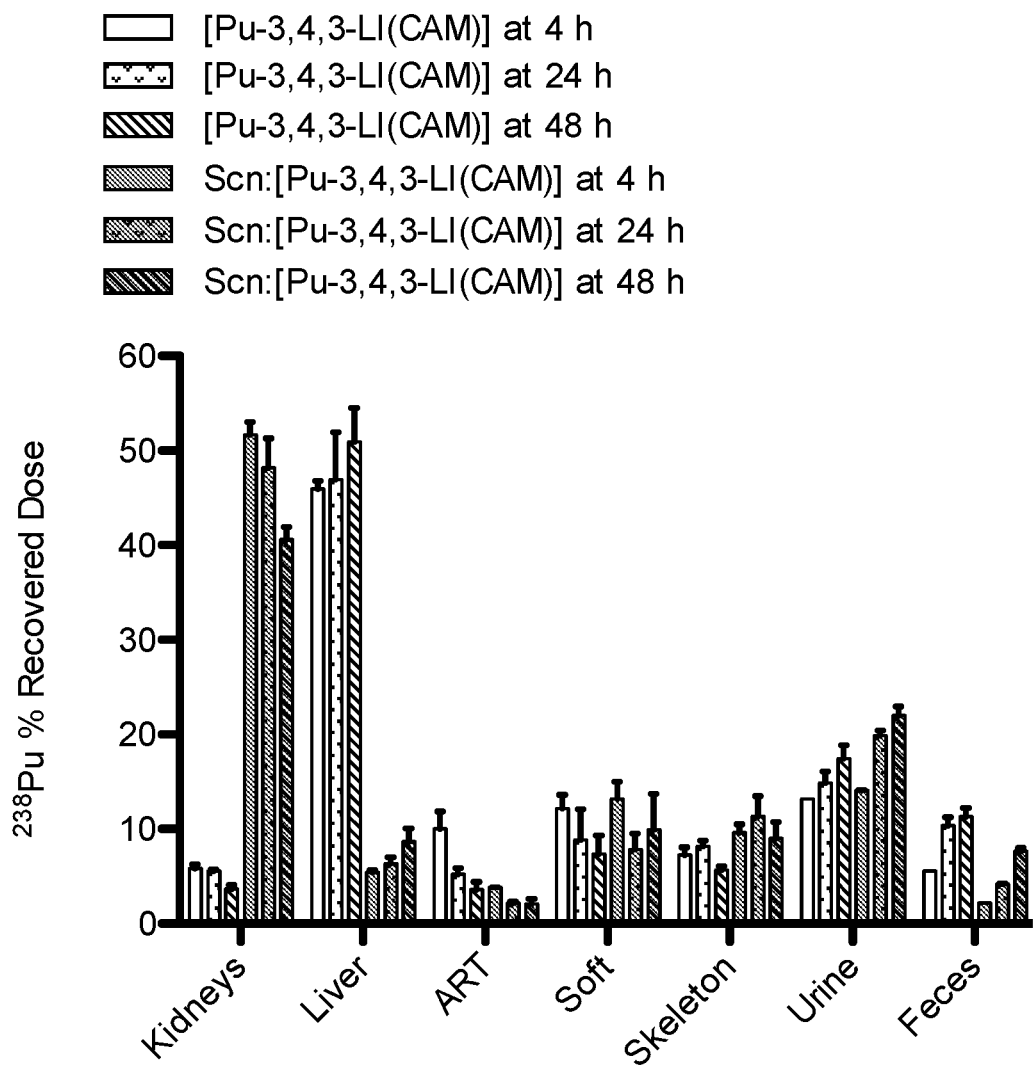
FIG. 14. Biodistribution of Pu(IV) when administered as a free or Scn-bound 3,4,3-LI(CAM) complex. Healthy mice injected intravenously with $^{238}$Pu-ligand and $^{238}$Pu-ligand-protein solutions (370 Bq/mouse); mice euthanized at 4, 24, or 48 h. "ART" and "Soft" stand for "abdominal remaining tissues" and other "soft tissues," respectively.

Biodistribution Evaluation. To evaluate the in vivo retention and excretion patterns of M(IV)-3,4,3-LI(CAM) complexes and their Scn adducts, $^{238}$Pu(IV) was used as a radiolabel. $^{238}$Pu(IV) likely behaves similarly to Th(IV) and Zr(IV) (the ionic radius of $Pu^{4+}$ is included between those of $Th^{4+}$ and $Zr^{4+}$) (Sturzbecher-Hoehne, et al., Inorganic Chemistry, 2015, 54 (7): 3462-3468) but allows for more accurate metabolic balance experiments due to its relatively long radioactive half-life (87.8 yr) and low specific activity (0.63 TBq/g), compared to the therapeutic $^{227}$Th (18.68 d; 1139 TBq/g) and imaging $^{89}$Zr (78.42 h; 16,630 TBq/g) isotopes. It is also important to note that other commonly available isotopes such as $^{232}$Th (14 Gyr; 4.07 kBq/g) would not exhibit enough activity to allow for radioanalysis. In this in vivo stability experiment, $^{238}$Pu-ligand complex solutions were formed in situ (Ligand:Pu and Scn:Chelator:Pu ratios of 100:1 and 100:100:1, respectively) and administered intravenously. Mice were euthanized 4, 24, or 48 h after the metal injection, and tissues and excreta were radioanalyzed for $^{238}$Pu content (FIG. 14).

Independent of the presence of Scn in the administered solution, 30% of the injected $^{238}$Pu was excreted by 48 hours and $^{238}$Pu excreta content steadily increased, suggesting delayed clearance of the complexes. The rate of $^{238}$Pu elimination observed for $^{238}$Pu-3,4,3-LI(CAM) is strikingly different from that observed for the $^{238}$Pu-3,4,3-LI(1,2-HOPO) complex in previous studies (albeit performed in a different strain of mice and with younger animals), in which quantitative excretion was observed by 24 h. In both Scn-bound and free $^{238}$Pu-3,4,3-LI(CAM) cases, and at all time points, more $^{238}$Pu was found in the urine than in the feces. However, the kidney and liver contents suggest a dramatic difference in excretion pattern: when free, the 3,4,3-LI(CAM) complex is predominantly found in the liver at early time points after administration and follows a biliary pathway, similar to what is known for HOPO complexes. However, insertion within the protein favors elimination through the renal system, with up to 52% of $^{238}$Pu found in the kidneys 4 h after administration of the Scn adducts, a burden that subsequently slowly decreases. Combined with significantly faster rates of excretion and considerably lower skeleton and soft tissue burden when compared with free $^{238}$Pu, this major difference between kidney vs. liver $^{238}$Pu retention of the Scn-bound vs. free complex evidences the high in vivo stability of the Scn:[$Pu^{IV}$(3,43-LI(CAM))] adduct.

Conclusion. The Scn:3,4,3-LI(CAM) system is a novel and highly promising chelator platform to develop new radiopharmaceuticals and imaging agents. Scn's highly specific binding to 3,4,3-LI(CAM)-$M^{IV}$ and 3,4,3-LI(CAM)-$M^{III}$ complexes eliminates the need for costly bioconjugation of chelators to targeting ligands as the protein may be encoded via well-established biochemical methods. Interestingly, one can envision a system where both imaging ($^{89}Zr^{IV}$) and therapeutic ($^{227}Th^{IV}$ or $^{225}Ac^{III}$) metallic radioisotopes may be used in conjunction for dual diagnostics/treatment applications. The described results illustrate the promise of this system.

Example 2

Tests with cut-off filters. The present example presents a separation process that uses size exclusion. Various systems are already commercially available for the purification of macromolecules (including proteins) from low-molecular weight molecules by size exclusion. These systems usually contain a porous membrane that lets the small molecules pass but retains the macromolecules.

"Cut-off" filters were used for the separation of tin ions ($Sn^{4+}$) from europium ions ($Eu^{3+}$). The aim of the tests described in this section was to obtain an experimental proof of principle of our separation process rather than determining the maximum efficacy or selectivity of the process.

Samples containing tin ions complexed to the composition (e.g., ligand) [3,4,3-LI(1,2-HOPO)]$^{4-}$ were passed through 3 kDa cut-off filters (2 filters from 2 different suppliers). As seen on FIG. 18, the majority of the tin ions passed through the filters. The same experiment was performed with samples containing europium ions ($Eu^{3+}$) complexed to the composition (e.g., ligand) [3,4,3-LI(1,2-HOPO)]$^{4-}$ and siderocalin. In this case, since a high molecular weight adduct is formed (Scn[Eu(III)L]), the majority of europium is retained by the filters.

Figure 18:
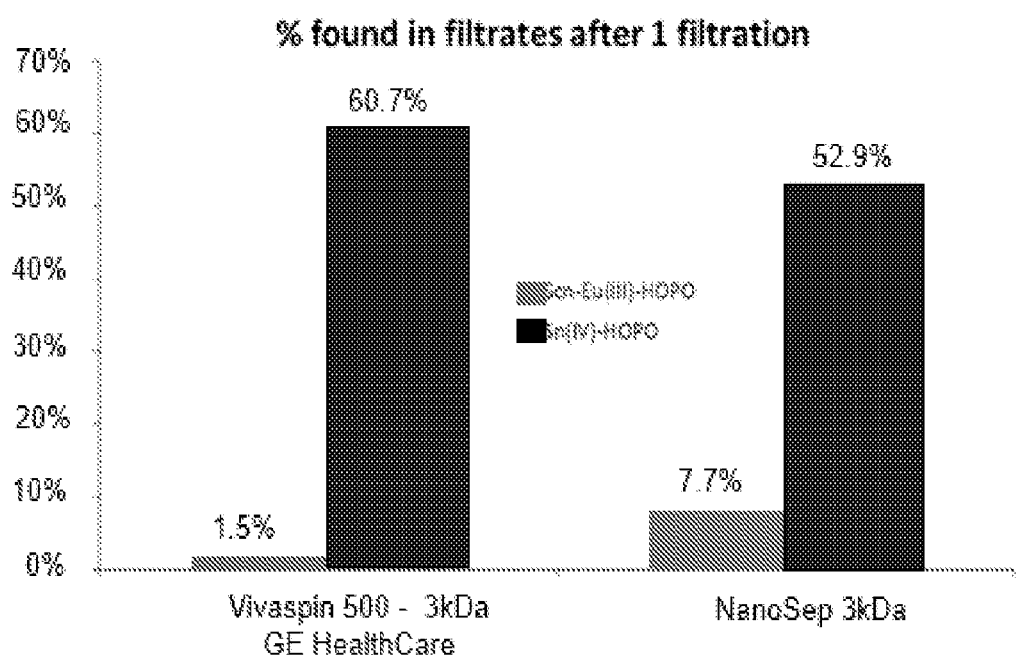
FIG. 18 depicts a bar graph showing the percentage of Sn(IV)-HOPO complex (right bar in each pair of experiments) or siderocalin-Eu(III)-3,4,3-LI(1,2-HOPO) passed through the cut-off filter. Left: filter from GE HealthCare, model "VivaSpin 500-3 kDa". Right: filter from NanoSep, model "3 kDa". Sample centrifuged 15 min at 10,000 rpm. T=22° C. Tin sample: [Sn(IV)]=25 μM, [3,4,3-LI(1,2-HOPO)]=25 μM, pH=7.4. Europium sample: [Eu(III)]=300 nM, [3,4,3-LI(1,2-HOPO)]=300 nM, [siderocalin]=350 nM, pH=7.4.

The performances obtained above are limited by the performance of the filters which are not designed for such applications. The fact that less than 100% of the tin ions passed through the filters is probably due to adsorption on the membrane. Nonetheless, the results displayed in FIG. 18 show that a good separation can be obtained between $M^{4+}$ and $M^{3+}$ ions and even for a 1-step process, which works at room temperature and under mild conditions (aqueous solution at pH=7.4). The separation factor Sn/Eu obtained is 41.4 in the case of the GE HealthCare filter and 6.9 for the "NanoSep' filter (FIG. 18).

Figure 19:
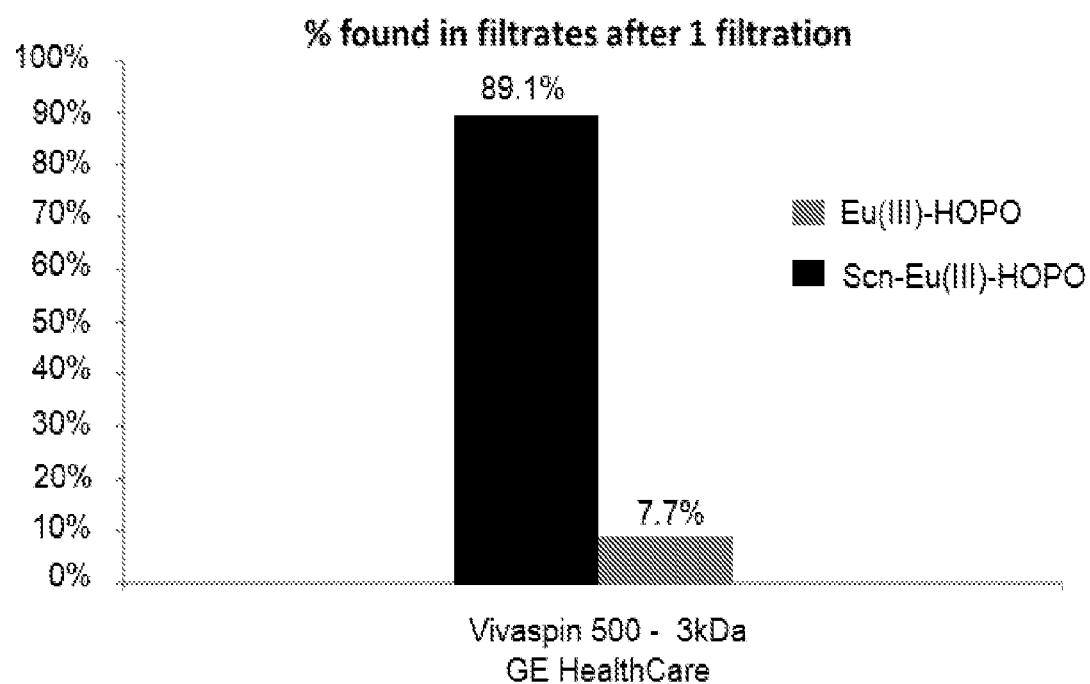
FIG. 19. Percentage of europium passed through the cut-off filter for samples containing Eu(III)-3,4,3-LI(1,2-HOPO) complex without (left) and with (right) siderocalin. Sample without siderocalin: [Eu(III)]=1 μM, [3,4,3-LI(1,2-HOPO)]=1 μM, pH=7.4. Sample without siderocalin: [Eu(III)]=0.3 μM, [3,4,3-LI(1,2-HOPO)]=0.3 μM, [siderocalin] =0.35 μM, pH=7.4. Sample centrifuged 15 min at 10,000 rpm. T=22° C. Cut-off filter from GE HealthCare, model "VivaSpin 500-3 kDa".

The influence of the protein itself on the filtration was clarified by preparing 2 samples: one containing only the complex [Eu(III)-3,4,3-LI(1,2-HOPO)]$^-$ and another containing the complex [Eu(III)-3,4,3-LI(1,2-HOPO)]$^-$ in addition to siderocalin. FIG. 19 shows that the addition of the protein allows to form a high-molecular weight adduct that is retained by the filter. Indeed, in the absence of the protein, 89% of the europium passed through the filter compared to only 7.7% under similar conditions but in the presence of the protein.

Example 3

Figure 20:
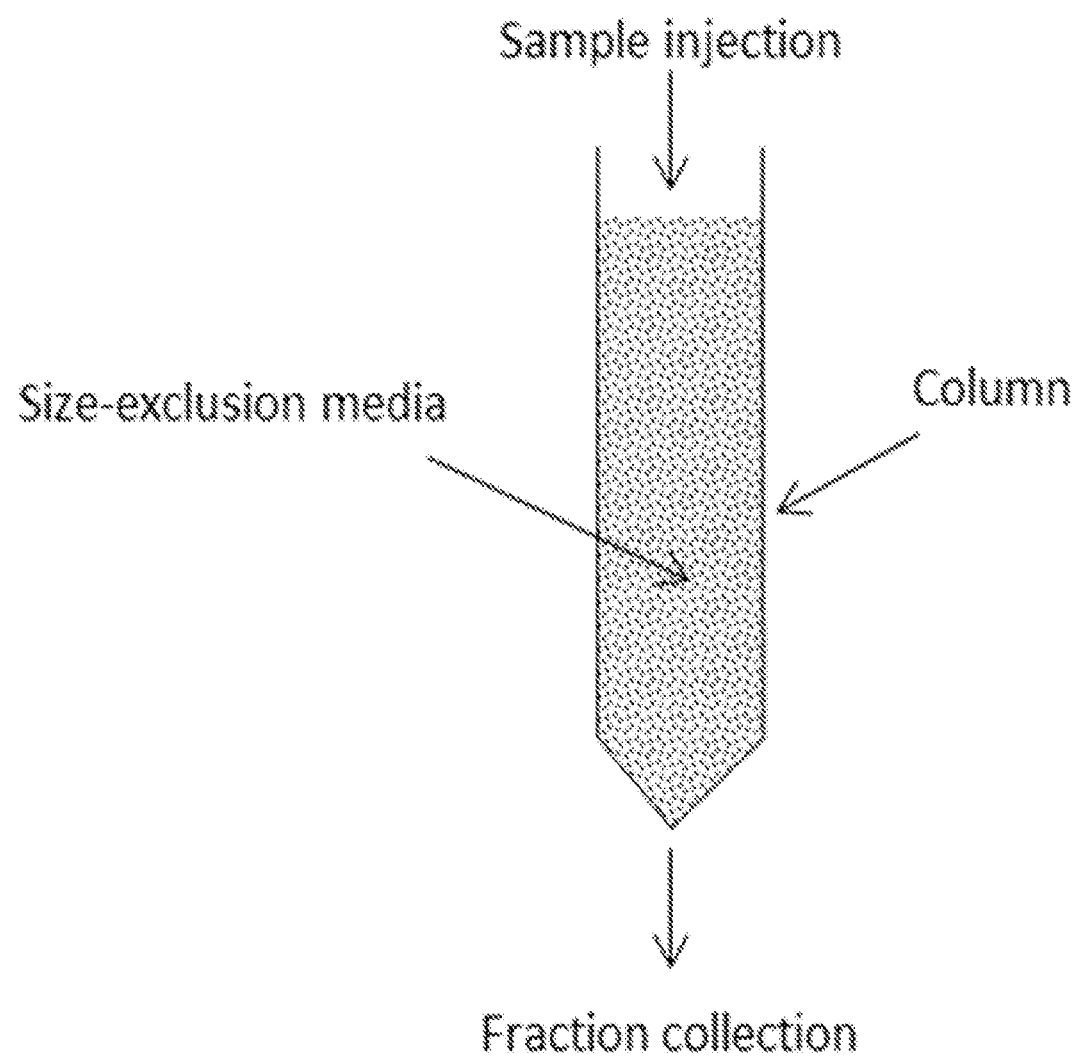
FIG. 20 depicts a scheme of the gravity column used for metal ions separation.

Tests with size exclusion column. An additional size exclusion system was tested. A chromatographic size-exclusion media, called "Sephadex G-25", was used to separate the low-molecular weight complex from the high-molecular weight adduct metal-composition (e.g., ligand)-protein. The Sephadex media is a classical porous size-exclusion media used in biology for protein purification. Macromolecules such as proteins are too big to go inside the pores of the media and are consequently not retained, whereas the small molecules can go inside the pores of the media and their elution is delayed compared to the protein. A scheme is give in FIG. 20. An advantage of such a system, besides being simple and robust, is that the recovery yields can reach 100%, as long as the column is flushed with the appropriate solution. Once the protein adduct is eluted, the other components of the initial samples (for example [M(IV)-3,4,3-LI(1,2-HOPO)] complexes) can therefore be recovered by passing more buffer to the column.

Figure 21:
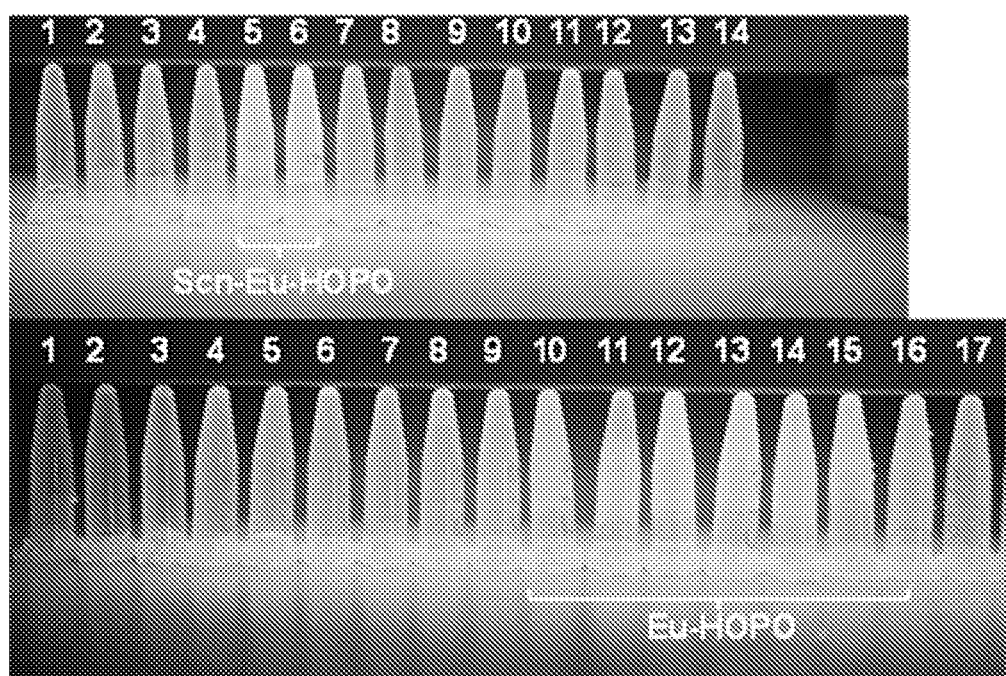
FIG. 21 is a picture of fractions collected from Sephadex G25 PD-10 column under UV irradiation (λ=312 nm). Top: initial sample containing $Eu^{3+}$ ions, $[3,4,3-LI(1,2-HOPO)]^{4-}$ and siderocalin. Bottom: initial sample containing $Eu^{3+}$ ions and $[3,4,3-LI(1,2-HOPO)]^{4-}$. The bracketed section is due to the presence of the complexes siderocalin-[Eu(III)-3,4,3-LI (1,2-HOPO)] (top) or [Eu(III)-3,4,3-LI(1,2-HOPO)]$^-$ (bottom) which are luminescent under UV irradiation. Each fraction is about 0.5 mL. pH=7.4. T=25° C. Samples eluted with TBS buffer.

Samples containing metal ions and the composition (e.g., ligand) [3,4,3-LI(1,2-HOPO)]$^{4-}$ in the presence or in the absence of siderocalin were injected in a gravity column at room temperature and ambient pressure. The samples were eluted at pH 7.4 with a classical TBS buffer and fractions were collected and analyzed. The first test was performed with europium ions ($Eu^{3+}$) in order to evaluate the applicability of this system. The [Eu(III)-3,4,3-LI(1,2-HOPO)]$^-$ complex and the siderocalin-[Eu(III)-3,4,3-LI(1,2-HOPO)] adduct are fluorescent under UV irradiation and can therefore be followed easily. FIG. 21 illustrates the separation of the low-molecular weight complex [Eu(l III)-3,4,3-LI(1,2-HOPO)]$^-$ from the siderocalin-[Eu(III)-3,4,3-LI(1,2-HOPO)] adduct. The adduct exits the column in the early fractions (5 and 6) whereas the small complex exits the column later in fractions 10 to 17.

Figure 22:
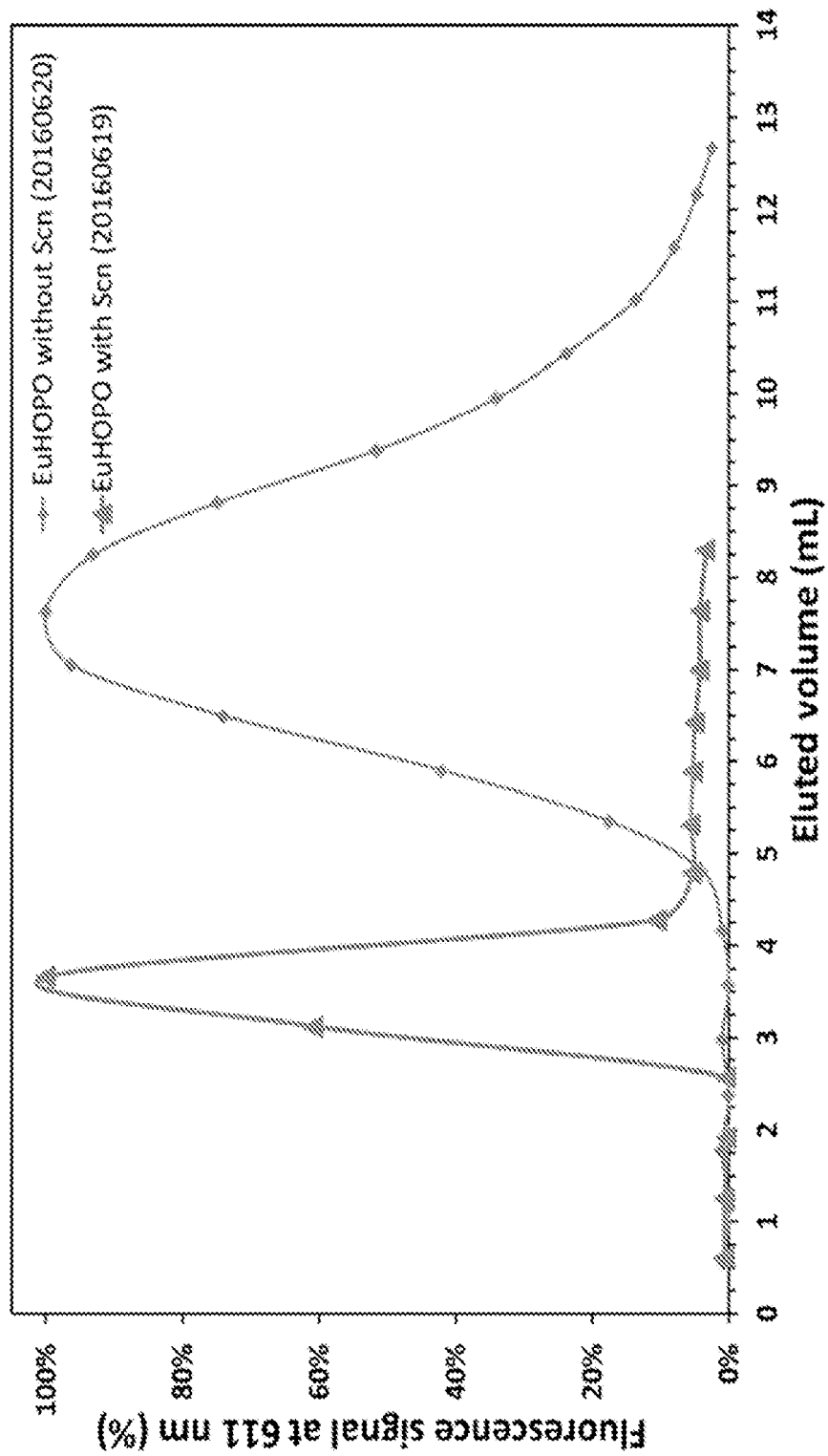
FIG. 22 is a graph showing the fluorescence analysis of the fraction depicted on FIG. 21. Triangles: sample with siderocalin; [Eu(III)]=0.3 μM, [3,4,3-LI(1,2-HOPO)]=0.3 μM, [siderocalin]=0.35 μM, pH=7.4. Diamonds: sample without siderocalin; [Eu(III)]=1.0 µM, [3,4,3-LI(1,2-HOPO)]=1.0 µM, pH=7.4. Gravity column: Sephadex G-25 PD-10 (GE HealthCare). Samples eluted with TBS at pH 7.4. T=22° C. Fluorescence signal measure at 611 nm after excitation of the samples at 325 nm.

A quantitative analysis of the fractions depicted above was performed by spectrofluorimetry (FIG. 22). The results given on FIG. 22 confirm the previous qualitative observation (FIG. 21) and show that the macromolecular adduct exits the column before the low molecular complex. These results therefore confirm that the presence of the protein clearly influence the elution time of the negatively charged complexes as exemplified here with [Eu(III)-3,4,3-LI(1,2-HOPO)]$^-$.

Figure 23:
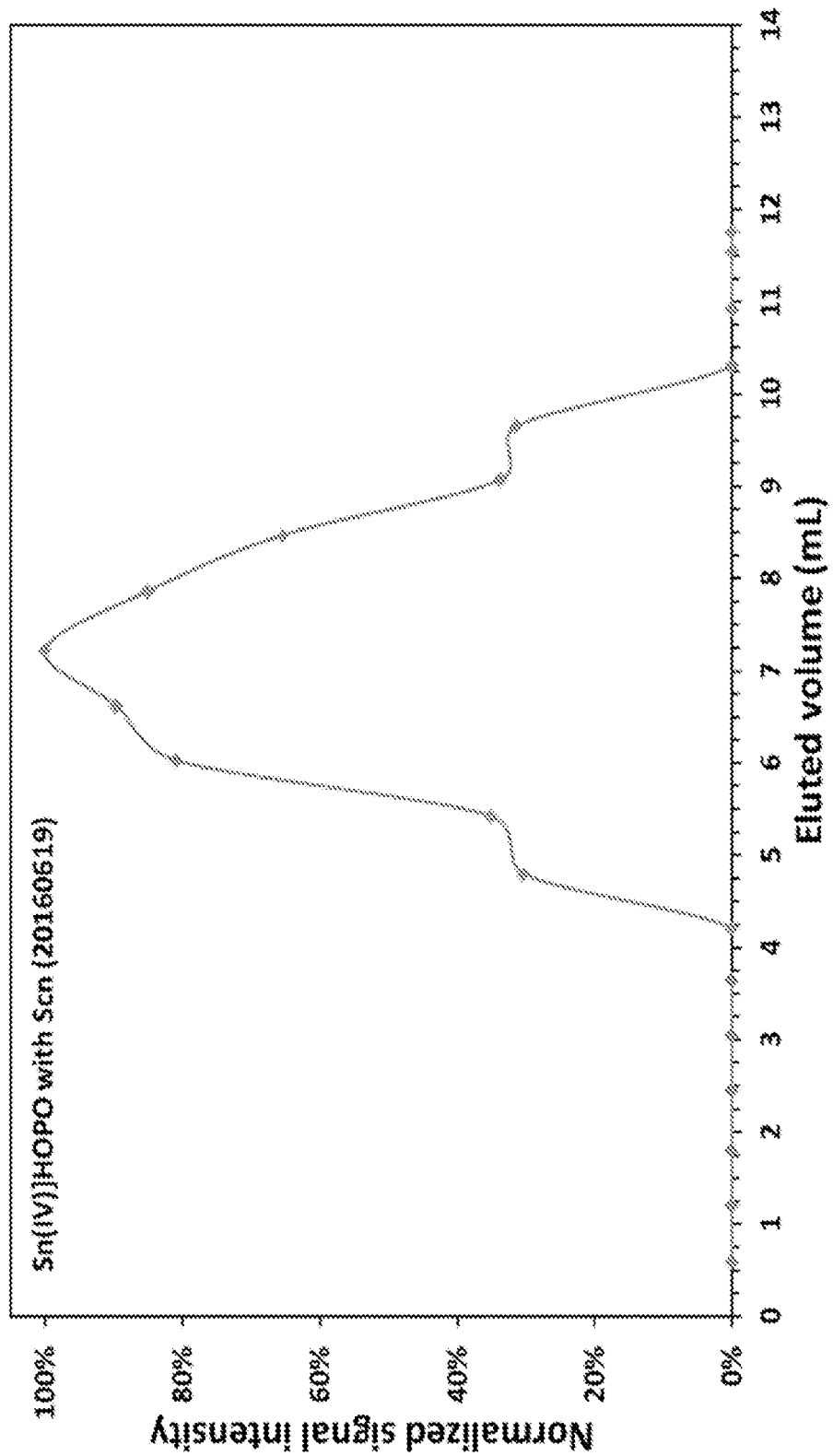
FIG. 23 is a graph depicting the UV-vis analysis of a tin(IV) sample passed through a Sephadex G25 PD-10 size-exclusion column. Initial sample containing $Sn^{4+}$ ions and $[3,4,3-LI(1,2-HOPO)]^{4-}$. The complex [Sn(IV)-3,4,3-LI(1,2-HOPO)] was detected by UV-vis at 304 nm which characteristic of this complex. Each fraction is about 0.5 mL. pH=7.4. T=25° C. Sample eluted with TBS buffer.

The size-exclusion column was also tested with the tin (IV) neutral complex [Sn(IV)-3,4,3-LI(1,2-HOPO)]. The elution of the complex was followed by UV-vis since the latter is neither luminescent nor radioactive but has a characteristic maximum absorbance at 304 nm. FIG. 23 shows that the elution of the tin(IV) complex is not recognized by the protein and that its elution is delayed compared to the macromolecular adducts (comparison FIG. 22 and FIG. 23). Based on the results obtained with Eu(III) and Sn(IV) it is clear that both metals can be separated since the Eu(III) complex is recognized by the protein and exits the column in the early fractions whereas the tin(IV) neutral complex is not recognized and elutes long after the macromolecular adduct.

Figure 24:
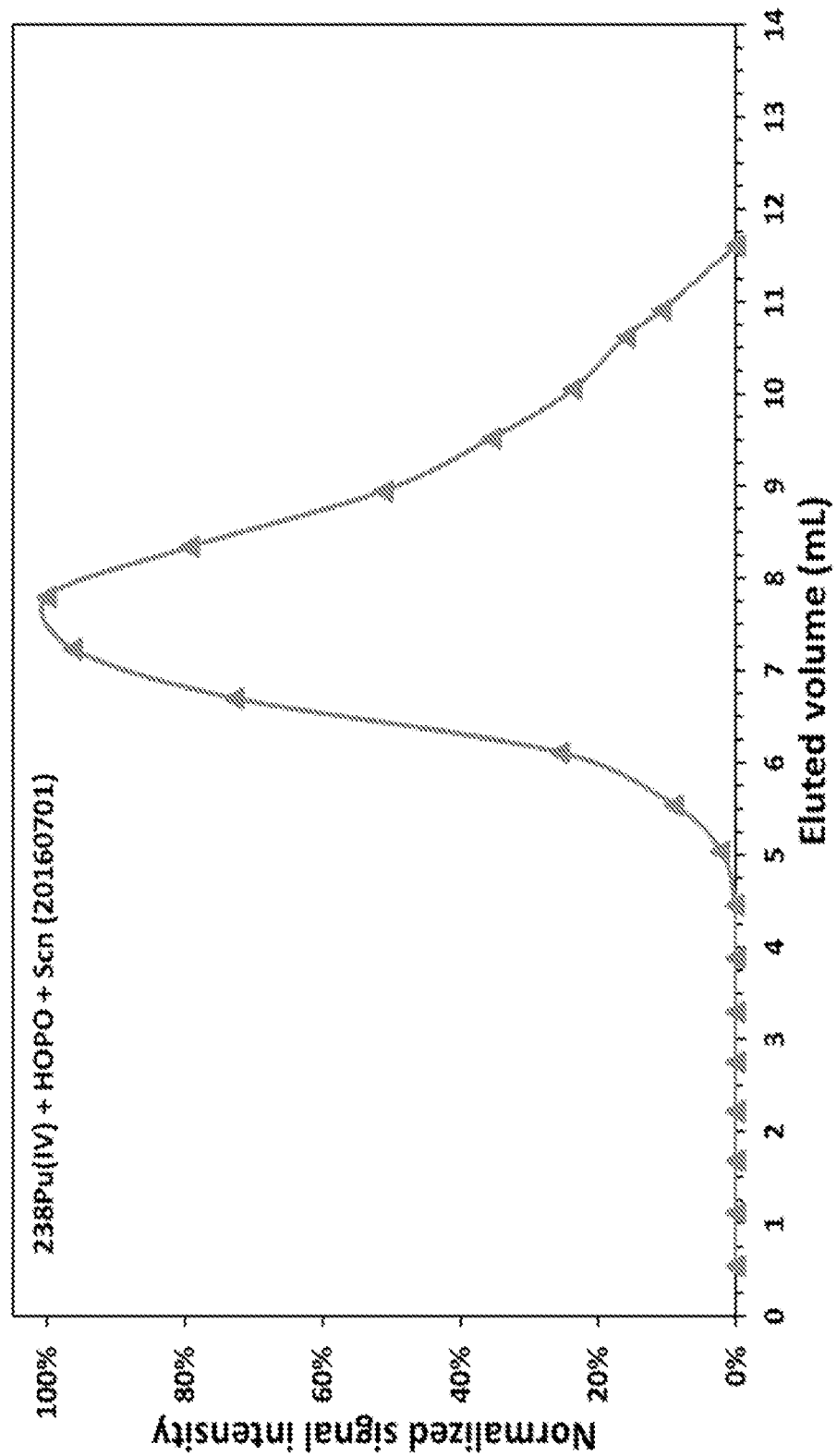
FIG. 24 is a graph depicting the liquid scintillation analysis of a $^{238}Pu(IV)$ sample passed through a Sephadex G25 PD-10 size-exclusion column. Initial sample containing $Pu^{4+}$ ions and $[3,4,3-LI(1,2-HOPO)]^{4-}$. The presence of plutonium in each fraction was controlled by liquid scintillation counting. Each fraction is about 0.5 mL. pH=7.4. T=25° C. Sample eluted with TBS buffer.

The system was then tested with plutonium ions ($Pu^{4+}$). A sample containing $^{238}Pu^{4+}$ ions, the composition (e.g., ligand) [3,4,3-LI(1,2-HOPO)]$^{4-}$ and siderocalin was eluted through a Sephadex column and followed by liquid scintillation since the isotope $^{238}Pu$ has a high specific activity (17.1 $Ci \cdot g^{-1}$). As for [Sn(IV)-3,4,3-LI(1,2-HOPO)], the plutonium neutral complex, [Pu(IV)-3,4,3-LI(1,2-HOPO)], is not recognized by siderocalin and elutes long after the Scn[Eu(III)L]macromolecular species (comparison of FIG. 24 and triangle curve on FIG. 22). It is clear from the results obtained here that Eu(III) ions can be separated from both Sn(IV) and Pu(IV) ions via by [3,4,3-LI(1,2-HOPO)]/siderocalin-based systems. The same conclusion can be drawn for the other rare earth ions.

Example 4

A separation experiment was performed for a sample containing both curium ions ($^{248}Cm^{3+}$) and plutonium ions ($^{238}Pu^{4+}$). Curium and plutonium separation is especially important in the frame of nuclear fuel cycles because these two actinides elements are present in the nuclear wastes and are difficult to separate. The plutonium-curium case is a good model for the separation of $Bk^{4+}$ ions from $Cf^{3+}$ and $Cm^{3+}$. The plutonium-curium separation is also a good model for the separation of actinium ($Ac^{3+}$) from thorium ($Th^{4+}$) which are two other actinides of interest in the context of medical applications.

The presence of plutonium in the different fractions was detected by liquid scintillation. Due to the low activity of the curium isotope used ($^{248}Cm$, specific activity of 4.3 $mCi \cdot g^{-}1$), the presence of curium couldn't be detected by liquid scintillation but was rather performed by spectrofluorimetry. Indeed, as for Eu(III), the [Cm(III)-3,4,3-LI(1,2-HOPO)]$^-$ complex and the siderocalin-Cm(III)-3,4,3-LI(1,2-HOPO)] adduct are fluorescent under UV irradiation. As expected, the complex formed with [3,4,3-LI(1,2-HOPO)]$^{4-}$ and $Cm^{3+}$ is recognized by siderocalin which yields a macro-species which elutes rapidly. On the contrary, the neutral [Pu(IV)-3,4,3-LI(1,2-HOPO)] complex is not up taken by siderocalin and stays longer in the column. It has to be underlined that the initial sample described on FIG. 25 had high ratio curium/plutonium with a value of 25 mol/mol. This ratio is clearly unfavorable to obtain high purity plutonium with classical separation processes. Nonetheless, as shown on FIG. 25, the two actinides elements species have readily different retention times and plutonium fractions without curium could be obtained.

Figure 25:
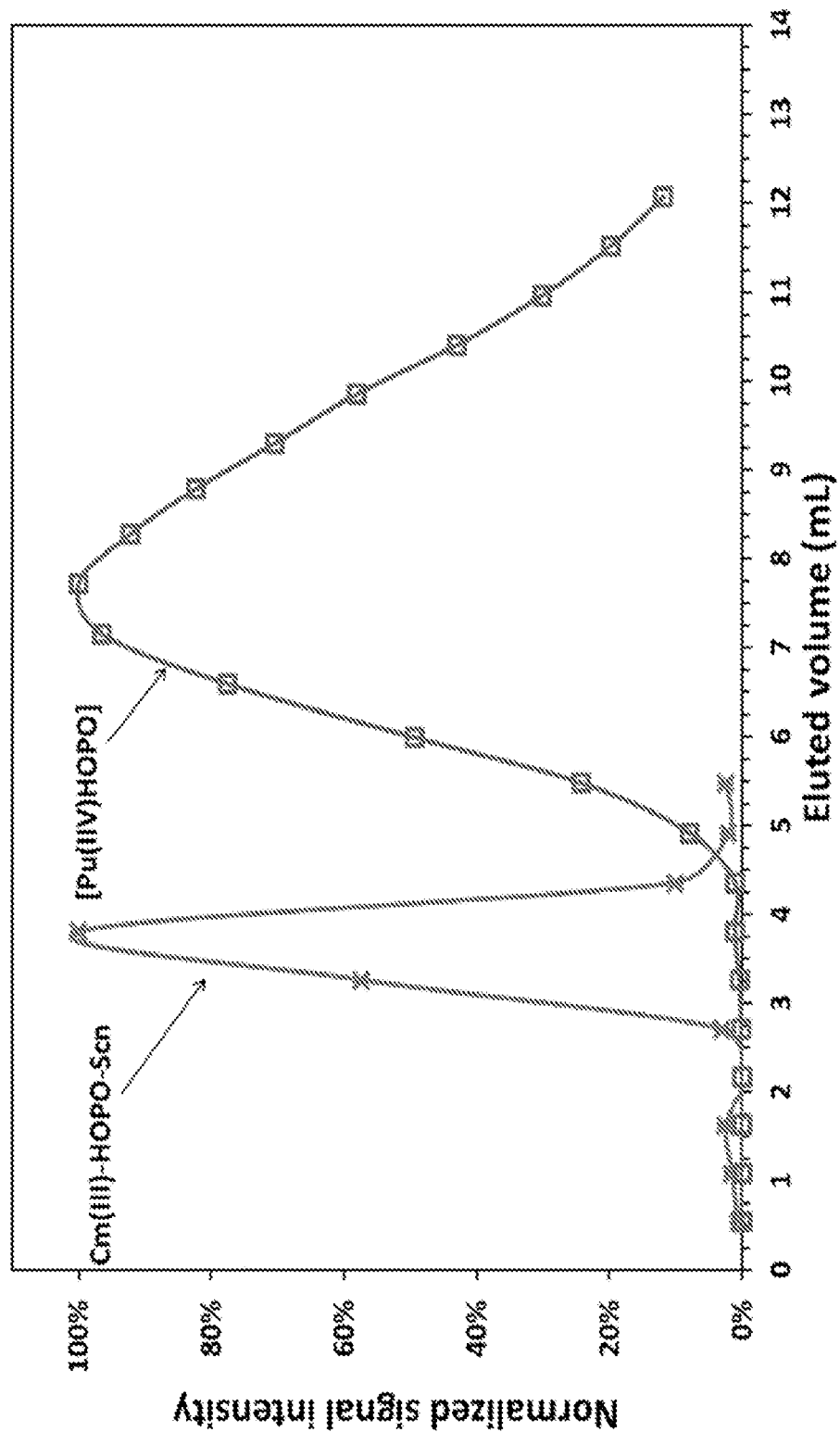
FIG. 25 is a graph depicting the analysis of the fractions collected after passing a sample containing $^{238}Pu^{4+}$ ions and $^{248}Cm^{3+}$ ions. Crosses: detection of $^{248}Cm^{3+}$ ions by fluorescence (Fluorescence signal measure at 614 nm after excitation of the samples at 325 nm). Squares: liquid scintillation analysis of $^{238}Pu$. Both fluorescence and liquid scintillation signals were normalized for comparison. Initial sample: [Cm]=0.500 µM, [Pu]=0.020 µM, [3,4,3-LI(1,2-HOPO)]=0.570 µM, [siderocalin]=0.6 µM, pH=7.4. Gravity column: Sephadex G-25 PD-10 (GE HealthCare). Samples eluted with TBS at pH 7.4. T=22° C.

Interestingly, the curium(III) retention time is similar to the europium(III) one (comparison of FIG. 25 and FIG. 22) whereas the plutonium(IV) retention time is similar to the tin(IV) one (comparison of FIG. 25 and FIG. 23). These results show that the separation doesn't depend on the nature of the metal ion but on the charge of its complex with the small composition (e.g., ligand) (here [3,4,3-LI(1,2-HOPO)]$^{4-}$).

The results described above demonstrate that ions can be separated in an efficient manner by using protein-composition (e.g., ligand) recognition and subsequent selective formation of high-molecular weight species. The proofs of concept given above pave the way for new separation or purification processes. All the separations described in these isolation experiments were performed at room temperature, at ambient pressure, using a one-step process and under mild chemical conditions (fully aqueous solvent, pH 7.4). Moreover, the chemical or biochemical reagents employed do not contain non-volatile elements which could allow the final recovery and concentration of the purified ion by simple techniques such as ignition. The system described above also exhibits a high selectivity and allows separating and purifying ions even for samples that present a very unfavorable metal ions ratio (as demonstrated in the $Cm^{3+}/Pu^{4+}$ experiment). The results also indicate that the system selectivity is generic for ions having the same electronic charge (for example $Cm^{3+}$ and $Eu^{3+}$ versus $Sn^{4+}$ and $Pu^{4+}$) which open ways to several applications.

Example 5

The oxidation state of Bk when bound to 3,4,3-L(1,2-HOPO) was unambiguously assigned through liquid chromatography (LC) coupled with high resolution mass spectrometry (MS). Analysis of 1:1 metal:ligand aqueous mixtures prepared under ambient conditions with $^{241}$Am, $^{248}$Cm and $^{249}$Cf, whose $M^{4+}/M^{3+}$ redox potentials are extremely high ([Am], +3.1 and +3.2 V, respectively), confirmed the formation of trivalent 3,4,3-LI(1,2-HOPO) complexes. For those three trans-Pu elements, the MS patterns are almost identical, with four mono-charged adducts detected ([$M^{III}LH_2$]$^+$, [$M^{III}LHNa$]$^+$, [$M^{III}LNa_2$]$^+$ and [$M^{III}LNaK$]$^+$), which clearly contrasts with the data obtained for tetravalent $^{242}$Pu and $^{232}$Th complexes. The MS spectrum of the $^{249}$Bk system assembled in situ from a BkCl$_3$ solution displayed [BkLH]$^+$, [BkLNa]$^+$ and [BkLK]$^+$ species, evidently demonstrating that the Bk complex contains a Bk(IV) ion and not Bk(III). Spontaneous oxidation of Bk(III) to Bk(IV) is thought to occur through air oxidation, similarly to the Ce system, which does not necessitate the addition of oxidizers or electrolytic oxidation required in previously proposed methods. The use of 3,4,3-LI(1,2-HOPO) as a chelation and oxidation-promoting agent for Bk also has the notable advantage of promoting the formation of M(IV) complexes over a wide pH-range: the Zr(IV), Ce(IV) and Pu(IV) complexes are formed in 1 M $H_2SO_4$ and are stable up to pH 11.

Liquid Chromatography-Mass Spectrometry. The experimental setting used for liquid chromatography-high resolution mass spectrometry assays (LC-HRMS) has been previously described (M. Sturzbecher-Hoehne, T. A. Choi, R. J. Abergel, Hydroxypyridinonate Complex Stability of Group (IV) Metals and Tetravalent f-Block Elements: The Key to the Next Generation of Chelating Agents for Radiopharmaceuticals, Inorg. Chem. 54 (2015) 3462-3468. doi:10.1021/acs.inorgchem.5b00033). LC-HRMS spectra were acquired on a UPLC Waters Xevo system interfaced with a QTOF mass spectrometer (Waters Corporation, Milford, Mass., USA) in Micromass Z-spray geometry. Chromatographic separation was achieved on an analytical Zorbax Eclipse column (Agilent Technologies, XDB-C18, 5 µm, 4.6×150 mm) maintained at ambient temperature (25° C.) with two mobile phases (water (A) and methanol (B)) containing 0.5% formic acid. Samples (10 µL injection) were eluted using a gradient initially held constant at 7% B for 6.0 min and were then progressed to 40% B in the next 6.0 min and held at 40% B for 10 min. Mobile phase B was then increased to 99% over 3.0 min, held constant at 99% for 5.0 min, and then rapidly switched to 7% B and held until 46 min for equilibration. The flow rate was maintained at 0.5 mL/min. The mass spectrometer equipped with an ESI source was operated in positive ion mode, and mass spectra were acquired in the continuum mode across the m/z range of 100-1200, at 5 s per scan, with a 14 ms interscan delay. Data acquisition and instrument control were accomplished using MassLynx software, version 4.1. Samples were infused into the ionization chamber from the LC system. The operating parameters were as follows: the nebulization gas flow rate was set to 600 L/h with a desolvation temperature of 375° C., the cone gas flow rate was set to 30 L/h, and the ion source temperature was 125° C. The capillary, sampling cone, and extraction cone voltages were tuned to 2.7 kV, 47 V, and 3.3 V, respectively. Liquid nitrogen served as nebulizer and argon was used as collision gas with collision energies up to 50 eV. A calibration check of the instrument was performed with 0.5 mM sodium formate, prior to sample analysis. Samples containing an equal concentration of actinide and 3,4,3-LI(1,2-HOPO) were prepared in 0.1 M HEPES buffer at pH 7.4 (for Cm, Cf and Bk) or in 0.5% formic acid at pH 2 (for Ce, Th, and Pu). The concentrations used were 10 µM for $^{243}$Am, $^{249}$Bk and $^{249}$Cf samples and 1 µM for Ce, $^{232}$Th, $^{242}$Pu, and $^{248}$Cm. For consistency, an addition of 0.1 µM of [$Zr^{IV}$3,4,3-LI(1,2-HOPO)] was performed in each sample in order to use the Zr complex as internal reference. The retention times of independent samples were then normalized using that of [$Zr^{IV}$3,4,3-L1(1,2-HOPO)].

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability of Scn, chelators, and radionuclides to form SCC complexes, and/or in the ability of a particular SCC complex to provide a therapeutically effective treatment according to an objective measure disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; +18% of the stated value; +17% of the stated value; +16% of the stated value; +15% of the stated value; ±14% of the stated value; +13% of the stated value; ±12% of the stated value; +11% of the stated value; +10% of the stated value; +9% of the stated value; ±8% of the stated value; +7% of the stated value; +6% of the stated value; ±5% of the stated value; +4% of the stated value; ±3% of the stated value; +2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials is individually incorporated herein by reference in their entirety for their referenced teaching.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention can be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

What is claimed is:

1. A method of treating cancer in a subject in need thereof comprising administering to the subject a therapeutically effective amount of a composition including a structure

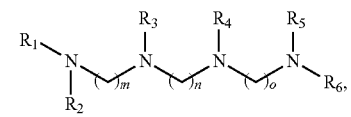

wherein:
at least one of $R_1$, $R_2$, $R_3$, $R_4$, and $R_6$, individually, are selected from the group consisting of a CAM group, a HA group, and a 1,2-HOPO group;
at least another one of $R_1$, $R_2$, $R_3$, $R_4$, and $R_6$, individually, are selected from the group consisting of H and an alkyl group having from 1 to 10 carbon atoms;
$R_6$ is selected from the group consisting of (i) H, (ii) an alkyl group having from 1 to 10 carbon atoms, and (iii) an alkyl group having from 1 to 10 carbon atoms and substituted by at least one of SH, $NH_2$, or C(=O)OH;
m is from 1 to 6;
n is from 1 to 6;
o is from 1 to 6; and
wherein the composition is bound to a siderocalin and a metal
wherein the siderocalin has
a sequence as set forth in any one of SEQ ID NOs: 1-8, 12-16, or 18-22,
a sequence as set forth in any one of SEQ ID NOs: 1-8, 12-14, 16, 18, or 22, with a threonine to cysteine mutation at position 54 or a serine to cysteine mutation at position 68,
a sequence as set forth in SEQ ID NOs: 15 or 20 with a threonine to cysteine mutation at position 54, or
a sequence as set forth in SEQ ID NO: 19 with a serine to cysteine mutation at position 68,
thereby treating the cancer in the subject in need thereof.

2. The method of claim 1, wherein the siderocalin is bound to the composition at position 54, position 68, or both position 54 and position 68 of the siderocalin.

3. The method of claim 1, wherein the metal is a radionuclide.

4. The method of claim 3, wherein the radionuclide is selected from the group consisting of $^{225}$Ac, $^{226}$Ac, $^{228}$Ac, $^{105}$Ag, $^{106}$mAg, $^{110}$mAg, $^{111}$Ag, $^{112}$Ag, $^{113}$Ag, $^{239}$Am, $^{240}$Am, $^{242}$Am, $^{244}$Am, $^{37}$Ar, $^{71}$As, $^{72}$As, $^{73}$As, $^{74}$As, $^{76}$As, $^{77}$As, $^{209}$At, $^{210}$At, $^{191}$Au, $^{192}$Au, $^{193}$Au, $^{194}$Au, $^{195}$Au, $^{196}$Au, $^{196}$m$^2$Au, $^{198}$Au, $^{198}$mAu, $^{199}$Au, $^{200}$mAu, $^{128}$Ba, $^{131}$Ba, $^{133}$mBa, $^{135}$mBa, $^{140}$Ba, $^{7}$Be, $^{203}$Bi, $^{204}$Bi, $^{205}$Bi, $^{206}$Bi, $^{210}$Bi, $^{212}$Bi, $^{243}$Bk, $^{244}$Bk, $^{245}$Bk, $^{246}$Bk, $^{248}$mBk, $^{250}$Bk, $^{76}$Br, $^{77}$Br, $^{80}$mBr, $^{82}$Br, $^{11}$C, $^{14}$C, $^{45}$Ca, $^{47}$Ca, $^{107}$Cd, $^{115}$Cd, $^{115}$mCd, $^{117}$mCd, $^{132}$Ce, $^{133}$mCe, $^{134}$Ce, $^{135}$Ce $^{137}$Ce, $^{137}$mCe, $^{139}$Ce, $^{141}$Ce, $^{143}$Ce, $^{144}$Ce, $^{246}$Cf, $^{247}$Cf, $^{253}$Cf, $^{254}$Cf, $^{240}$Cm, $^{241}$Cm, $^{242}$Cm, $^{252}$Cm, $^{55}$Co, $^{56}$Co, $^{57}$Co, $^{58}$Co, $^{58}$mCo, $^{60}$Co, $^{48}$Cr, $^{51}$Cr, $^{127}$Cs, $^{129}$Cs, $^{131}$Cs, $^{132}$Cs, $^{136}$Cs, $^{137}$Cs, $^{61}$Cu, $^{62}$Cu, $^{64}$Cu, $^{67}$Cu, $^{153}$Dy, $^{155}$Dy, $^{157}$Dy, $^{159}$Dy, $^{165}$Dy, $^{166}$Dy, $^{160}$Er, $^{161}$Er, $^{165}$Er, $^{169}$Er, $^{171}$Er, $^{172}$Er, $^{250}$Es, $^{251}$Es, $^{253}$Es, $^{254}$Es, $^{254}$mEs, $^{255}$Es, $^{256}$mEs, $^{145}$Eu, $^{146}$Eu, $^{147}$Eu, $^{148}$Eu, $^{149}$Eu, $^{150}$mEu, $^{152}$mEu, $^{156}$Eu, $^{157}$Eu, $^{52}$Fe, $^{59}$Fe, $^{251}$Fm, $^{252}$Fm, $^{253}$Fm, $^{254}$Fm, $^{255}$Fm, $^{257}$Fm, $^{66}$Ga, $^{67}$Ga, $^{68}$Ga, $^{72}$Ga, $^{73}$Ga, $^{146}$Gd, $^{147}$Gd, $^{149}$Gd, $^{151}$Gd, $^{153}$Gd, $^{159}$Gd, $^{68}$Ge, $^{69}$Ge, $^{71}$Ge, $^{77}$Ge, $^{170}$Hf, $^{171}$Hf, $^{173}$Hf, $^{175}$Hf, $^{179}$m$^2$Hf, $^{180}$mHf, $^{181}$Hf, $^{184}$Hf, $^{192}$Hg, $^{193}$Hg, $^{193}$mHg, $^{195}$Hg, $^{195}$mHg, $^{197}$Hg, $^{197}$mHg, $^{203}$Hg, $^{160}$mHo, $^{166}$Ho, $^{167}$Ho, $^{123}$I, $^{124}$I, $^{126}$I, $^{130}$I, $^{132}$I, $^{133}$I, $^{135}$I, $^{109}$In, $^{110}$In, $^{111}$In, $^{114}$mIn, $^{115}$mIn, $^{184}$Ir, $^{185}$Ir, $^{186}$Ir, $^{187}$Ir, $^{188}$Ir, $^{189}$Ir, $^{190}$Ir, $^{190}$m$^2$Ir, $^{192}$Ir, $^{193}$mIr, $^{194}$Ir, $^{194}$m$^2$Ir, $^{195}$mIr, $^{42}$K, $^{43}$K, $^{76}$Kr, $^{79}$Kr, $^{81}$mKr, $^{85}$mKr, $^{132}$La, $^{133}$La, $^{135}$La, $^{140}$La, $^{141}$La, $^{262}$Lr, $^{169}$Lu, $^{170}$Lu, $^{171}$Lu, $^{172}$Lu, $^{174}$mLu, $^{176}$mLu, $^{177}$Lu, $^{177}$mLu, $^{179}$Lu, $^{257}$Md, $^{258}$Md, $^{260}$Md, $^{28}$Mg, $^{52}$Mn, $^{90}$Mo, $^{93}$mMo, $^{99}$Mo, $^{13}$N, $^{24}$Na, $^{90}$Nb, $^{91}$mNb, $^{92}$mNb, $^{95}$Nb, $^{95}$mNb, $^{96}$Nb, $^{138}$Nd, $^{139}$mNd, $^{140}$Nd, $^{147}$Nd, $^{56}$Ni, $^{57}$Ni, $^{66}$Ni, $^{234}$Np, $^{236}$mNp, $^{238}$Np, $^{239}$Np, $^{15}$O, $^{182}$Os, $^{183}$Os, $^{183}$mOs, $^{185}$Os, $^{189}$mOs, $^{191}$Os, $^{191}$mOs, $^{193}$Os, $^{32}$P, $^{33}$P, $^{228}$Pa, $^{229}$Pa, $^{230}$Pa, $^{232}$Pa, $^{233}$Pa, $^{234}$Pa, $^{200}$Pb, $^{201}$Pb, $^{202}$mPb, $^{203}$Pb, $^{209}$Pb, $^{212}$Pb, $^{100}$Pd, $^{101}$Pd, $^{103}$Pd, $^{109}$Pd, $^{111}$mPd, $^{112}$Pd, $^{143}$Pm, $^{148}$Pm, $^{148}$mPm, $^{149}$Pm, $^{151}$Pm, $^{204}$Po, $^{206}$Po, $^{207}$Po, $^{210}$Po, $^{139}$Pr, $^{142}$Pr, $^{143}$Pr, $^{145}$Pr, $^{188}$Pt, $^{189}$Pt, $^{191}$Pt, $^{193}$mPt, $^{195}$mPt, $^{197}$Pt, $^{200}$Pt, $^{202}$Pt, $^{234}$Pu, $^{237}$Pu, $^{243}$Pu, $^{245}$Pu, $^{246}$Pu, $^{247}$Pu, $^{223}$Ra, $^{224}$Ra, $^{225}$Ra, $^{81}$Rb, $^{82}$Rb, $^{82}$mRb, $^{83}$Rb, $^{84}$Rb, $^{86}$Rb, $^{181}$Re, $^{182}$Re, $^{182}$mRe, $^{183}$Re, $^{184}$Re, $^{184}$mRe, $^{186}$Re, $^{188}$Re, $^{189}$Re, $^{190}$mRe, $^{99}$Rh, $^{99}$mRh, $^{100}$Rh, $^{101}$mRh, $^{102}$Rh, $^{103}$mRh, $^{105}$Rh, $^{211}$Rn, $^{222}$Rn, $^{97}$Ru, $^{103}$Ru, $^{105}$Ru, $^{35}$S, $^{118}$mSb, $^{119}$Sb, $^{120}$Sb, $^{120}$mSb, $^{122}$Sb, $^{124}$Sb, $^{126}$Sb, $^{127}$Sb, $^{128}$Sb, $^{129}$Sb, $^{43}$Sc, $^{44}$Sc, $^{44}$mSc, $^{46}$Sc, $^{47}$Sc, $^{48}$Sc, $^{72}$Se, $^{73}$Se, $^{75}$Se, $^{153}$Sm, $^{156}$Sm, $^{110}$Sn, $^{113}$Sn, $^{117}$mSn, $^{119}$mSn, $^{121}$Sn, $^{123}$Sn, $^{125}$Sn, $^{82}$Sr, $^{83}$Sr, $^{85}$Sr, $^{89}$Sr, $^{91}$Sr, $^{173}$Ta, $^{175}$Ta, $^{176}$Ta, $^{177}$Ta, $^{180}$Ta, $^{182}$Ta, $^{183}$Ta, $^{184}$Ta, $^{149}$Tb, $^{150}$Tb, $^{151}$Tb, $^{152}$Tb, $^{153}$Tb, $^{154}$Tb, $^{154}$mTb, $^{154}$m$^2$Tb, $^{155}$Tb, $^{156}$Tb, $^{156}$mTb, $^{156}$m$^2$Tb, $^{160}$Tb, $^{161}$Tb, $^{94}$Tc, $^{95}$Tc, $^{95}$mTc, $^{96}$Tc, $^{97}$mTc, $^{99}$mTc, $^{118}$Te, $^{119}$Te, $^{119}$mTe, $^{121}$Te, $^{121}$mTe, $^{123}$mTe, $^{125}$mTe, $^{127}$Te, $^{127}$mTe, $^{129}$mTe, $^{131}$mTe, $^{132}$Te, $^{227}$Th, $^{231}$Th, $^{234}$Th, $^{45}$Ti, $^{198}$Tl, $^{199}$Tl, $^{200}$Tl, $^{201}$Tl, $^{202}$Tl, $^{204}$Tl, $^{165}$Tm, $^{166}$Tm, $^{167}$Tm, $^{168}$Tm, $^{170}$Tm, $^{172}$Tm, $^{173}$Tm, $^{230}$U, $^{231}$U, $^{237}$U, $^{240}$U, $^{48}$V, $^{178}$W, $^{181}$W, $^{185}$W, $^{187}$W, $^{188}$W, $^{122}$Xe, $^{125}$Xe, $^{127}$Xe, $^{129}$mXe, $^{131}$mXe, $^{133}$Xe, $^{133}$mXe, $^{135}$Xe, $^{85}$mY, $^{86}$Y, $^{87}$Y, $^{87}$mY, $^{88}$Y, $^{90}$Y, $^{90}$mY, $^{91}$Y, $^{92}$Y, $^{93}$Y, $^{166}$Yb, $^{169}$Yb, $^{175}$Yb, $^{62}$Zn, $^{65}$Zn, $^{69}$mZn, $^{71}$mZn, $^{72}$Zn, $^{86}$Zr, $^{88}$Zr, $^{89}$Zr, $^{95}$Zr, and $^{97}$Zr.

5. The method of claim 1, further comprising obtaining an image after the administering using positron emission tomography (PET), single photon emission computed tomography, radioisotope renography, or scintigraphy.

6. The method of claim 1, wherein cellular proliferation is reduced in the subject after administering the composition as compared to cellular proliferation in the subject following diagnosis with the cancer but before administering the composition.

7. The method of claim 1, wherein the cancer is adrenal cancer, bladder cancer, blood cancer, bone cancer, brain cancer, breast cancer, carcinoma, cervical cancer, colon cancer, colorectal cancer, corpus uterine cancer, ear, nose and throat (ENT) cancer, endometrial cancer, esophageal cancer, gastrointestinal cancer, head and neck cancer, Hodgkin's disease cancer, intestinal cancer, kidney cancer, larynx cancer, leukemia, liver cancer, lymph node cancer, lymphoma, lung cancer, melanoma, mesothelioma, myeloma, nasopharynx cancer, neuroblastoma, non-Hodgkin's lymphoma, oral cancer, ovarian cancer, pancreatic cancer, penile cancer, pharynx cancer, prostate cancer, rectal cancer, sarcomcancer, seminomcancer, skin cancer, stomach cancer, teratomcancer, testicular cancer, thyroid cancer, uterine cancer, vaginal cancer, and vascular tumor cancer.

8. The method of claim 1, wherein the structure is:

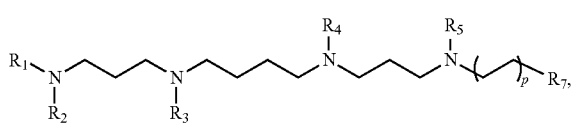

wherein:
at least one of $R_1$, $R_3$, $R_4$, or $R_5$ $R_1$, $R_2$, $R_3$, $R_4$, and $R_5$, individually, are a CAM group, a HA group, or a 1,2-HOPO group;
optionally, another one of $R_1$, $R_3$, $R_4$, or $R_5$ $R_1$, $R_2$, $R_3$, $R_4$, and $R_5$, individually, are H or an alkyl group having from 1 to 10 carbon atoms;
$R_2$ is H or an alkyl group including from 1 to 5 carbon atoms;
$R_7$ is SH, C(=O)OH, or $NH_2$; and
p is from 0 to 4.

9. The method of claim 8, wherein:
$R_1$ is a CAM group or a 1,2-HOPO group;
$R_3$ and $R_4$, individually, are a HA group; and
$R_5$ is a CAM group, a 1,2-HOPO group, or a HA group.

10. The method of claim 1, wherein the structure is:

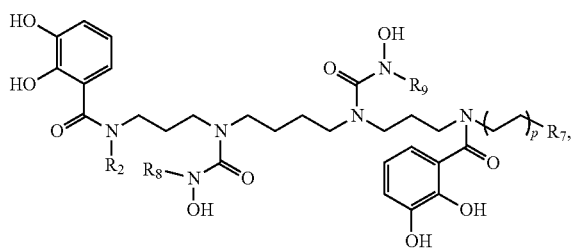

wherein:
$R_7$ is SH, $NH_2$, or C(=O)OH;
$R_2$, $R_8$, and $R_9$, individually, are H, OH, or an alkyl group including from 1 to 5 carbon atoms; and
p is from 0 to 4.

11. The method of claim 1, wherein the structure is:

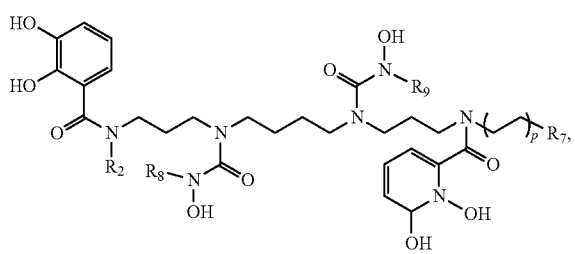

wherein:
$R_7$ is SH, $NH_2$, or C(=O)OH;
$R_2$, $R_8$, and $R_9$, individually, are H, OH, or an alkyl group including from 1 to 5 carbon atoms; and
p is from 0 to 4.

12. The method of claim 1, wherein the structure is:

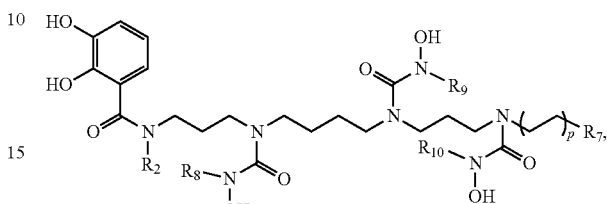

wherein:
$R_7$ is SH, $NH_2$, or C(=O)OH;
$R_2$, $R_8$, $R_9$, and $R_{10}$, individually, are H, OH, or an alkyl group including from 1 to 5 carbon atoms; and
p is from 0 to 4.

13. The method of claim 1, wherein the structure is:

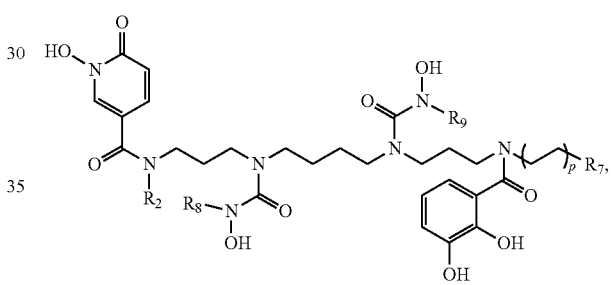

wherein:
$R_7$ is SH, $NH_2$, or C(=O)OH;
$R_2$, $R_8$, and $R_9$, individually, are H, OH, or an alkyl group including from 1 to 5 carbon atoms; and
p is from 0 to 4.

14. The method of claim 1, wherein the structure is:

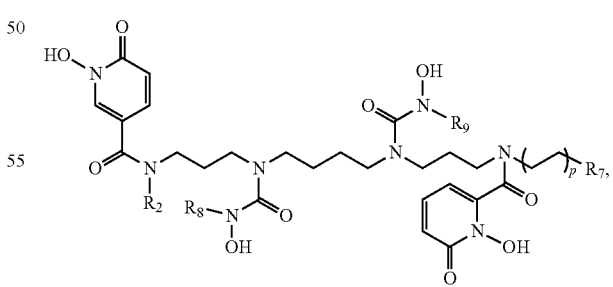

wherein:
$R_7$ is SH, $NH_2$, or C(=O)OH;
$R_2$, $R_8$, and $R_9$, individually, are H, OH, or an alkyl group including from 1 to 5 carbon atoms; and
p is from 0 to 4.

15. The method of claim 1, wherein the structure is:

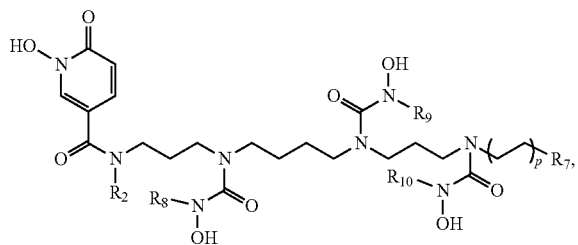

wherein:
$R_7$ is SH, $NH_2$, or $C(=O)OH$;
$R_2$, $R_8$, $R_9$, and $R_{10}$, individually, are H, OH, or an alkyl group including from 1 to 5 carbon atoms; and
p is from 0 to 4.

16. The method of claim 1, wherein the structure is:

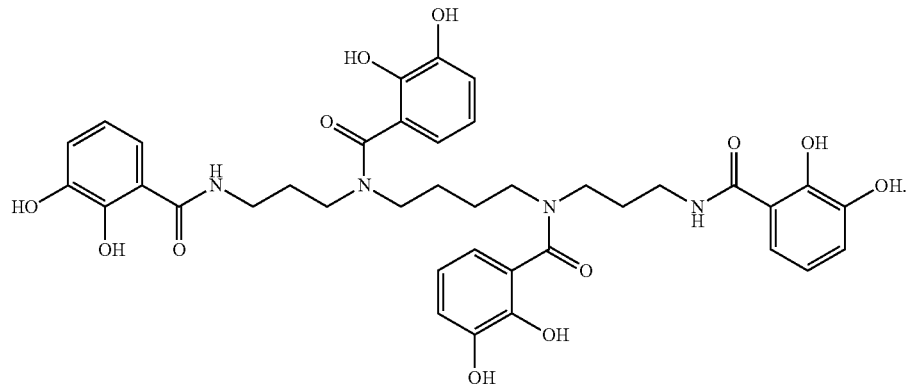 [SMILES: O=C(NCCCN(CCCCN(CCCNC(=O)c1cccc(O)c1O)C(=O)c1cccc(O)c1O)C(=O)c1cccc(O)c1O)c1cccc(O)c1O]

17. The method of claim 1, wherein the structure is:

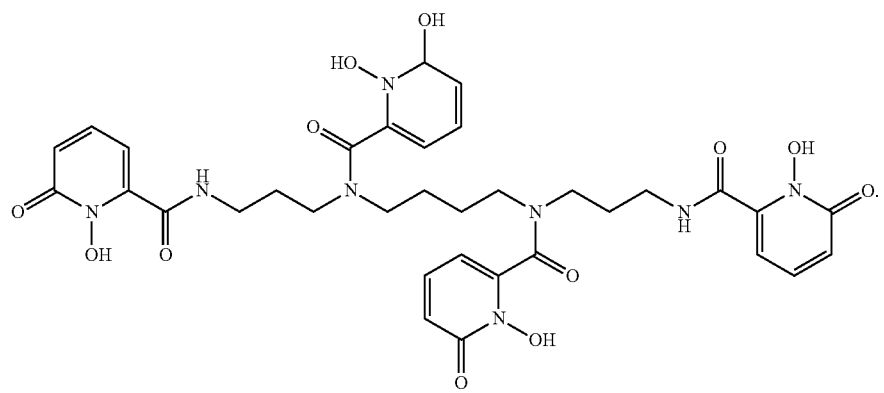 [SMILES: O=C(NCCCN(CCCCN(CCCNC(=O)c1cccc(=O)n1O)C(=O)c1cccc(=O)n1O)C(=O)C1=CC=CC(O)N1O)c1cccc(=O)n1O]

18. A method of treating a thyroid disease, a blood disorder, or restenosis in a subject in need thereof comprising administering to the subject a therapeutically effective amount of a composition including a structure

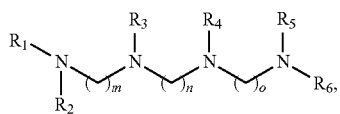

wherein:

at least one of $R_1$, $R_2$, $R_3$, $R_4$, and $R_6$, individually, are selected from the group consisting of a CAM group, a HA group, and a 1,2-HOPO group;

at least another one of $R_1$, $R_2$, $R_3$, $R_4$, and $R_6$, individually, are selected from the group consisting of H and an alkyl group having from 1 to 10 carbon atoms;

$R_6$ is selected from the group consisting of (i) H, (ii) an alkyl group having from 1 to 10 carbon atoms, and (iii) an alkyl group having from 1 to 10 carbon atoms and substituted by at least one of SH, $NH_2$, or $C(=O)OH$;

m is from 1 to 6;

n is from 1 to 6;

o is from 1 to 6; and wherein the composition is bound to a siderocalin and a metal wherein the siderocalin has
  a sequence as set forth in any one of SEQ ID NOs: 1-25,
  a sequence as set forth in any one of SEQ ID NOs: 1-8, 10, 12-14, 16, 18, 22, 23, or 25 with a threonine to cysteine mutation at position 54 or a serine to cysteine mutation at position 68, a sequence as set forth in SEQ ID NOs: 15 or 20 with a threonine to cysteine mutation at position 54, or a sequence as set forth in SEQ ID NOs: 11 or 19 with a serine to cysteine mutation at position 68, thereby treating the thyroid disease, the blood disorder, or the restenosis in the subject in need thereof.

19. The method of claim 18, wherein the thyroid disease is hyperthyroidism or thyrotoxicosis.

20. The method of claim 18, wherein the blood disorder is Polycythemia vera.

21. The method of claim 18, wherein the restenosis follows balloon angioplasty and/or stent placement.

* * * * *